US012807720B2

(12) United States Patent
Daly et al.

(10) Patent No.: US 12,807,720 B2
(45) **Date of Patent: *Nov. 24, 2026**

(54) ANTI-FGFR2 ANTIBODIES AND METHODS OF USE THEREOF

(71) Applicant: Regeneron Pharmaceuticals, Inc., Tarrytown, NY (US)

(72) Inventors: Christopher Daly, New York, NY (US); Frank Delfino, Poughquag, NY (US); Amy Han, Hockessin, DE (US); Thomas Nittoli, Orangeburg, NY (US); Li Zhang, Baldwin Place, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 504 days.

This patent is subject to a terminal disclaimer.

(21) Appl. No.: 18/462,692

(22) Filed: Sep. 7, 2023

(65) Prior Publication Data

US 2024/0190973 A1 Jun. 13, 2024

Related U.S. Application Data

(63) Continuation of application No. 17/507,138, filed on Oct. 21, 2021, now Pat. No. 11,866,502.

(60) Provisional application No. 63/253,858, filed on Oct. 8, 2021, provisional application No. 63/220,948, filed on Jul. 12, 2021, provisional application No. 63/104,377, filed on Oct. 22, 2020.

(51) Int. Cl.

| | |
|---|---|
| ***C07K 16/28*** | (2006.01) |
| ***A61K 39/00*** | (2006.01) |
| ***A61K 45/06*** | (2006.01) |
| ***A61K 47/68*** | (2017.01) |
| ***A61P 35/00*** | (2006.01) |
| ***C07K 16/30*** | (2006.01) |

(52) U.S. Cl.

CPC .......... *C07K 16/2863* (2013.01); *A61K 45/06* (2013.01); *A61K 47/68033* (2023.08); *A61K 47/68037* (2023.08); *A61K 47/6849* (2017.08); *A61P 35/00* (2018.01); *C07K 16/30* (2013.01); *A61K 2039/505* (2013.01)

(58) Field of Classification Search

None

See application file for complete search history.

(56) References Cited

U.S. PATENT DOCUMENTS

| | | | |
|---|---|---|---|
| 5,208,020 | A | 5/1993 | Chari et al. |
| 5,714,586 | A | 2/1998 | Kunstmann et al. |
| 6,596,541 | B2 | 7/2003 | Murphy et al. |
| 7,087,411 | B2 | 8/2006 | Daly et al. |
| 7,582,298 | B2 | 9/2009 | Stevens et al. |
| 7,750,116 | B1 | 7/2010 | Doronina et al. |
| 7,754,681 | B2 | 7/2010 | Feng |
| 9,950,076 | B2 | 4/2018 | Nittoli et al. |
| 10,143,186 | B2 | 12/2018 | McWhirter et al. |
| 10,570,151 | B2 | 2/2020 | Nittoli |
| 11,866,502 | B2 | 1/2024 | Daly et al. |
| 2007/0258987 | A1 | 11/2007 | Francisco et al. |
| 2008/0305497 | A1 | 12/2008 | Kosmeder et al. |
| 2009/0142354 | A1 | 6/2009 | Papadopoulos et al. |
| 2010/0129314 | A1 | 5/2010 | Singh et al. |
| 2010/0331527 | A1 | 12/2010 | Davis et al. |
| 2011/0027286 | A1 | 2/2011 | Thurston et al. |
| 2013/0101546 | A1 | 4/2013 | Yurkovetskiy et al. |
| 2014/0322220 | A1 | 10/2014 | Harrenga et al. |
| 2016/0317656 | A1 | 11/2016 | Urano et al. |
| 2016/0354482 | A1 | 12/2016 | Nittoli et al. |
| 2016/0375147 | A1 | 12/2016 | Nittoli |
| 2017/0145102 | A1 | 5/2017 | Pierce et al. |
| 2017/0209591 | A1 | 7/2017 | Nittoli et al. |
| 2019/0153105 | A1 | 5/2019 | Kim et al. |
| 2021/0260208 | A1 | 8/2021 | Han et al. |

FOREIGN PATENT DOCUMENTS

| | | |
|---|---|---|
| WO | WO 2005/089808 | 9/2005 |
| WO | WO 2008/122039 | 10/2008 |
| WO | WO 2010/010324 | 1/2010 |
| WO | WO 2011/018611 | 2/2011 |
| WO | WO 2011/130598 | 10/2011 |
| WO | WO 2012/059882 | 5/2012 |
| WO | WO 2012/166559 | 12/2012 |
| WO | WO 2013/053872 | 4/2013 |
| WO | WO 2013/053873 | 4/2013 |
| WO | WO 2013/055990 | 4/2013 |
| WO | WO 2013/055993 | 4/2013 |

(Continued)

OTHER PUBLICATIONS

Felgenhauer et al. (Nucleic Acids Res. 1990 18(16): 4927) (Year: 1990).*

Sambrook et al. (Molecular Cloning A laboratory Manual, 2nd edition, Cold Spring Harbor, N.Y. 1989, pp. 16.3-16.36) (Year: 1989).*

Dondelinger et al. (2018) Understanding the Significance and Implications of Antibody Numbering and Antigen-Binding Surface/Residue Definition, Frontiers in Immunology, 9: 2278, pp. 1-15, doi: 10.3389/fimmu2018.02278. eCollection 2018.

(Continued)

*Primary Examiner* — Peter J Reddig

(74) *Attorney, Agent, or Firm* — FisherBroyles, LLP; Cara L. Crowley-Weber; Haiou Qin

(57) ABSTRACT

Provided herein are monoclonal antibodies, and antigen-binding fragments thereof, that bind fibroblast growth factor receptor 2 (FGFR2), and methods of use thereof and methods of use thereof. Also included are antibody-drug conjugates (ADCs) comprising the anti-FGFR2 antibodies or antigen-binding fragments thereof linked to a cytotoxic agent, radionuclide, or other moiety, as well as methods of treatment using the same.

37 Claims, 14 Drawing Sheets

Specification includes a Sequence Listing.

(56) References Cited

FOREIGN PATENT DOCUMENTS

| | | |
|---|---|---|
| WO | WO 2013/068874 | 5/2013 |
| WO | WO 2013/076186 | 5/2013 |
| WO | WO 2013/085925 | 6/2013 |
| WO | WO 2014/065661 | 5/2014 |
| WO | WO 2014/089193 | 6/2014 |
| WO | WO 2014/121087 | 8/2014 |
| WO | WO 2014/145090 | 9/2014 |
| WO | WO 2015/031396 A1 | 3/2015 |
| WO | WO 2015/155998 | 10/2015 |
| WO | WO 2018/089373 A2 | 5/2018 |
| WO | WO 2022/087243 | 4/2022 |

OTHER PUBLICATIONS

Gonzales et al. (2005) "Minimizing the Immunogenicity of Antibodies for Clinical Application", Tumor Biology, 26, pp. 31-43, doi: 10.1159/000084184.

Kunik et al. (2012) "Structural Consensus among Antibodies Defines the AntigenBinding Site", PLoS Computational Biology, 8(2): e1002388, pp. 1-12.

Panka et al. (1988) "Variable Region Framework Differences Result in Decreased or Increased Affinity of Variant Anti-Digoxin Antibodies", Proc. Natl. Acad. Sci, USA, 85, pp. 3080-3084.

Park et al. (2011) "Abstract 5056: HuGAL-FR21, a Humanized Monoclonal Antibody to Fibroblast Growth Factor Receptor 2, Effectively Inhibits the Growth of Gastric Tumor Xenografts", Poster Presentations—Proffered Abstracts| Apr. 15, 2011, Cancer Res. 8 Supplement:5056, 71 (8_Supplement): 5056. https://doi.org/10.1158/1538-7445.AM2011-5056.

Sela-Culang et al. (2013) "The Structural Basis of Antibody-Antigen Recognition", Frontiers in Immunology, 4: Article 302, pp. 1-13, doi:10.3389/fimmu.2013.00302.

Wark et al. (2006) "Latest Technologies for the Enhancement of Antibody Affinity", Advanced Drug Delivery Reviews 58, pp. 657-670.

Moon et al. (2016) "Substitution of Heavy Complementarity Determining Region 3 (CDR-H3) Residues Can Synergistically Enhance Functional Activity of Antibody and Its Binding Affinity to HER2 Antigen", Molecules and Cells, 39(3): 217-228.

Winter and Harris (1993) "Humanized Antibodies", Immunology Today, 14(6): 243-246.

Accession No. NP_075259.4 To: Protein [Internet]. Bethesda (MD): National Library of Medicine (US), National Center for Biotechnology Information; [1988]—Accession No. NP_075259.4, "Fibroblast Growth Factor Receptor 2 Isoform 2 Precursor [*Homo sapiens*]", cited on Jan. 9, 2022, [online], [retrieved on Jan. 27, 2022]. Retrieved from: https://www.ncbi.nlm.nihm.gov/protein/NP_075259.4, 4 pages.

Accession No. P01863 To: Protein [Internet]. Bethesda (MD): National Library of Medicine (US), National Center for Biotechnology Information; [1988]—Accession No. P01863, "RecName: Full=Ig Gamma-2A Chain C Region, A Allele; AltName: Full=Immunoglobulin Heavy Chain Gamma Polypeptide", cited on Jun. 2, 2021, [online], [retrieved on Jan. 27, 2022]. Retrieved from: https://www.ncbi.nlm.nihm.gov/protein/P01863, 4 pages.

Agarwal et al. (2013) "A Pictet-Spengler Ligation for Protein Chemical Modification," Proc. National Acad. Sci., USA, 110: 46-51.

Al-Lazikani et al. (1997) "Standard Conformations for the Canonical Structures of Immunoglobulins," J. Mol. Biol., 273: 927-948.

Altschul et al. (1990) "Basic Local Alignment Search Tool," J. Mol. Biol., 215: 403-410.

Altschul et al. (1997) "Gapped Blast and PSI-Blast: A New Generation of Protein Database Search Programs," Nucleic Acids Res., 25: 3389-3402.

Baskin et al. (2007) "Copper-Free Click Chemistry for Dynamic in vivo Imaging," PNAS, 104(43): 16793-16797.

Boersma and Pluckthun (2011) "DARPins and Other Repeat Protein Scaffolds: Advances in Engineering and Applications," Curr. Opin. Biotechnol., 22: 849-857.

Carrico et al (2007) "Introducing Genetically Encoded Aldehydes into Proteins," Nat. Chem. Biol., 3(6): 321-322.

Cha et al. (2009) "Aberrant Receptor Internalization and Enhanced FRS2-Dependent Signaling Contribute to The Transforming Activity of The Fibroblast Growth Factor Receptor 2iiib C3 Isoform," J. Biol. Chem., 284(10): 6227-6240.

Dennler, et al. (2014) "Transglutaminase-Based Chemo-Enzymatic Conjugation Approach Yields Homogeneous Antibody-Drug Conjugates," Bioconjugate Chem., 25(3): 569-578.

Doronina et al. (2003) "Development of Potent Monoclonal Antibody Auristatin Conjugates for Cancer Therapy," Nature Biotech, 21(7): 778-784.

Ducry and Stump (2010) "Antibody-Drug Conjugates: Linking Cytotoxic Payloads to Monoclonal Antibodies," Bioconjugate Chem., 21: 5-13.

Ducry Eds. (2013) "Antibody-Drug Conjugates," Humana Press, Methods in Molecular Biology, Springer Protocols, 315 pages.

Ehring (1999) "Hydrogen Exchange/Electrospray Ionization Mass Spectrometry Studies of Structural Features of Proteins and Protein/Protein Interactions," Analytical Biochemistry, 267(2): 252-259.

Engen and Smith (2001) "The Basics of Ion Chromatography," Anal. Chem., 73: 256A-265A.

Gemo et al. (2014) "FPA144: A Therapeutic Antibody for Treating Patients with Gastric Cancers Bearing FGFR2 Gene Amplification," Cancer Res, 74(19 Suppl): AACR Abstract ID 5446.

Gonnet et al. (1992) "Exhaustive Matching of the Entire Protein Sequence Database," Science, 256: 1443-1445.

Hamblett et al. (2004) "Effects of Drug Loading on the Antitumor Activity of a monoclonal Antibody Drug Conjugate," American Association for Cancer Research., 10(20): 7063-7070.

Hofer et al. (2008) "An Engineered Selenocysteine Defines a unique Class of Antibody Derivatives," Proc. Natl. Acad. Sci., USA, 105: 12451-12456.

Hollander et al. (2008) "Selection of Reaction Additives Used in the Preparation of Monomeric Antibody-Calicheamicin Conjugates," Bioconjugate Chem., 19: 358-361.

International Search Report and The Written Opinion of International Application No. PCT/US2021/056018 mailed Apr. 8, 2022, 20 pages.

Jeger et al. (2010) "Site-Specific and Stoichiometric Modification of Antibodies by Bacterial Transglutaminase," Angew Chemie Inter Ed., 49(51): 9995-9997.

Junghans et al. (1990) "Anti-Tac-H, a Humanized Antibody to the Interleukin 2 Receptor with New Features for Immunotherapy in Malignant and Immune Disorders," Cancer Res., 50: 1495-1502.

Kabat et al. (1991) "Sequences of Proteins of Immunological Interest," Fifth Edition, National Institutes of Health, Bethesda, Md., 37 pages.

Kazane et al. (2013) "Self-Assembled Antibody Multimers Through Peptide Nucleic Acid Conjugation," J. Amm. Chem. Soc. [Epub: Dec. 4, 2012] 135: 240-246.

Klein et al. (2012) "Progress in Overcoming the Chain Association Issue in Bispecific Heterodimeric IgG Antibodies," mAbs, 4:6, 1-11.

Kufer et al. (2004) "A Revival of Bispecific Antibodies," Trends Biotechnol., 22(5): 238-244.

Lee et al. (2016) "Antitumor Activity and Safety of FPA144, an ADCC-Enhanced, FGFR2b Isoform-Selective Monoclonal Antibody, in Patients with FGFR2b+ Gastric Cancer and Advanced Solid Tumors," J Clin Oncol 34(15 Suppl): ASCO Abstract ID 2502.

Li et al. (2016) "A Biparatopic HER2-Targeting Antibody-Drug Conjugate Induces Tumor Regression in Primary Models Refractory or Ineligible for HER2-Targeted Therapy," Cancer Cell, 29: 117-129.

Lorenzi et al., (1997) "Ligand-Independent Activation of Fibroblast Growth Factor Receptor-2 By Carboxyl Terminal Alterations," Oncogene, 15: 817-826.

Martin et al. (1989) "Modeling Antibody Hypervariable Loops: A Combined Algorithm," Proc. Natl. Acad. Sci. USA, 86: 9268-9272.

Pearson (1994) "Using the FASTA Program to Search Protein and DNA Sequence Databases," Methods Mol. Biol., 24: 307-331.

(56) References Cited

OTHER PUBLICATIONS

Pearson (2000) "Flexible Sequence Similarity Searching with the FASTA3 Program Package," Methods in Molecular Biology, 132: 185-219.
Ponziani et al. (2020) "Antibody-Drug Conjugates: The New Frontier of Chemotherapy," Int. J. Mol. Sci., 21(5510): 1-26.
Powers et al. (2016) "FPA144, A Therapeutic Monoclonal Antibody Targeting the FGFR2b Receptor, Promotes Antibody Dependent Cell-Mediated Cytotoxicity and Stimulates Sensitivity to PD-1 in the 4T1 Syngeneic Tumor Model," Cancer Res 76(14 Suppl): AACR Abstract ID 1407.
Rabuka et al. (2012) "Site-Specific Chemical Protein Conjugation Using Genetically Encoded Aldehyde Tags," Nat. Protocols, 7(6): 1052-1067.
Reineke (2004) "Antibody Epitope Mapping Using Arrays of Synthetic Peptides," Methods Mol Biol, 248: 443-463.
Ryan et al. (2001) "Polyclonal Antibody Production Against Chito-Oligosaccharides," Food & Agriculture Immunology, 13: 127-130.
Sapra et al. (2013) "Monoclonal Antibody-Based Therapies in Cancer: Advances and Challenges," Pharmacol. & Therapeutics, 138: 452-469.
Schumacher et al. (2016) "Current Status: Site-Specific Antibody Drug Conjugates," J. Clin. Immunol., 26(Suppl 1): S100-S107.
Shaunak et al. (2006) "Site-Specific PEGylation of Native Disulfide Bonds in Therapeutic Proteins," Nat. Chem. Biol., 2(6): 312-313.
Shield et al. (2002) "Lack of Fucose on Human IgG1 N-Linked Oligosaccharide Improves Binding to Human FcyRIII and Antibody-Dependent Cellular Toxicity," JBC 277(30): 26733-26740.
Sommer et al. (2014) "FGFR2-ADC Potently and Selectively Inhibits Growth of Gastric and Breast Cancer Xenograft Models," Cancer Res., 74(19 Suppl): AACR Abstract ID 4491.
Sommer et al. (2016) "Preclinical Efficacy of the Auristatin-Based Antibody-Drug Conjugate Bay 1187982 for the Treatment of FGFR2-Positive Solid Tumors," Cancer Res., 76(21): 6331-6339.
Takeda et al., (2007) "AZD2171 Shows Potent Antitumor Activity Against Gastric Cancer Over-Expressing Fibroblast Growth Factor Receptor 2/Keratinocyte Growth Factor Receptor, "Clin Cancer Research, 13(10): 3051-3057.
Taylor et al. (1992) "A Transgenic Mouse that Expresses a Diversity of Human Sequence Heavy and Light Chain Immunoglobulins," Nucl. Acids Res., 20: 6287-6295.
Tomer (2000) "Characterization of a Discontinuous Epitope of the Human Immunodeficiency Virus (HIV)Core Protein p24 by Epitope Excision and Differential Chemical Modification followed by Mass Spectrometric Peptide Mapping Analysis," Protein Science 9: 487-496.
Tutt et al. (1991) "Trispecific F(ab')3 Derivatives That Use Cooperative Signaling Via The TCR/CD3 Complex and CD2 to Activate and Redirect Resting Cytotoxic T Cells," J. Immunol., 147: 60-69.
Wickstroem et al. (2019) "Preclinical Combination Studies of an FGFR2 Targeted Thorium Conjugate and the ATR Inhibitor Bay 1895344," Int J Radiat Oncol Biol Phys., 105(2): 410-422.
Wittemer-Rump et al. (2014) "Pharmacokinetic and Pharmacodynamic (PK/PD) Modeling of Preclinical Data of a Novel Anti-Fibroblast Growth Factor Receptor 2 (FGFR2) Antibody (Bay 1179470) to Guide Dosing in Phase 1," Cancer Res., 74(19 Suppl): AACR Abstract ID 672.

* cited by examiner

Figure 1A. Anti FGFR2 mAb-PEG$_3$-N$_3$-LP1
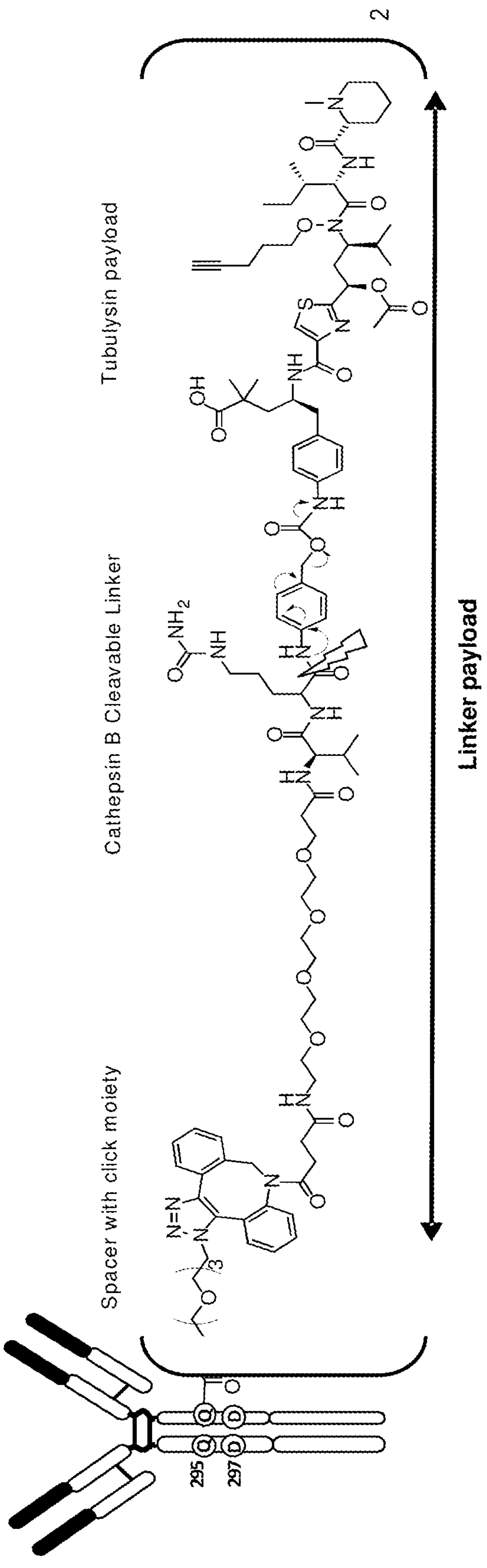

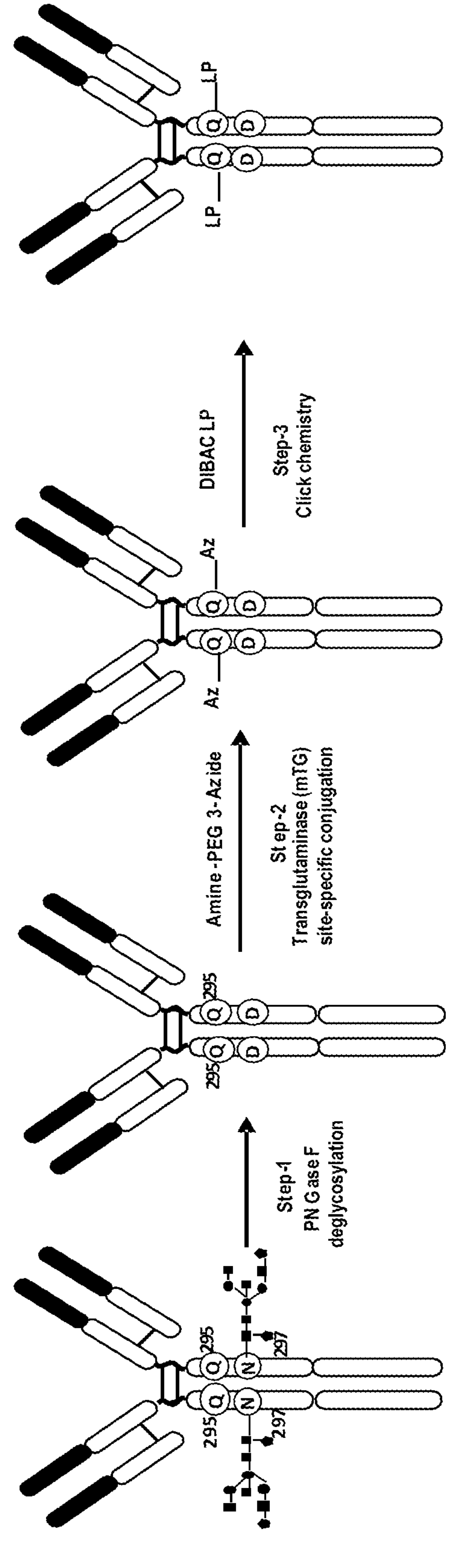
Figure 1B. 3-step site-specific conjugation

Figure 2. SEC-HPLC monomer purity analysis
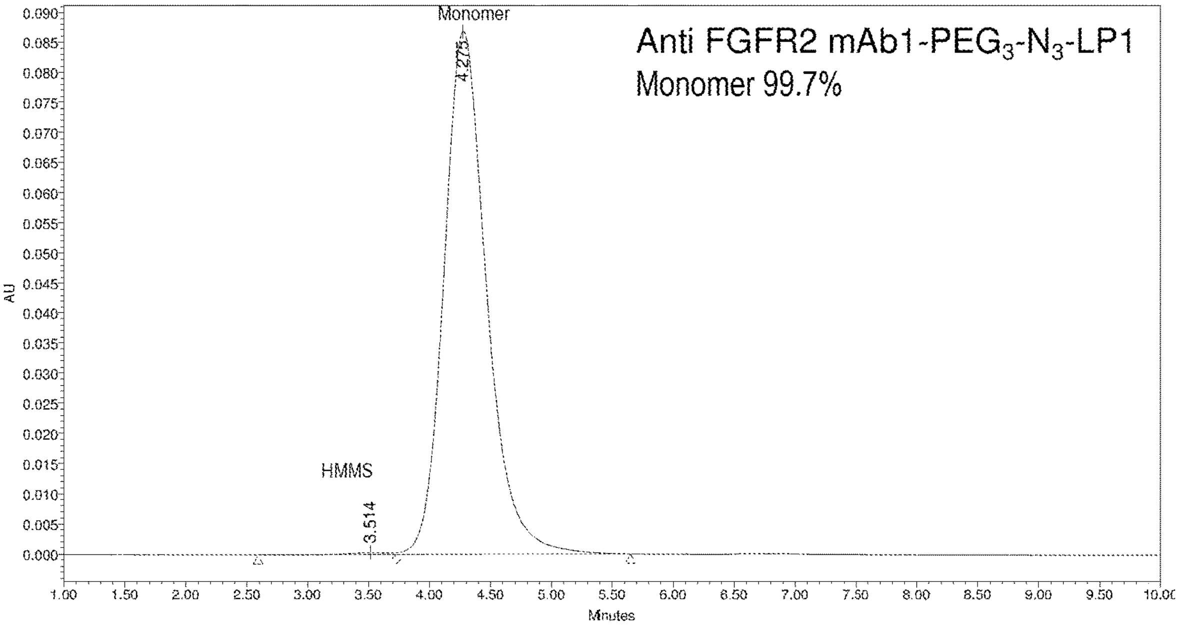

Figure 8
| General structure | DAR | L1-B' (NH2-L1-B' can be chosen from **Table 1**) | |
|---|---|---|---|
| | | L1 | B' |
| 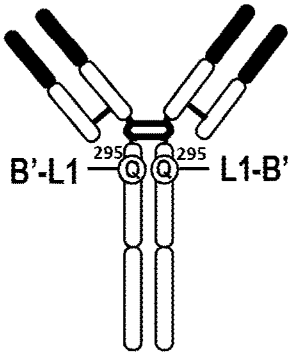 | 2 | Peptides | -N3 |
| | | 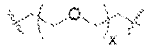 | |
| | | 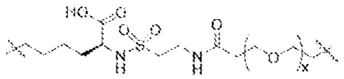 | |
| | | 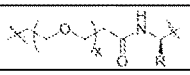 | |
| | | 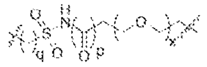 | |
| 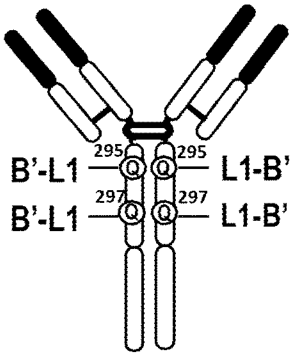 | 4 | 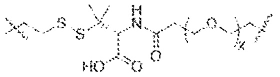 | |
| | | 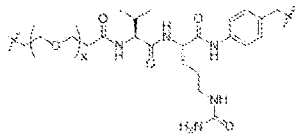 | |

Figure 9
| General structure | group | n | L1 |
|---|---|---|---|
| 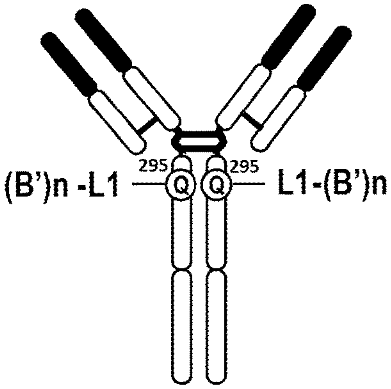  | A | 2 | 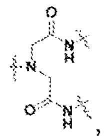 , 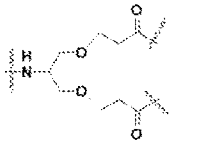 |
| | B | 3 | 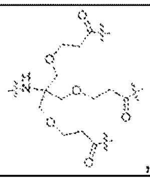 , 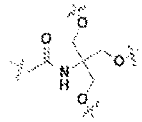 |
| | C | 4 | 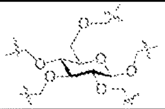 |
| | D | 6 | 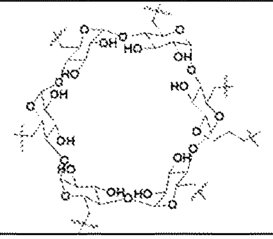 |
| 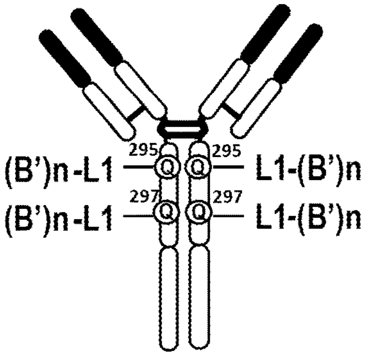  | E | | 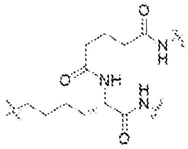 , 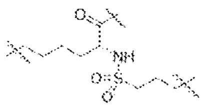 |

ANTI-FGFR2 ANTIBODIES AND METHODS OF USE THEREOF

CROSS-REFERENCE TO RELATED APPLICATIONS

This application is a continuation of U.S. patent application Ser. No. 17/507,138, filed on Oct. 21, 2021, which claims the benefit under 35 U.S.C § 119(e) of U.S. Provisional Application Ser. No. 63/253,858, filed Oct. 8, 2021; U.S. Provisional Application Ser. No. 63/220,948 filed Jul. 12, 2021; and U.S. Provisional Application Ser. No. 63/104,377 filed Oct. 22, 2020, which are herein incorporated by reference in their entirety.

TECHNICAL FIELD

The present invention relates to antibodies and antigen-binding fragments thereof, as well as antibody-drug conjugates of such antibodies, which specifically bind fibroblast growth factor receptor 2 (FGFR2), and methods of use thereof.

SEQUENCE LISTING

An official copy of the sequence listing is submitted concurrently with the specification electronically via Patent Center. The contents of electronic sequence listing (10680US02_Sequence_Listing_ST26.xml; Size 86,016 bytes; and Date of Creation: Sep. 7, 2023) is part of the specification and is herein incorporated by reference in its entirety.

BACKGROUND

The fibroblast growth factor (FGF) receptor tyrosine kinase (RTK) family consists of fibroblast growth factor receptor 1 (FGFR1), FGFR2, FGFR3, and FGFR4, and encompasses high affinity receptors for as many as 18 different FGF ligands. The receptor is a transmembrane tyrosine kinase, and FGFR signaling drives downstream pathways, including the mitogen-activated protein kinase (MAPK) and AKT pathways, which are crucial for cell proliferation, differentiation, survival, and migration. Binding of the FGF ligand to the receptor induces dimerization of the FGF:FGFR complex. Dimerization leads to kinase activation and autophosphorylation of multiple tyrosine residues in the cytoplasmic domain of the receptor, and activation of downstream signaling of the phosphoinositide 3-kinase (PI3K)-AKT and MAPK-extracellular signal-regulated kinase (ERK) pathways. Alternative splicing of the IgIII loop in FGFR1-3 generates the FGFRIIIb or the FGFRIIIc isoforms.

FGFR2 amplification has been reported in various cancers. FGFR2 amplification affects signaling without altering the intrinsic kinase activity of the receptor. Signaling through overexpressed FGFR2 also shows evidence of being ligand-independent and sensitive to FGFR inhibitors (Lorenzi, 1997, Ligand-independent activation of fibroblast growth factor receptor-2 by carboxyl terminal alterations, Oncogene; Takeda, 1999, AZD2171 shows potent antitumor activity against gastric cancer over-expressing fibroblast growth factor receptor 2/keratinocyte growth factor receptor, Clin Cancer Research; Cha, 2009, Aberrant receptor internalization and enhanced FRS2-dependent signaling contribute to the transforming activity of the fibroblast growth factor receptor 2 IIIb C3 isoform, J. Biol. Chem).

Furthermore, the FGFR2 protein is overexpressed in about 3% of breast cancers, including triple negative breast cancer, and about 10% of gastric/esophageal cancers. FGFR2 overexpression is also found in other cancers, including colon, hepatocellular, pancreatic, ovary, uterine, cervical, endometrial, bladder, lung, colon, glioma, and head and neck cancers. In addition, mutations of the FGFR2 gene have been reported in about 12% of endometrial carcinomas. FGFR2 overexpression has been associated with poor survival in patients with gastric cancer.

There is significant interest in FGFR2 as a therapeutic target across tumor types. In patients with gastric cancer carrying FGFR2 amplification, therapeutic intervention using small molecule FGFR inhibitors, such as TAS-120 and AZD4547, has been suggested.

Both preclinical and clinical studies have demonstrated that FGFR-amplified tumors are sensitive to FGFR inhibition and therefore susceptible to therapeutic targeting. Treatment of FGFR2 positive tumors with anti-FGFR2 therapies such as Bemarituzumab (aka HGS1036, HGS 1036, FP-1039, FPA144, GSK3052230) reportedly leads to improvements in early survival and advanced disease. (Gemo et al. (2014) "FPA144: A Therapeutic Antibody for Treating Patients with Gastric Cancers Bearing FGFR2 Gene Amplification" AACR Abstract ID 5446; Powers et al. (2016) "FPA144, A Therapeutic Monoclonal Antibody Targeting the FGFR2b Receptor, Promotes Antibody Dependent Cell-Mediated Cytotoxicity and Stimulates Sensitivity to PD-1 in the 4T1 Syngeneic Tumor Model" AACR Abstract ID 1407; and Lee et al. (2016) "Antitumor Activity and Safety of FPA144, an ADCC-Enhanced, FGFR2b Isoform-Selective Monoclonal Antibody, in Patients with FGFR2b+ Gastric Cancer and Advanced Solid Tumors" ASCO Abstract ID 2502).

Some FGFR2 antibodies are conjugated to cytotoxic payloads, including thorium-227 (Aprutumab, aka BAY1179470, BAY2304058) and auristatin (Aprutumab ixadotin, aka BAY1187982, BAY1179470 ADC). Aprutumab-TTC (anti-FGFR2 antibody, a chelator moiety covalently conjugated to the antibody, and the alpha particle-emitting radionuclide thorium-227) reportedly inhibited tumor growth in several xenograft models. (Wickstroem et al. (2019) "Preclinical Combination Studies of an FGFR2 Targeted Thorium Conjugate and the ATR Inhibitor Bay 1895344" Int J Radiat Oncol Biol Phys 105(2):410-422; Wittemer-Rump et al. (2014) "Pharmacokinetic and Pharmacodynamic (PK/PD) Modeling of Preclinical Data of a Novel Anti-Fibroblast Growth Factor Receptor 2 (FGFR2) Antibody (BAY 1179470) to Guide Dosing in Phase 1" AACR Abstract ID 672). In clinical testing, Aprutumab ixodotin was poorly tolerated, with a minimum tolerated dose found to be below the therapeutic threshold estimated preclinically; therefore, the trial was terminated early. (Sommer et al. (2016) "Preclinical Efficacy of the Auristatin-Based Antibody-Drug Conjugate BAY 1187982 for the Treatment of FGFR2-Positive Solid Tumors" Cancer Res 76(21):6331-6339; Sommer et al. (2014) "FGFR2-ADC Potently and Selectively Inhibits Growth of Gastric and Breast Cancer Xenograft Models" AACR Abstract ID 4491)

There remains a significant unmet medical need for improved anti-cancer drugs that are effective in FGFR2 expressing cancers.

BRIEF SUMMARY

Provided herein are antibodies and antigen-binding fragments thereof that bind human FGF receptor 2 protein (FGFR2). The antibodies are useful, inter alia, for targeting tumor cells that express FGFR2. The anti-FGFR2 antibodies, and antigen-binding portions thereof, may be used alone in unmodified form, or may be included as part of an antibody-drug conjugate.

Other embodiments will become apparent from a review of the ensuing detailed description.

BRIEF DESCRIPTION OF THE FIGURES

FIG. 1A and FIG. 1 B. FIG. 1A depicts a monoclonal antibody with a click moiety spacer, a cathepsin B cleavable linker, and a tubulysin payload. FIG. 1 B depicts a process for site specific conjugation on the antibody.

FIG. 2 provides SEC-HPLC analyses of the anti-FGFR2 antibody —tubulysin conjugate.

FIG. 8 depicts basic component structures of non-limiting exemplary azide amine linkers.

FIG. 9 depicts basic component structures of exemplary non-limiting branched-alkyl azide amine linkers.

DETAILED DESCRIPTION

Figure 3:
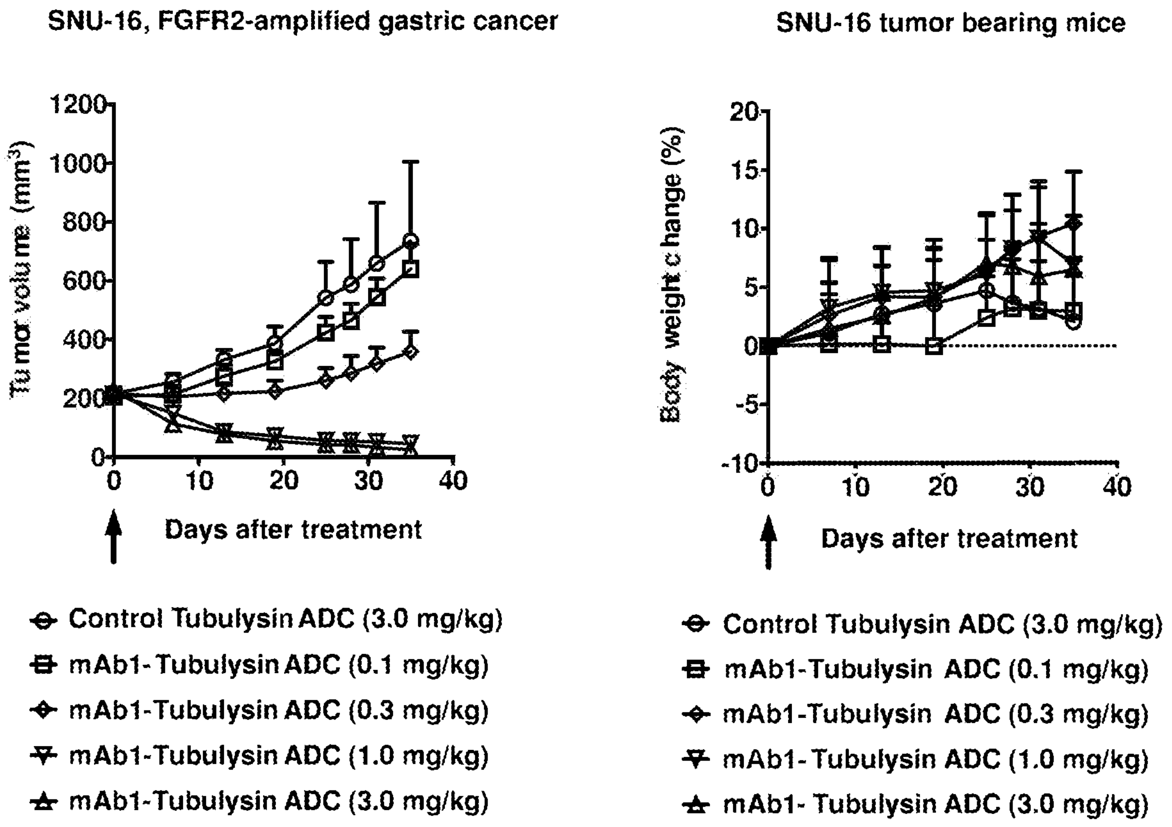
FIG. 3 shows change in tumor volume and body weight in human gastric cancer xenografts over time with treatment using different dosages of Anti-FGFR2 antibody-tubulysin conjugate. Anti-FGFR2 tubulysin ADC demonstrated significant anti-tumor efficacy against SNU-16 human gastric cancer xenografts.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

FGFR2 Protein

The expressions "FGFR2" and the like, as used herein, refer to a tyrosine protein kinase that acts as a cell-surface receptor for fibroblast growth factors. The protein is also known as keratinocyte growth factor receptor and CD332. FGFR2b can refer to the amino acid sequence as set forth in SEQ ID NO: 55, and/or having the amino acid sequence as set forth in NCBI accession No. NP_075259.4, and is encoded by the FGFR2 gene residing on chromosome 10.

The epithelial splicing regulatory protein 1 (ESRP1) isoform is responsible for the FGFR2 splicing and consequent expression of the epithelial FGFR2b isoform.

FGFR2 is a tyrosine-protein kinase that acts as cell-surface receptor for fibroblast growth factors and plays an essential role in the regulation of cell proliferation, differentiation, migration and apoptosis, and in the regulation of embryonic development. Activation of FGFR2 results in phosphorylation of PLCG1, FRS2, and PAK4 and activation of several signaling cascades. Activation of PLCG1 leads to the production of the cellular signaling molecules diacylglycerol and inositol 1,4,5-trisphosphate. Phosphorylation of FRS2 triggers recruitment of GRB2, GAB1, PIK3R1 and SOS1, and mediates activation of RAS, MAPK1/ERK2, MAPK3/ERK1 and the MAP kinase signaling pathway, as well as of the AKT1 signaling pathway. FGFR2 signaling is down-regulated by ubiquitination, internalization and degradation. Mutations that lead to constitutive kinase activation or impair normal FGFR2 maturation, internalization and degradation lead to aberrant signaling. Likewise, over-expressed FGFR2 promotes activation of STAT1.

All references to proteins, polypeptides and protein fragments herein are intended to refer to the human version of the respective protein, polypeptide or protein fragment unless explicitly specified as being from a non-human species. Thus, the expression "FGFR2" means human FGFR2 unless specified as being from a non-human species, e.g., "mouse FGFR2" "monkey FGFR2," etc.

As used herein, the expression "cell surface-expressed FGFR2" means one or more FGFR2 protein(s), or the extracellular domain thereof, that is/are expressed on the surface of a cell in vitro or in vivo, such that at least a portion of a FGFR2 protein is exposed to the extracellular side of the cell membrane and is accessible to an antigen-binding portion of an antibody. A "cell surface-expressed FGFR2" can comprise or consist of an FGFR2 protein expressed on the surface of a cell which normally expresses FGFR2 protein. Alternatively, "cell surface-expressed FGFR2" can comprise or consist of FGFR2 protein expressed on the surface of a cell that normally does not express human FGFR2 on its surface but has been artificially engineered to express FGFR2 on its surface.

ANTI-FGFR2 Antibodies and Antigen-Binding Fragments Thereof

The term "antibody", as used herein, means any antigen-binding molecule or molecular complex comprising at least one complementarity determining region (CDR) that specifically binds to or interacts with a particular antigen (e.g., FGFR2). The term "antibody" includes immunoglobulin molecules comprising four polypeptide chains, two heavy chains (HC) and two light chains (LC) inter-connected by disulfide bonds, as well as multimers thereof (e.g., IgM). The term "antibody" also includes immunoglobulin molecules consisting of four polypeptide chains, two HC and two LC inter-connected by disulfide bonds. Each HC comprises a heavy chain variable region (abbreviated herein as HCVR or $V_H$) and a heavy chain constant region. The heavy chain constant region comprises three domains, $C_{H1}$, $C_{H2}$ and $C_{H3}$. Each LC comprises a light chain variable region (abbreviated herein as LCVR or $V_L$) and a light chain constant region. The light chain constant region comprises one domain ($C_{1L}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order FR1, CDR1, FR2, CDR2, FR3, CDR3, FR4. In different embodiments of the invention, the FRs of the anti-FGFR2 antibody (or antigen-binding portion thereof) may be identical to the human germline sequences, or may be naturally or artificially modified. An amino acid consensus sequence may be defined based on a side-by-side analysis of two or more CDRs.

Likewise, the term "antibody" includes immunoglobulin molecules comprising eight polypeptide chains, four HC and four LC inter-connected by disulfide bonds, i.e., a bi-specific antibody. The term "antibody" also includes immunoglobulin molecules consisting of eight polypeptide chains, four HC and four LC inter-connected by disulfide bonds.

Furthermore, the term "antibody" includes functionalized immunoglobulin molecules comprising at least one HC, wherein the HC comprises an azido-$PEG_3$-amine. In some aspects, the azido-$PEG_3$-amine is located at a Q295 site on the antibody HC. In some aspects, the azido-$PEG_3$-amine is located at a Q297 site on the antibody. In some aspects, the antibody has two HCs functionalized with azido-$PEG_3$-amines located at both Q295 sites in the HCs. In some aspects, the antibody has two HCs functionalized with azido-$PEG_3$-amines located at both Q297 sites in the HCs. In some aspects, the antibody has two HCs functionalized with azido-$PEG_3$-amines located at both Q295 sites and at both Q297 sites in the HCs. The Q297 sites in the HCs are obtained by modifying the N297 to a Q297, also referred to herein as an N297Q modification.

According to one aspect, anti-FGFR2 antibodies are provided. Exemplary anti-FGFR2 antibodies according to this aspect are listed in Tables 3 and 4 herein. Table 3 sets forth the amino acid sequence identifiers of the heavy chain variable regions (HCVRs), light chain variable regions (LCVRs), heavy chain complementarity determining regions (HCDR1, HCDR2 and HCDR3), light chain complementarity determining regions (LCDR1, LCDR2 and LCDR3), heavy chains (HC), and light chains (LC) of the anti-FGFR2 antibodies, or antigen-binding fragments thereof, disclosed herein. Table 4 sets forth the nucleic acid sequence identifiers of the HCVRs, LCVRs, HCDR1, HCDR2, HCDR3, LCDR1, LCDR2, LCDR3, HC, and LC of the exemplary antibodies.

Provided herein are antibodies or antigen-binding fragments thereof that specifically bind FGFR2, comprising the CDRs within an HCVR comprising an amino acid sequence selected from any of the HCVR amino acid sequences listed in Table 3, or a substantially similar sequence thereof having at least 90%, at least 95%, at least 98% or at least 99% sequence identity thereto.

Provided herein are antibodies or antigen-binding fragments thereof that specifically bind FGFR2, comprising an HCVR comprising an amino acid sequence selected from any of the HCVR amino acid sequences listed in Table 3, or a substantially similar sequence thereof having at least 90%, at least 95%, at least 98% or at least 99% sequence identity thereto.

Provided herein are antibodies or antigen-binding fragments thereof that specifically bind FGFR2, comprising the CDRs within an LCVR comprising an amino acid sequence selected from any of the LCVR amino acid sequences listed in Table 3, or a substantially similar sequence thereof having at least 90%, at least 95%, at least 98% or at least 99% sequence identity thereto.

Provided herein are antibodies or antigen-binding fragments thereof that specifically bind FGFR2, comprising an LCVR comprising an amino acid sequence selected from any of the LCVR amino acid sequences listed in Table 3, or a substantially similar sequence thereof having at least 90%, at least 95%, at least 98% or at least 99% sequence identity thereto.

Provided herein are antibodies or antigen-binding fragments thereof that specifically bind FGFR2, comprising the CDRs within an HCVR and an LCVR amino acid sequence pair (HCVR/LCVR) comprising any of the HCVR amino acid sequences listed in Table 3 paired with any of the LCVR amino acid sequences listed in Table 3. Also provided herein are antibodies or antigen-binding fragments thereof that specifically bind FGFR2, comprising an HCVR/LCVR amino acid sequence pair comprising any of the HCVR amino acid sequences listed in Table 3 paired with any of the LCVR amino acid sequences listed in Table 3. In certain embodiments, an HCVR/LCVR amino acid sequence pair is selected from the group consisting of: SEQ ID NO: 2/10, 22/28, and 40/44.

Also provided are antibodies or antigen-binding fragments thereof that specifically bind FGFR2, comprising a heavy chain CDR1 (HCDR1) comprising an amino acid sequence selected from any of the HCDR1 amino acid sequences listed in Table 3 or a substantially similar sequence thereof having at least 90%, at least 95%, at least 98% or at least 99% sequence identity.

Also provided are antibodies or antigen-binding fragments thereof that specifically bind FGFR2, comprising a heavy chain CDR2 (HCDR2) comprising an amino acid sequence selected from any of the HCDR2 amino acid sequences listed in Table 3 or a substantially similar sequence thereof having at least 90%, at least 95%, at least 98% or at least 99% sequence identity.

Also provided are antibodies or antigen-binding fragments thereof that specifically bind FGFR2, comprising a heavy chain CDR3 (HCDR3) comprising an amino acid sequence selected from any of the HCDR3 amino acid sequences listed in Table 3 or a substantially similar sequence thereof having at least 90%, at least 95%, at least 98% or at least 99% sequence identity.

Also provided are antibodies or antigen-binding fragments thereof that specifically bind FGFR2, comprising a light chain CDR1 (LCDR1) comprising an amino acid sequence selected from any of the LCDR1 amino acid sequences listed in Table 3 or a substantially similar sequence thereof having at least 90%, at least 95%, at least 98% or at least 99% sequence identity.

Also provided are antibodies or antigen-binding fragments thereof that specifically bind FGFR2, comprising a light chain CDR2 (LCDR2) comprising an amino acid sequence selected from any of the LCDR2 amino acid sequences listed in Table 3 or a substantially similar sequence thereof having at least 90%, at least 95%, at least 98% or at least 99% sequence identity.

Also provided are antibodies or antigen-binding fragments thereof that specifically bind FGFR2, comprising a light chain CDR3 (LCDR3) comprising an amino acid sequence selected from any of the LCDR3 amino acid sequences listed in Table 3 or a substantially similar sequence thereof having at least 90%, at least 95%, at least 98% or at least 99% sequence identity.

Also provided are antibodies or antigen-binding fragments thereof that specifically bind FGFR2, comprising an HCDR1 and an LCDR1 amino acid sequence pair (HCDR1/LCDR1) comprising any of the HCDR1 amino acid sequences listed in Table 3 paired with any of the LCDR1 amino acid sequences listed in Table 3. According to certain embodiments, antibodies or antigen-binding fragments thereof comprise at least one HCDR1/LCDR1 amino acid sequence pair contained within any of the exemplary anti-FGFR2 antibodies listed in Table 3. In certain embodiments, the HCDR1/LCDR1 amino acid sequence pair is selected from the group consisting of: SEQ ID NO: 4/12, 24/30, and 24/46.

Also provided are antibodies or antigen-binding fragments thereof that specifically bind FGFR2, comprising an HCDR2 and an LCDR2 amino acid sequence pair (HCDR2/LCDR2) comprising any of the HCDR2 amino acid sequences listed in Table 3 paired with any of the LCDR2 amino acid sequences listed in Table 3. According to certain embodiments, the antibodies or antigen-binding fragments thereof comprise at least one HCDR2/LCDR2 amino acid sequence pair contained within any of the exemplary anti-FGFR2 antibodies listed in Table 3. In certain embodiments, the HCDR2/LCDR2 amino acid sequence pair is selected from the group consisting of: SEQ ID NO: 6/GAS-4-4 and SEQ ID NO: 6/KAS.

Also provided herein are antibodies or antigen-binding fragments thereof that specifically bind FGFR2, comprising an HCDR3 and an LCDR3 amino acid sequence pair (HCDR3/LCDR3) comprising any of the HCDR3 amino acid sequences listed in Table 3 paired with any of the LCDR3 amino acid sequences listed in Table 3. According to certain embodiments the antibodies or antigen-binding fragments thereof comprise at least one HCDR3/LCDR3 amino acid sequence pair contained within any of the exemplary anti-FGFR2 antibodies listed in Table 3. In certain embodiments, the HCDR3/LCDR3 amino acid sequence pair is selected from the group consisting of: SEQ ID NO: 8/16, 26/34, and 42/34.

Also provided herein are antibodies or antigen-binding fragments thereof that specifically bind FGFR2, comprising a set of six CDRs (i.e., HCDR1-HCDR2-HCDR3-LCDR1-LCDR2-LCDR3) contained within any of the exemplary anti-FGFR2 antibody sequences listed in Table 3. In certain embodiments, the HCDR1-HCDR2-HCDR3-LCDR1-LCDR2-LCDR3 amino acid sequence sets are selected from the group consisting of: SEQ ID NOs: 4-6-8-12-GAS-SEQ ID NO: 16, SEQ ID NOs: 24-6-26-30-KAS SEQ ID NO: 34, and SEQ ID NOs: 24-6-42-46-KAS-SEQ ID NO: 34.

In a related embodiment, antibodies or antigen-binding fragments thereof that specifically bind FGFR2 comprise a set of six CDRs (i.e., HCDR1-HCDR2-HCDR3-LCDR1-LCDR2-LCDR3) contained within an HCVR/LCVR amino acid sequence pair as defined by any of the exemplary anti-FGFR2 antibody sequences listed in Table 3. For example, anti-FGFR2 antibodies or antigen-binding fragments thereof can comprise an HCDR1-HCDR2-HCDR3-LCDR1-LCDR2-LCDR3 amino acid sequence set contained within an HCVR/LCVR amino acid sequence pair selected from the group consisting of: SEQ ID NOs: 2/10, 22/28, and 40/44.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); AI-Lazikani et al., *J. Mol. Biol.* 273:927-948 (1997); and Martin et al., *Proc. Natl. Acad. Sci. USA* 86:9268-9272 (1989).

Public databases are also available for identifying CDR sequences within an antibody. Provided herein are antibodies or antigen-binding fragments thereof that specifically bind FGFR2, comprising a heavy chain (HC) comprising an amino acid sequence selected from any of the HC amino acid sequences listed in Table 3, or a substantially similar sequence thereof having at least 90%, at least 95%, at least 98% or at least 99% sequence identity thereto. For example, provided herein are antibodies or antigen-binding fragments thereof that specifically bind FGFR2, comprising a HC comprising an amino acid sequence selected from any of the HC amino acid sequences listed in Table 3, but comprising an N297Q modification, or an equivalent modification. Illustratively, provided herein is an antibody or antigen-binding fragment thereof having a heavy chain comprising an N297Q modification within a HC amino acid sequence selected from the group consisting of SEQ ID NOs: 18, 36, and 49. In some aspects, the antibody or antigen-binding fragment thereof comprises a HC comprising an N297Q modification within the HC amino acid sequence of SEQ ID NO: 18. In some aspects, the antibody or antigen-binding fragment thereof comprises a HC comprising an N297Q modification within the HC amino acid sequence of SEQ ID NO: 36. In some aspects, the antibody or antigen-binding fragment thereof comprises a HC comprising an N297Q modification within the HC amino acid sequence of SEQ ID NO: 49.

In some aspects, the antibody or antigen-binding fragment thereof comprises a HC amino acid sequence selected from the group consisting of SEQ ID NOs: 52, 53, and 54. Such HC sequences comprise the equivalent of the N297Q modification.

Provided herein are antibodies or antigen-binding fragments thereof that specifically bind FGFR2, comprising a light chain (LC) comprising an amino acid sequence selected from any of the LC amino acid sequences listed in Table 3, or a substantially similar sequence thereof having at least 90%, at least 95%, at least 98% or at least 99% sequence identity thereto.

Provided herein are antibodies or antigen-binding fragments thereof that specifically bind FGFR2, comprising an HC and an LC amino acid sequence pair (HC/LC) comprising any of the HC amino acid sequences listed in Table 3 paired with any of the LC amino acid sequences listed in Table 3. According to certain embodiments, the antibodies comprise two HC/LC amino acid sequence pairs contained within any of the exemplary anti-FGFR2 antibodies listed in Table 3. In certain embodiments, an HC/LC amino acid sequence pair is selected from the group consisting of: SEQ ID NO: 18/20, 36/38, and 49/51. In some aspects, the HC comprises an N297Q modification as provided above. As such, HC/LC amino acid sequence pair is selected from the group consisting of: SEQ ID NO: 52/20, 53/38, and 54/51.

Also provided herein are nucleic acid molecules encoding anti-FGFR2 antibodies or portions thereof. For example, the present invention provides nucleic acid molecules encoding any of the HCVR amino acid sequences listed in Table 3; in certain embodiments the nucleic acid molecule comprises a polynucleotide sequence selected from any of the HCVR nucleic acid sequences listed in Table 4, or a substantially similar sequence thereof having at least 90%, at least 95%, at least 98% or at least 99% sequence identity thereto.

Also provided are nucleic acid molecules encoding any of the LCVR amino acid sequences listed in Table 3; in certain embodiments the nucleic acid molecule comprises a polynucleotide sequence selected from any of the LCVR nucleic acid sequences listed in Table 4, or a substantially similar sequence thereof having at least 90%, at least 95%, at least 98% or at least 99% sequence identity thereto.

Also provided are nucleic acid molecules encoding any of the HCDR1 amino acid sequences listed in Table 3; in certain embodiments the nucleic acid molecule comprises a polynucleotide sequence selected from any of the HCDR1 nucleic acid sequences listed in Table 4, or a substantially similar sequence thereof having at least 90%, at least 95%, at least 98% or at least 99% sequence identity thereto.

Also provided are nucleic acid molecules encoding any of the HCDR2 amino acid sequences listed in Table 3; in certain embodiments the nucleic acid molecule comprises a polynucleotide sequence selected from any of the HCDR2 nucleic acid sequences listed in Table 4, or a substantially similar sequence thereof having at least 90%, at least 95%, at least 98% or at least 99% sequence identity thereto.

Also provided are nucleic acid molecules encoding any of the HCDR3 amino acid sequences listed in Table 3; in certain embodiments the nucleic acid molecule comprises a polynucleotide sequence selected from any of the HCDR3 nucleic acid sequences listed in Table 4, or a substantially similar sequence thereof having at least 90%, at least 95%, at least 98% or at least 99% sequence identity thereto.

Also provided are nucleic acid molecules encoding any of the LCDR1 amino acid sequences listed in Table 3; in certain embodiments the nucleic acid molecule comprises a polynucleotide sequence selected from any of the LCDR1 nucleic acid sequences listed in Table 4, or a substantially similar sequence thereof having at least 90%, at least 95%, at least 98% or at least 99% sequence identity thereto.

Also provided are nucleic acid molecules encoding any of the LCDR2 amino acid sequences listed in Table 3; in certain embodiments the nucleic acid molecule comprises a polynucleotide sequence selected from any of the LCDR2 nucleic acid sequences listed in Table 4, or a substantially similar sequence thereof having at least 90%, at least 95%, at least 98% or at least 99% sequence identity thereto.

Also provided are nucleic acid molecules encoding any of the LCDR3 amino acid sequences listed in Table 3; in certain embodiments the nucleic acid molecule comprises a polynucleotide sequence selected from any of the LCDR3 nucleic acid sequences listed in Table 4, or a substantially similar sequence thereof having at least 90%, at least 95%, at least 98% or at least 99% sequence identity thereto.

Also provided are nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-FGFR2 antibodies listed in Table 3.

Also provided are nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-FGFR2 antibodies listed in Table 3.

Also provided are nucleic acid molecules encoding both an HCVR and an LCVR, wherein the HCVR comprises an amino acid sequence of any of the HCVR amino acid sequences listed in Table 3, and wherein the LCVR comprises an amino acid sequence of any of the LCVR amino acid sequences listed in Table 3. In certain embodiments, the nucleic acid molecule comprises a polynucleotide sequence selected from any of the HCVR nucleic acid sequences listed in Table 4, or a substantially similar sequence thereof having at least 90%, at least 95%, at least 98% or at least 99% sequence identity thereto, and a polynucleotide sequence selected from any of the LCVR nucleic acid sequences listed in Table 4, or a substantially similar sequence thereof having at least 90%, at least 95%, at least 98% or at least 99% sequence identity thereto. In certain embodiments according to this aspect, the nucleic acid molecule encodes an HCVR and LCVR, wherein the HCVR and LCVR are both derived from the same anti-FGFR2 antibody listed in Table 3.

Also provided are nucleic acid molecules encoding any of the HC amino acid sequences listed in Table 3; or encoding a substantially similar sequence thereof having at least 90%, at least 95%, at least 98% or at least 99% sequence identity thereto. For example, the nucleic acid molecules can encode any of the HC amino acid sequences listed in Table 3, wherein the HC has an N297Q modification.

Also provided are nucleic acid molecules encoding any of the LC amino acid sequences listed in Table 3; or encoding a substantially similar sequence thereof having at least 90%, at least 95%, at least 98% or at least 99% sequence identity thereto.

Also provided herein are recombinant expression vectors capable of expressing a polypeptide comprising a heavy or light chain variable region of an anti-FGFR2 antibody. For example, recombinant expression vectors comprise any of the nucleic acid molecules mentioned herein, i.e., nucleic acid molecules encoding any of the HCVR, LCVR, and/or CDR sequences as set forth in Table 3. Also included within the scope of the present disclosure are host cells into which such vectors have been introduced, as well as methods of producing the antibodies or portions thereof by culturing the host cells under conditions permitting production of the antibodies or antibody fragments, and recovering the antibodies and antibody fragments so produced.

Provided herein are anti-FGFR2 antibodies or antigen-binding fragments thereof having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

Antigen-Binding Domains

As used herein, the expression "antigen-binding domain" means any peptide, polypeptide, nucleic acid molecule, scaffold-type molecule, peptide display molecule, or polypeptide-containing construct that is capable of specifically binding a particular antigen of interest (e.g., human FGFR2). The term "specifically binds" or the like, as used herein, means that the antigen-binding domain forms a complex with a particular antigen characterized by a dissociation constant ($K_D$) of 500 pM or less, and does not bind other unrelated antigens under ordinary test conditions. "Unrelated antigens" are proteins, peptides or polypeptides that have less than 95% amino acid identity to one another.

Exemplary categories of antigen-binding domains that can be used in the context of the present disclosure include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen, antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, 2011, *Curr. Opin. Biotechnol.* 22:849-857, and references cited therein]), and aptamers or portions thereof.

Methods for determining whether two molecules specifically bind one another are well known in the art and include, for example, equilibrium dialysis, surface plasmon resonance, and the like. For example, an antigen-binding domain, as used in the context of the present disclosure, includes polypeptides that bind a particular antigen (e.g., a target molecule [T] or an internalizing effector protein [E]) or a portion thereof with a $K_D$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, NJ).

The term "$K_D$ ", as used herein, means the equilibrium dissociation constant of a particular protein-protein interaction (e.g., antibody-antigen interaction). Unless indicated otherwise, the $K_D$ values disclosed herein refer to $K_D$ values determined by surface plasmon resonance assay at 25° C.

As indicated above, an "antigen-binding domain" may comprise or consist of an antibody or antigen-binding fragment of an antibody. The term "antibody," as used herein, means any antigen-binding molecule or molecular complex comprising at least one complementarity determining region (CDR) that specifically binds to or interacts with a particular antigen (e.g., human FGFR2). The term "antibody" includes immunoglobulin molecules comprising two polypeptide chains, one heavy (H) chain and one light (L) chain interconnected by disulfide bonds, as well as multimers thereof (e.g., IgM). The heavy chain comprises a heavy chain variable region (abbreviated herein as HCVR or $V_H$) and a heavy chain constant region. The heavy chain constant region comprises three domains, $C_H1$, $C_H2$ and $C_H3$. The light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the antibodies provided herein (or antigen-binding portion thereof) may be identical to the human germline sequences, or may be naturally or artificially modified. An amino acid consensus sequence may be defined based on a side-by-side analysis of two or more CDRs.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_{H2}$; (iii) $V_H$-$C_H3$; (iv) $V_H$-$C_H1$-$C_H2$; (v) $V_H$-$C_H1$-$C_H2$-$C_H3$; (vi) $V_H$-$C_H2$—$C_H3$; (vii) $V_H$-$C_L$; (viii) $V_L$-$C_H1$; (iX) $V_L$-$C_H2$; (X) $V_L$-$C_H3$; (xi) $V_L$-$C_H1$—$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The antibodies provided herein may comprise or consist of human antibodies and/or recombinant human antibodies, or fragments thereof. The term "human antibody", as used herein, includes antibodies having variable and constant regions derived from human germline immunoglobulin sequences. Human antibodies may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies or antigen-binding fragments thereof of the present disclosure may comprise or consist of recombinant human antibodies or antigen-binding fragments thereof. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created, or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$sequences, may not naturally exist within the human antibody germline repertoire in vivo.

The anti-FGFR2 antibodies or antigen-binding fragments thereof provided herein may be "isolated." An "isolated anti-FGFR2 antibody" as used herein, means an antibody or antigen-binding fragment thereof that has been identified and separated and/or recovered from at least one component of its natural environment. For example, an antibody or antigen-binding fragment thereof that has been separated or removed from at least one component of an organism, or from a tissue or cell in which the antibody is produced, is an "isolated anti-FGFR2 antibody" for purposes of the present disclosure. An isolated anti-FGFR2 antibody or antigen-binding fragment thereof also includes molecules in situ within a recombinant cell. Isolated antibodies or antigen-binding fragments thereof are molecules that have been subjected to at least one purification or isolation step. According to certain embodiments, an isolated anti-FGFR2 antibody or antigen-binding fragment thereof may be substantially free of other cellular material and/or chemicals.

Variants

The anti-FGFR2 antibodies and antigen-binding fragments thereof disclosed herein may comprise one or more amino acid substitutions, insertions, and/or deletions in the framework and/or CDR regions of the heavy and light chain variable domains as compared to the corresponding germline sequences from which the antibodies or antigen-binding fragments thereof were derived. Such mutations can be readily ascertained by comparing the amino acid sequences disclosed herein to germline sequences available from, for example, public antibody sequence databases. The present disclosure includes antibodies or antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations").

A person of ordinary skill in the art, starting with the heavy and light chain variable region sequences disclosed herein, can easily produce numerous antibodies or antigen-binding fragments thereof, which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived).

Furthermore, the antibodies or antigen-binding fragments thereof of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies or antigen-binding fragments thereof that contain one or more germline mutations can be easily tested for one or more desired property such as, improved binding specificity, increased binding affinity, improved or enhanced antagonistic or agonistic biological properties (as the case may be), reduced immunogenicity, etc. Antibodies or antigen-binding fragments thereof obtained in this general manner are encompassed within the present disclosure.

Typically, an antibody or antigen-binding fragment provided herein which is modified in some way retains the ability to specifically bind to FGFR2, e.g., retains at least 10% of its FGFR2 binding activity (when compared to the parental antibody) when that activity is expressed on a molar basis. In some aspects, an antibody or antigen-binding fragment of the disclosure retains at least 20%, 50%, 70%, 80%, 90%, 95% or 100% or more of the FGFR2 binding affinity as the parental antibody. It is also intended that an antibody or antigen-binding fragment of the present disclosure can include conservative or non-conservative amino acid substitutions (referred to as "conservative variants" or "function conserved variants" of the antibody) that do not substantially alter its biologic activity.

A "variant" of a polynucleotide refers to a polynucleotide comprising a nucleotide sequence that is at least about 70-99.9% (e.g., at least about 70, 72, 74, 75, 76, 79, 80, 81, 82, 83, 84, 85, 86, 87, 88, 89, 90, 91, 92, 93, 94, 95, 96, 97, 98, 99, 99.5, or 99.9%) identical to a referenced nucleotide sequence that is set forth herein (e.g., SEQ ID NOs: 1, 3, 5, 7, 9, 11, 15, 17, 19, 21, 23, 25, 27, 29, 33, 35, 37, 39, 41, 43, 45, 47, 48, and 50, GGTGCATCC and AAGGCGTCT); when the comparison is performed by a BLAST algorithm wherein the parameters of the algorithm are selected to give the largest match between the respective sequences over the entire length of the respective reference sequences (e.g., expect threshold: 10; word size: 28; max matches in a query range: 0; match/mismatch scores: 1, -2; gap costs: linear).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

A "variant" of a polypeptide, such as an immunoglobulin chain (e.g., mAb1 $V_H$, $V_L$, HC, or LC, mAb2 $V_H$, $V_L$, HC, or LC, or mAb3 $V_H$, $V_L$, HC, or LC), refers to a polypeptide comprising an amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a referenced amino acid sequence that is set forth herein (e.g., SEQ ID NO: 2, 10, 18, 20, 22, 28, 36, 38, 40, 44, 49, or 51); when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment).

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservatively modified variant" or a "conservative substitution" refers to a variant wherein there is one or more substitutions of amino acids in a polypeptide with other amino acids having similar characteristics (e.g., charge, side-chain size, hydrophobicity/hydrophilicity, backbone conformation and rigidity, etc.). Such changes can frequently be made without significantly disrupting the biological activity of the antibody or fragment. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4th Ed.)). In addition, substitutions of structurally or functionally similar amino acids are less likely to significantly disrupt biological activity.

In cases where two or more amino acid sequences differ from each other by conservative substitutions, the percent or degree of similarity may be adjusted upwards to correct for the conservative nature of the substitution. Means for making this adjustment are well known to those of skill in the art. (See, e.g., Pearson (1994) Methods Mol. Biol. 24: 307-331). Examples of groups of amino acids that have side chains with similar chemical properties include 1) aliphatic side chains: glycine, alanine, valine, leucine and isoleucine; 2)

aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et aL. (1992) Science 256: 1443 45. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions, and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence provided herein to a database containing a large number of sequences from different organisms is the computer program BLAST, especially BLASTP or TBLASTN, using default parameters. See, e.g., Altschul et aL. (1990) J. Mol. Biol. 215: 403-410 and Altschul et aL. (1997) Nucleic Acids Res. 25:3389-3402, each incorporated by reference herein.

The present disclosure also includes anti-FGFR2 antibodies and antigen-binding fragments thereof comprising variants of any of the HCVR, LCVR, and/or CDR amino acid sequences disclosed herein. Exemplary variants included within this aspect include variants of any of the HCVR, LCVR, and/or CDR amino acid sequences disclosed herein having one or more substitutions, for example, conservative substitutions. In some aspects, the present disclosure includes anti-FGFR2 antibodies and antigen-binding fragments thereof having HCVR, LCVR, and/or CDR amino acid sequences with, e.g., 10 or fewer, 8 or fewer, 6 or fewer, 4 or fewer, 3 or fewer, 2, or 1 amino acid substitutions relative to any of the HCVR, LCVR, and/or CDR amino acid sequences set forth in Table 3 herein, where the modified antibodies and antigen-binding fragments thereof maintain the binding activity against FGFR2.

Anti-FGFR2 antigen-binding proteins, e.g., antibodies and antigen-binding fragments thereof of the present disclosure, in one embodiment, include a heavy chain immunoglobulin variable region having at least 70% (e.g., 80%, 85%, 90%, 95%, 99%) amino acid sequence identity to the amino acids set forth in SEQ ID NO: 2, 22, or 40; and/or a light chain immunoglobulin variable region having at least 70% (e.g., 80%, 85%, 90%, 95%, 99%) amino acid sequence identity to the amino acids set forth in SEQ ID NO: 10, 28, or 44.

In addition, a variant anti-FGFR2 antigen-binding protein may include a polypeptide comprising an amino acid sequence that is set forth herein except for one or more (e.g., 1, 2, 3, 4, 5, 6, 7, 8, 9 or 10) mutations such as, for example, missense mutations (e.g., conservative substitutions), nonsense mutations, deletions, or insertions. For example, the present disclosure includes antigen-binding proteins which include an immunoglobulin heavy chain variant comprising the amino acid sequence set forth in SEQ ID NO: 2, 22, or 40 but having one or more of such mutations and/or an immunoglobulin light chain variant comprising the amino acid sequence set forth in SEQ ID NO: 10, 28, or 44 but having one or more of such mutations. In an embodiment of the disclosure, a variant anti-FGFR2 antigen-binding protein includes an immunoglobulin heavy chain variant comprising HCDR1, HCDR2, and HCDR3 wherein one or more (e.g., 1 or 2 or 3) of such CDRs has one or more of such mutations (e.g., conservative substitutions) and/or an immunoglobulin light chain variant comprising LCDR1, LCDR2, and LCDR3 wherein one or more (e.g., 1 or 2 or 3) of such CDRs has one or more of such mutations (e.g., conservative substitutions).

The disclosure further provides variant anti-FGFR2 antigen-binding proteins, e.g., antibodies or antigen-binding fragments thereof, comprising one or more variant CDRs (e.g., any one or more of HCDR1, HCDR2, HCDR3, LCDR1, LCDR2, and/or LCDR3) that are set forth herein with at least 70%, 75%, 80%, 85%, 90%, 95%, 98%, 99% or 99.9% sequence identity or similarity to, e.g., SEQ ID NOs: 4, 6, 8, 12, 16, and/or GAS; or SEQ ID NOs: 24, 6, 26, 30, 34, and/or KAS; or SEQ ID NOs: 24, 6, 42, 46, 34, and/or KAS.

Embodiments of the present disclosure also include variant antigen-binding proteins, e.g., anti-FGFR2 antibodies and antigen-binding fragments thereof, that comprise immunoglobulin $V_H$s and $V_L$S, or HCs and LCs, which comprise an amino acid sequence having 70% or more (e.g., 80%, 85%, 90%, 91%, 92%, 93%, 94%, 95%, 96%, 97%, 98%, or 99%) overall amino acid sequence identity or similarity to the amino acid sequences of the corresponding $V_H$s, $V_L$s, HCs or LCs specifically set forth herein, but wherein the HCDR1, HCDR2, HCDR3, LCDR1, LCDR2, and/or LCDR3 of such immunoglobulins are not variants and comprise the amino acid sequence set forth in SEQ ID NOs: 4, 6, 8, 12, 16, and/or GAS; or SEQ ID NOs: 24, 6, 26, 30, 34, and/or KAS; or SEQ ID NOs: 24, 6, 42, 46, 34, and/or KAS, respectively. Thus, in such embodiments, the CDRs within variant antigen-binding proteins are not, themselves, variants.

In some aspects, provided herein is an anti-FGFR2 antibody or antigen-binding fragment thereof comprising: three heavy chain CDRs (HCDR1, HCDR2, and HCDR3) contained within the heavy chain variable region (HCVR) amino acid sequence of SEQ ID NO: 2, or an amino acid sequence that is at least 90% identical thereto; and three light chain CDRs (LCDR1, LCDR2, and LCDR3) contained within the light chain variable region (LCVR) amino acid sequence of SEQ ID NO: 10, or an amino acid sequence that is at least 90% identical thereto.

In some aspects, the HCDR1 comprises the amino acid sequence of SEQ ID NO: 4 or an amino acid sequence of SEQ ID NO: 4 comprising two or fewer amino acid substitutions; the HCDR2 comprises the amino acid sequence of SEQ ID NO: 6 or an amino acid sequence of SEQ ID NO: 6 comprising two or fewer amino acid substitutions; the HCDR3 comprises the amino acid sequence of SEQ ID NO: 8 or an amino acid sequence of SEQ ID NO: 8 comprising two or fewer amino acid substitutions; the LCDR1 comprises the amino acid sequence of SEQ ID NO: 12 or an amino acid sequence of SEQ ID NO: 12 comprising two or fewer amino acid substitutions; the LCDR2 comprises the amino acid sequence of GAS or an amino acid sequence of GAS comprising two or fewer amino acid substitutions; and the LCDR3 comprises the amino acid sequence of SEQ ID NO: 16 or an amino acid sequence of SEQ ID NO: 16 comprising two or fewer amino acid substitutions.

In some aspects, the HCDR1 comprises the amino acid sequence of SEQ ID NO: 4; the HCDR2 comprises the amino acid sequence of SEQ ID NO: 6; the HCDR3 comprises the amino acid sequence of SEQ ID NO: 8; the LCDR1 comprises the amino acid sequence of SEQ ID NO: 12; the LCDR2 comprises the amino acid sequence of GAS; and the LCDR3 comprises the amino acid sequence of SEQ ID NO: 16.

In some aspects, the anti-FGFR2 antibody or antigen-binding fragment thereof comprises an HCVR comprising the amino acid sequence of SEQ ID NO: 2 or an amino acid sequence that is at least 95% identical thereto; and an LCVR comprising the amino acid sequence of SEQ ID NO: 10 or an amino acid sequence that is at least 95% identical thereto.

In some aspects, the anti-FGFR2 antibody or antigen-binding fragment thereof comprises an HCVR comprising the amino acid sequence of SEQ ID NO: 2; and an LCVR comprising the amino acid sequence of SEQ ID NO: 10.

In some aspects, the anti-FGFR2 antibody or antigen-binding fragment thereof comprises three heavy chain CDRs (HCDR1, HCDR2, and HCDR3) contained within the heavy chain variable region (HCVR) amino acid sequence of SEQ ID NO: 22, or an amino acid sequence that is at least 90% identical thereto; and three light chain CDRs (LCDR1, LCDR2, and LCDR3) contained within the light chain variable region (LCVR) amino acid sequence of SEQ ID NO: 28, or an amino acid sequence that is at least 90% identical thereto.

In some aspects, the HCDR1 comprises the amino acid sequence of SEQ ID NO: 24 or an amino acid sequence of SEQ ID NO: 24 comprising two or fewer amino acid substitutions; the HCDR2 comprises the amino acid sequence of SEQ ID NO: 6 or an amino acid sequence of SEQ ID NO: 6 comprising two or fewer amino acid substitutions; the HCDR3 comprises the amino acid sequence of SEQ ID NO: 26 or an amino acid sequence of SEQ ID NO: 26 comprising two or fewer amino acid substitutions; the LCDR1 comprises the amino acid sequence of SEQ ID NO: 30 or an amino acid sequence of SEQ ID NO: 30 comprising two or fewer amino acid substitutions; the LCDR2 comprises the amino acid sequence of KAS or an amino acid sequence of KAS comprising two or fewer amino acid substitutions; and the LCDR3 comprises the amino acid sequence of SEQ ID NO: 34 or an amino acid sequence of SEQ ID NO: 34 comprising two or fewer amino acid substitutions.

In some aspects, the HCDR1 comprises the amino acid sequence of SEQ ID NO: 24; the HCDR2 comprises the amino acid sequence of SEQ ID NO: 6; the HCDR3 comprises the amino acid sequence of SEQ ID NO: 26; the LCDR1 comprises the amino acid sequence of SEQ ID NO: 30; the LCDR2 comprises the amino acid sequence of KAS; and the LCDR3 comprises the amino acid sequence of SEQ ID NO: 34.

In some aspects, the anti-FGFR2 antibody or antigen-binding fragment thereof comprises an HCVR comprising the amino acid sequence of SEQ ID NO: 22 or an amino acid sequence that is at least 95% identical thereto; and an LCVR comprising the amino acid sequence of SEQ ID NO: 28 or an amino acid sequence that is at least 95% identical thereto.

In some aspects, the anti-FGFR2 antibody or antigen-binding fragment thereof comprises an HCVR comprising the amino acid sequence of SEQ ID NO: 22; and an LCVR comprising the amino acid sequence of SEQ ID NO: 28.

Function-conservative variants of the anti-FGFR2 antibodies and antigen-binding fragments thereof are also part of the present invention. Any of the variants of the anti-FGFR2 antibodies and antigen-binding fragments thereof (as discussed herein) may be "function-conservative variants". Such function-conservative variants may, in some cases, also be characterized as conservatively modified variants. "Function-conservative variants," as used herein, refers to variants of the anti-FGFR2 antibodies or antigen-binding fragments thereof in which one or more amino acid residues have been changed without significantly altering one or more functional properties of the antibody or fragment. In an embodiment of the invention, a function-conservative variant of an anti-FGFR2 antibody or antigen-binding fragment thereof of the present disclosure comprises a variant amino acid sequence and exhibits one or more of the following functional properties:

binds to FGFR2b with a $K_D$ equal to or less than $2.5\times10^{-8}$ M as measured by surface plasmon resonance;

selectively binds hFGFR2b over hFGFR2c; and/or has a half-life (t1/2) of greater than about 10 minutes as measured by surface plasmon resonance.

Anti-FGFR2 Antibodies or Antigen-Binding Fragments Thereof Comprising Fc Variants According to certain embodiments provided herein, anti-FGFR2 antibodies or antigen-binding fragments thereof are provided comprising an Fc domain comprising one or more mutations which enhance or diminish antibody binding to the FcRn receptor, e.g., at acidic pH as compared to neutral pH. For example, the present disclosure includes anti-FGFR2 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 2500 and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, provided herein are anti-FGFR2 antibodies comprising an Fc domain comprising one or more pairs or groups of mutations selected from the group consisting of: 2500 and 248L (e.g., T250Q and M248L); 252Y, 254T and 256E (e.g., M252Y, S254T and T256E); 428L and 434S (e.g., M428L and N434S); 257I and 311I (e.g., P257I and Q3111); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations and other mutations within the antibody variable domains disclosed herein are contemplated within the scope of the present disclosure.

The present disclosure also includes anti-FGFR2 antibodies comprising a chimeric heavy chain constant ($C_H$) region, wherein the chimeric $C_H$ region comprises segments derived from the $C_H$ regions of more than one immunoglobulin isotype. For example, the antibodies of the disclosure may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies provided herein comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013).

Multi-Specific Antibodies

The antibodies provided herein may be mono-specific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

Any of the multi-specific antigen-binding molecules provided herein, or variants thereof, may be constructed using standard molecular biological techniques (e.g., recombinant DNA and protein expression technology), as will be known to a person of ordinary skill in the art.

In some embodiments, FGFR2-specific antibodies are generated in a bi-specific format (a "bi-specific") in which variable regions binding to distinct domains of FGFR2 are linked together to confer dual antigen specificity within a single binding molecule. Appropriately designed bi-specifics may enhance overall FGFR2 inhibitory efficacy through increasing both specificity and binding avidity. Variable regions with specificity for individual domains, or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domain and a second target, such as, but not limited to, for example, a second different anti-FGFR antibody, may be prepared in a bi-specific format using techniques described herein, or other techniques known to those skilled in the art. Antibody variable regions binding to distinct regions may be linked together with variable regions that bind to relevant sites on, for example, FGFR2, to confer dual-antigen specificity within a single binding molecule. Appropriately designed bi-specifics of this nature serve a dual function. Variable regions with specificity for one antigen are combined with variable regions with specificity for FGFR2 and are paired on a structural scaffold that allows each variable region to bind to the separate antigens.

An exemplary bi-specific antibody format that can be used in the context of the present disclosure involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V821 (by IMGT; D356E, L358M, N384S, K392N, V397M, and V422I by EU) in the case of IgG1 antibodies; N44S, K52N, and V821 (IMGT; N384S, K392N, and V422I by EU) in the case of IgG2 antibodies; and Q15R, N44S, K52N, V57M, R69K, E79Q, and V821 (by IMGT; Q355R, N384S, K392N, V397M, R409K, E419Q, and V422I by EU) in the case of IgG4 antibodies. Variations on the bi-specific antibody format described above are contemplated within the scope of the present disclosure.

Other exemplary bi-specific formats that can be used in the context of the present disclosure include, without limitation, e.g., scFv-based or diabody bi-specific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and $Mab^2$ bi-specific formats (see, e.g., Klein et aL. 2012, mAbs 4:6, 1-11, and references cited therein, for a review of the foregoing formats). Bi-specific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency, and geometry. (See, e.g., Kazane et aL., *J. Am. Chem. Soc.* [Epub: Dec. 4, 2012]).

As such, contemplated herein are bi-specific antibodies comprising at least one antigen-binding domain which binds with FGFR2. Methods for making bi-specific antibodies are known in the art and may be used to construct bi-specific antigen-binding molecules disclosed herein.

Exemplary antigen-binding domains that can be included in an anti-FGFR2 bi-specific antigen-binding molecule include one or more antigen-binding domains derived from any of the anti-FGFR2 sequences disclosed herein. For example, the present disclosure includes FGFR2 x FGFR2 bi-specific antigen-binding molecules comprising a D1 and/or D2 antigen-binding domain comprising an HCVR comprising an amino acid sequence selected from any of the HCVR amino acid sequences listed in Table 3, or a substantially similar sequence thereof having at least 90%, at least 95%, at least 98% or at least 99% sequence identity thereto. Also provided herein are FGFR2 x FGFR2 bi-specific antigen-binding molecules comprising a D1 and/or D2 antigen-binding domain comprising an LCVR comprising an amino acid sequence selected from any of the LCVR amino acid sequences listed in Table 3, or a substantially similar sequence thereof having at least 90%, at least 95%, at least 98% or at least 99% sequence identity thereto.

Biological Characteristics of the Antigen-Binding Molecules Provided Herein

Provided herein are anti-FGFR2 antibodies and antigen binding fragments thereof that bind human FGFR2 (e.g., hFGFR2b.mmh) with high affinity. For example, the present disclosure includes anti-FGFR2 antibodies and antigen binding fragments thereof that bind human FGFR2 with a $K_D$ of less than about 25 nM as measured by surface plasmon resonance at 25° C., e.g., using an assay format as defined in Example 3 herein, or a substantially similar assay. According to certain embodiments, anti-FGFR2 antibodies and antigen-binding fragments thereof are provided that bind human FGFR2 at 25° C. with a $K_D$ of less than about 25 nM, less than about 20 nM, less than about 18 nM, less than about 15 nM, less than about 12 nM, less than about 10 nM, less than about 9 nM, or less than about 8 nM, as measured by surface plasmon resonance, e.g., using an assay format as defined in Example 3 herein, or a substantially similar assay.

Also provided herein are anti-FGFR2 antibodies and antigen binding fragments thereof that bind human FGFR2 (e.g., hFGFR2b.mmh) with a dissociative half-life (t1/2) of greater than about 10 minutes as measured by surface plasmon resonance at 25° C., e.g., using an assay format as defined in Example 3 herein, or a substantially similar assay. According to certain embodiments, anti-FGFR2 antibodies and antigen-binding fragments thereof are provided that bind human FGFR2 at 25° C. with a t/2 of greater than about 12 minutes, greater than about 14 minutes, greater than about 16 minutes, greater than about 18 minutes, greater than about 20 minutes, greater than about 22 minutes, greater than about 24 minutes, or greater than about 25 minutes, or longer, as measured by surface plasmon resonance, e.g., using an assay format as defined in Example 3 herein, or a substantially similar assay.

As such, provided herein are isolated monoclonal antibodies or antigen-binding fragments thereof that bind to FGFR2, wherein the antibodies or antigen-binding fragments thereof exhibit one or more of the following characteristics:

(a) are fully human monoclonal antibodies;

(b) bind to FGFR2b with a $K_D$ equal to or less than $2.5\times10^{-8}$ M as measured by surface plasmon resonance;

(c) selectively bind hFGFR2b over hFGFR2c; and (d) comprise three heavy chain CDRs (HCDR1, HCDR2, and HCDR3) contained within the heavy chain variable region (HCVR) amino acid sequence of SEQ ID NO: 2 or SEQ ID NO: 22, or an amino acid sequence that is at least 90% identical thereto; and three light chain CDRs (LCDR1, LCDR2, and LCDR3) contained within the light chain variable region (LCVR) amino acid sequence of SEQ ID NO: 10 or SEQ ID NO: 28, or an amino acid sequence that is at least 90% identical thereto.

Also provided herein are anti-FGFR2 antibodies or antigen-binding fragments thereof having one or more of the following characteristics:

(a) are fully human monoclonal antibodies;

(b) bind to FGFR2b with a $K_D$ equal to or less than $2.5\times10^{-8}$ M as measured by surface plasmon resonance;

(c) have a half-life (t1/2) of greater than about 10 minutes as measured by surface plasmon resonance; and (d) selectively bind hFGFR2b over hFGFR2c.

Also provided herein are anti-FGFR2 antibodies or antigen-binding fragments thereof having one or more of the following characteristics:

(a) are fully human monoclonal antibodies;

(b) bind to FGFR2b with a $K_D$ equal to or less than $8.9\times10^{-9}$ M as measured by surface plasmon resonance;

(c) have a half-life (t1/2) of greater than about 25 minutes as measured by surface plasmon resonance; and (d) selectively bind hFGFR2b over hFGFR2c.

Also provided herein are anti-FGFR2 antibodies or antigen-binding fragments thereof conjugated to a cytotoxin, having one or more of the following characteristics:

(a) are selectively cytotoxic to hFGFR2b expressing cells over hFGFR2c expressing cells;

(b) bind to FGFR2b with a $K_D$ equal to or less than $4.8\times10^{-8}$ M as measured by surface plasmon resonance;

(c) have a half-life (t1/2) of greater than about 7 minutes as measured by surface plasmon resonance; and (d) induce regression of FGFR2b positive tumors in a dose dependent manner.

Also provided herein are anti-FGFR2 antibodies or antigen-binding fragments thereof that, when conjugated to a cytotoxin, are weakly cytotoxic to low FGFR2b expressing but high FGFR2c expressing cells; are weakly cytotoxic to non-FGFR2 expressing cells; and/or are cytotoxic to FGFR2b positive cells. According to certain embodiments, provided herein are anti-FGFR2 antibodies and antigen-binding fragments thereof that, when conjugated to a cytotoxin, are weakly cytotoxic to low FGFR2b but high FGFR2c expressing NCI-H716 cells, i.e. have an IC50 of greater than about 20 nM; are weakly cytotoxic to non-FGFR2 expressing IM-9 cells, i.e. have an IC50 of greater than about 20 nM; and/or are cytotoxic to FGFR2b positive MFM-223 or SNU-16 cells, i.e. have an IC50 of less than about 270 pM, for example, less than about 268 pM, less than about 214 pM, less than about 206 pM, less than about 172 pM, less than about 125 pM, less than about 63 pM, less than about 43.4 pM or less than about 37 pM, using an in vitro cytotoxicity assay format as defined in Example 6 herein, or a substantially similar assay.

Also provided herein are anti-FGFR2 antibodies or antigen-binding fragments thereof that, when conjugated to a cytotoxin, reduce tumor growth in FGFR2b positive tumors. Also provided herein are anti-FGFR2 antibodies or antigen-binding fragments thereof that, when conjugated to a cytotoxin, cause tumor regression in FGFR2b positive tumors. Reduction in tumor growth and tumor regression can be ascertained using tumor xenografts implanted in SCID mice as described in Example 7 herein, or a substantially similar assay.

According to certain embodiments, provided herein are anti-FGFR2 antibodies and antigen-binding fragments thereof that, when conjugated to a cytotoxin such as tubulysin 1ALP, reduce SNU-16 xenograft tumor growth by at least 16.2% in mice administered 0.1 mg/kg anti-FGFR2 antibody as a one-time subcutaneous injection. According to certain embodiments, provided herein are anti-FGFR2 antibodies and antigen-binding fragments thereof that, when conjugated to a cytotoxin such as tubulysin 1ALP, reduce SNU-16 xenograft tumor growth by at least 72.7% in mice administered 0.3 mg/kg anti-FGFR2 antibody as a one-time subcutaneous injection. According to certain embodiments, provided herein are anti-FGFR2 antibodies and antigen-binding fragments thereof that, when conjugated to a cytotoxin such as tubulysin 1ALP, reduce SNU-16 xenograft tumor growth by at least 132.5% in mice administered 1.0 mg/kg anti-FGFR2 antibody as a one-time subcutaneous injection. According to certain embodiments, provided herein are anti-FGFR2 antibodies and antigen-binding fragments thereof that, when conjugated to a cytotoxin such as tubulysin 1ALP, reduce SNU-16 xenograft tumor growth by at least 139% in mice administered 3.0 mg/kg anti-FGFR2 antibody as a one-time subcutaneous injection.

According to certain embodiments, provided herein are anti-FGFR2 antibodies and antigen-binding fragments thereof that, when conjugated to a cytotoxin such as maytansinoid 1ALP, reduce SNU-16 xenograft tumor growth by at least 63.9% in mice administered 1.0 mg/kg anti-FGFR2 antibody as a one-time subcutaneous injection. According to certain embodiments, provided herein are anti-FGFR2 antibodies and antigen-binding fragments thereof that, when conjugated to a cytotoxin such as maytansinoid 1ALP, reduce SNU-16 xenograft tumor growth by at least 89.2% in mice administered 3 mg/kg anti-FGFR2 antibody as a one-time subcutaneous injection. According to certain embodiments, provided herein are anti-FGFR2 antibodies and antigen-binding fragments thereof that, when conjugated to a cytotoxin such as maytansinoid 1ALP, reduce SNU-16 xenograft tumor growth by at least 102.3% in mice administered 10 mg/kg anti-FGFR2 antibody as a one-time subcutaneous injection. According to certain embodiments, provided herein are anti-FGFR2 antibodies and antigen-binding fragments thereof that, when conjugated to a cytotoxin such as maytansinoid 1ALP, reduce SNU-16 xenograft tumor growth by at least 100.4% in mice administered 15 mg/kg anti-FGFR2 antibody as a one-time subcutaneous injection.

According to certain embodiments, provided herein are anti-FGFR2 antibodies and antigen-binding fragments thereof that, when conjugated to a cytotoxin such as Camptothecin LP1 (8 DAR), reduce SNU-16 xenograft tumor growth by at least 99% in mice administered 1.0 mg/kg anti-FGFR2 antibody as a one-time subcutaneous injection. According to certain embodiments, provided herein are anti-FGFR2 antibodies and antigen-binding fragments thereof that, when conjugated to a cytotoxin such as Camptothecin LP1 (8 DAR), reduce SNU xenograft tumor growth by at least 131% in mice administered 3 mg/kg anti-FGFR2 antibody as a one-time subcutaneous injection. According to certain embodiments, provided herein are anti-FGFR2 antibodies and antigen-binding fragments thereof that, when conjugated to a cytotoxin such as Camptothecin LP1 (8 DAR), reduce SNU xenograft tumor growth by at least 131% in mice administered 10 mg/kg anti-FGFR2 antibody as a one-time subcutaneous injection.

According to certain embodiments, provided herein are anti-FGFR2 antibodies and antigen-binding fragments thereof that, when conjugated to a cytotoxin such as Camptothecin LP2 (4 DAR), reduce SNU-16 xenograft tumor growth by at least 72% in mice administered 0.3 mg/kg anti-FGFR2 antibody by subcutaneous injection on day 0 and day 7. According to certain embodiments, provided herein are anti-FGFR2 antibodies and antigen-binding fragments thereof that, when conjugated to a cytotoxin such as Camptothecin LP2 (4 DAR), reduce SNU xenograft tumor growth by at least 106% in mice administered 1 mg/kg anti-FGFR2 antibody by subcutaneous injection on day 0 and day 7. According to certain embodiments, provided herein are anti-FGFR2 antibodies and antigen-binding fragments thereof that, when conjugated to a cytotoxin such as Camptothecin LP2 (4 DAR), reduce SNU xenograft tumor growth by at least 137% in mice administered 3 mg/kg anti-FGFR2 antibody by subcutaneous injection on day 0 and day 7.

The antigen-binding proteins of the present disclosure may possess one or more of the aforementioned biological characteristics, or any combination thereof. The foregoing list of biological characteristics of the antibodies is not intended to be exhaustive. Other biological characteristics of the antibodies provided herein will be evident to a person of ordinary skill in the art from a review of the present disclosure including the working Examples herein.

Antibody-Drug Conjugates (ADCs)

Provided herein are antibody-drug conjugates (ADCs) comprising an anti-FGFR2 antibody or antigen-binding fragment thereof conjugated to a therapeutic moiety such as a cytotoxic agent (i.e., a cytotoxin), a chemotherapeutic drug, or a radioisotope.

Cytotoxic agents include any agent that is detrimental to the growth, viability, or propagation of cells, including, but not limited to, tubulin-interacting agents and DNA-damaging agents. In some embodiments, the cytotoxic agent is a tubulin inhibitor. In particular embodiments, the tubulin inhibitor inhibits tubulin polymerization. In some embodiments, the cytotoxic payload is a topoisomerase I inhibitor. In some embodiments, the cytotoxic agent is a maytansinoid, an auristatin, a hemiasterlin, a vinblastine, a vincristine, a pyrrolobenzodiazepine, a paclitaxel, a docetaxel, a cryptophycin, a tubulysin, or a camptothecin analog. Examples of suitable cytotoxic agents and chemotherapeutic agents that can be conjugated to anti-FGFR2 antibodies in accordance with this aspect of the disclosure also include, e.g., 1-(2chloroethyl)-1,2-dimethanesulfonyl hydrazide, 1,8-dihydroxy-bicyclo[7.3.1]trideca-4,9-diene-2,6-diyne-13-one, 1-dehydrotestosterone, 5-fluorouracil, 6-mercaptopurine, 6-thioguanine, 9-amino camptothecin, actinomycin D, amanitins, aminopterin, anguidine, anthracycline, anthramycin (AMC), bleomycin, busulfan, butyric acid, calicheamicins (e.g., calicheamicin $\gamma_1$), camptothecin, carminomycins, carmustine, cemadotins, cisplatin, colchicin, combretastatins, cyclophosphamide, cytarabine, cytochalasin B, Dxd or derivative thereof, dactinomycin, daunorubicin, decarbazine, diacetoxypentyldoxorubicin, dibromomannitol, dihydroxy anthracin dione, disorazoles, dolastatin (e.g., dolastatin 10), doxorubicin, duocarmycin, echinomycins, eleutherobins, emetine, epothilones, esperamicin, estramustines, ethidium bromide, etoposide, fluorouracils, geldanamycins, gramicidin D, glucocorticoids, irinotecans, kinesin spindle protein (KSP) inhibitors, leptomycins, leurosines, lidocaine, lomustine (CCNU), maytansinoids, mechlorethamine, melphalan, mercatopurines, methopterins, methotrexate, mithramycin, mitomycin, mitoxantrone, N8-acetyl spermidine, podophyllotoxins, procaine, propranolol, pteridines, puromycin, pyrrolobenzodiazepines (PBDs), rhizoxins, streptozotocin, tallysomycins, taxol, tenoposide, tetracaine, thioepa chlorambucil, tomaymycins, topotecans, tubulysin, vinblastine, vincristine, vindesine, vinorelbines, and derivatives of any of the foregoing. According to certain embodiments, the cytotoxic agent that is conjugated to an anti-FGFR2 antibody is a maytansinoid such as DM1 or DM4, a tomaymycin derivative, or a dolastatin derivative. According to certain embodiments, the cytotoxic agent that is conjugated to an anti-FGFR2 antibody is an auristatin such as MMAE, MMAF, or derivatives thereof. In some embodiments, the cytotoxic agent is Dxd or a derivative thereof. In some embodiments, the cytotoxic agent is AZ13599185 (see, e.g., Li et. al., 2016 Cancer Cell29, 117-129). Other cytotoxic agents known in the art are contemplated within the scope of the present disclosure, including, e.g., protein toxins such ricin, *C. difficile* toxin, pseudomonas exotoxin, ricin, diphtheria toxin, botulinum toxin, bryodin, saporin, pokeweed toxins (i.e., phytolaccatoxin and phytolaccigenin), and others such as those set forth in Sapra et al., *Pharmacol. & Therapeutics,* 2013, 138:452-469. In some embodiments, the cytotoxic agent is a tubulysin, a maytansinoid, or a camptothecin, or an analog thereof.

In certain embodiments, the cytotoxic agent is a tubulysin. Suitable tubulysins include those described in U.S. patent application Ser. No. 16/724,164 filed Dec. 20, 2019. In some embodiments, the tubulysin is Compound IVa, IVa', IVb, IVc, IVd, IVe, IVf, IVg, IVh, IVj, IVk, IV-I, IVm, IVn, IVo, IVp, IVq, IVr, IVs, IVt, IVu, IVvA, IVvB, IVw, IVx, IVy, Va, Va', Vb, Vc, Vd, Ve, Vf, Vg, Vh, Vi, Vj, Vk, Via, VIb, VIc, VId, VIe, VIf, VIg, VIh, VI, VIi, VII, VIII, IX, X, D-5a, or D-5c from U.S. patent application Ser. No. 16/724,164 filed Dec. 20, 2019. In certain embodiments, the tubulysin is Compound Ve in U.S. patent application Ser. No. 16/724,164 filed Dec. 20, 2019. In some embodiments, the tubulysin has the following structure:

Tubulysin 1A

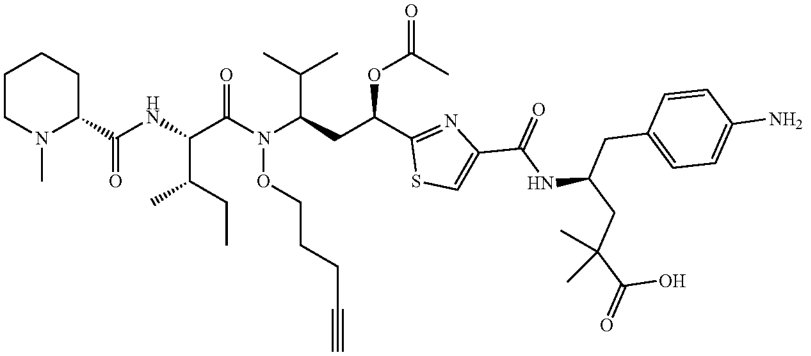

Tubulysin 1A can be prepared using the methods disclosed in U.S. Ser. No. 16/724,164 filed Dec. 20, 2019.

In some embodiments, the payload of the present disclosure is camptothecin. In certain embodiments, the payloads of the present disclosure are camptothecin analogs and/or derivatives.

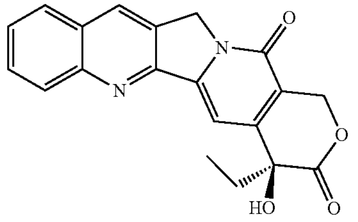

Camptothecin

In some embodiments, a suitable camptothecin analog is topotecan, irinotecan, belotecan, or deruxtecan (Dxd).

In one embodiment, the payload of the present disclosure is deruxtecan (Dxd):

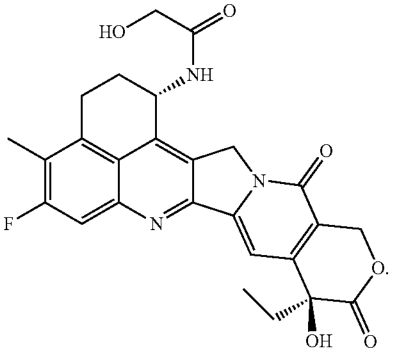 [SMILES: CC[C@@]1(O)C(=O)OCc2c1cc1n(c2=O)Cc2c-1nc1cc(F)c(C)c3c1c2[C@@H](NC(=O)CO)CC3]

In another embodiment, the payload is exatecan:

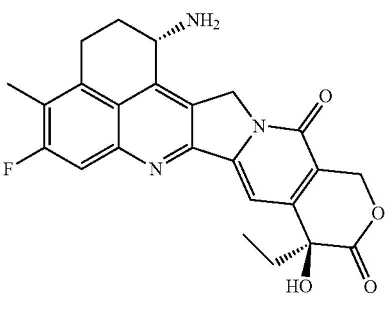 [SMILES: CC[C@@]1(O)C(=O)OCc2c1cc1n(c2=O)Cc2c-1nc1cc(F)c(C)c3c1c2[C@@H](N)CC3]

In certain embodiments, the payload of the present disclosure is a camptothecin analog having the structure P-I:

(P-I)

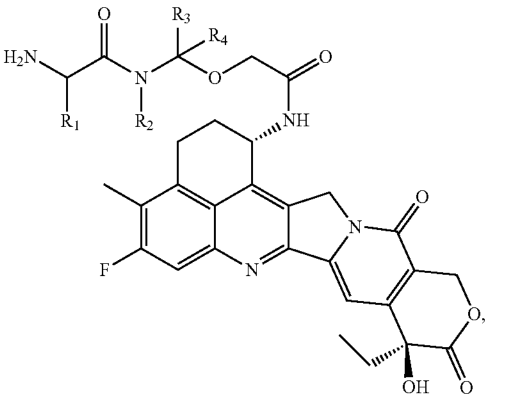

wherein $R_1$, $R_2$, and $R_3$, and $R_4$ are independently a hydrogen or an alkyl, e.g., a $C_1$-$C_{12}$ alkyl, or a $C_1$-$C_8$ alkyl, or a $C_1$-$C_6$ alkyl, or a $C_1$-$C_4$ alkyl, or wherein $R_2$ and $R_3$ together form a 5-membered or a 6-membered ring, or a pharmaceutically acceptable salt thereof.

In one embodiment, $R_1$ is a hydrogen. In one embodiment, $R_2$ is a hydrogen. In one embodiment, $R_2$ is a $C_1$-$C_4$ alkyl. In one embodiment, $R_3$ is a hydrogen. In one embodiment, $R_3$ is a $C_1$-$C_4$ alkyl. In one embodiment, $R_4$ is a hydrogen. In one embodiment, $R_4$ is a $C_1$-$C_4$ alkyl. In one embodiment, $R_1$, $R_2$, and $R_3$, and $R_4$ are a hydrogen in each occurrence. In one embodiment, the compound of the present disclosure is P-IA:

(P-IA)

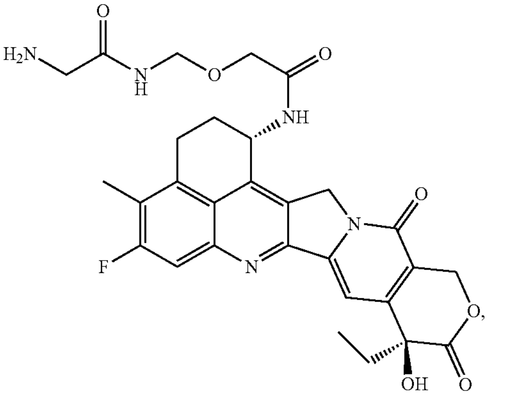

or a pharmaceutically acceptable salt thereof. In some embodiments, P-IA is converted into dxd. In some aspects, P-IA is converted to dxd in vivo. In some aspects, the ADC delivers the payload to a FGFR2b expressing tissue, such as an FGFR2b expressing tumor, and in some aspects, P-IA is converted in the local environment to dxd. In some aspects, the ADC comprises P-1A, and the ADC is converted in the local environment to dxd.

In one embodiment, $R_2$ and $R_3$ together form a 5-membered ring. In one embodiment, $R_2$ and $R_3$ together are $—(CH_2)_3—$.

In one embodiment, $R_2$ and $R_3$ together form a 6-membered ring. In one embodiment, $R_2$ and $R_3$ together are $—(CH_2)_4—$.

In one embodiment, $R_1$ is a hydrogen, and $R_2$ and $R_s$ together form a 5-membered ring.

In one embodiment, the compound of the present disclosure has a structure according to Formula (P-II):

(P-II)

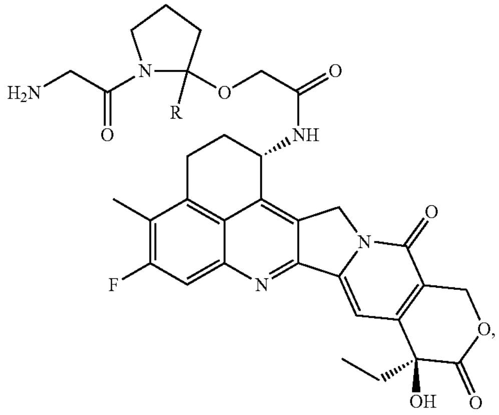

wherein R is a hydrogen or an alkyl, e.g., a $C_1$-$C_{12}$ alkyl, or a $C_1$-$C_8$ alkyl, or a $C_1$-$C_6$ alkyl, or a $C_1$-$C_4$ alkyl, or a pharmaceutically acceptable salt thereof.

It should be understood by one of skill in the art that the compound P-II depicted above is also meant to include all isomeric (e.g., enantiomeric, diastereomeric, and geometric (or conformational)) forms of the structure. For example, the R and S configurations for each asymmetric center, are within the scope of the present disclosure. By way of an example, the two isomers depicted below are within the scope of the present disclosure:

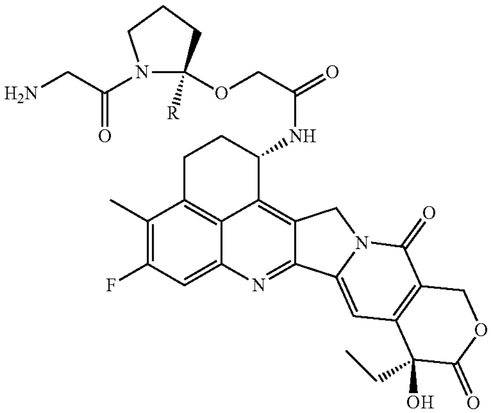

and

-continued

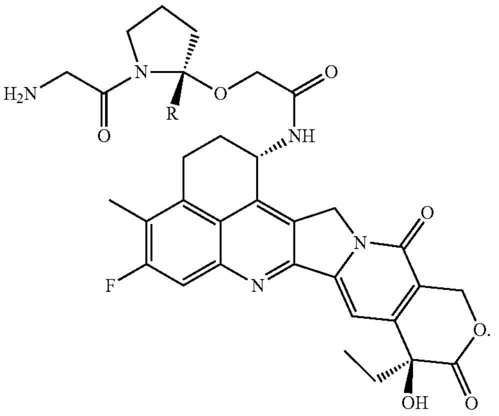

In one embodiment, the compound of the present disclosure is

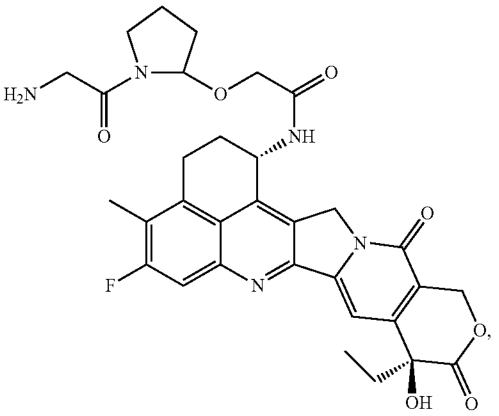 [SMILES: CC[C@@]1(O)C(=O)OCc2c1cc1n(c2=O)Cc2c-1nc1cc(F)c(C)c3c1c2[C@@H](NC(=O)COC1CCCN1C(=O)CN)CC3]

or a pharmaceutically acceptable salt thereof.

In one embodiment, the payload according to the disclosure is conjugated to form a protein-drug conjugate (e.g., an anti-FGFR2 antibody-drug conjugate). In one embodiment, the payload is covalently attached to a moiety M. In one embodiment, the payload is M-Dxd. In one embodiment, M-Dxd has a structure selected from the group consisting of

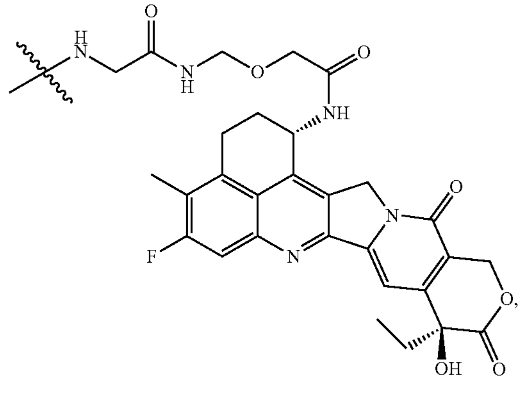 [SMILES: *NCC(=O)NCOCC(=O)N[C@H]1CCc2c(C)c(F)cc3nc4c(c1c23)Cn1c-4cc2c(c1=O)COC(=O)[C@]2(O)CC]

and

-continued

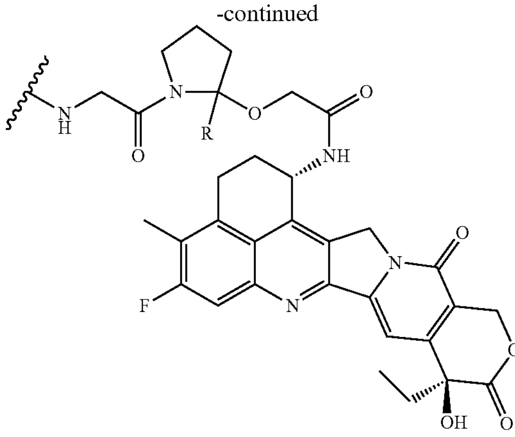

wherein R is a hydrogen or a $C_1$-$C_4$ alkyl, and where ~ represents the point of attachment to $L_2$.

In one embodiment, the payload according to the disclosure is:

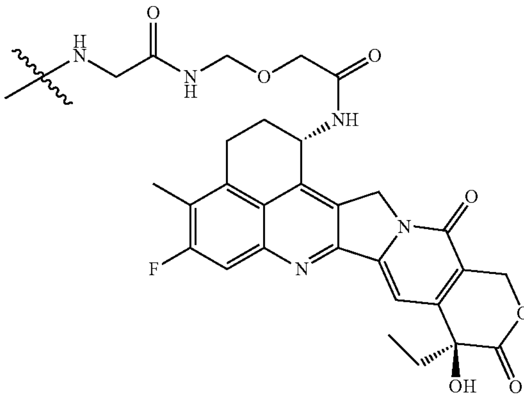

where ~ represents the point of attachment to a linker.

Provided herein is an anti-FGFR2 antibody or antigen binding fragment thereof conjugated through a linker to a payload having the following structure:

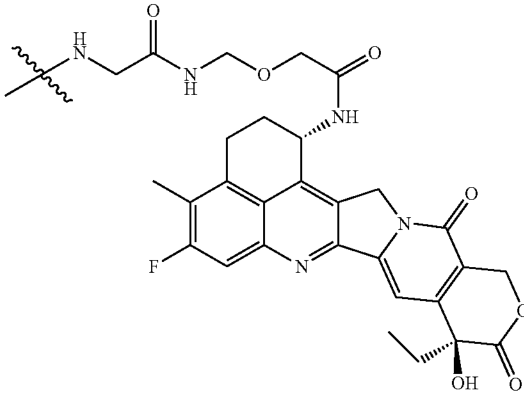

wherein the anti-FGFR2 antibody or antigen-binding fragment thereof comprises an HCDR1-HCDR2-HCDR3-LCDR1-LCDR2-LCDR3 amino acid sequence set contained within an HCVR/LCVR amino acid sequence pair selected from the group consisting of: SEQ ID NOs: 2/10, 22/28, and 40/44.

Provided herein is an anti-FGFR2 antibody or antigen binding fragment thereof conjugated through a linker to a payload having the following structure:

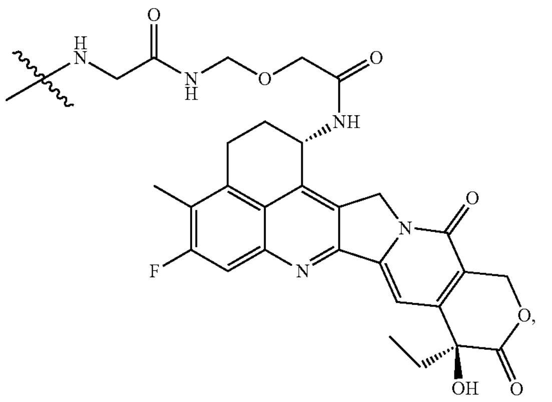 [SMILES: *NCC(=O)NCOCC(=O)N[C@H]1CCc2c(C)c(F)cc3nc4c(c1c23)Cn1c-4cc2c(c1=O)COC(=O)[C@]2(O)CC]

wherein the anti-FGFR2 antibody or antigen-binding fragment thereof comprises an HCDR1-HCDR2-HCDR3-LCDR1-LCDR2-LCDR3 amino acid sequence set selected from the group consisting of SEQ ID NOs: 4-6-8-12-GAS SEQ ID NO: 16, SEQ ID NOs: 24-6-26-30-KAS SEQ ID NO: 34, and SEQ ID NOs: 24-6-42-46-KAS SEQ ID NO: 34.

Provided herein is an anti-FGFR2 antibody or antigen binding fragment thereof conjugated through a linker to a payload having the following structure:

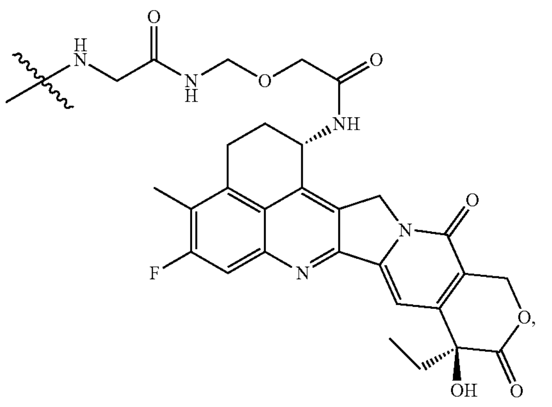 [SMILES: *NCC(=O)NCOCC(=O)N[C@H]1CCc2c(C)c(F)cc3nc4c(c1c23)Cn1c-4cc2c(c1=O)COC(=O)[C@]2(O)CC]

wherein the anti-FGFR2 antibody or antigen-binding fragment thereof comprises an HCVR/LCVR amino acid sequence pair selected from the group consisting of: SEQ ID NOs: 2/10, 22/28, and 40/44.

Provided herein is an anti-FGFR2 antibody or antigen binding fragment thereof conjugated through a linker to a payload having the following structure:

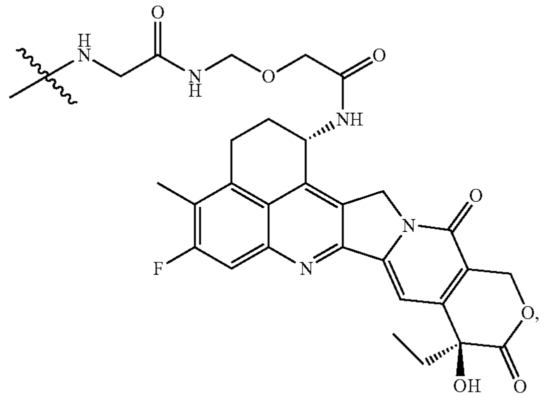 [SMILES: *NCC(=O)NCOCC(=O)N[C@H]1CCc2c(C)c(F)cc3nc4c(c1c23)Cn1c-4cc2c(c1=O)COC(=O)[C@]2(O)CC]

wherein the anti-FGFR2 antibody or antigen-binding fragment thereof comprises a heavy chain amino acid sequence selected from the group consisting of SEQ ID NO: 18, 36, 49, 52, SEQ ID NO: 53, and SEQ ID NO: 54. In some aspects, the anti-EGFR2 antibody or antigen-binding fragment thereof comprises a heavy chain/light chain amino acid sequence pair selected from the group consisting of SEQ ID NOs: 18/20, 36/38, 49/51, 52/20, 53/38, and 54/51.

In certain embodiments, the cytotoxic agent is a maytansinoid, e.g., derivative of maytansine. Suitable maytansinoids include DM1, DM4, or derivatives, stereoisomers, or isotopologues thereof. Suitable maytansinoids also include, but are not limited to, those disclosed in WO 2014/145090A1, WO 2015/031396A1, US 2016/0375147A1, U.S. Pat. No. 10,570,151 (e.g., compound 6 therein) and US 2017/0209591A1, incorporated herein by reference in their entireties. In some embodiments, the maytansinoid is DM1.

In some embodiments, the maytansinoid has the following structure:

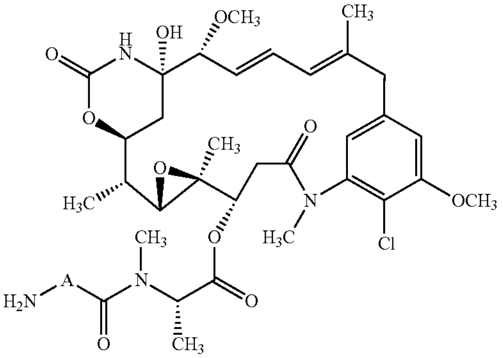

wherein A is an optionally substituted arylene or heteroarylene.

In some embodiments, the maytansinoid has the following structure:

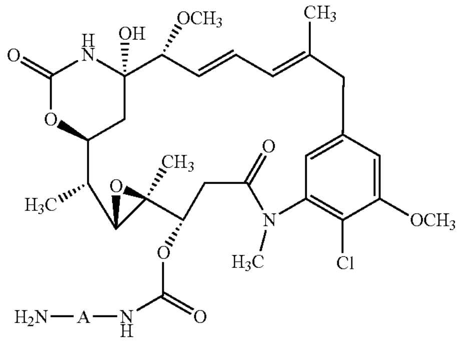
wherein A is an optionally substituted arylene or heteroarylene.
In some embodiments, the maytansinoid has the following structure:
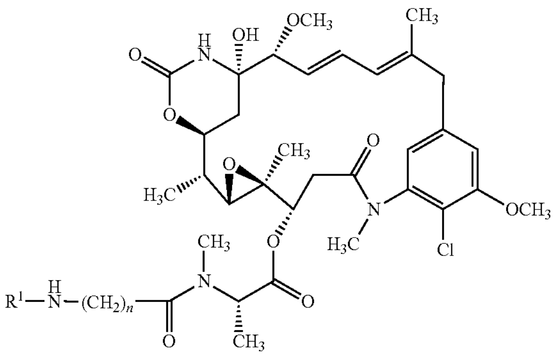
wherein n is an integer from 1-12 and $R^1$ is alkyl.
In some embodiments, the maytansinoid is:
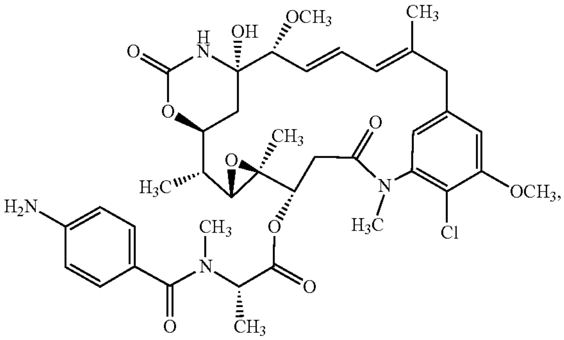
,
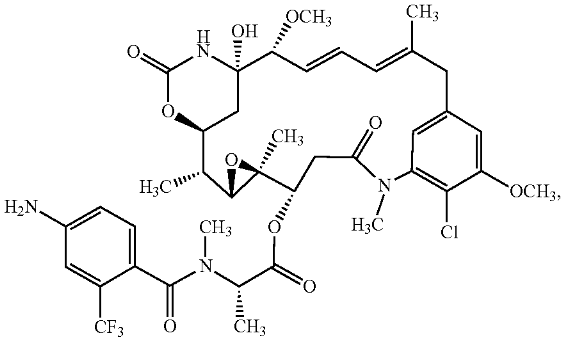
,
-continued
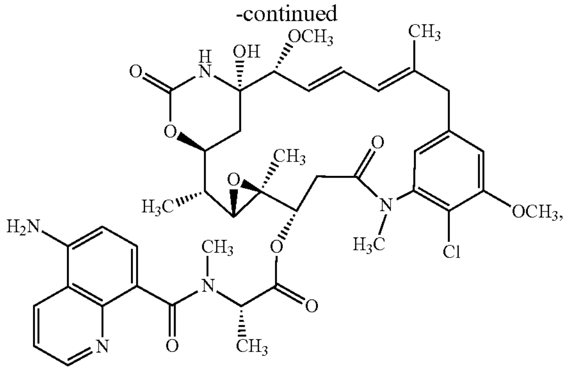
,
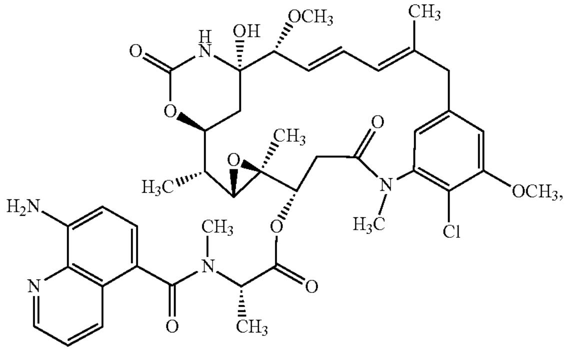
,
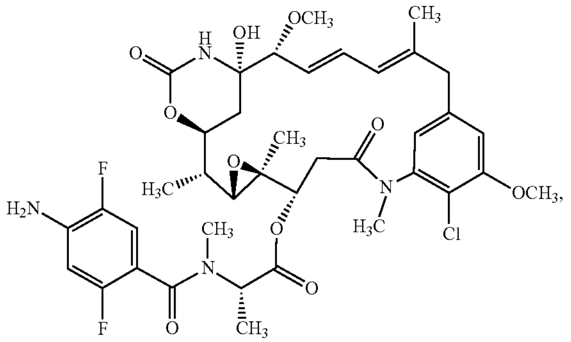
,
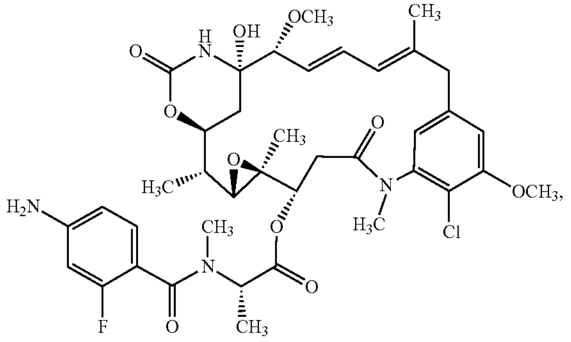
,
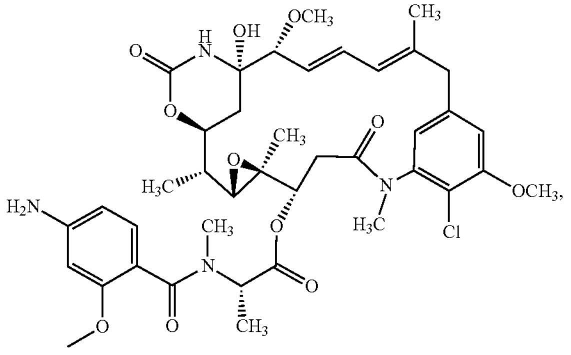
, -continued
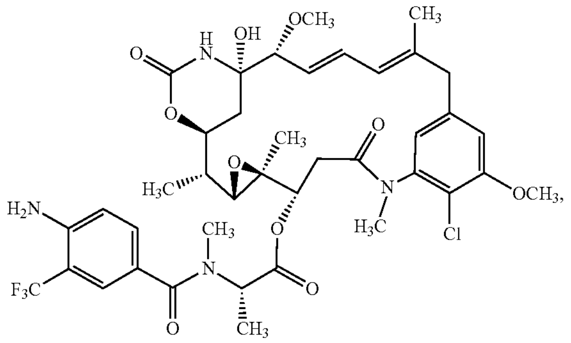
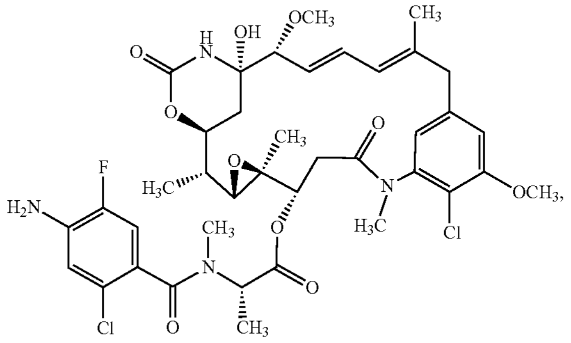
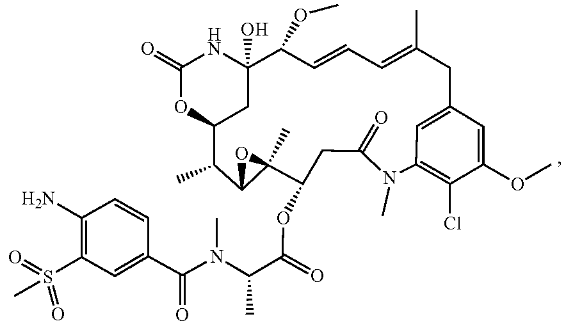
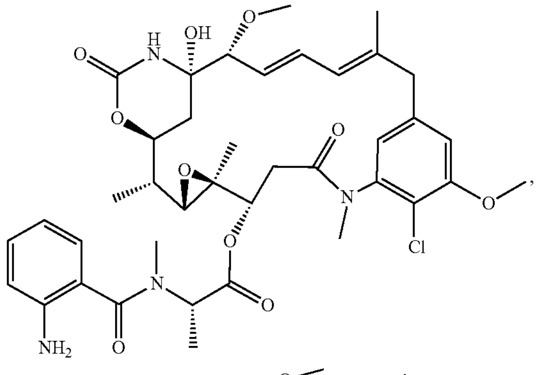
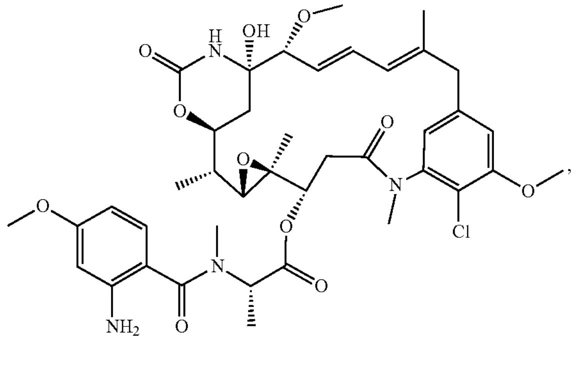
-continued
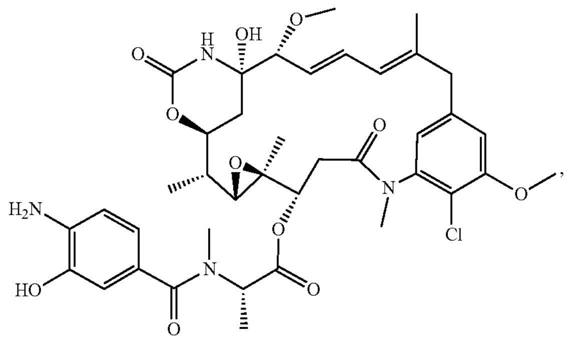
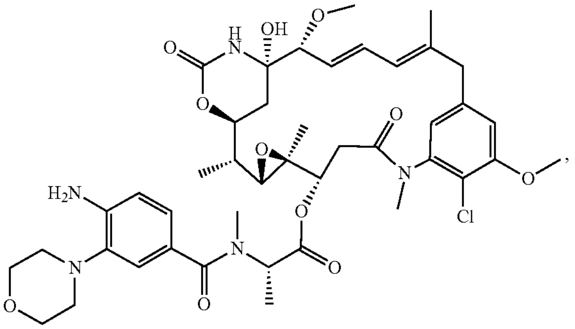
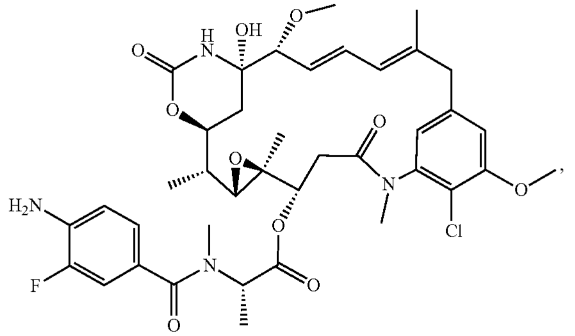
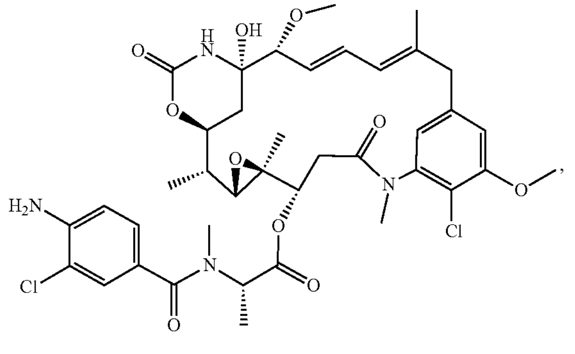
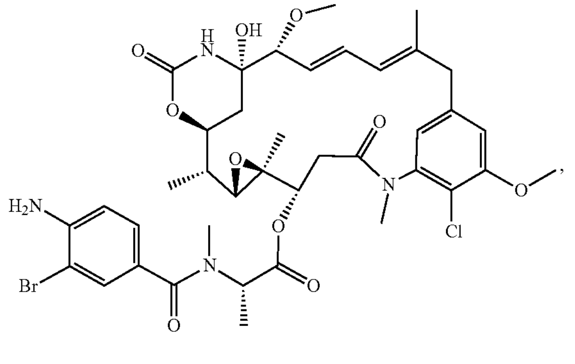

-continued
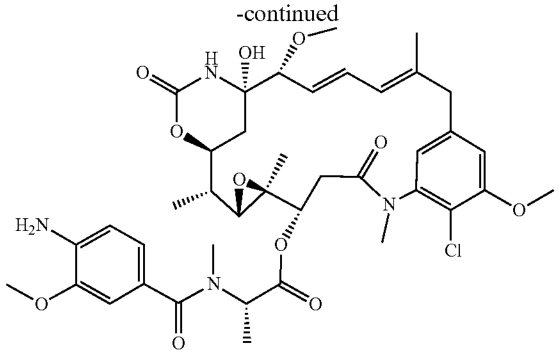
,
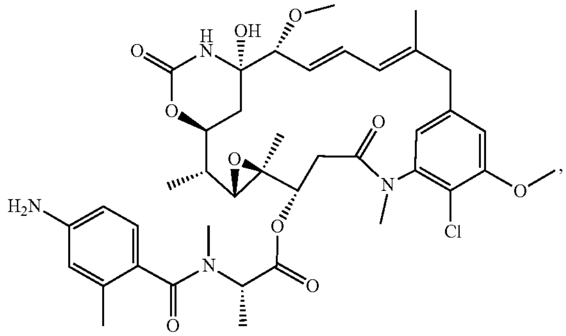
,
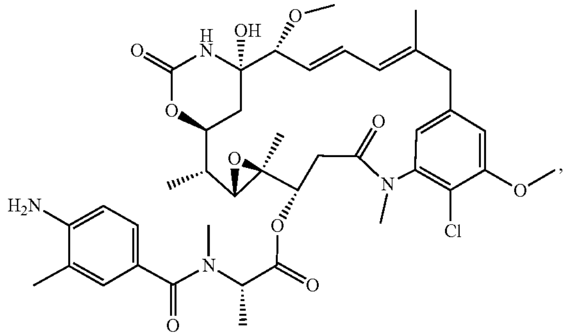
,
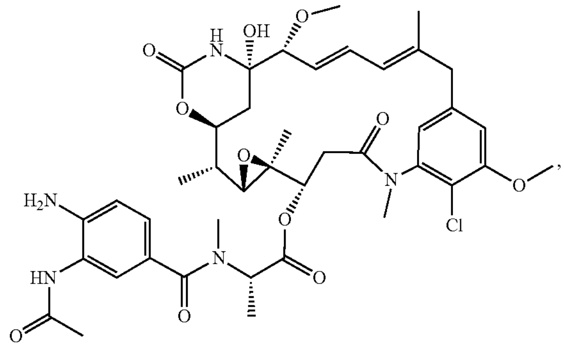
,
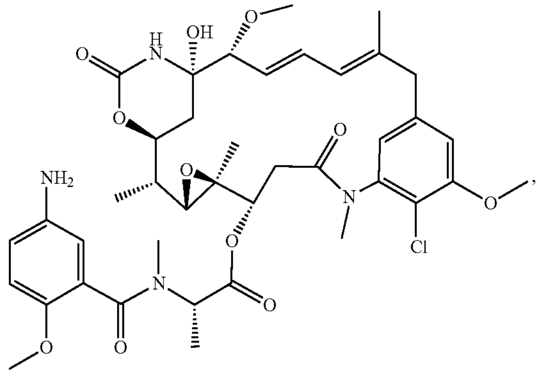
,
-continued
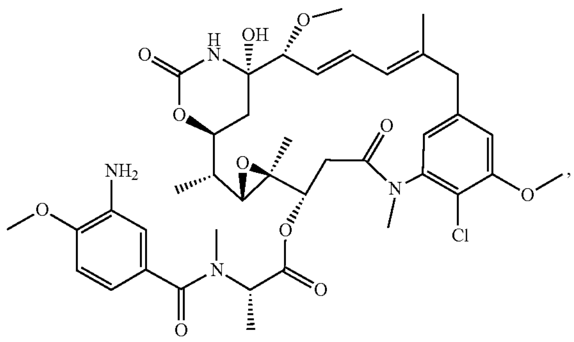
,
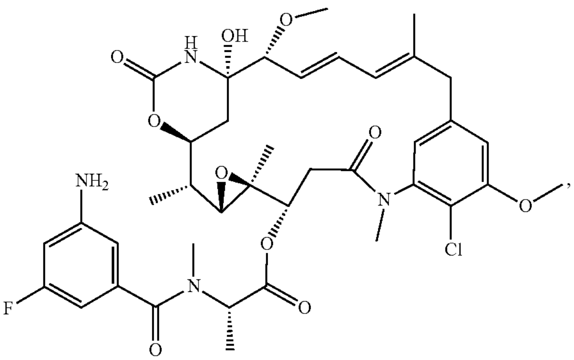
,
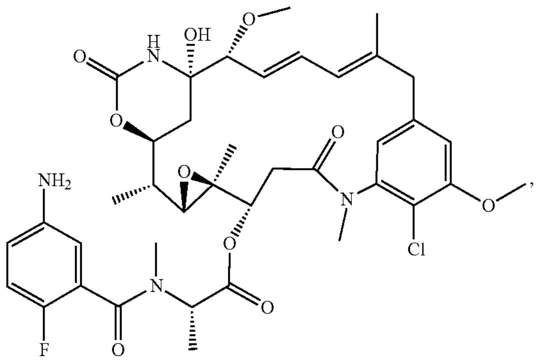
,
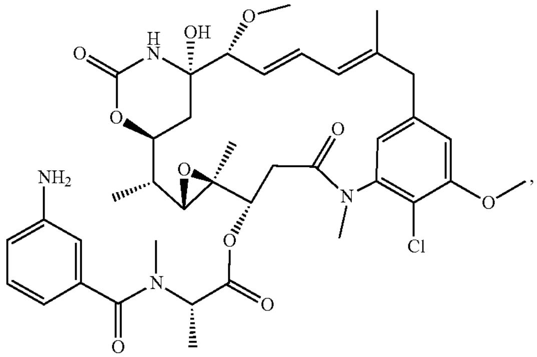
, -continued
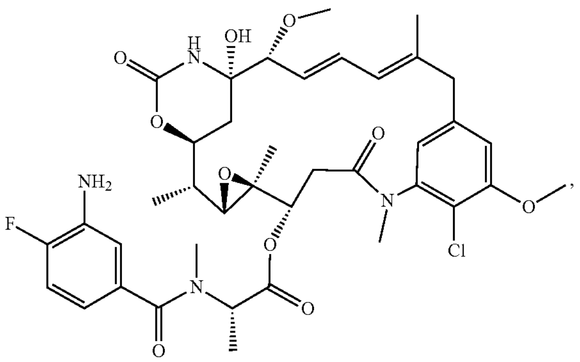
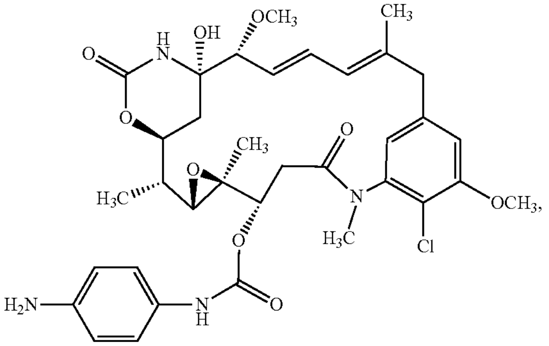
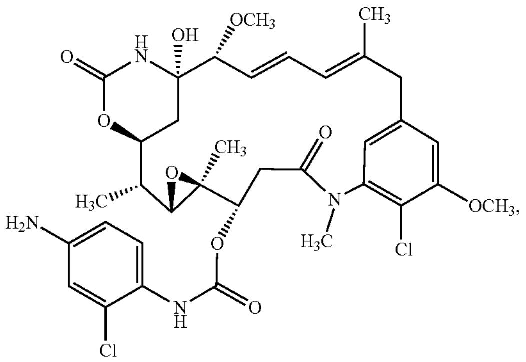
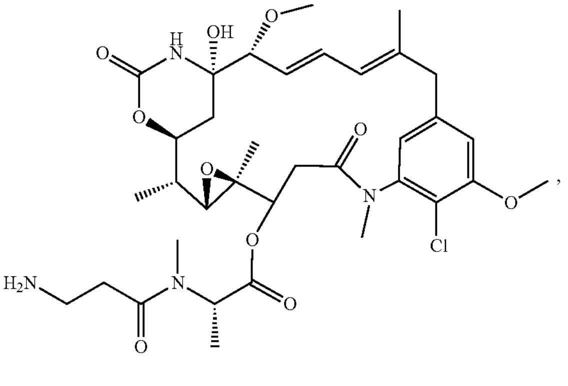
-continued
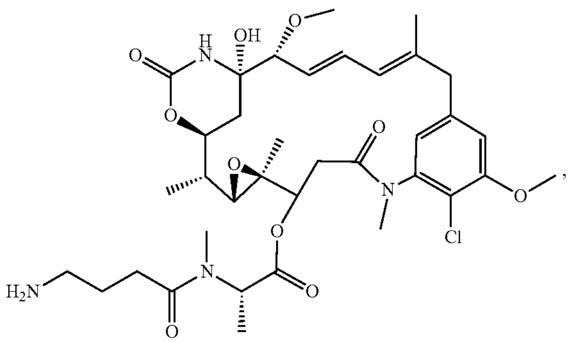
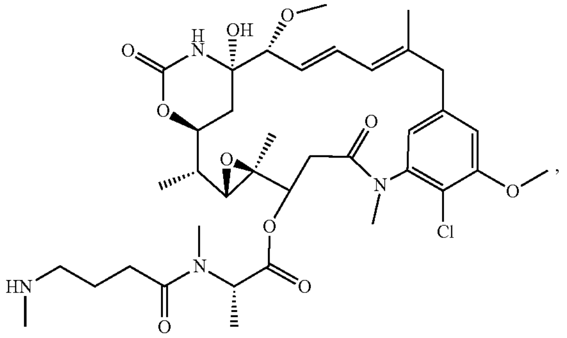
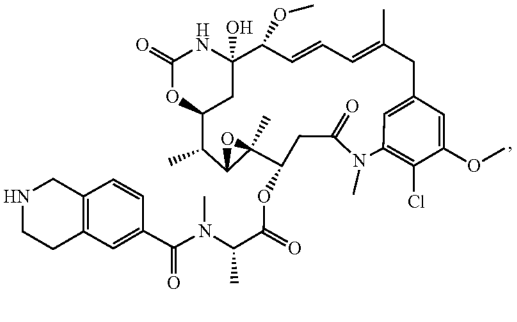
or -continued

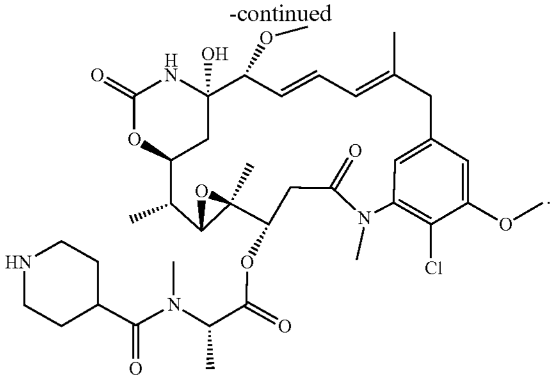

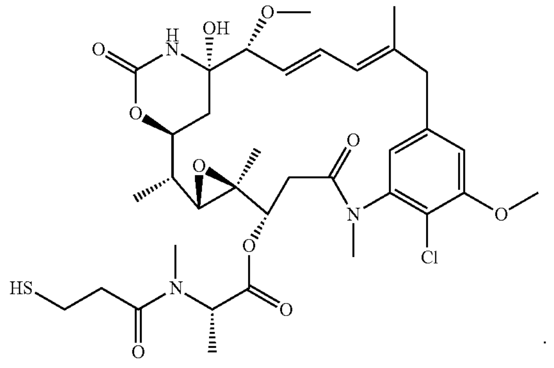 [SMILES: COc1cc2cc(c1Cl)N(C)C(=O)C[C@H](OC(=O)[C@H](C)N(C)C(=O)CCS)[C@]1(C)O[C@H]1[C@H](C)[C@@H]1C[C@@](O)(NC(=O)O1)[C@H](OC)/C=C/C=C(\C)C2]

In some embodiments, the maytansinoid is a compound having the formula Maytansinoid 1A:

Maytansinoid 1A

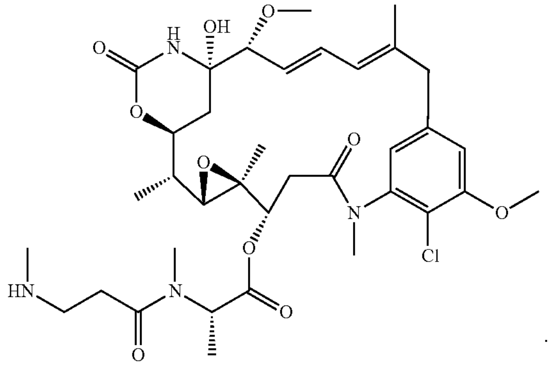

Provided herein is also an antibody-drug conjugate comprising an anti-FGFR2 antibody or antigen binding fragment thereof conjugated to Maytansinoid 1A, wherein the antibody-drug conjugate has the following structure:

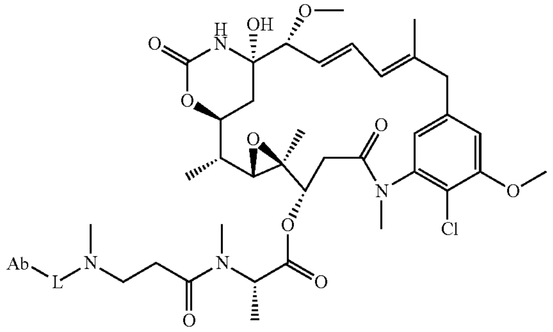

wherein the Ab is the anti-FGFR2 antibody or antigen binding fragment thereof and L is a linker. In some embodiments, the Ab is an anti-FGFR2 antibody or antigen-binding fragment thereof comprising the CDRs within the HCVR amino acid sequence of SEQ ID NO: 2 and the CDRs within the LCVR amino acid sequence of SEQ ID NO: 10. In some embodiments, the Ab is an anti-FGFR2 antibody or antigen-binding fragment thereof comprising an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS; and an LCDR3 amino acid sequence of SEQ ID NO: 16. In some embodiments, the Ab is an anti-FGFR2 antibody or antigen-binding fragment thereof comprising the CDRs within the HCVR amino acid sequence of SEQ ID NO: 22 and the CDRs within the LCVR amino acid sequence of SEQ ID NO: 28. In some embodiments, the Ab is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the Ab is an anti-FGFR2 antibody or antigen-binding fragment thereof comprising the CDRs within the HCVR amino acid sequence of SEQ ID NO: 40 and the CDRs within the LCVR amino acid sequence of SEQ ID NO: 44. In some embodiments, the Ab is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KAS; and an LCDR3 amino acid sequence of SEQ ID NO: 34.

Provided herein is also an antibody-drug conjugate comprising an anti-FGFR2 antibody or antigen binding fragment thereof conjugated to Tubulysin 1A, wherein the antibody-drug conjugate has the following structure:

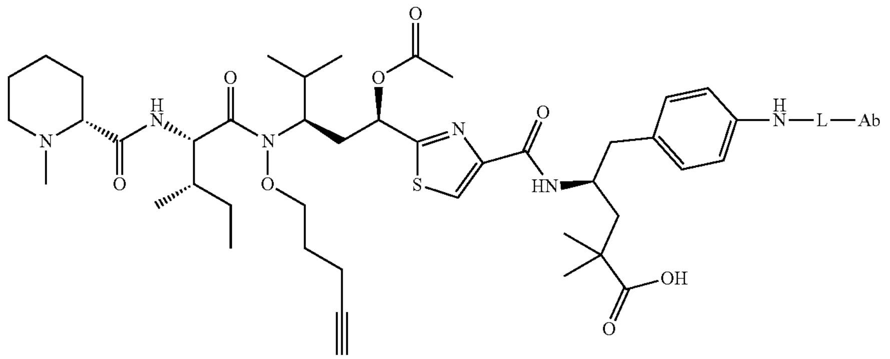

wherein the Ab is the anti-FGFR2 antibody or antigen binding fragment thereof and L is a linker. In some embodiments, the Ab is an anti-FGFR2 antibody or antigen-binding fragment thereof comprising the CDRs within the HCVR amino acid sequence of SEQ ID NO: 2 and the CDRs within the LCVR amino acid sequence of SEQ ID NO: 10. In some embodiments, the Ab is an anti-FGFR2 antibody or antigen-binding fragment thereof comprising an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS; and an LCDR3 amino acid sequence of SEQ ID NO: 16. In some embodiments, the Ab is an anti-FGFR2 antibody or antigen-binding fragment thereof comprising the CDRs within the HCVR amino acid sequence of SEQ ID NO: 22 and the CDRs within the LCVR amino acid sequence of SEQ ID NO: 28. In some embodiments, the Ab is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the Ab is an anti-FGFR2 antibody or antigen-binding fragment thereof comprising the CDRs within the HCVR amino acid sequence of SEQ ID NO: 40 and the CDRs within the LCVR amino acid sequence of SEQ ID NO: 44. In some embodiments, the Ab is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KAS; and an LCDR3 amino acid sequence of SEQ ID NO: 34.

Provided herein is also an antibody-drug conjugate comprising an anti-FGFR2 antibody or antigen binding fragment thereof conjugated to a camptothecin analog, wherein the antibody-drug conjugate has the following structure:

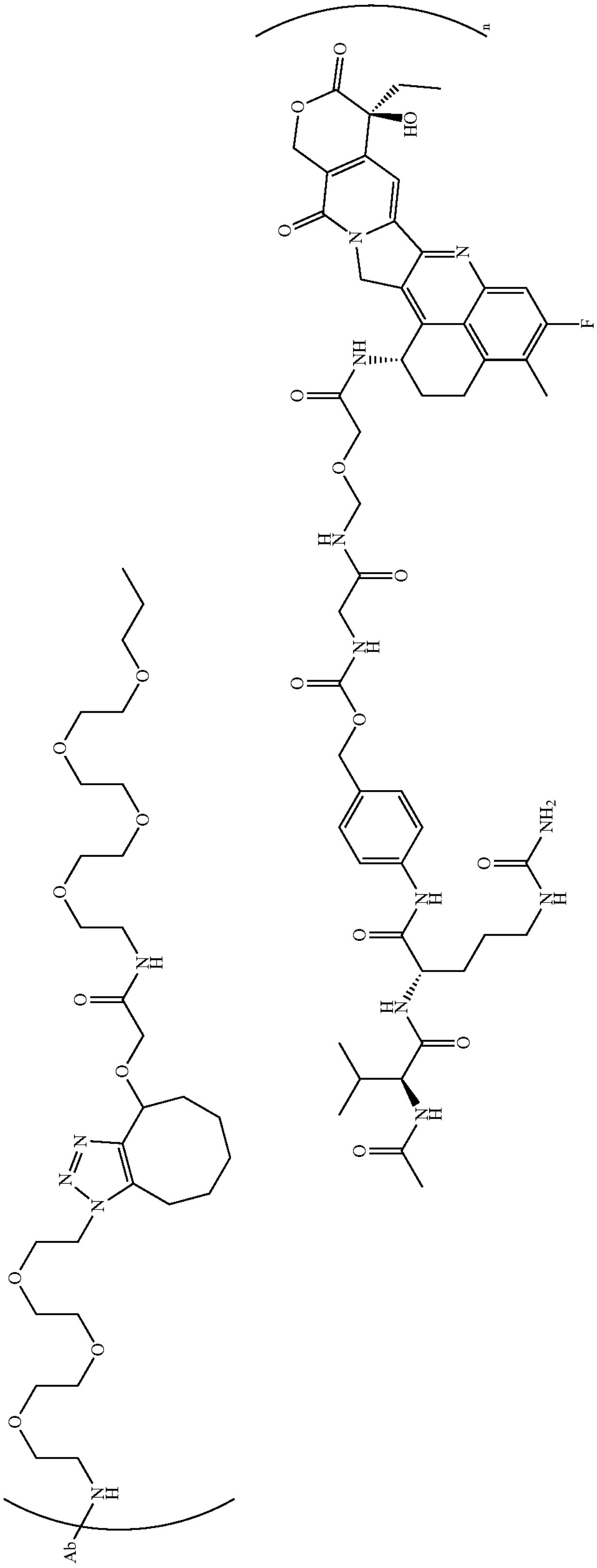
or

-continued
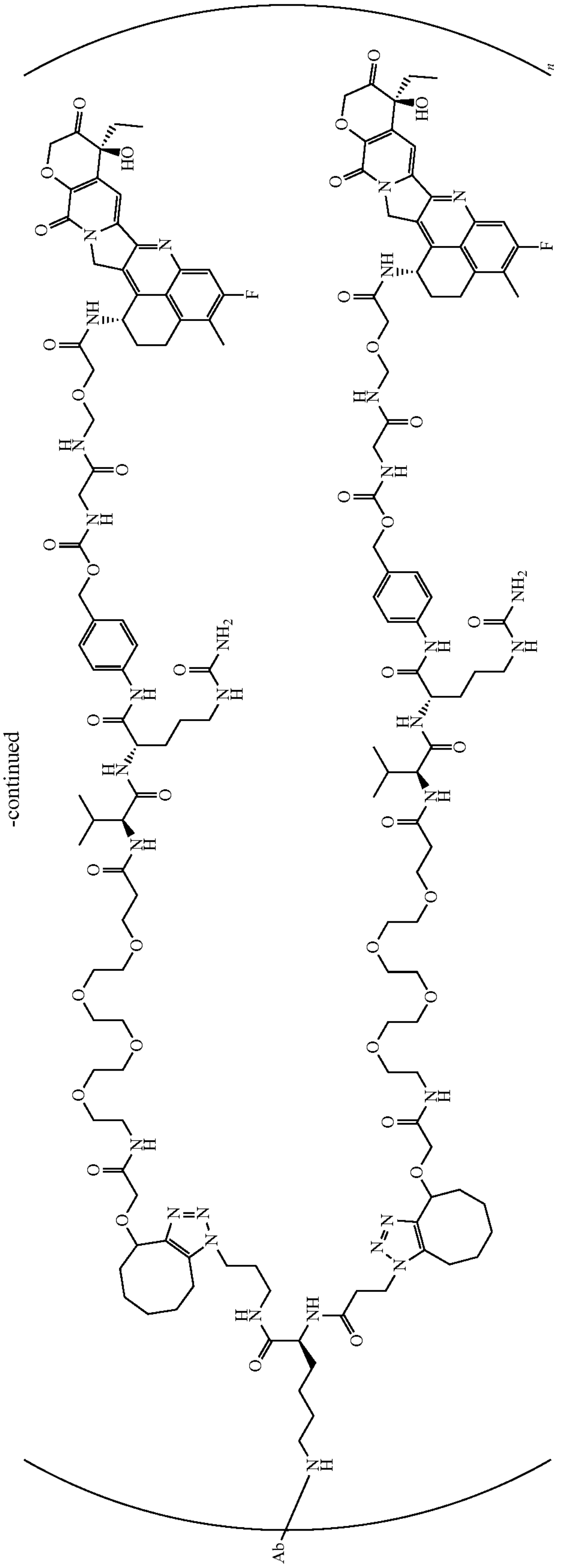

wherein the Ab is the anti-FGFR2 antibody or antigen binding fragment thereof, and n is 2 or 4. In particular embodiments, n is 2. In particular embodiments, n is 4. In some embodiments, the Ab is an anti-FGFR2 antibody or antigen-binding fragment thereof comprising the CDRs within the HCVR amino acid sequence of SEQ ID NO: 2 and the CDRs within the LCVR amino acid sequence of SEQ ID NO: 10. In some embodiments, the Ab is an anti-FGFR2 antibody or antigen-binding fragment thereof comprising an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS; and an LCDR3 amino acid sequence of SEQ ID NO: 16. In some embodiments, the Ab is an anti-FGFR2 antibody or antigen-binding fragment thereof comprising the CDRs within the HCVR amino acid sequence of SEQ ID NO: 22 and the CDRs within the LCVR amino acid sequence of SEQ ID NO: 28. In some embodiments, the Ab is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the Ab is an anti-FGFR2 antibody or antigen-binding fragment thereof comprising the CDRs within the HCVR amino acid sequence of SEQ ID NO: 40 and the CDRs within the LCVR amino acid sequence of SEQ ID NO: 44. In some embodiments, the Ab is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KASSEQ 4D NO: 2; and an LCDR3 amino acid sequence of SEQ ID NO: 34. n is a value between 2 and 12, for example, 2, 3, 4, 5, 6, 7, 8, 9, 10, 11, or 12.

Also provided herein are antibody-radionuclide conjugates (ARCs) comprising anti-FGFR2 antibodies conjugated to one or more radionuclides. Exemplary radionuclides that can be used in the context of this aspect of the disclosure include, but are not limited to, e.g., $^{225}Ac$, $^{212}Bi$, $^{213}Bi$, $^{131}I$, $^{186}Re$, $^{227}Th$, $^{222}Rn$, $^{223}Ra$, $^{224}Ra$, and $^{90}Y$.

In certain embodiments provided herein, ADCs are provided comprising an anti-FGFR2 antibody or antigen-binding fragment thereof conjugated to a cytotoxic agent (e.g., any of the cytotoxic agents disclosed above) via a linker. Linkers are any group or moiety that links, connects, or bonds the antibody or antigen-binding proteins described herein with a therapeutic moiety, e.g., cytotoxic agent. Suitable linkers may be found, for example, in *Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. Generally, suitable binding agent linkers for the antibody conjugates described herein are those that are sufficiently stable to exploit the circulating half-life of the antibody and, at the same time, capable of releasing its payload upon antigen binding and/or antigen-mediated internalization of the conjugate. Linkers can be cleavable or non-cleavable. Cleavable linkers include linkers that are cleaved by intracellular metabolism following internalization, e.g., cleavage via hydrolysis, reduction, or enzymatic reaction. Non-cleavable linkers include linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citrulline units, and para-aminobenzyl (PAB) units. In some aspects, the linker comprises one of more PEG groups.

Any linker molecule or linker technology known in the art can be used to create or construct an ADC of the present disclosure. In certain embodiments, the linker is a cleavable linker, e.g., a cathepsin B cleavable linker. According to other embodiments, the linker is a non-cleavable linker. Exemplary linkers that can be used in the context of the present disclosure include, linkers that comprise or consist of e.g., MC (6-maleimidocaproyl), MP (maleimidopropanoyl), val-cit (valine-citrulline), val-ala (valine-alanine), dipeptide site in protease-cleavable linker, ala-phe (alanine-phenylalanine), dipeptide site in protease-cleavable linker, PAB (p-aminobenzyloxycarbonyl), SPP (N-Succinimidyl 4-(2-pyridylthio) pentanoate), SMCC (N-Succinimidyl 4-(N-maleimidomethyl)cyclohexane-1 carboxylate), SIAB (N-Succinimidyl (4-iodo-acetyl)aminobenzoate), and variants and combinations thereof. Additional examples of linkers that can be used in the context of the present disclosure are provided, e.g., in U.S. Pat. No. 7,754,681 and in Ducry, Bioconjugate Chem., 2010, 21:5-13, and the references cited therein, the contents of which are incorporated by reference herein in their entireties.

In certain embodiments, the linkers are stable in physiological conditions. In certain embodiments, the linkers are cleavable, for instance, able to release at least the payload portion in the presence of an enzyme or at a particular pH range or value. In some embodiments, a linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the linker comprises a non-cleavable moiety.

Suitable linkers also include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. In some embodiments, the linker comprises two amino acids. In some embodiments, the linker comprises three amino acids. In some embodiments, the linker comprises four amino acids. Suitable amino acids include natural, non-natural, standard, non-standard, proteinogenic, non-proteinogenic, and L-or D-u.-amino acids. In some embodiments, the linker comprises alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or combination thereof. In certain embodiments, one or more side chains of the amino acids is linked to a side chain group, described below. In some embodiments, the linker comprises valine and citrulline. In some embodiments, the linker comprises lysine, valine, and citrulline. In some embodiments, the linker comprises lysine, valine, and alanine. In some embodiments, the linker comprises valine and alanine. In some embodiments, the linker comprises a dipeptide, tripeptide, or tetrapeptide. In some embodiments, the linker comprises a peptide, wherein the peptide is valine-citrulline (val-cit or VC), glutamic acid-valine-citrulline (EVC), glycine-glycine-phenylalanine (GGF), or glycine-glycine-phenylalanine-glycine (GGFG).

In some embodiments, the linker comprises a self-immolative group. The self-immolative group can be any such group known to those of skill. In particular embodiments, the self-immolative group is p-aminobenzyl (PAB), or a derivative thereof. Useful derivatives include p-aminobenzyloxycarbonyl (PABC). In some embodiments, the linker comprises a moiety having the following structure:

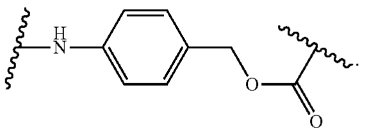 [SMILES: *Nc1ccc(COC(*)=O)cc1]

In some embodiments, the linker is:

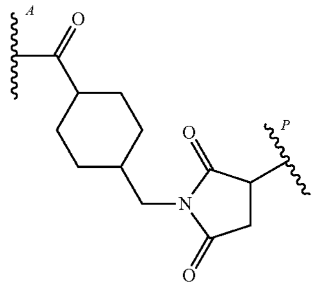

wherein

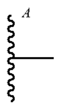

is a bond to the antibody or antigen-binding protein (e.g., via lysine residue) and

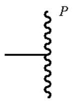

is a bond to the cytotoxic agent (e.g., DM1). In some embodiments, the linker is:

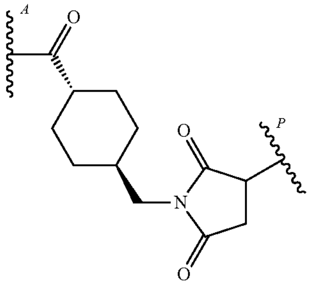

wherein

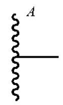

is a bond to the antibody or antigen-binding protein (e.g., via lysine residue) and

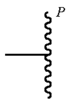

is a bond to the cytotoxic agent (e.g., DM1). In certain embodiments, the linker is:

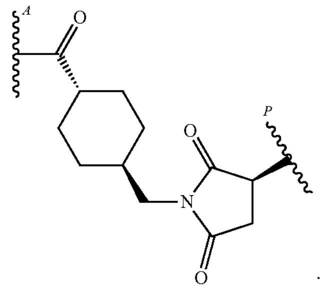

In certain embodiments, the linker is:

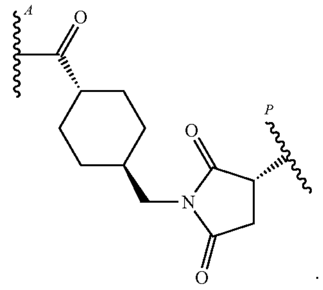

In some embodiments, the linker is derived from maleimidylmethyl-4-trans-cyclohexanecarboxysuccinate:

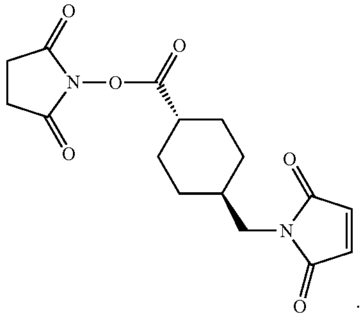 [SMILES: O=C1C=CC(=O)N1C[C@H]1CC[C@H](C(=O)ON2C(=O)CCC2=O)CC1]

.

In some embodiments, the linker is:

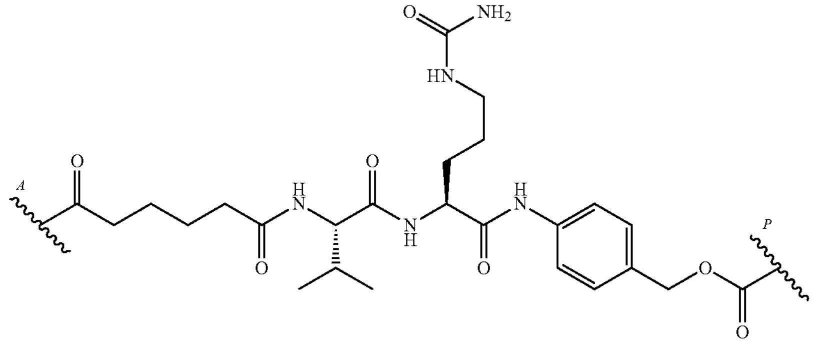

wherein

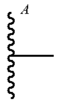

is a bond to the antibody or antigen-binding protein (e.g., via lysine residue) and

is a bond to the cytotoxic agent (e.g., a compound having the following formula:

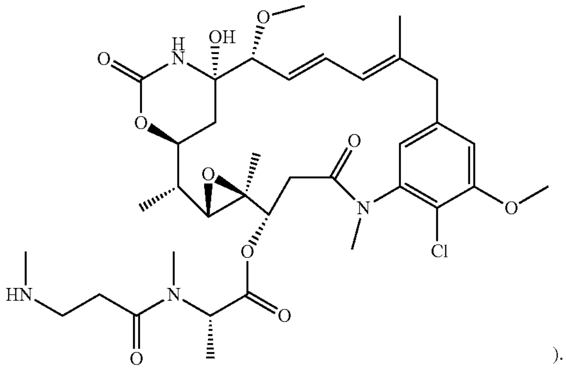 [SMILES: CNCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

).

Suitable linkers also include, but are not limited to, linkers that comprise one or more cyclic moieties. In some embodiments, the cyclic moiety is derived from a cycloaddition reaction. In certain embodiments, the cyclic moiety is derived from a 1-3-cycloaddition reaction between an azide and alkyne, e.g., cycloalkyne. In some embodiments, the cyclic moiety is

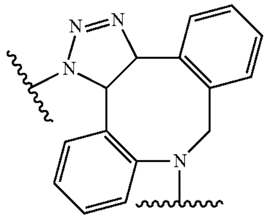 [SMILES: *N1Cc2ccccc2C2N=NN(*)C2c2ccccc21]

or its cycloaddition regioisomer:

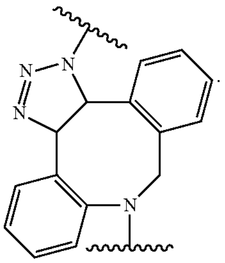 [SMILES: *N1Cc2ccccc2C2C(N=NN2*)c2ccccc21]

.

As used herein, "regioisomer," "regioisomers," or "mixture of regioisomers" refers to the product(s) of 1,3-cycloadditions or strain-promoted alkyne-azide cycloadditions (SPAACs)-otherwise known as click reactions-that derive from suitable azides (e.g., —$N_3$, or -PEG-$N_3$ derivatized antibodies) treated with suitable alkynes. In certain embodiments, for example, regioisomers and mixtures of regioisomers are characterized by the click reaction products shown below:

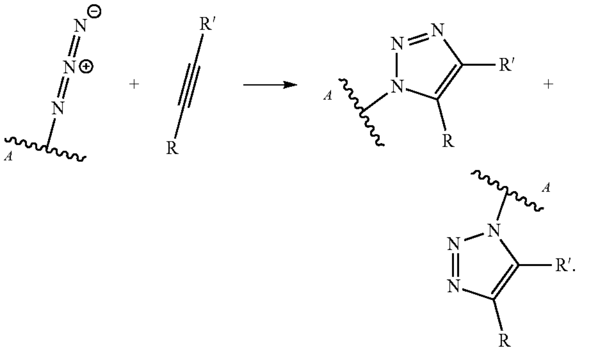

In certain embodiments, more than one suitable azide and more than one suitable alkyne can be utilized within a synthetic scheme en route to a product, where each pair of azide-alkyne can participate in one or more independent click reactions to generate a mixture of regioisomeric click reaction products. For example, a person of skill will recognize that a first suitable azide may independently react with a first suitable alkyne, and a second suitable azide may independently react with a second suitable alkyne, en route to a product, resulting in the generation of four possible click reaction regioisomers or a mixture of the four possible click reaction regioisomers.

In certain embodiments, such cycloaddition reactions facilitate conjugation of an antibody functionalized with one of more azido groups with a payload comprising a linker moiety comprising an alkyne. In some embodiments, the anti-FGFR2 antibodies described herein are functionalized with one or more azido groups. When the antibodies are specifically functionalized with azido groups at specific amino acid residues, e.g., Q295, such antibodies can be site-specifically conjugated with payloads having linker moieties comprising an alkyne that is capable of undergoing a cycloaddition reaction with said azido groups. In some embodiments, the anti-FGFR2 antibody is functionalized at Q295 by reacting said antibody with a primary amine compound comprising an azido group and transglutaminase. Antibodies that are conjugated through glutamine residues are bonded through a —CONH— moiety, e.g., that results from reaction of the glutamine residue with a primary amine compound. The bond connecting a linker-payload to such conjugated glutamine residue is depicted herein in some embodiments as

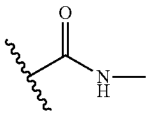
or
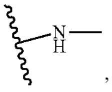
, both representing the resulting —C(O)NH— moiety that links the antibody to the linker payloads described herein. In some embodiments, the primary amine compound comprising an azido group comprises a PEG group. In certain embodiments, said primary amine compound is:

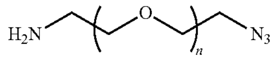

wherein n is 1-12. In certain embodiments, said primary amine compound is:

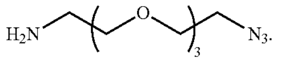

In some embodiments, the linker comprises one or more spacers. Suitable spacers include moieties that link, e.g., covalently or through ionic interaction, two linker portions, a linker portion with a payload, or a linker portion with an antibody. In certain embodiments, the spacer is a PEG group.

The present disclosure comprises ADCs in which a linker connects an anti-FGFR2 antibody or antigen-binding fragment thereof to a drug or cytotoxin through an attachment at a particular amino acid within the antibody or antigen-binding molecule. Exemplary amino acid attachments that can be used in the context of this aspect, e.g., lysine (see, e.g., U.S. Pat. No. 5,208,020; US 2010/0129314; Hollander et al., *Bioconjugate Chem.,* 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA,* 2008, 105:12451-12456), formyl glycine (see, e.g., Carrico et al., *Nat. Chem. Biol.,* 2007, 3:321-322; Agarwal et al., *Proc. Natl. Acad. Sci., USA,* 2013, 110:46-51, and Rabuka et al., *Nat. Protocols,* 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, and Ryan et al., *Food & Agriculture Immunol.,* 2001, 13:127-130) and disulfide linkers (see, e.g., WO 2013/085925, WO 2010/010324, WO 2011/018611, and Shaunak et al., *Nat. Chem. Biol.,* 2006, 2:312-313). Site specific conjugation techniques can also be employed to direct conjugation to particular residues of the antibody or antigen binding protein (see, e.g., Schumacher et al. *J Clin Immunol* (2016) 36(Suppl 1): 100). Site specific conjugation techniques include, but are not limited to, glutamine conjugation via transglutaminase (see e.g., Schibli, Angew Chemie Inter Ed. 2010, 49,9995).

According to certain embodiments, the present disclosure provides ADCs, wherein an anti-FGFR2 antibody or antigen-binding fragment thereof as described herein is conjugated to a linker-drug composition as set forth in International Patent Publication WO2014/145090, (e.g., compound "7" disclosed therein), the disclosure of which is hereby incorporated by reference herein in its entirety:

7

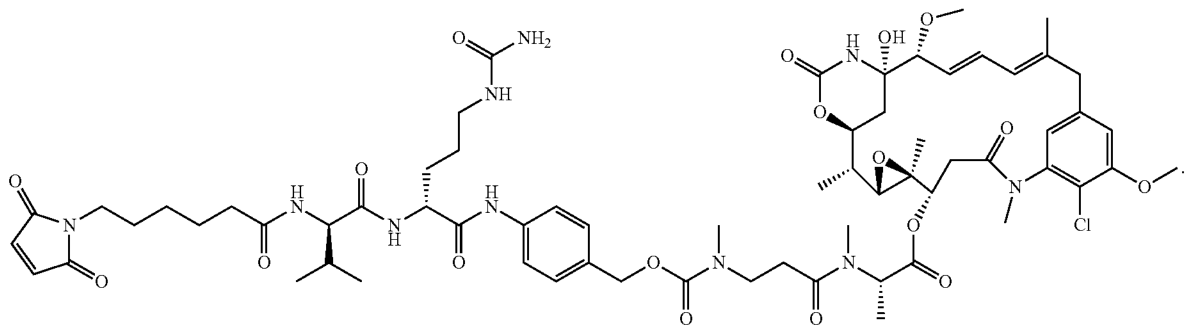

Provided herein are also antibody-drug conjugates comprising the anti-FGFR2 antibodies disclosed herein, where said antibody is conjugated to a cytotoxic agent. In certain embodiments, the cytotoxic agent is a maytansinoid. In certain embodiments, the maytansinoid is a compound having the following formula:

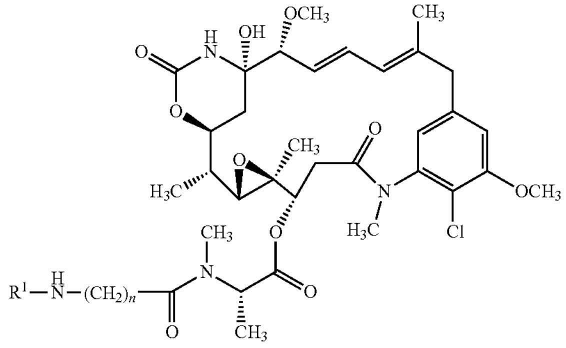

wherein n is an integer from 1-12 and $R^1$ is alkyl. In certain embodiments, the maytansinoid is

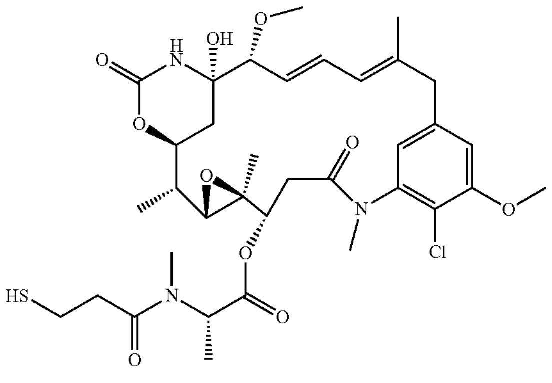

.

In some embodiments, the maytansinoid is Maytansinoid 1A:

Maytansinoid 1A

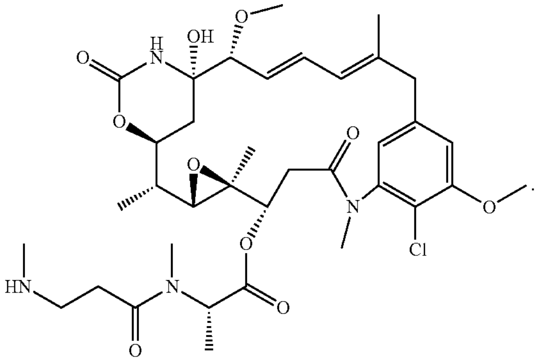

In certain embodiments, the cytotoxic agent is a maytansinoid, and the maytansinoid is covalently attached to the antibody via non-cleavable linker. In certain embodiments, the cytotoxic agent is a maytansinoid, and the maytansinoid is covalently attached to the anti-FGFR2 antibody or antigen-binding fragment thereof via cleavable linker.

An exemplary cleavable linker is the cathepsin B cleavable linker. In certain embodiments, the cytotoxic agent is a maytansinoid, and the maytansinoid is covalently attached to the anti-FGFR2 antibody or antigen-binding fragment thereof via a cathepsin B cleavable linker. In one embodiment, the anti-FGFR2 antibody or antigen-binding fragment thereof is conjugated to a maytansinoid via cleavable linker, wherein the linker comprises a dipeptide. In another embodiment, the anti-FGFR2 antibody or antigen-binding fragment thereof is conjugated to a maytansinoid via cleavable linker, wherein the linker comprises a valine-citrulline dipeptide. In another embodiment, the anti-FGFR2 antibody or antigen-binding fragment thereof is conjugated to a maytansinoid via cleavable linker, wherein the linker comprises a valine-citrulline dipeptide and PAB group. In one embodiment, the anti-FGFR2 antibody or antigen-binding fragment thereof is conjugated to:

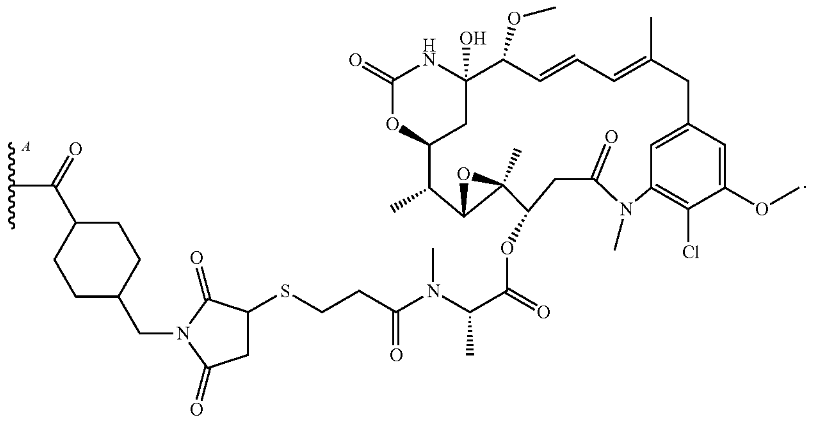

wherein

is a bond to the antibody. In some embodiments, the antibody is an anti-FGFR2 antibody or antigen-binding fragment thereof comprising the CDRs within the HCVR amino acid sequence of SEQ ID NO: 2 and the CDRs within the LCVR amino acid sequence of SEQ ID NO: 10. In some embodiments, the antibody is an anti-FGFR2 antibody or antigen-binding fragment thereof comprising an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS; and an LCDR3 amino acid sequence of SEQ ID NO: 16. In some embodiments, the antibody is an anti-FGFR2 antibody or antigen-binding fragment thereof comprising the CDRs within the HCVR amino acid sequence of SEQ ID NO: 22 and the CDRs within the LCVR amino acid sequence of SEQ ID NO: 28. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the antibody is an anti-FGFR2 antibody or antigen-binding fragment thereof comprising the CDRs within the HCVR amino acid sequence of SEQ ID NO: 40 and the CDRs within the LCVR amino acid sequence of SEQ ID NO: 44. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KAS; and an LCDR3 amino acid sequence of SEQ ID NO: 34.

In one embodiment, the anti-FGFR2 antibody or antigen-binding fragment thereof is conjugated to:

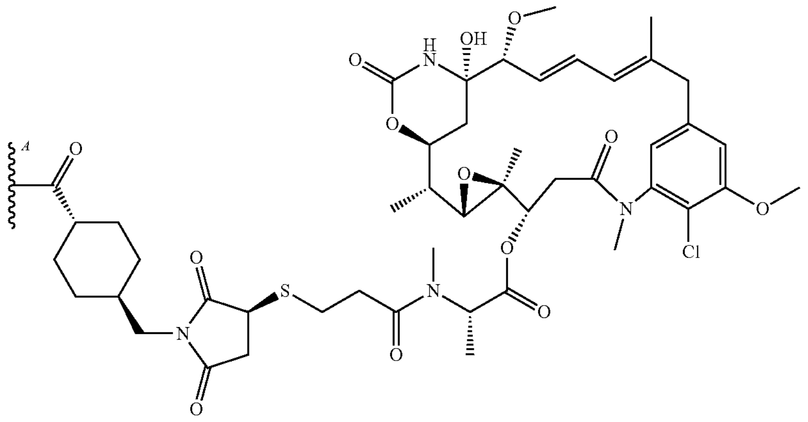

wherein

is a bond to the antibody. In some embodiments, the antibody is an anti-FGFR2 antibody or antigen-binding fragment thereof comprising the CDRs within the HCVR amino acid sequence of SEQ ID NO: 2 and the CDRs within the LCVR amino acid sequence of SEQ ID NO: 10. In some embodiments, the antibody is an anti-FGFR2 antibody or antigen-binding fragment thereof comprising an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS; and an LCDR3 amino acid sequence of SEQ ID NO: 16. In some embodiments, the antibody is an anti-FGFR2 antibody or antigen-binding fragment thereof comprising the CDRs within the HCVR amino acid sequence of SEQ ID NO: 22 and the CDRs within the LCVR amino acid sequence of SEQ ID NO: 28. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the antibody is an anti-FGFR2 antibody or antigen-binding fragment thereof comprising the CDRs within the HCVR amino acid sequence of SEQ ID NO: 40 and the CDRs within the LCVR amino acid sequence of SEQ ID NO: 44. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KAS; and an LCDR3 amino acid sequence of SEQ ID NO: 34.

In one embodiment, the anti-FGFR2 antibody or antigen-binding fragment thereof is conjugated to:

wherein

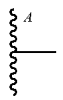

is a bond to the antibody. In some embodiments, the antibody is an anti-FGFR2 antibody or antigen-binding fragment thereof comprising the CDRs within the HCVR amino acid sequence of SEQ ID NO: 2 and the CDRs within the LCVR amino acid sequence of SEQ ID NO: 10. In some embodiments, the antibody is an anti-FGFR2 antibody or antigen-binding fragment thereof comprising an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS; and an LCDR3 amino acid sequence of SEQ ID NO: 16. In some embodiments, the antibody is an anti-FGFR2 antibody or antigen-binding fragment thereof comprising the CDRs within the HCVR amino acid sequence of SEQ ID NO: 22 and the CDRs within the LCVR amino acid sequence of SEQ ID NO: 28. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the antibody is an anti-FGFR2 antibody or antigen-binding fragment thereof comprising the CDRs within the HCVR amino acid sequence of SEQ ID NO: 40 and the CDRs within the LCVR amino acid sequence of SEQ ID NO: 44. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KAS; and an LCDR3 amino acid sequence of SEQ ID NO: 34.

In one embodiment, the anti-FGFR2 antibody or antigen-binding fragment thereof is conjugated to:

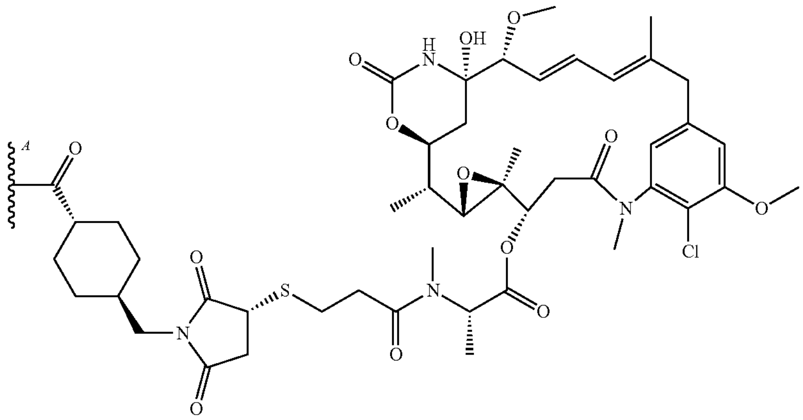

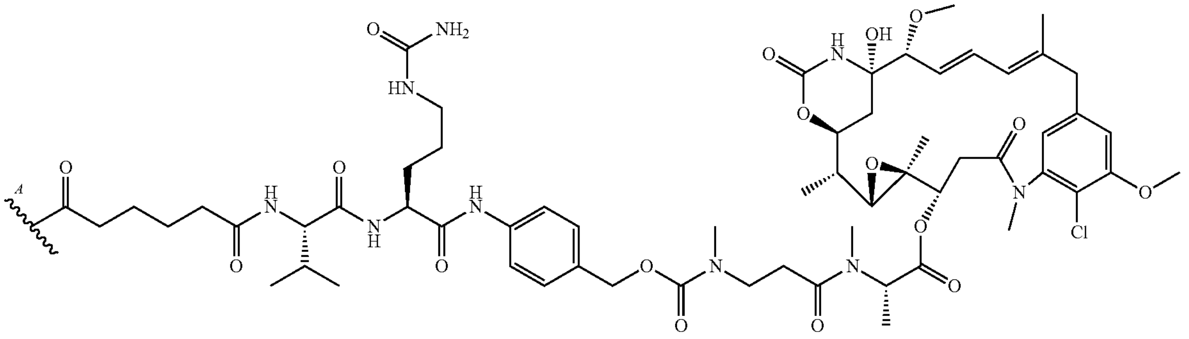

wherein

is a bond to the antibody. In some embodiments, the antibody is an anti-FGFR2 antibody or antigen-binding fragment thereof comprising the CDRs within the HCVR amino acid sequence of SEQ ID NO: 2 and the CDRs within the LCVR amino acid sequence of SEQ ID NO: 10. In some embodiments, the antibody is an anti-FGFR2 antibody or antigen-binding fragment thereof comprising an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS; and an LCDR3 amino acid sequence of SEQ ID NO: 16. In some embodiments, the antibody is an anti-FGFR2 antibody or antigen-binding fragment thereof comprising the CDRs within the HCVR amino acid sequence of SEQ ID NO: 22 and the CDRs within the LCVR amino acid sequence of SEQ ID NO: 28. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the antibody is an anti-FGFR2 antibody or antigen-binding fragment thereof comprising the CDRs within the HCVR amino acid sequence of SEQ ID NO: 40 and the CDRs within the LCVR amino acid sequence of SEQ ID NO: 44. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KAS; and an LCDR3 amino acid sequence of SEQ ID NO: 34.

In some embodiments, the anti-FGFR2 antibody or antigen-binding fragment thereof is conjugated to BAY1187982; see Sommer et al., 2016, Cancer Res, 76 (21), 6631-6639, doi: 10.1 158/0008-5472.CAN-1 6-0180. In some embodiments, the anti-FGFR2 antibody or antigen binding fragment thereof is conjugated to

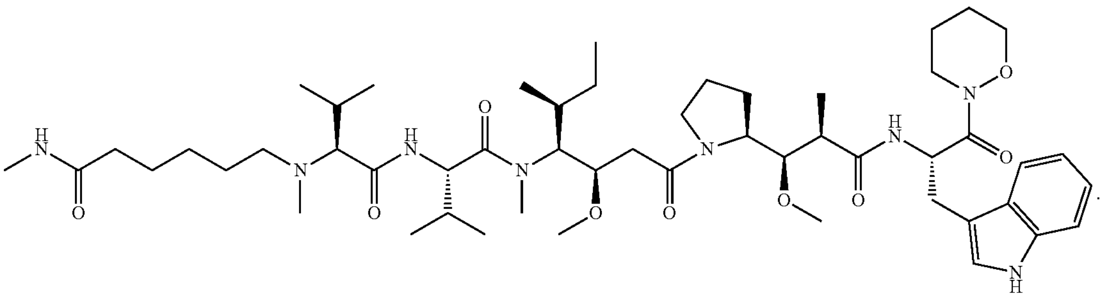 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@H](C(C)C)N(C)CCCCCC(=O)NC)C(C)C]

In some embodiments, the anti-FGFR2 antibody or antigen-binding fragment thereof is conjugated to:

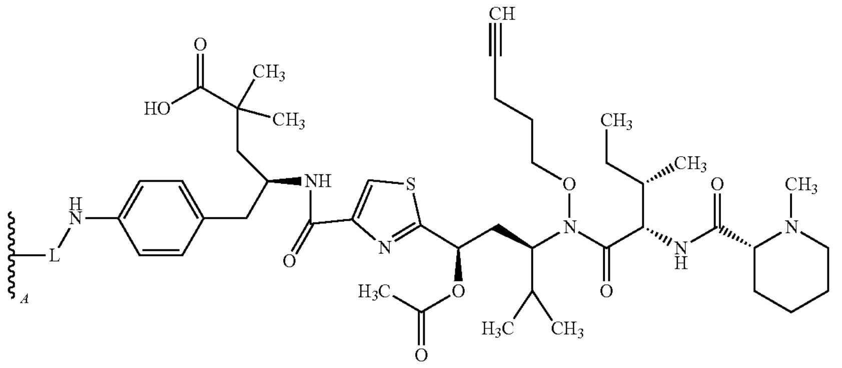

wherein L is a linker and

is a bond to the antibody. In some embodiments, the antibody is an anti-FGFR2 antibody or antigen-binding fragment thereof comprising the CDRs within the HCVR amino acid sequence of SEQ ID NO: 2 and the CDRs within the LCVR amino acid sequence of SEQ ID NO: 10. In some embodiments, the antibody is an anti-FGFR2 antibody or antigen-binding fragment thereof comprising an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS ; and an LCDR3 amino acid sequence of SEQ ID NO: 16. In some embodiments, the antibody is an anti-FGFR2 antibody or antigen-binding fragment thereof comprising the CDRs within the HCVR amino acid sequence of SEQ ID NO: 22 and the CDRs within the LCVR amino acid sequence of SEQ ID NO: 28. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the antibody is an anti-FGFR2 antibody or antigen-binding fragment thereof comprising the CDRs within the HCVR amino acid sequence of SEQ ID NO: 40 and the CDRs within the LCVR amino acid sequence of SEQ ID NO: 44. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KAS; and an LCDR3 amino acid sequence of SEQ ID NO: 34.

In some embodiments, the anti-FGFR2 antibody or antigen-binding fragment thereof is conjugated to:

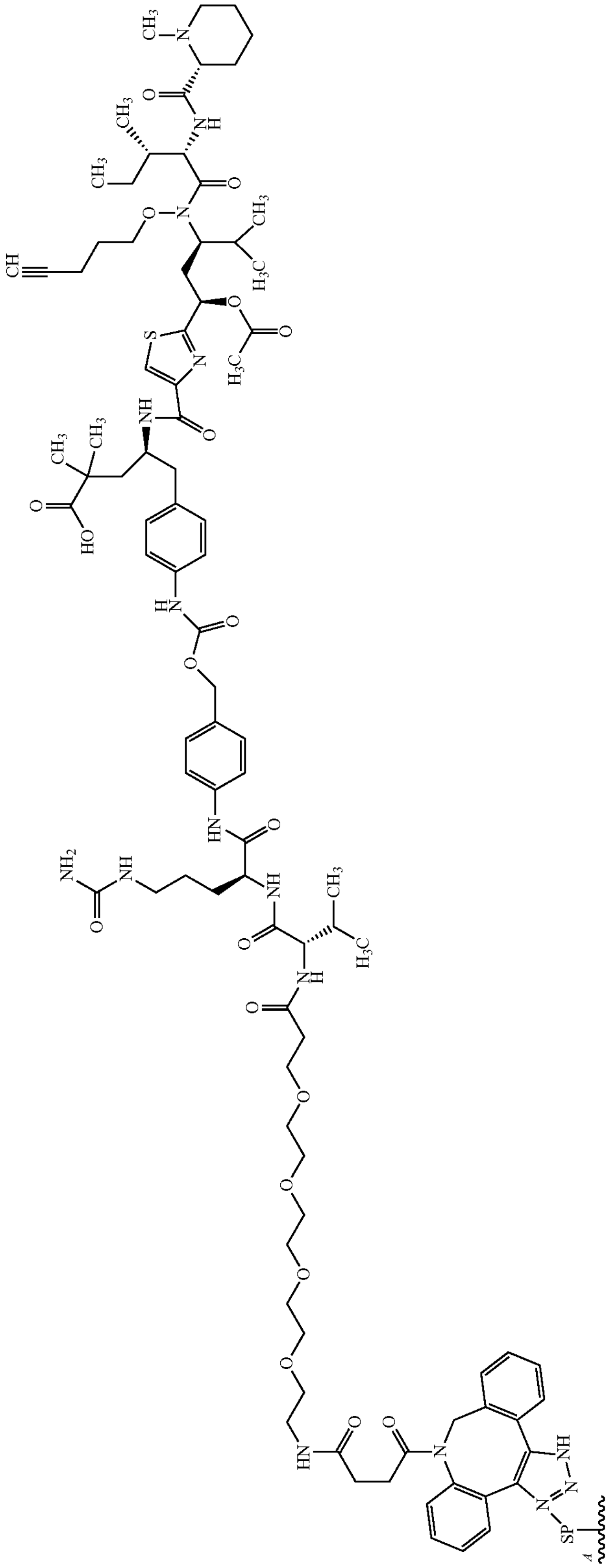

or its cycloaddition regioisomer thereof, wherein SP is a spacer and

is a bond to the antibody. In some embodiments, the

is a bond to a glutamine residue of the antibody. In particular embodiments, the glutamine residue is Q295. In some embodiments, the antibody is conjugated at Q295 and Q297. In some embodiments, the antibody is an anti-FGFR2 antibody or antigen-binding fragment thereof comprising the CDRs within the HCVR amino acid sequence of SEQ ID NO: 2 and the CDRs within the LCVR amino acid sequence of SEQ ID NO: 10. In some embodiments, the antibody is an anti-FGFR2 antibody or antigen-binding fragment thereof comprising an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS; and an LCDR3 amino acid sequence of SEQ ID NO: 16. In some embodiments, the antibody is an anti-FGFR2 antibody or antigen-binding fragment thereof comprising the CDRs within the HCVR amino acid sequence of SEQ ID NO: 22 and the CDRs within the LCVR amino acid sequence of SEQ ID NO: 28. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the antibody is an anti-FGFR2 antibody or antigen-binding fragment thereof comprising the CDRs within the HCVR amino acid sequence of SEQ ID NO: 40 and the CDRs within the LCVR amino acid sequence of SEQ ID NO: 44. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KAS; and an LCDR3 amino acid sequence of SEQ ID NO: 34.

In some embodiments, the anti-FGFR2 antibody or antigen-binding fragment thereof is conjugated to:

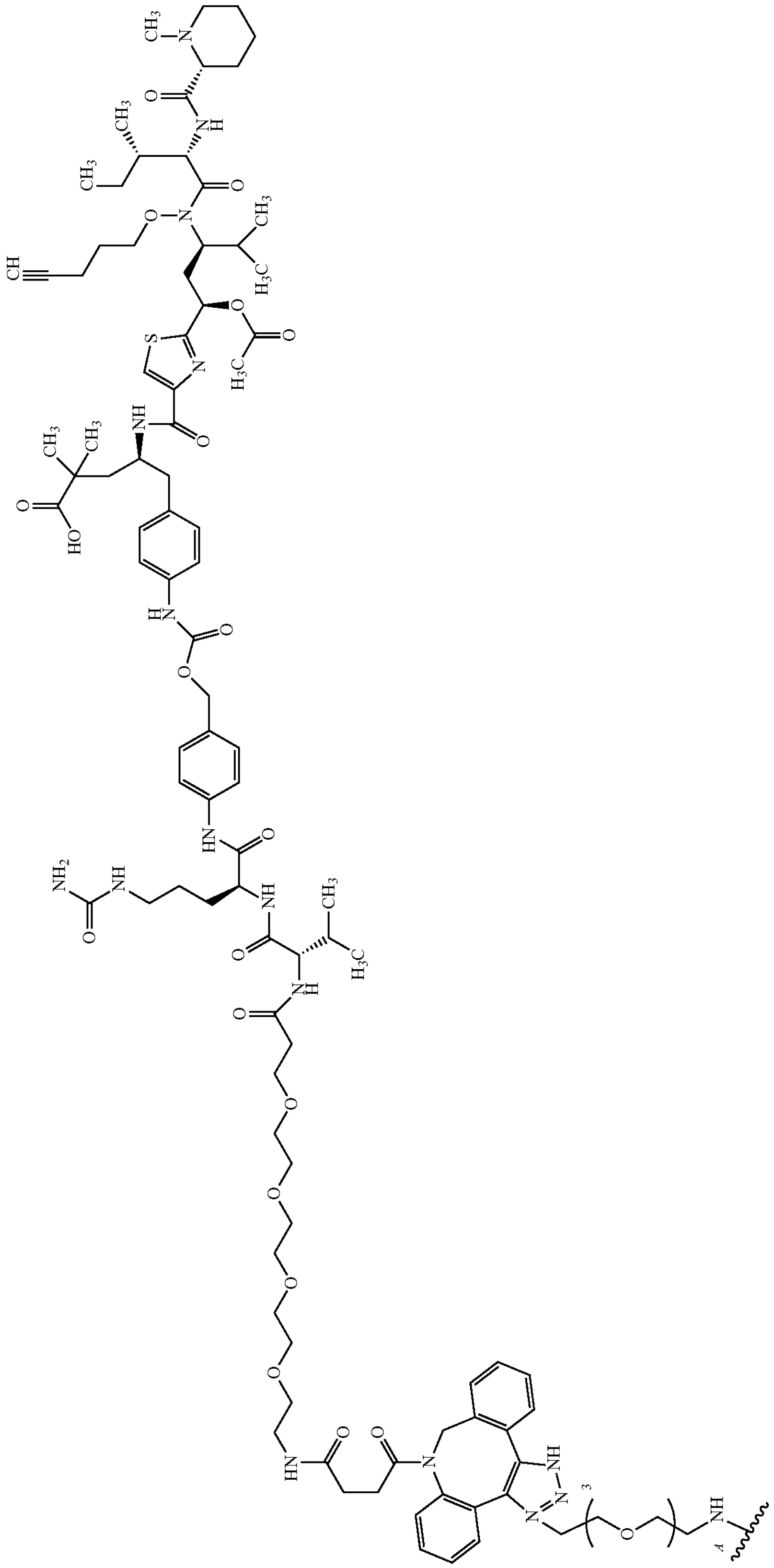

or its cycloaddition regioisomer thereof:

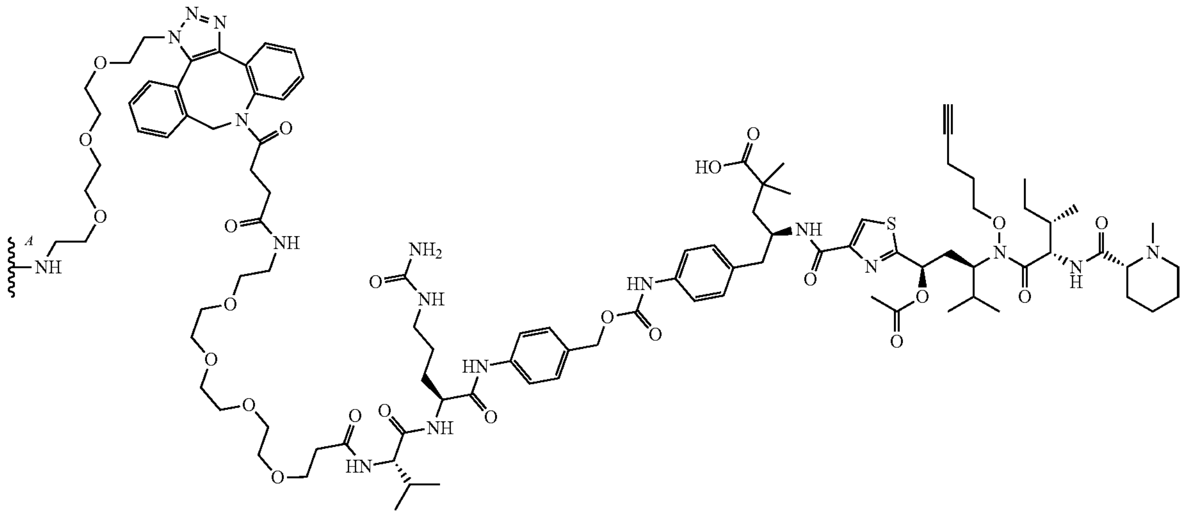

wherein

is a bond to a glutamine residue of the antibody. In certain embodiments, the glutamine is a heavy chain Q295 glutamine. In certain embodiments, the anti-FGFR2 antibody comprises a heavy chain having Q295 and Q297, wherein said Q297 is derived from an N297Q mutation. In some aspects, the anti-FGFR2 antibody comprises a heavy chain (HC) selected from the group consisting of SEQ ID NOs: 52, 53, and 54. In some embodiments, the antibody is an anti-FGFR2 antibody or antigen-binding fragment thereof comprising the CDRs within the HCVR amino acid sequence of SEQ ID NO: 2 and the CDRs within the LCVR amino acid sequence of SEQ ID NO: 10. In some embodiments, the antibody is an anti-FGFR2 antibody or antigen-binding fragment thereof comprising an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS; and an LCDR3 amino acid sequence of SEQ ID NO: 16. In some embodiments, the antibody is an anti-FGFR2 antibody or antigen-binding fragment thereof comprising the CDRs within the HCVR amino acid sequence of SEQ ID NO: 22 and the CDRs within the LCVR amino acid sequence of SEQ ID NO: 28. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the antibody is an anti-FGFR2 antibody or antigen-binding fragment thereof comprising the CDRs within the HCVR amino acid sequence of SEQ ID NO: 40 and the CDRs within the LCVR amino acid sequence of SEQ ID NO: 44. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KAS; and an LCDR3 amino acid sequence of SEQ ID NO: 34.

In some embodiments, the anti-FGFR2 antibody or antigen-binding fragment thereof is conjugated through a linker to:

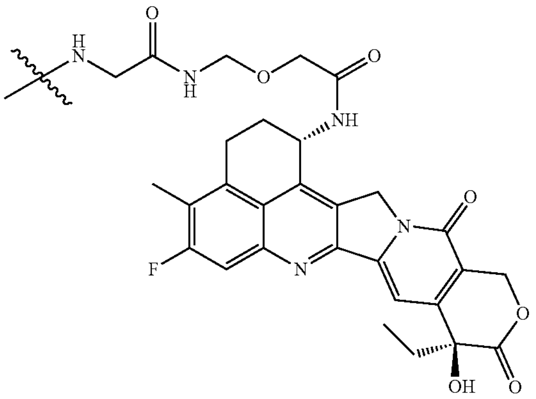 [SMILES: *NCC(=O)NCOCC(=O)N[C@H]1CCc2c(C)c(F)cc3nc4c(c1c23)Cn1c-4cc2c(c1=O)COC(=O)[C@]2(O)CC]

where represents the point of attachment to a linker. In some embodiments, the linker is attached to one or more glutamine residue(s) of the antibody or antigen-binding fragment thereof. In some embodiments, the antibody is an anti-FGFR2 antibody or antigen-binding fragment thereof comprising the CDRs within the HCVR amino acid sequence of SEQ ID NO: 2 and the CDRs within the LCVR amino acid sequence of SEQ ID NO: 10. In some embodiments, the antibody is an anti-FGFR2 antibody or antigen-binding fragment thereof comprising an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS; and an LCDR3 amino acid sequence of SEQ ID NO: 16. In some embodiments, the antibody is an anti-FGFR2 antibody or antigen-binding fragment thereof comprising the CDRs within the HCVR amino acid sequence of SEQ ID NO: 22 and the CDRs within the LCVR amino acid sequence of SEQ ID NO: 28. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the antibody is an anti-FGFR2 antibody or antigen-binding fragment thereof comprising the CDRs within the HCVR amino acid sequence of SEQ ID NO: 40 and the CDRs within the LCVR amino acid sequence of SEQ ID NO: 44. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KAS; and an LCDR3 amino acid sequence of SEQ ID NO: 34.

In some embodiments, the conjugates have the following structure:

A*b*-[L-Pa*y*]$_n$ wherein:

Ab is an anti-FGFR2 antibody or antigen-binding fragment thereof as described herein;

L is a linker;

Pay is a cytotoxic agent; and n is an integer from 1-12.

In some embodiments, n is 2. In some embodiments, n is 4. In some embodiments, Pay is:

(Tubulysin 1a)

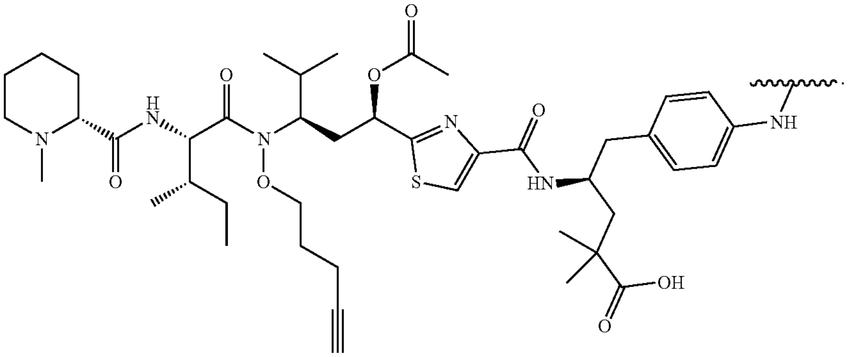

In some embodiments, L is a cleavable linker. In some embodiments, L comprises a peptide. In some embodiments, L comprises val-cit. In some embodiments, L comprises

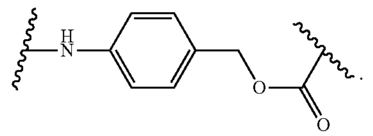

In some embodiments, L comprises a PEG group.

In some embodiments, L comprises a cyclic moiety. In certain embodiments, the cyclic moiety is the product of a 1,3-cycloaddition between an azide and a cycloalkyne. In some embodiments, -L-Pay is

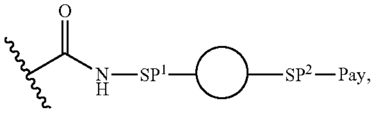

wherein $SP^1$ and $SP^2$ are each independently a spacer,

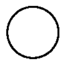

is a cyclic moiety, and

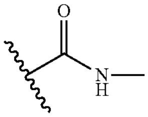 [SMILES: *C(=O)NC]

is a glutamine residue of an antibody. In some embodiments, the glutamine is a Q295 glutamine. In some embodiments, n is 2, wherein two L-Pay are conjugated to Q295. In some embodiments, n is 4, wherein two L-Pay are conjugated to Q295 and two L-Pay are conjugated to Q297. In some embodiments, the cyclic moiety is a product of a cycloaddition reaction. In certain embodiments, the cyclic moiety is a product of a cycloaddition reaction between an azide and cycloalkyne. In certain embodiments, the cyclic moiety is

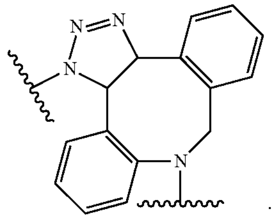 [SMILES: *N1Cc2ccccc2C2N=NN(*)C2c2ccccc21]

In certain embodiments, $SP^1$ comprises a PEG moiety. In some embodiments, the PEG comprises 1-12 ethylene glycol units. In certain embodiments, $SP^2$ comprise a dipeptide. In certain embodiments, $SP^2$ comprises val-cit. In certain embodiments, $SP^2$ comprises

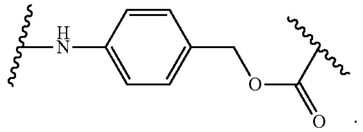 [SMILES: *Nc1ccc(COC(*)=O)cc1]

In certain embodiments, $SP^2$ comprises a PEG moiety. In some embodiments, $SP^2$-Pay is:

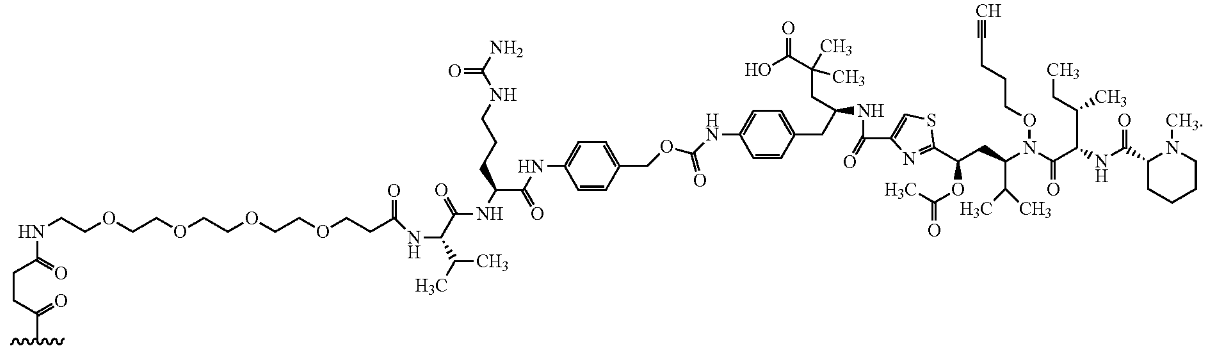 [SMILES: *C(=O)CCC(=O)NCCOCCOCCOCCOCCC(=O)N[C@H](C(=O)N[C@@H](CCCNC(N)=O)C(=O)Nc1ccc(COC(=O)Nc2ccc(C[C@@H](CC(C)(C)C(=O)O)NC(=O)c3csc([C@@H](C[C@H](C(C)C)N(OCCCC#C)C(=O)[C@@H](NC(=O)[C@H]4CCCCN4C)[C@@H](C)CC)OC(C)=O)n3)cc2)cc1)C(C)C]

In certain embodiments,

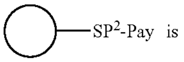

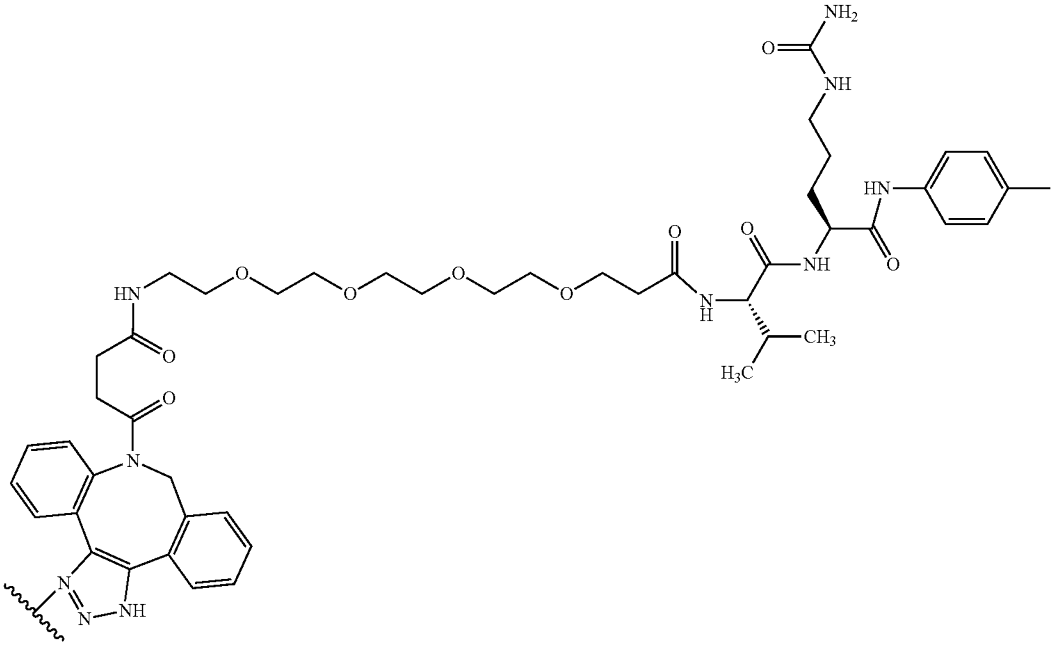

-continued
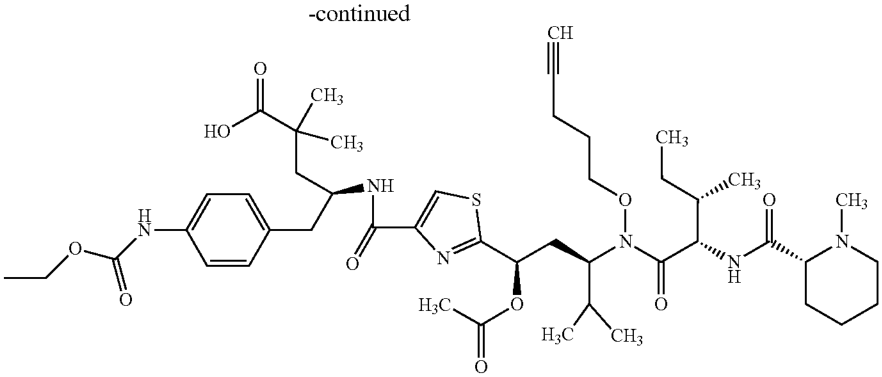
or a cycloaddition regioisomer thereof.
In certain embodiments,
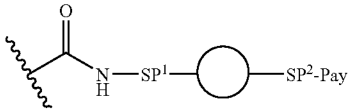 is
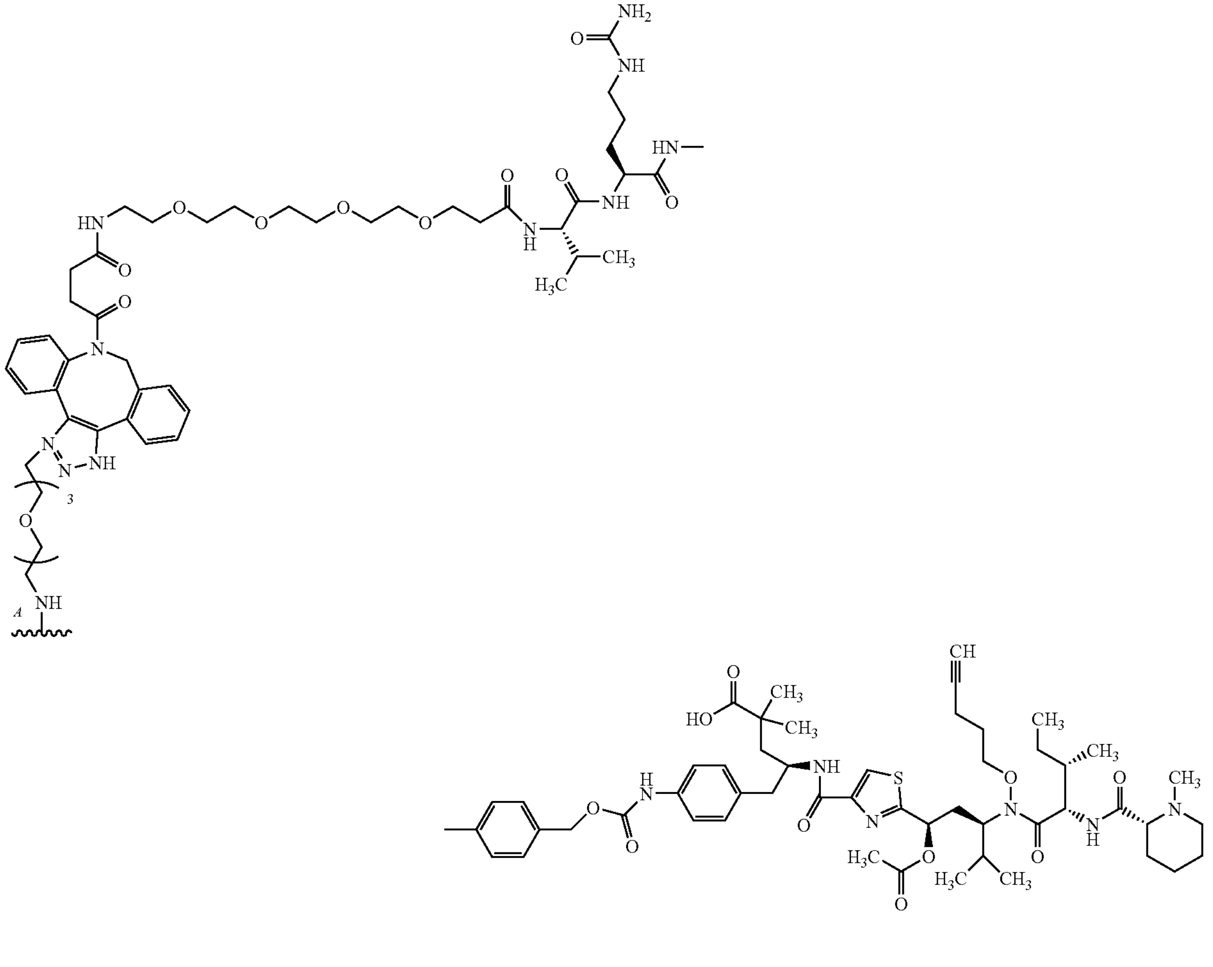
or a regioisomer thereof:

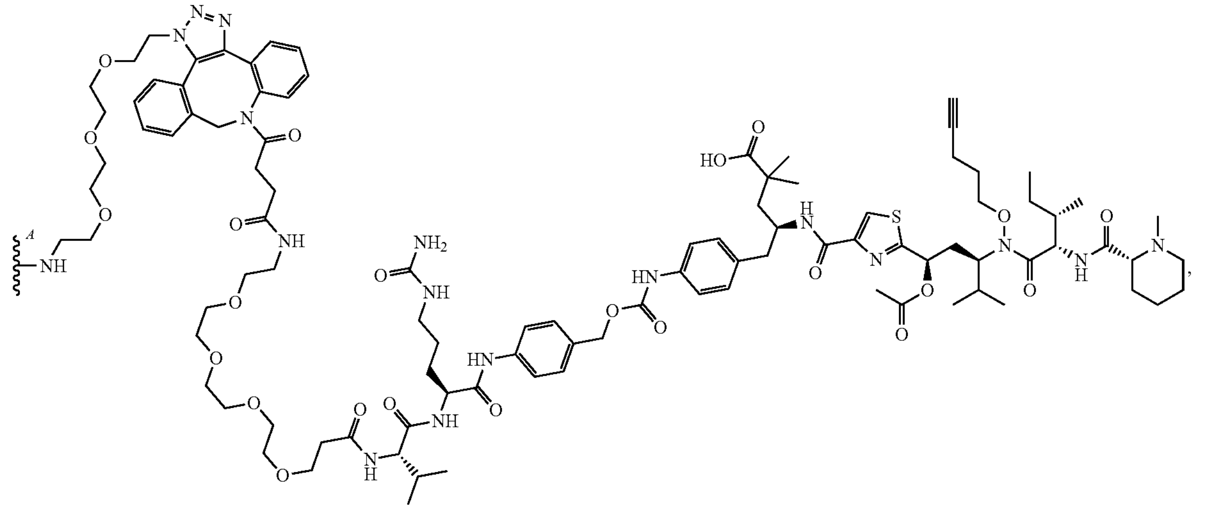

wherein

is a bond to a glutamine residue of the antibody. In some embodiments, the antibody is an anti-FGFR2 antibody or antigen-binding fragment thereof comprising the CDRs within the HCVR amino acid sequence of SEQ ID NO: 2 and the CDRs within the LCVR amino acid sequence of SEQ ID NO: 10. In some embodiments, the antibody is an anti-FGFR2 antibody or antigen-binding fragment thereof comprising an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS; and an LCDR3 amino acid sequence of SEQ ID NO: 16. In some embodiments, the antibody is an anti-FGFR2 antibody or antigen-binding fragment thereof comprising the CDRs within the HCVR amino acid sequence of SEQ ID NO: 22 and the CDRs within the LCVR amino acid sequence of SEQ ID NO: 28. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the antibody is an anti-FGFR2 antibody or antigen-binding fragment thereof comprising the CDRs within the HCVR amino acid sequence of SEQ ID NO: 40 and the CDRs within the LCVR amino acid sequence of SEQ ID NO: 44. In some embodiments, the antibody is an anti-FGFR2 antibody or antigen-binding fragment thereof comprising an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KAS; and an LCDR3 amino acid sequence of SEQ ID NO: 34.

In one aspect, the present disclosure provides a compound having a structure according to Formula (A):

$$BA\text{-}(Gln\text{-}NH\text{-}L1\text{-}B\text{-}(\text{-}L2\text{-}(\text{-}M\text{-}Dxd)_m)_k)_n \quad \text{(A), wherein:}$$

BA is an anti-FGFR2 antibody or an antigen-binding fragment thereof;

Gln is a glutamine residue;

L1 is absent or a first linker;

B is a branching unit comprising at least one adduct of group B' and group B", wherein one of the groups B' and B" is selected from —$N_3$ and

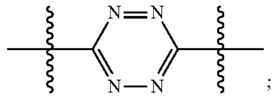 [SMILES: *c1nnc(*)nn1]

;

and the other of the groups B' and B" is selected from

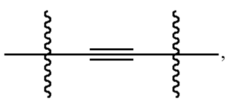

,

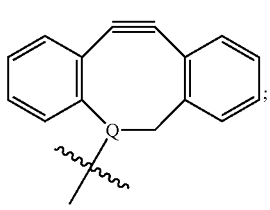

; and

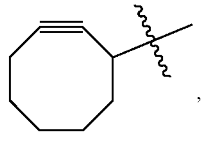

, where Q is C or N;

L2 is a second linker covalently attached to the branching unit B via the at least one group B";

M is absent or a moiety having the structure

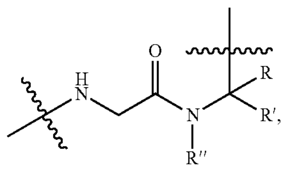

where R, R', and R" are independently at each occurrence hydrogen or a $C_1$-$C_4$ alkyl, or wherein R' and R" together form a 5-membered or a 6-membered ring;

Dxd is an anti-tumor agent having a structure according to Formula (P):

(P)

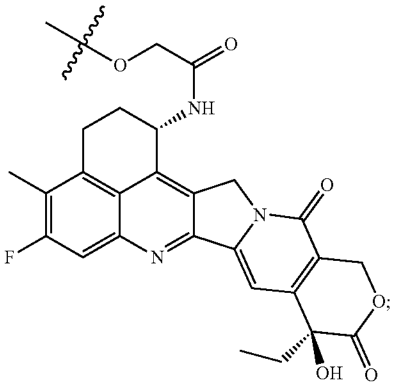

k is an integer from 1 to 12;

m is an integer from 1 to 30, and n is an integer from 1 to 30.

In one embodiment, the anti-FGFR2 antibody-drug conjugate according to the present disclosure comprises an anti-FGFR2 antibody, or antigen-binding fragment thereof, and a linker-payload, wherein the linker-payload comprises the structure:

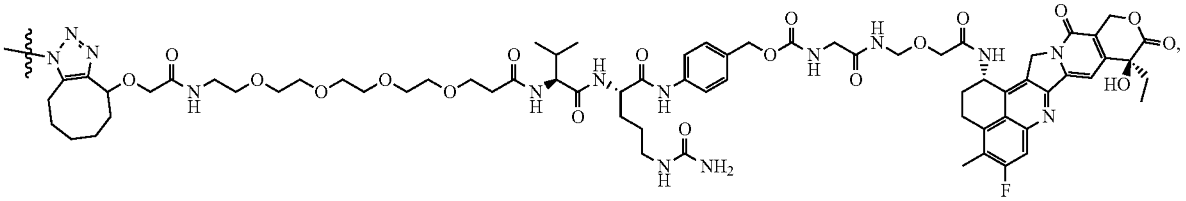 [SMILES: *n1nnc2c1CCCCCC2OCC(=O)NCCOCCOCCOCCOCCC(=O)N[C@H](C(=O)N[C@@H](CCCNC(N)=O)C(=O)Nc1ccc(COC(=O)NCC(=O)NCOCC(=O)N[C@H]2CCc3c(C)c(F)cc4nc5c(c2c34)Cn2c-5cc3c(c2=O)COC(=O)[C@]3(O)CC)cc1)C(C)C]

or a pharmaceutically acceptable salt thereof, where ∿∿ represents the point of attachment to the antibody, directly or through a second linker.

In one embodiment, the compound according to the disclosure has the following structure:

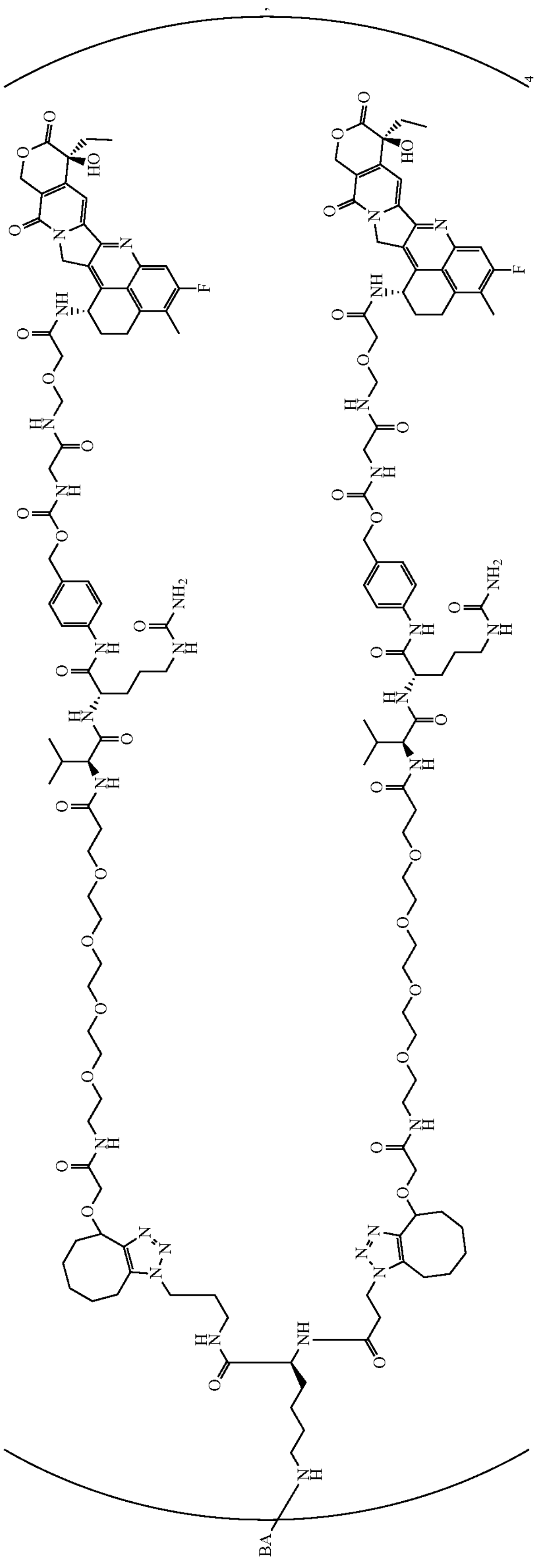

wherein BA is an anti-FGFR2 antibody or an antigen-binding fragment thereof.

In some embodiments, the anti-FGFR2 antibody or antigen-binding fragment thereof, i.e., BA, comprises the CDRs within the HCVR amino acid sequence of SEQ ID NO: 2 and the CDRs within the LCVR amino acid sequence of SEQ ID NO: 10. In some embodiments, the anti-FGFR2 antibody or antigen-binding fragment thereof comprises an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS; and an LCDR3 amino acid sequence of SEQ ID NO: 16. In some embodiments, the anti-FGFR2 antibody or antigen-binding fragment thereof comprises the CDRs within the HCVR amino acid sequence of SEQ ID NO: 22 and the CDRs within the LCVR amino acid sequence of SEQ ID NO: 28. In some embodiments, the anti-FGFR2 antibody or antigen-binding fragment thereof comprises an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the anti-FGFR2 antibody or antigen-binding fragment thereof comprises the CDRs within the HCVR amino acid sequence of SEQ ID NO: 40 and the CDRs within the LCVR amino acid sequence of SEQ ID NO: 44. In some embodiments, the anti-FGFR2 antibody or antigen-binding fragment thereof comprises an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KAS; and an LCDR3 amino acid sequence of SEQ ID NO: 34.

In one embodiment, the compound according to the disclosure has the following structure:

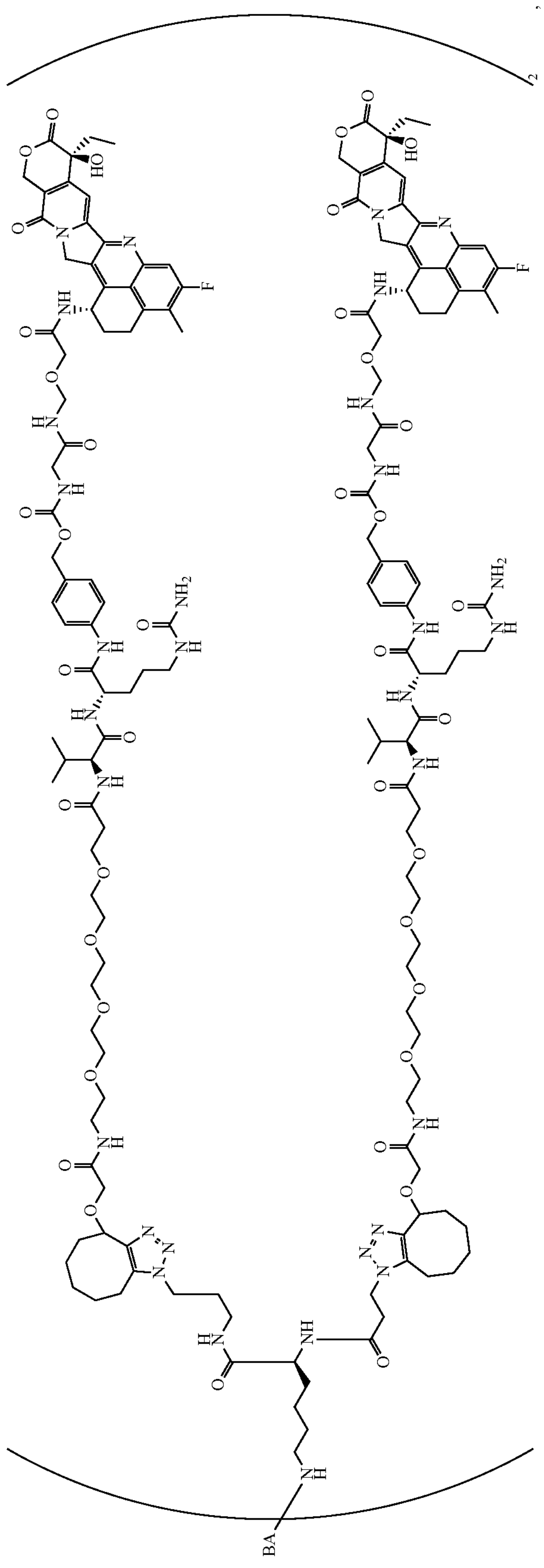

wherein BA is an anti-FGFR2 antibody or an antigen-binding fragment thereof.

In one embodiment, the compound according to the disclosure has the following structure:

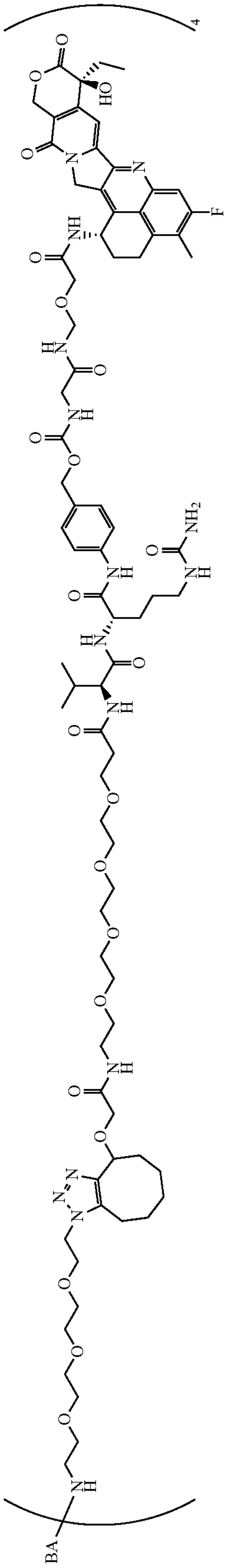

wherein BA is an anti-FGFR2 antibody or an antigen-binding fragment thereof.

In some embodiments, the anti-FGFR2 antibody or antigen-binding fragment thereof, i.e., BA, comprises the CDRs within the HCVR amino acid sequence of SEQ ID NO: 2 and the CDRs within the LCVR amino acid sequence of SEQ ID NO: 10. In some embodiments, the anti-FGFR2 antibody or antigen-binding fragment thereof comprises an HCDR1 amino acid sequence of SEQ ID NO: 4; an HCDR2 amino acid sequence of SEQ ID NO: 6; an HCDR3 amino acid sequence of SEQ ID NO: 8; an LCDR1 amino acid sequence of SEQ ID NO: 12; an LCDR2 amino acid sequence of GAS; and an LCDR3 amino acid sequence of SEQ ID NO: 16. In some embodiments, the anti-FGFR2 antibody or antigen-binding fragment thereof comprises the CDRs within the HCVR amino acid sequence of SEQ ID NO: 22 and the CDRs within the LCVR amino acid sequence of SEQ ID NO: 28. In some embodiments, the anti-FGFR2 antibody or antigen-binding fragment thereof comprises an HCDR1 amino acid sequence of SEQ ID NO: 24; an HCDR2 amino acid sequence of SEQ ID NO: 6; an HCDR3 amino acid sequence of SEQ ID NO: 26; an LCDR1 amino acid sequence of SEQ ID NO: 30; an LCDR2 amino acid sequence of KAS; and an LCDR3 amino acid sequence of SEQ ID NO: 34. In some embodiments, the anti-FGFR2 antibody or antigen-binding fragment thereof comprises the CDRs within the HCVR amino acid sequence of SEQ ID NO: 40 and the CDRs within the LCVR amino acid sequence of SEQ ID NO: 44. In some embodiments, the anti-FGFR2 antibody or antigen-binding fragment thereof comprises an HCDR1 amino acid sequence of SEQ ID NO: 24; an HCDR2 amino acid sequence of SEQ ID NO: 6; an HCDR3 amino acid sequence of SEQ ID NO: 42; an LCDR1 amino acid sequence of SEQ ID NO: 46; an LCDR2 amino acid sequence of KAS; and an LCDR3 amino acid sequence of SEQ ID NO: 34.

In one embodiment, the compound according to the disclosure has the following structure:

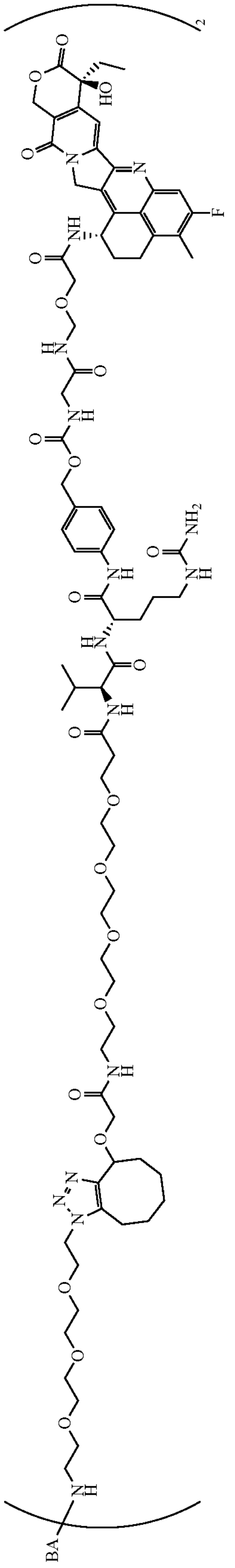

wherein BA is an anti-FGFR2 antibody or an antigen-binding fragment thereof).

Linker L1

In certain embodiments, linker L1 is absent.

In certain embodiments, linker L1 is present and is covalently attached to the amine of a glutamine residue of the anti-FGFR2 antibody.

In certain embodiments, linker L1 comprises an alkyl (e.g., a $C_{1-20}$ alkyl, or a $C_{1-12}$ alkyl, or a $C_{1-6}$ alkyl), —NH—, —C(O)—, —$(CH_2)_u$—NH—C(O)—, —$(CH_2)_u$—C(O)—NH—, —$(CH_2$—$CH_2$—$O)_v$—, —$(CH_2)_u$—(O—$CH_2$—$CH_2)_v$-C(O)—NH—, a peptide unit comprising from 2 to 4 amino acids, or combinations thereof, each of which may be optionally substituted with one or more of —S—, —$S(O_2)$—, —C(O)—, —$C(O_2)$—; or —$CO_2H$, wherein subscripts u and v are independently an integer from 1 to 8.

In certain embodiments, the free (unconjugated) linker L1 comprises a primary amine for attachment to the glutamine residue via a transglutamination reaction.

In one embodiment, linker L1 comprises one or more polyethylene glycol (PEG) units. In one embodiment, L1 comprises 2, or 3, or 4, or 5, or 6, or 7, or 8, or 9, or 10 PEG units.

In one embodiment, linker L1 comprises a disulfide (—S—S—) bond.

In one embodiment, linker L1 comprises a —$S(O_2)$— moiety.

In one embodiment, one or more carbons on linker L1 is substituted with —$CO_2H$.

In one embodiment, linker L1 comprises a peptide unit comprising from 2 to 4 amino acids, or a peptide unit comprising 2 amino acids, a peptide unit comprising 3 amino acids, or a peptide unit comprising 4 amino acids.

In one embodiment, linker L1 comprises a peptide unit comprising 2 amino acids selected from glycine, valine, phenylalanine, proline, glutamic acid, and citrulline, and combinations thereof.

In one particular embodiment, linker L1 comprises a valine-citrulline unit.

In one embodiment, linker L1 is selected from the group consisting of:

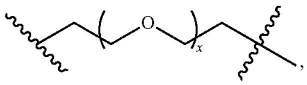
,
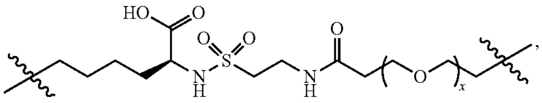
,
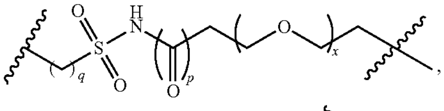
,
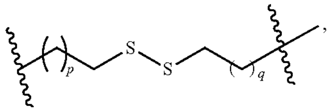
,
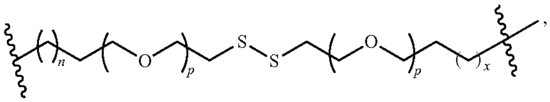
,
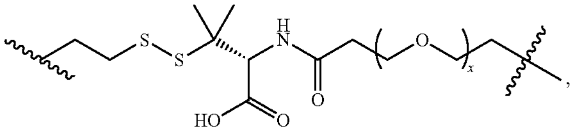
, -continued

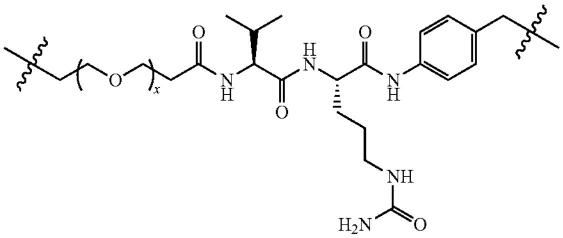
,
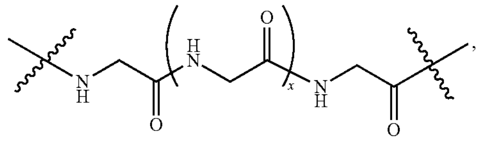
, and
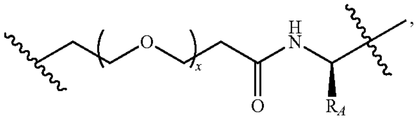
, wherein $R_A$ is a group comprising an alkyne, an azide, a tetrazine, a trans-cyclooctene, a maleimide, an amine, a ketone, an aldehyde, a carboxylic acid, an ester, a thiol, a sulfonic acid, a tosylate, a halide, a silane, a cyano group, a carbohydrate group, a biotin group, a lipid residue, and wherein subscripts x, n, p and q are independently an integer from 0 to 12, and combinations thereof.

Branching Unit B

In one aspect, branching unit B comprises at least one adduct of group B'. In certain embodiments, B comprises one adduct of group B'. In certain embodiments, B comprises two adducts of group B'. In certain embodiments, B comprises three adducts of group B'.

In certain embodiments, B comprises at least four adducts of group B'. In certain embodiments, B comprises four adducts of group B'. In certain embodiments, B comprises five adducts of group B'. In certain embodiments, B comprises six adducts of group B'.

Generally, an adduct of group B' according to the present disclosure encompasses any moiety comprising the product of an addition reaction of group B', independent of the synthetic steps taken to produce the moiety.

In some embodiments, the adduct of group B' may be a product of a substituted maleimide and, e.g., a thiol, or a substituted trans-cyclooctene, e.g.:

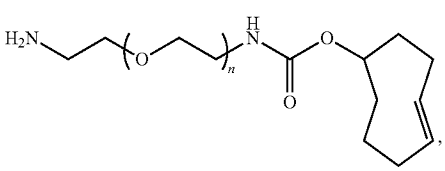
, where n is an integer from 0 to 12 and, e.g., a tetrazine.

In some embodiments, the adduct of group B' may be the product of a 1,3-cycloaddition reaction between an azide and an alkyne moiety. Without wishing to be bound by theory, the azide-alkyne cycloaddition is a 1,3-dipolar cycloaddition between an azide and a terminal or internal alkyne to give a 1,2,3-triazole.

More specifically, an adduct of group B' selected from $-N_3$, 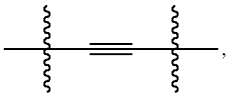, 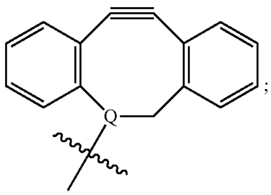;

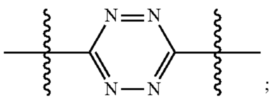; and 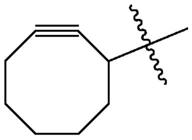, where Q is C or N, may encompass a 1,3-cycloaddition adduct of the group B' and the group B" selected from $-N_3$, 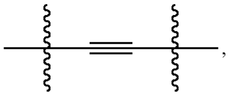, 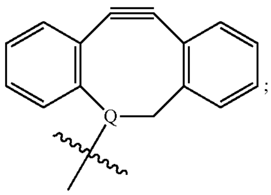;

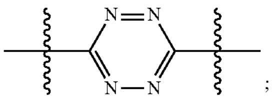; and 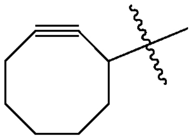, where Q is C or N, wherein the group B" is complementary to the group B' to form a 1,3-cycloaddition adduct.

By way of a non-limiting example, group B' may be an azide ($-N_3$), and group B" may be an alkyne-containing group, e.g.,

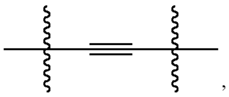, 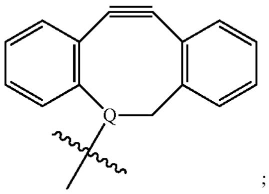; or

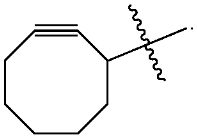.

By way of another non-limiting example, group B' may be an alkyne-containing group, e.g.,

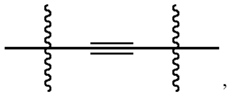, 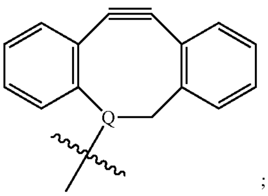; or

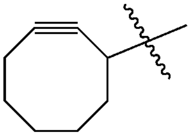

or and group B" may be an azide.

In one embodiment, the adduct of the group B' and the group B" comprises a triazole moiety. In one particular embodiment, the adduct of the group B' and the group B" has a structure selected from the group consisting of:

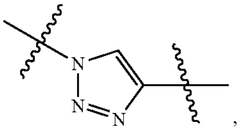, 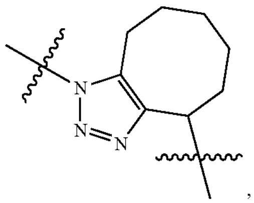, and

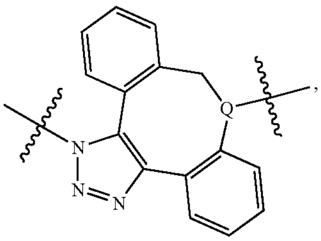, wherein Q is C or N.

As stated above, in one embodiment, B comprises one adduct of the group B'.

In specific embodiments, L1-B is selected from the group consisting of:

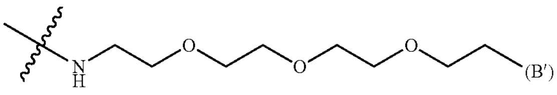

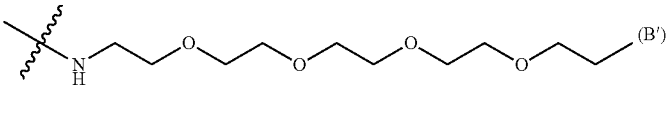

-continued

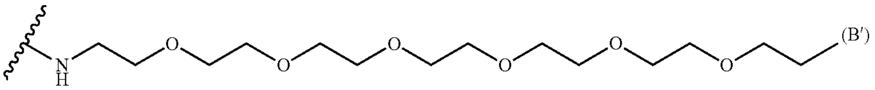

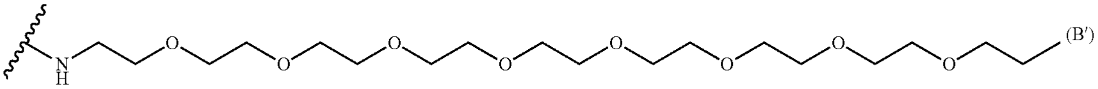

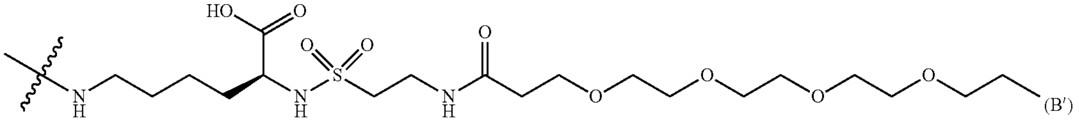

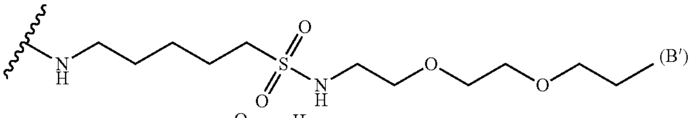

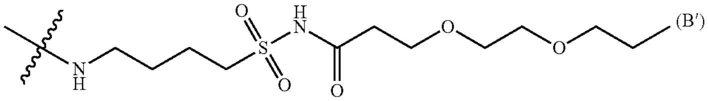

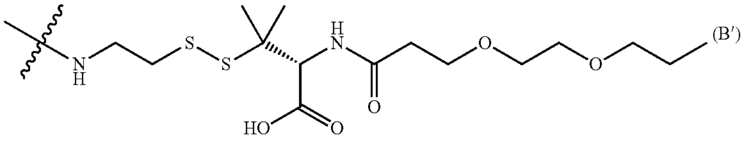

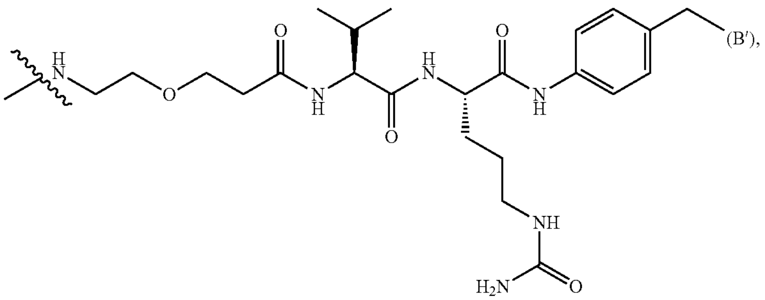

where the

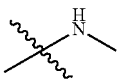 [SMILES: *NC]

is the amino point of attachment to the glutamine residue of the anti-FGFR2 antibody, and (B') is the adduct of the group B'.

In one embodiment, the group B' is an azide (—$N_3$), and the adduct of the group B' comprises a triazole.

According to one embodiment of the present disclosure, linkers L1-B may be azide amine linkers (AL), which comprise an amine group which directly attaches to the antibody, a PEG-containing base structure, and an azide functional group B' (n=1).

The basic component structures of non-limiting exemplary azide amine linkers are listed shown in FIG. 8 Specific structures synthesized as examples are provided in Table 1.

In one embodiment, B comprises at least two adducts of the group B'. In specific embodiments, B comprises:

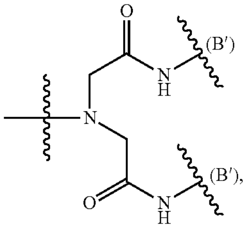

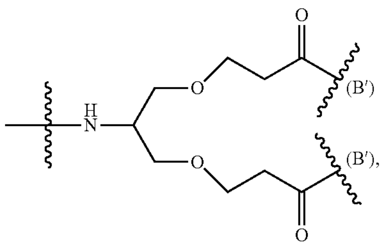

-continued
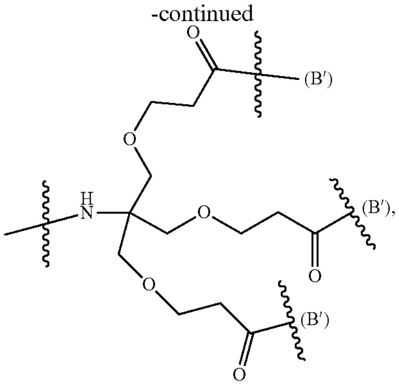
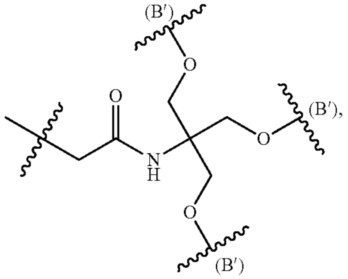
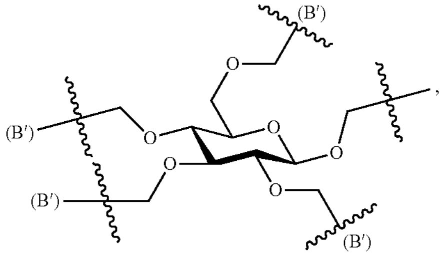
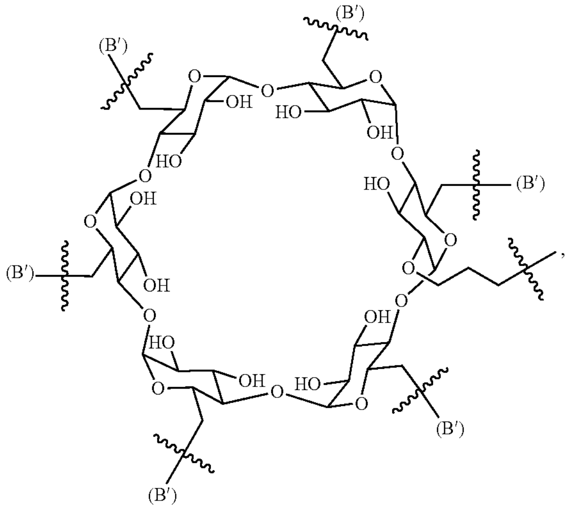
-continued
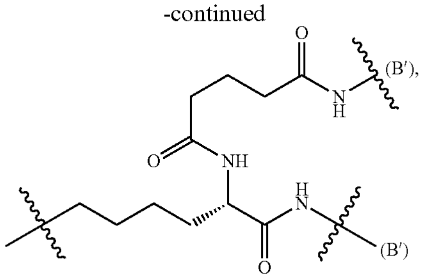
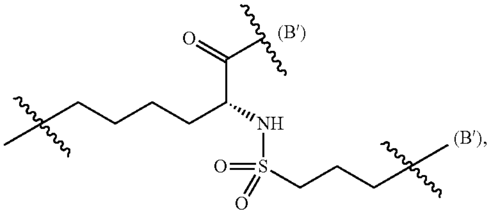
and
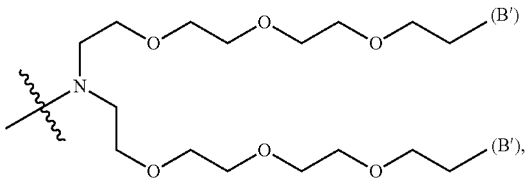
where (B') comprises points of attachment of the adduct of the group B'.
In specific embodiments, B is selected from the group consisting of:
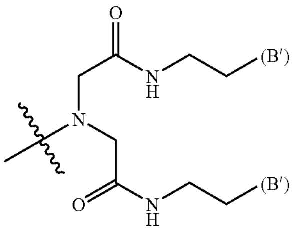
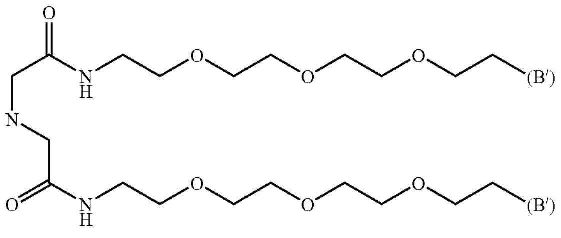

-continued
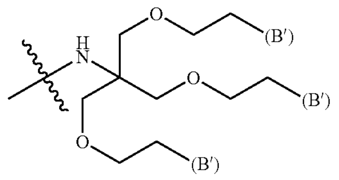
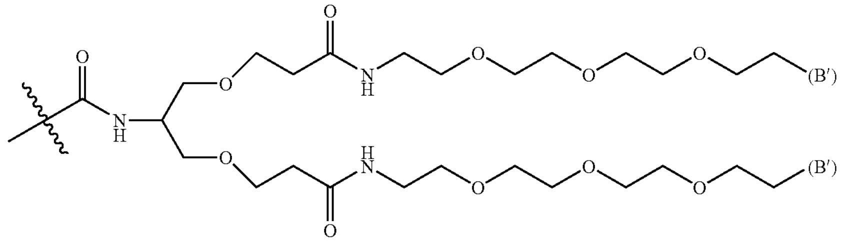
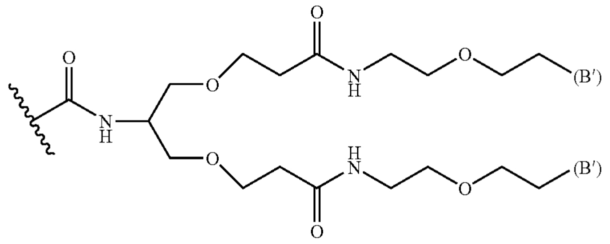
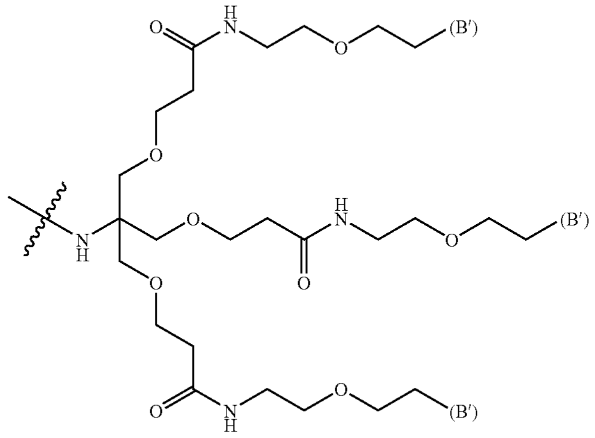
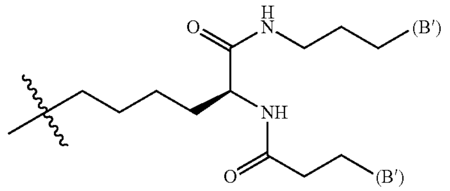

-continued
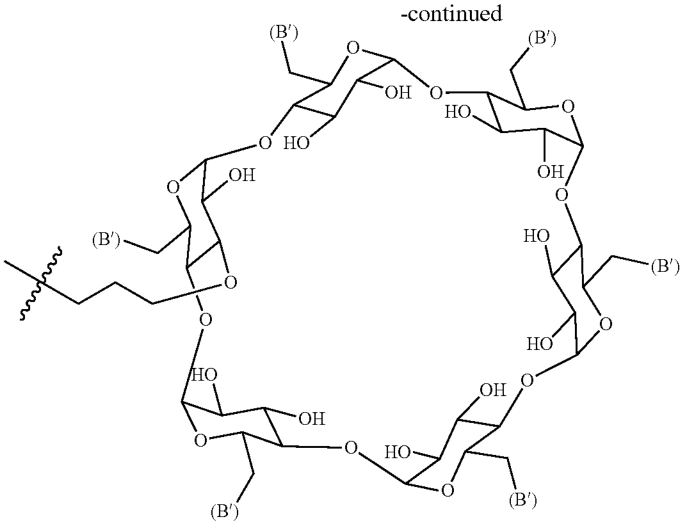
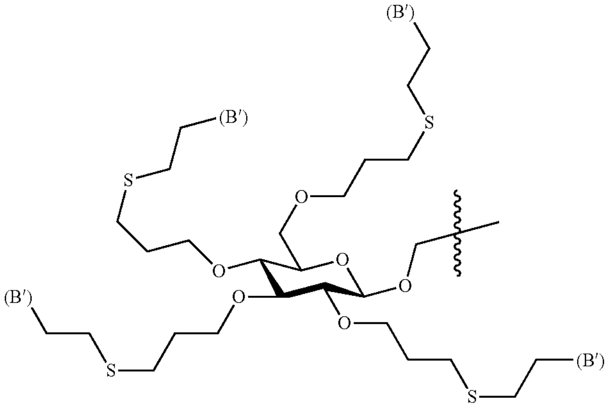
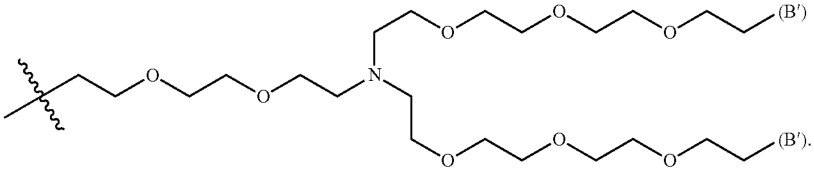
In specific embodiments, L1-B is selected from the group consisting of:
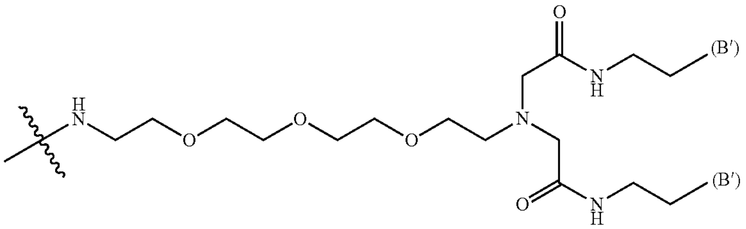
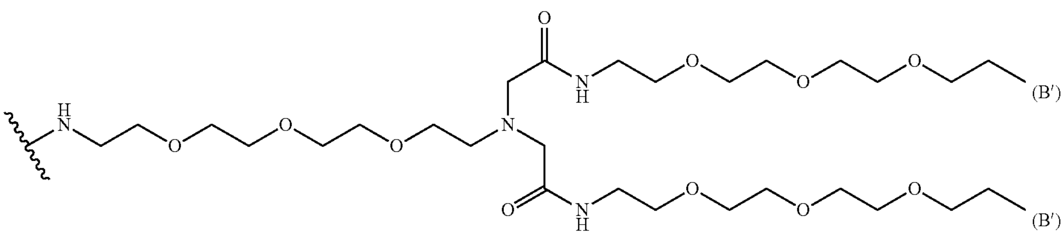

-continued
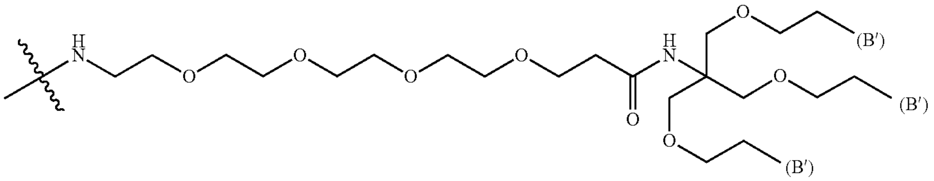
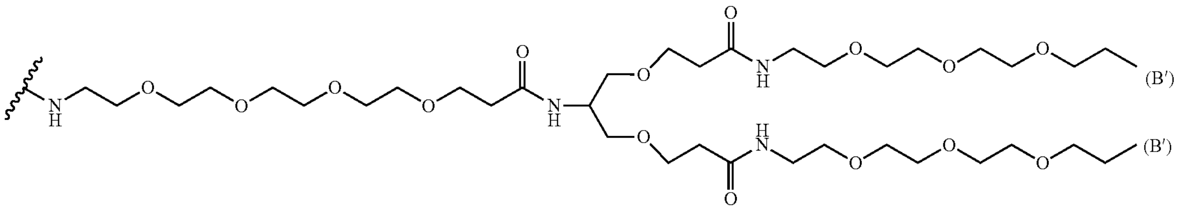
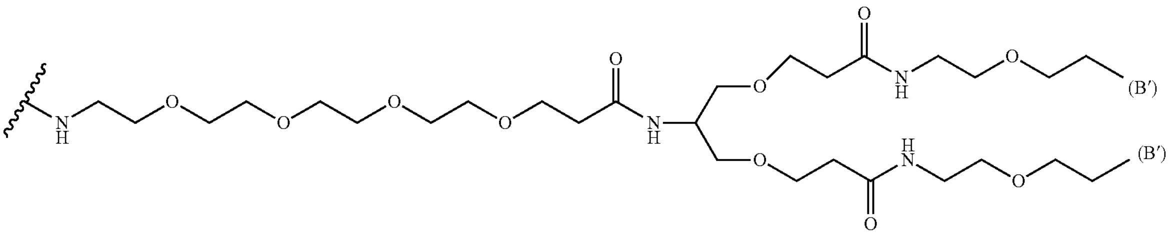
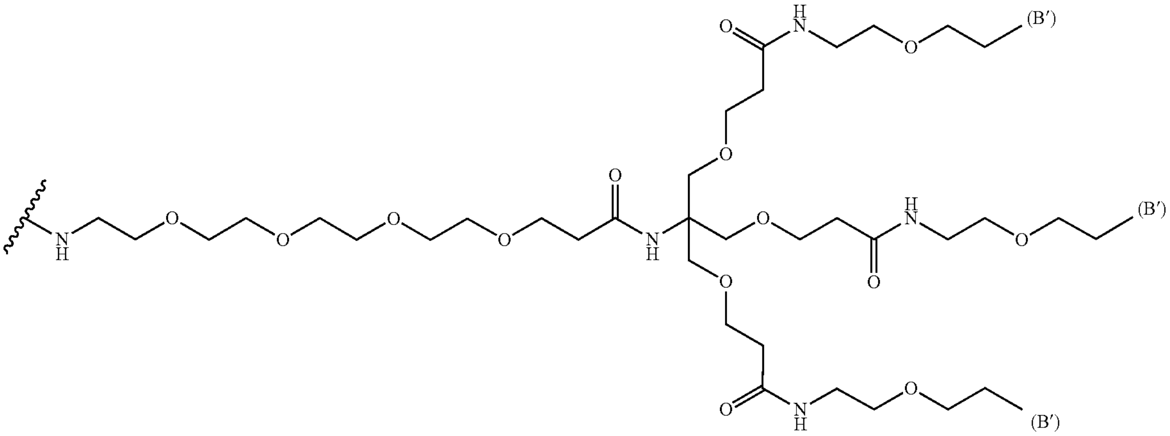
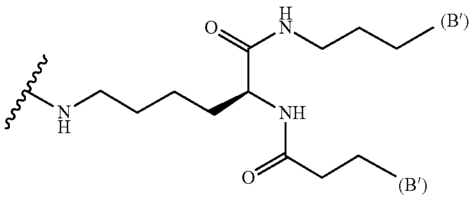

-continued

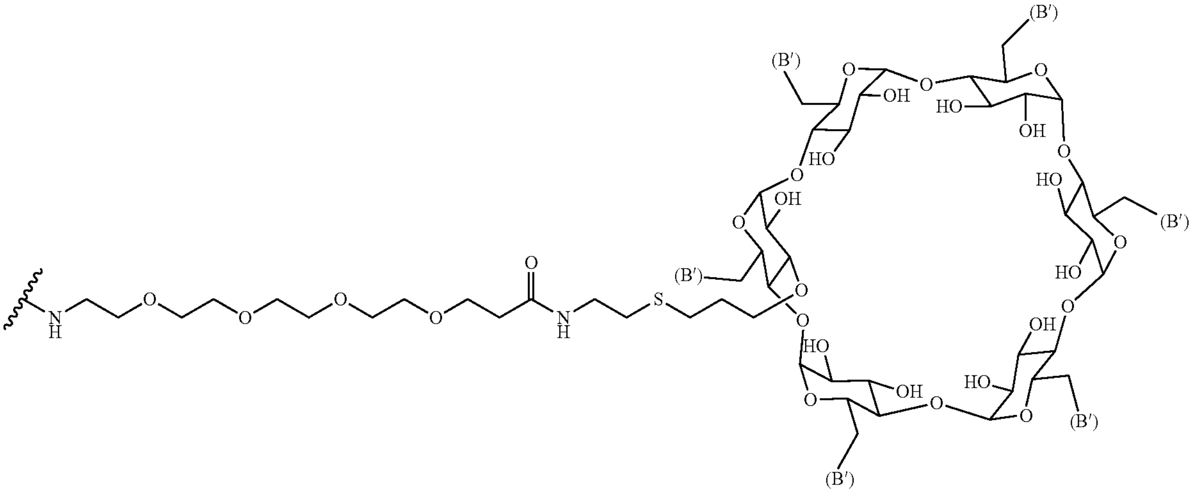

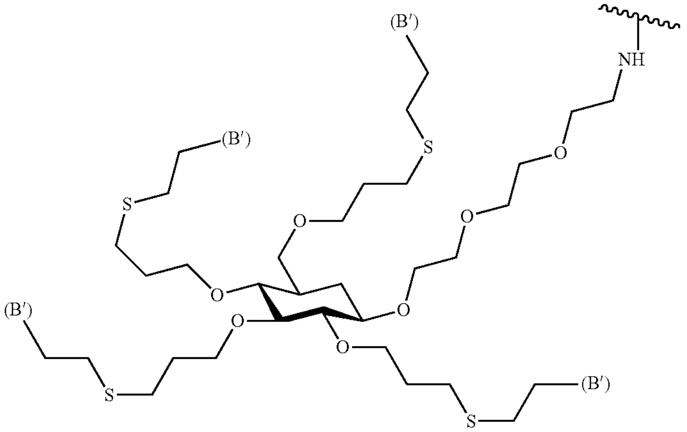

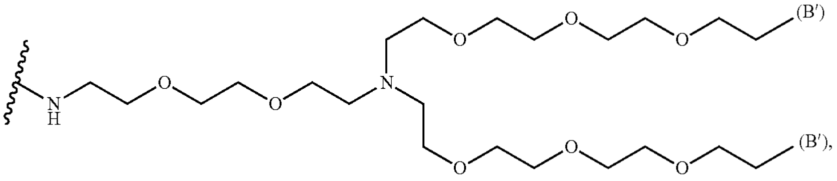

where the

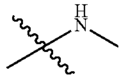 [SMILES: *NC]

is the amino point of attachment to the glutamine residue of the anti-FGFR2 antibody.

According to another embodiment of the present disclosure, linkers L1-B may be branched-alkyl azide amine linkers (BL) comprising an amine group which directly attaches to the anti-FGFR2 antibody, a branched-alkyl PEG containing base structure, and 2 to 6 azide functional groups B' (n=2-6).

The basic component structures of exemplary non-limiting branched-alkyl azide amine linkers are listed in FIG. 9 Specific structures synthesized as examples are provided in Table 2.

Linker L2

In certain embodiments of the present disclosure, L2 has a structure according to Formula (L2):

$$B''\text{-}SP^1\text{-}B2\text{-}(\text{-}SP^2\text{-}AA\text{-}SP^3)_p \text{ (L2)},$$

wherein:

B" is a group capable of covalently attaching to the group B';

$SP^1$ is absent or a first spacer unit;

B2 is absent or a branching unit;

$SP^2$ is absent or a second spacer unit;

AA is absent or a peptide unit comprising from 2 to 4 amino acids;

$SP^3$ is absent or a third spacer unit, and p is an integer from 1 to 12.

In certain embodiments of the present disclosure, L2 has a structure according to Formula (L2'):

$$H_2N\text{-}SP^1\text{-}B2\text{-}(\text{-}SP^2\text{-}AA\text{-}SP^3)_p \text{ (L2')},$$

wherein:

$SP^1$ is absent or a first spacer unit;

B2 is absent or a branching unit;

$SP^2$ is absent or a second spacer unit;

AA is absent or a peptide unit comprising from 2 to 4 amino acids;

$SP^3$ is absent or a third spacer unit, and p is an integer from 1 to 12.

In certain embodiments of the present disclosure, L2 has a structure according to Formula (L2"):

Maleimide-N-$SP^1$-B2-(-$SP^2$-AA-$SP^3$)$_p$ (L2"), wherein:
- $SP^1$ is absent or a first spacer unit;
- B2 is absent or a branching unit;
- $SP^2$ is absent or a second spacer unit;
- AA is absent or a peptide unit comprising from 2 to 4 amino acids;
- $SP^3$ is absent or a third spacer unit, and
- p is an integer from 1 to 12.

In certain embodiments wherein the linker L2 has the structure according to L2' or L2", the linker L2 may be directly covalently attached to an anti-FGFR2 antibody, e.g., via a TGase-mediated glutamine ligation (linker L2') or a cysteine ligation (linker L2").

In certain embodiments, the linker L2 comprises a group B" capable of covalently attaching to the group B' as described above.

In certain embodiments, the group B" is selected from $-N_3$, 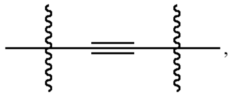, 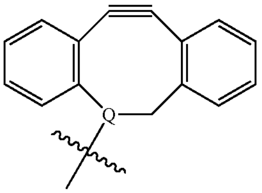;

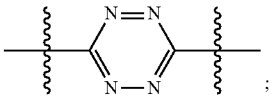; and 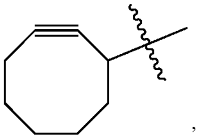, where Q is C or N.

By way of a non-limiting example, group B" may be an alkyne-containing group, e.g.,

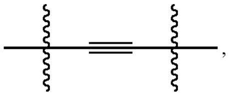,

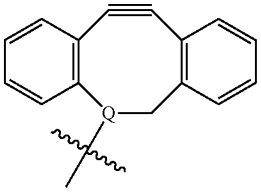; or 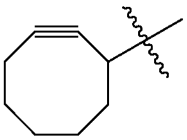.

By way of another non-limiting example, group B" may be an azide.

In one embodiment, the adduct of the group B' and the group B" comprises a triazole moiety. In one particular embodiment, the adduct of the group B' and the group B" has a structure selected from the group consisting of:

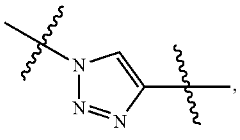,

-continued

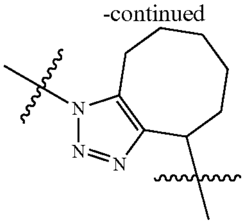, and

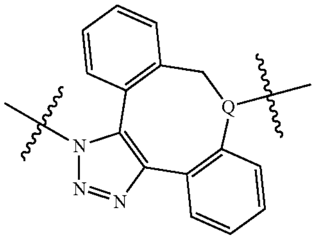, wherein Q is C or N.

In one embodiment, the first spacer $SP^1$ is absent.

In another embodiment, $SP^1$ is selected from the group consisting of and

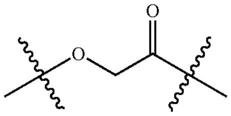 and

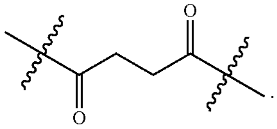.

In one embodiment, the second spacer $SP^2$ is absent.

In another embodiment, $SP^2$ is selected from the group consisting of an alkyl (e.g., a $C_{1-20}$ alkyl, or a $C_{1-12}$ alkyl, or a $C_{1-10}$ alkyl, or a $C_{1-8}$ alkyl, or a $C_{1-6}$ alkyl), $-(CH_2-CH_2-O)_v-$, $-NH-$, $-C(O)-$, $-NH-C(O)-$, $-NH-(CH_2)_u-$, $-NH-(CH_2)_u-C(O)-$, $-NH-(CH_2\text{-}CH_2\text{-}O)_v-$, $-NH-(CH_2\text{-}CH_2-O)_v-C(O)-$, $-NH-(CH_2\text{-}CH_2-O)_v-(CH_2)_u-$, $-NH-(CH_2-CH_2\text{-}O)_v\text{-}(CH_2)_u-C(O)-$, $-(CH_2)_u-NH-C(O)-$, $-NH-(CH_2)_u-NH-C(O)-$, $-NH-(CH_2)_u-C(O)-NH-$, or combinations thereof; wherein subscripts u and v are independently an integer from 1 to 8.

In certain embodiments, AA is a peptide unit comprising from 2 to 4 amino acids selected from glycine, valine, phenylalanine, proline, glutamic acid, lysine, phenylalanine, and citrulline, and combinations thereof.

In one embodiment, AA is a peptide unit comprising 2 amino acids. In one embodiment, AA is a peptide unit comprising 3 amino acids. In one embodiment, AA is a peptide unit comprising 4 amino acids.

In one particular embodiment, AA is valine-citrulline, valine-alanine, or phenylalanine-lysine.

In another particular embodiment, AA is selected from the group consisting of glycine-glycine-glycine (GGG), glycine-glycine-glycine-glycine (GGGG), glycine-glycine-phenylalanine (GGF), and glycine-glycine-phenylalanine-glycine (GGFG) and glutamic acid-valine-citrulline (EVC).

In one embodiment, the third spacer $SP^3$ is absent.

In another embodiment, $SP^3$ is selected from the group consisting of

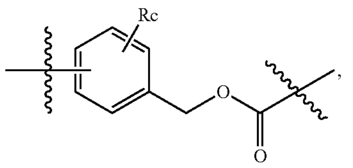

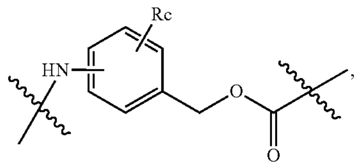

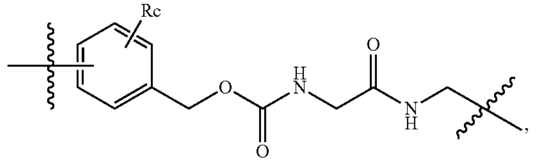

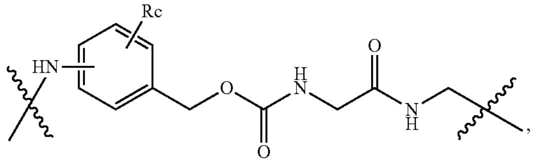

and combinations thereof, wherein $R_c$ is independently at each occurrence absent or a group selected from

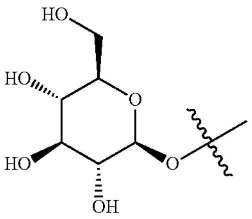

and

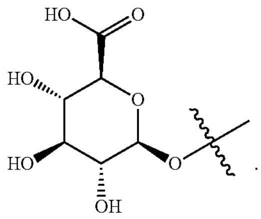

In one embodiment, the spacer $SP^3$ is covalently attached to the camptothecin analog, e.g., Dxd or M-Dxd.

In one embodiment, the linker L2 comprises from about 1 to about 12, or from about 1 to about 10, or from about 1 to about 8, or from about 1 to about 6, or from about 1 to about 4, or from about 1 to about 2 ($SP^2$-AA-$SP^3$) moieties, and the linker-payload L2-Dxd comprises from about 1 to about 12, or from about 1 to about 10, or from about 1 to about 8, or from about 1 to about 6, or from about 1 to about 4, or from about 1 to about 2 Dxd payload molecules.

Moiety M

In certain embodiments, moiety M is absent.

In certain embodiments, M is present and has a structure

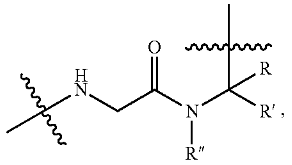

where R, R', and R" are independently at each occurrence hydrogen or alkyl, or wherein R' and R" together form a ring, e.g., a 3-membered to an 8-membered ring.

In certain embodiments, M is present and has a structure

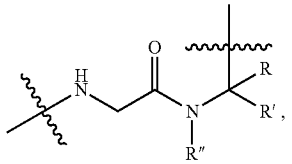

where R, R', and R" are independently at each occurrence hydrogen or a $C_1$-$C_4$ alkyl, or wherein R' and R" together form a 5-membered or a 6-membered ring.

In one embodiment, R is a hydrogen.

In one embodiment, R' is a hydrogen. In one embodiment, R' is a $C_1$-$C_4$ alkyl.

In one embodiment, R" is a hydrogen. In one embodiment, R" is a $C_1$-$C_4$ alkyl.

In one embodiment, R' and R" together form a 5-membered ring. In one embodiment, R' and R" together are $-(CH_2)_3-$.

In one embodiment, R' and R" together form a 6-membered ring. In one embodiment, R' and R" together are $-(CH_2)_4-$.

In one embodiment, R, R', and R" are hydrogens at each occurrence, i.e., M is

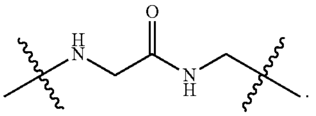 [SMILES: *CNC(=O)CN*]

In another embodiment, R is hydrogen and R' and R" together form a 5-membered ring, e.g., R' and R" together are $-(CH_2)_3-$ and M is

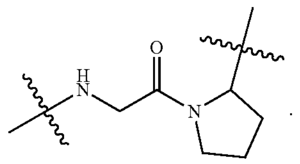 [SMILES: *NCC(=O)N1CCCC1*]

Linker-Payloads (L2-P)

In another aspect, the present disclosure provides a compound according to Formula (L2-P), (L2'-P), or (L2"-P):

B"-$SP^1$-(-$SP^2$-AA-$SP^3$-M-Dxd)$_p$ (L2-P), $H_2N$-$SP^1$-(-$SP^2$-AA-$SP^3$-M-Dxd)$_p$ (L2'-P), or

Maleimide-N-$SP^1$-(-$SP^2$-AA-$SP^3$-M-Dxd)$_p$ (L2'-P), wherein:

B" is selected from the group consisting of

—$N_3$, 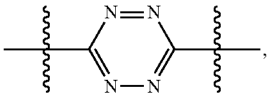,

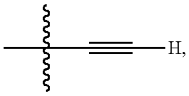, 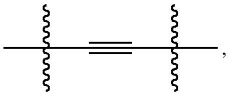,

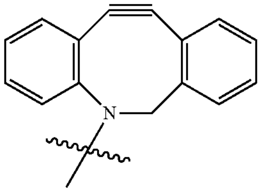

and

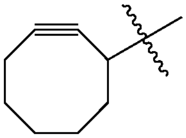

;

$SP^1$ is absent or a first spacer unit selected from the group consisting of and

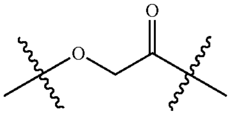

and

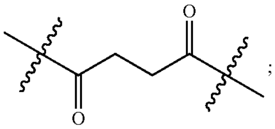

;

$SP^2$ is absent or a second spacer unit selected from the group consisting of a $C_{1-6}$ alkyl, $—(CH_2—CH_2—O)_v—$, —NH—, —C(O)—, —NH—C(O)—, $—NH—(CH_2)_u—$, $—NH—(CH_2)_u—C(O)—$, $—NH—(CH_2—CH_2—O)_v—$, $—NH—(CH_2—CH_2—O)_v—C(O)—$, $—NH—(CH_2—CH_2—O)_v—(CH_2)_u—$, $—NH—(CH_2—CH_2—O)_v—(CH_2)_u—C(O)—$, $—(CH_2)_u—NH—C(O)—$, $—NH—(CH_2)_u—NH—C(O)—$, $—NH—(CH_2)_u—C(O)—NH—$, or combinations thereof; wherein subscripts u and v are independently an integer from 1 to 8;

AA is absent or a peptide unit comprising from 2 to 4 amino acids;

$SP^3$ is absent or a third spacer unit selected from the group consisting of,

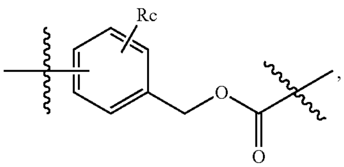

,

-continued

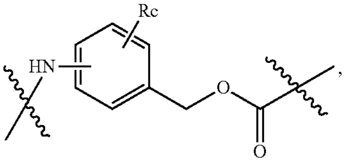

,

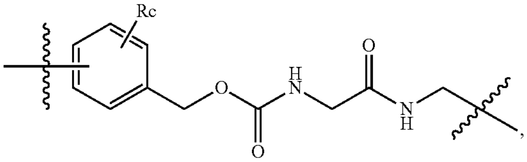

,

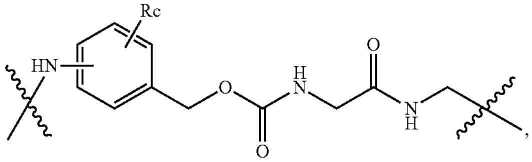

, wherein $R_c$ is independently at each occurrence absent or a group selected from OH and

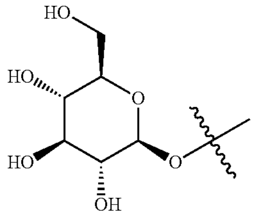

and

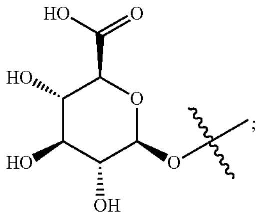

;

M is absent or

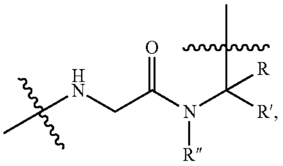

, where R, R', and R" are independently at each occurrence hydrogen or a $C_1$-$C_4$ alkyl, or wherein R' and R" together form a 5-membered or a 6-membered ring; and Dxd is an anti-tumor agent having a structure according to Formula (P):

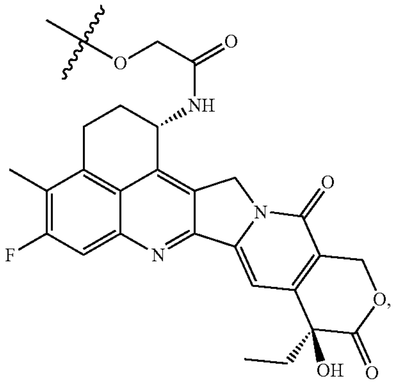

(P)

and p is an integer from 1 to 12.

In certain embodiments wherein L2-P has the structure according to L2'-P or L2"-P, the linker-payload may be directly covalently attached to an anti-FGFR2 antibody, e.g., via a TGase-mediated glutamine ligation (L2'-P) or a cysteine ligation (L2"-P).

In one embodiment, the product of a direct attachment of L2'-P to an anti-FGFR2 antibody (BA) might have the following structure:

$$BA\text{-}(G\mathit{ln}\text{-}NH\text{-}SP^1\text{-}B2\text{-}(\text{-}SP^2\text{-}AA\text{-}SP^3\text{-}M\text{-}D\mathit{xd})_p)_n.$$

In certain embodiments, the linker-payload L2-P, L2'-P, or L2"-P according to the disclosure has a structure selected from the group consisting of:

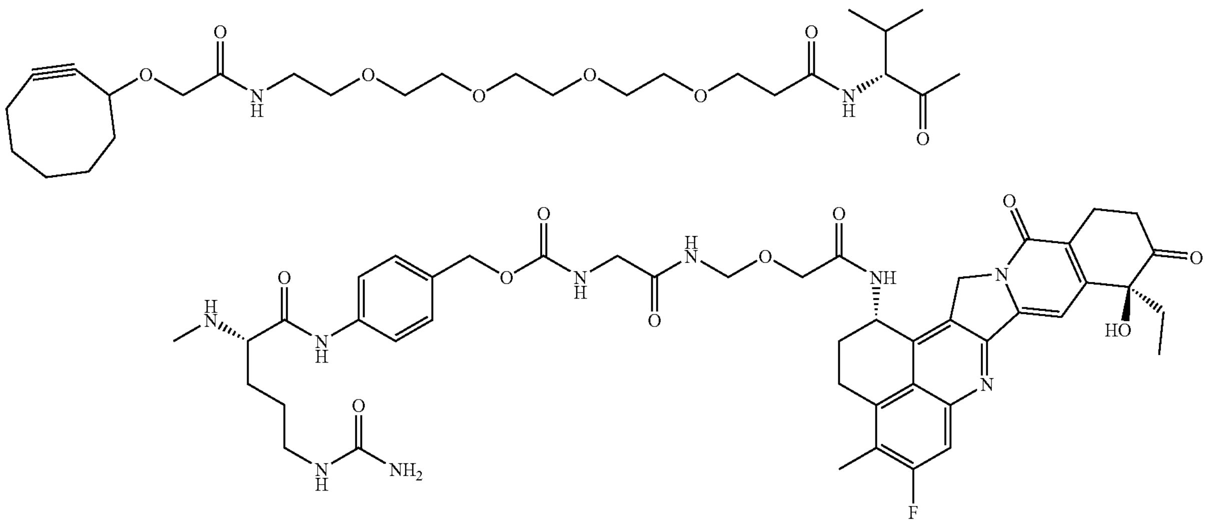

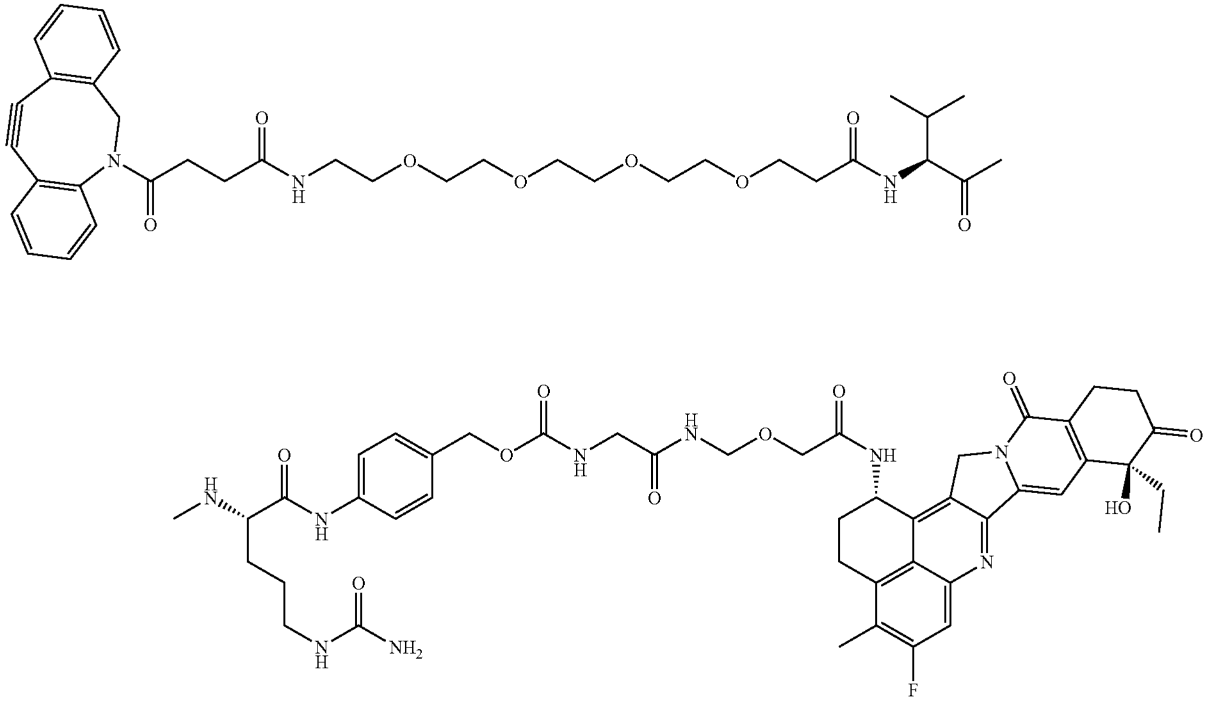

-continued
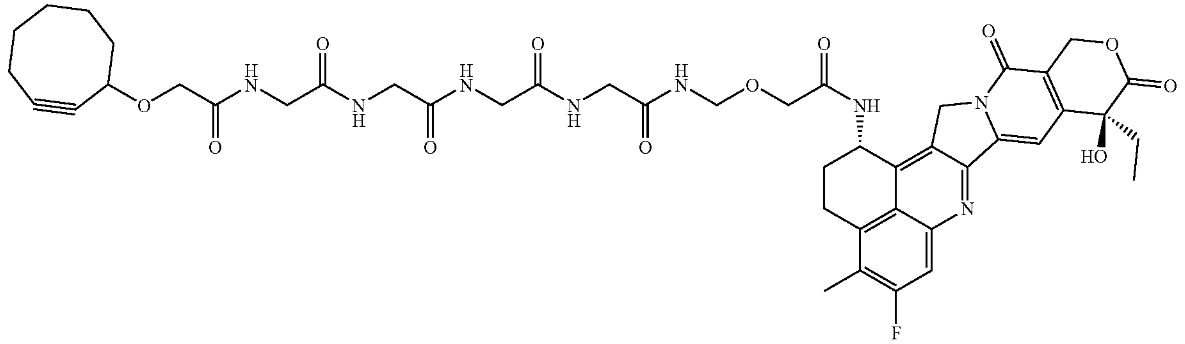
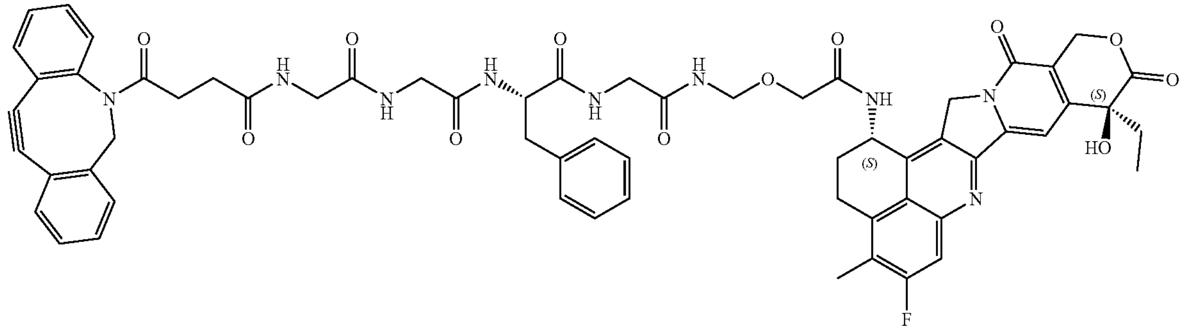
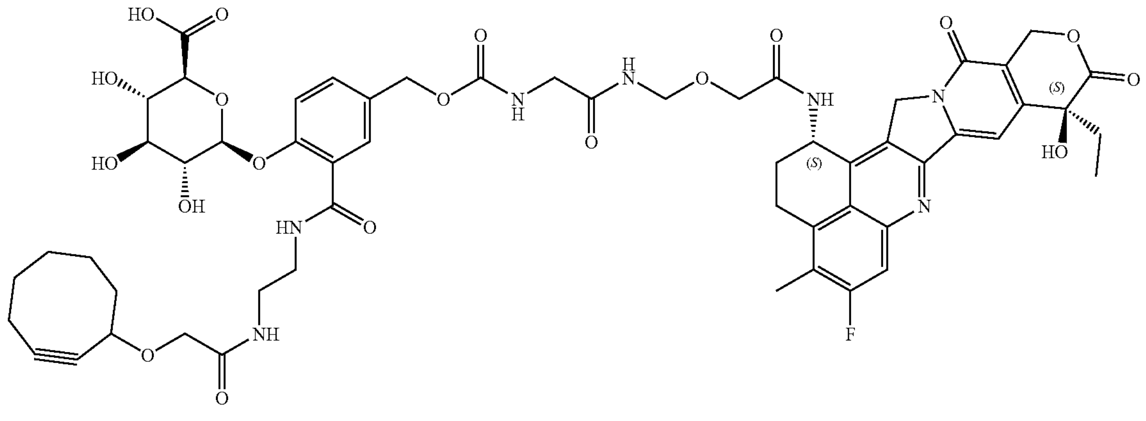
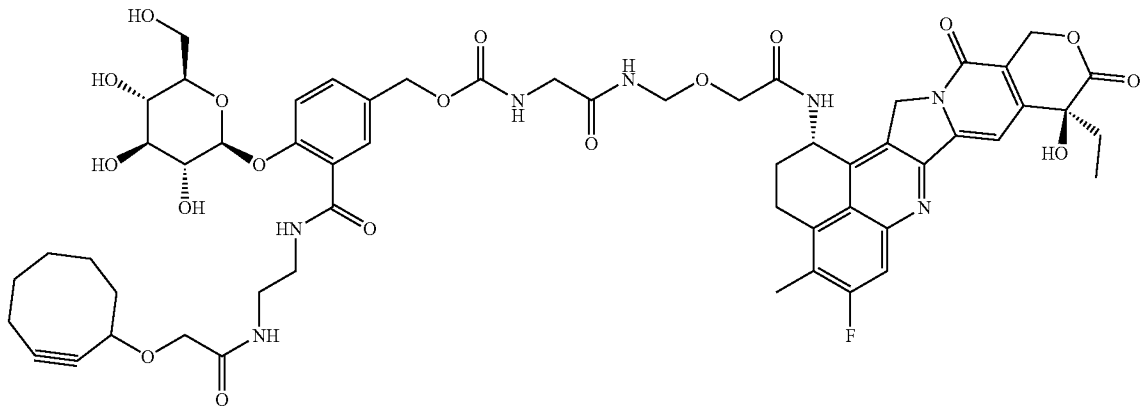

-continued
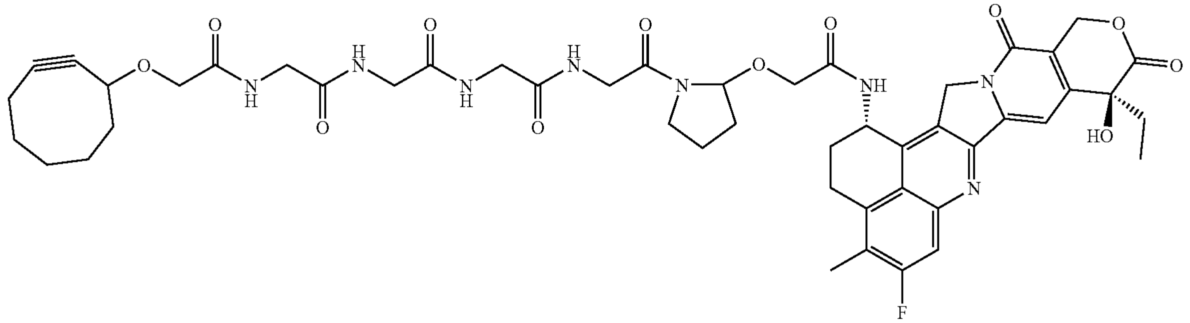
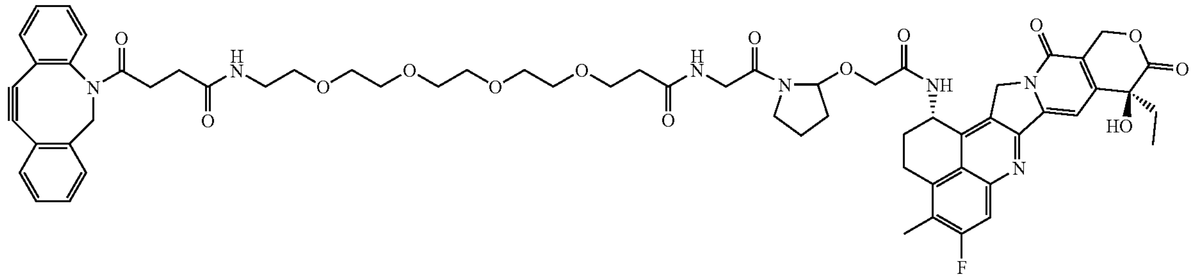
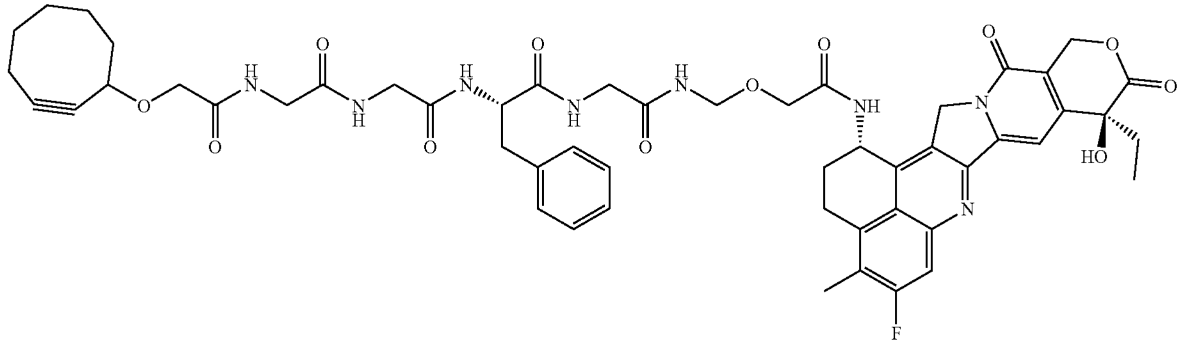
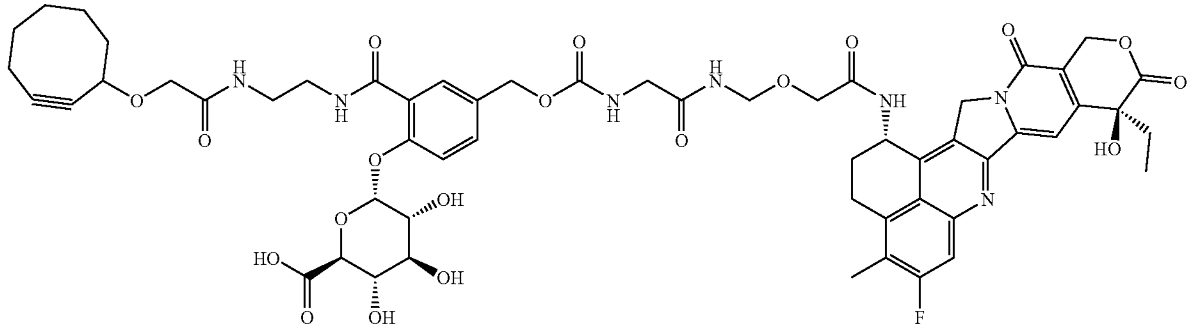
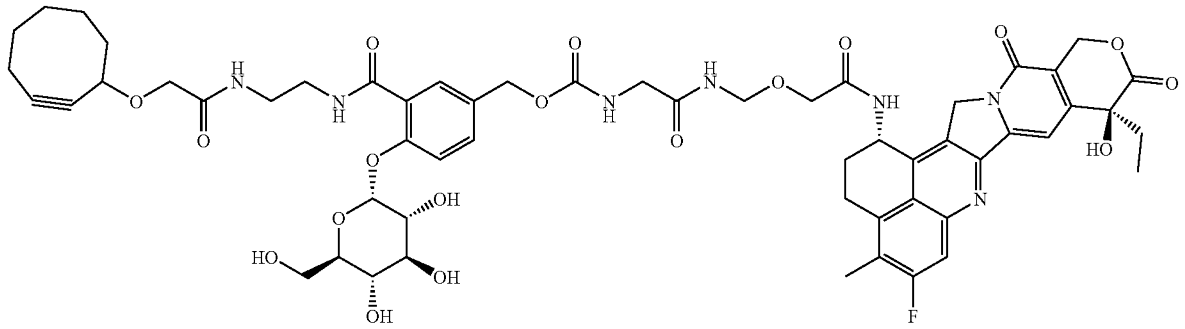

-continued
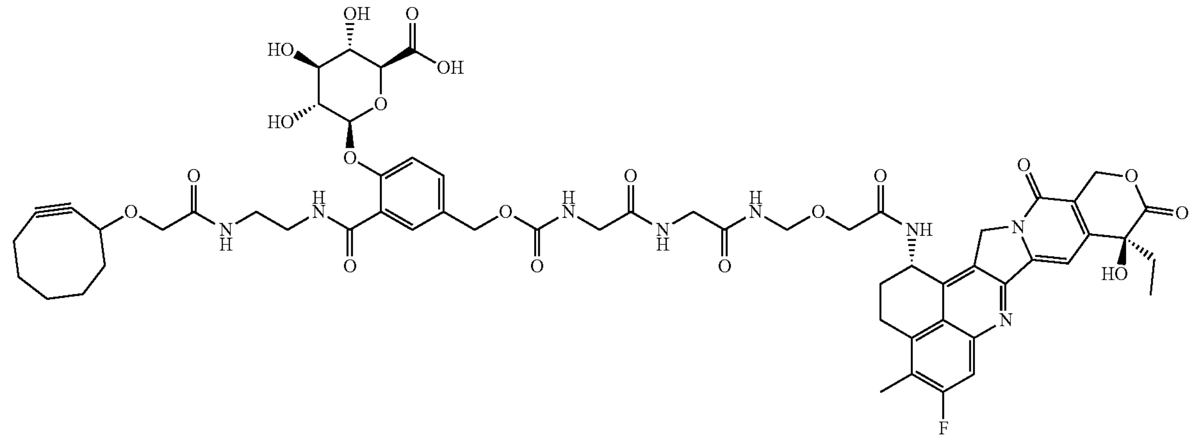
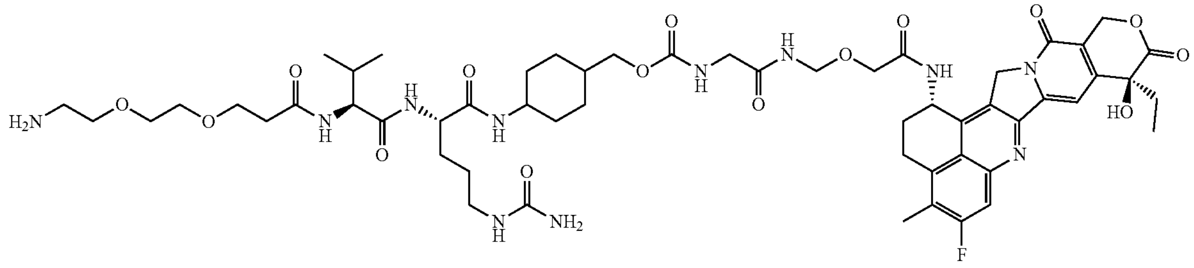
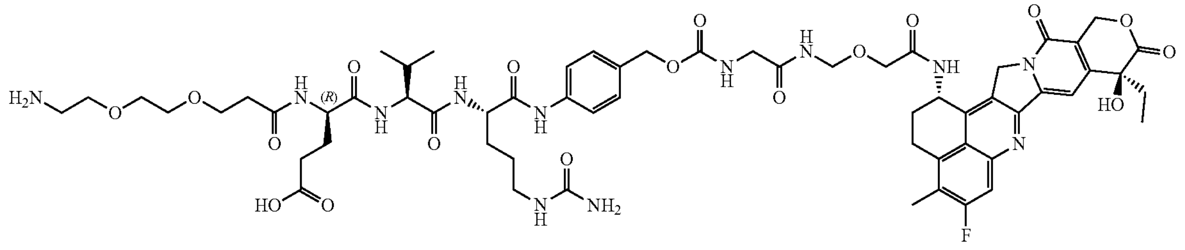
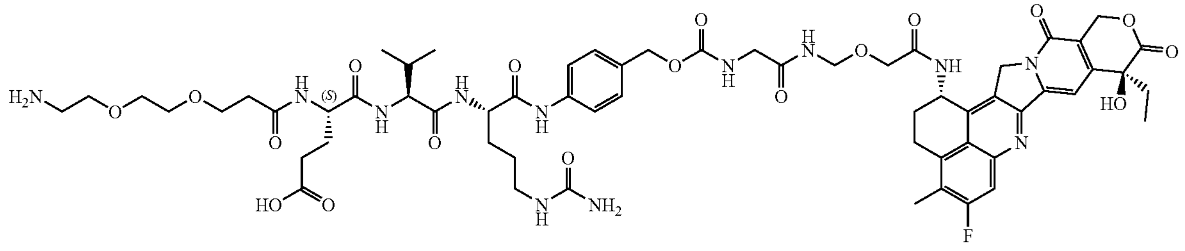
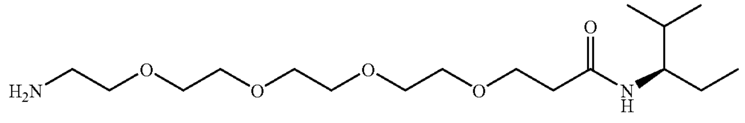
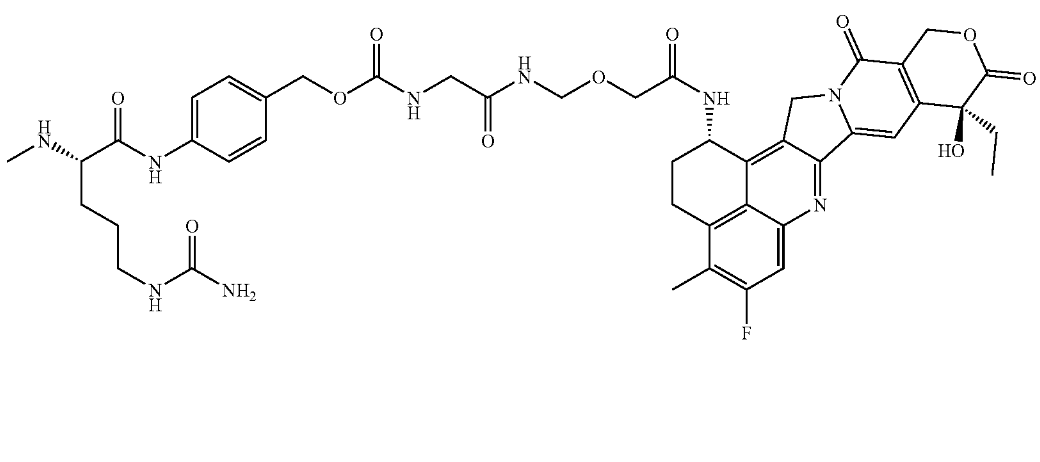

-continued
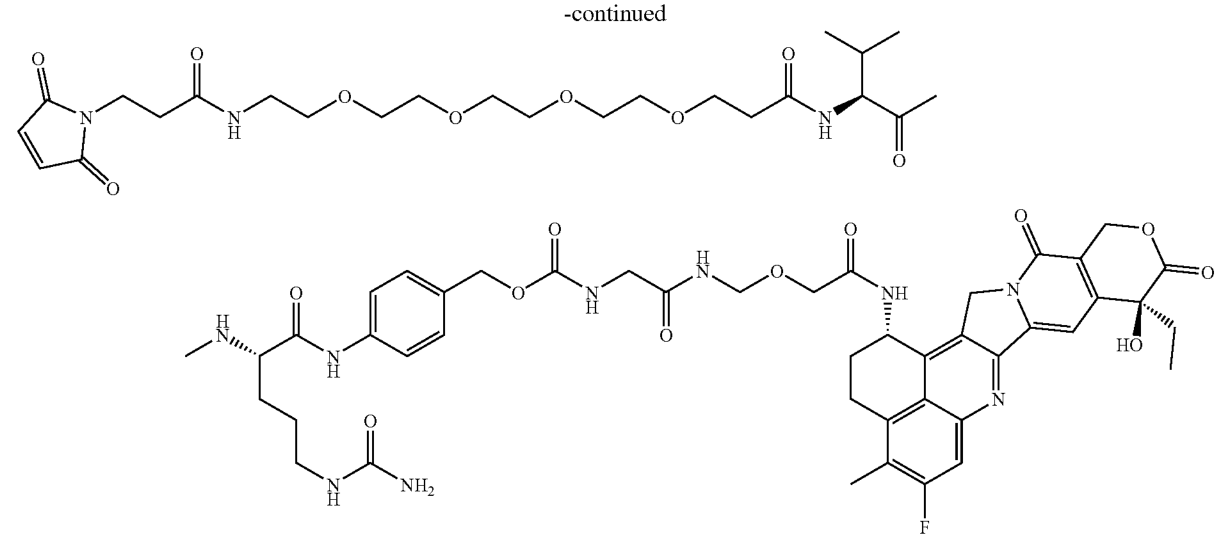
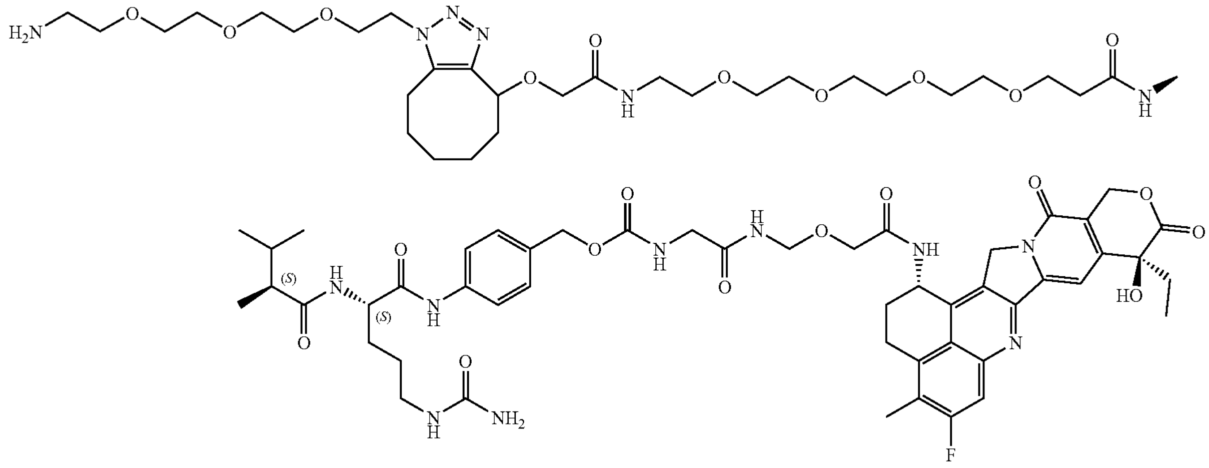
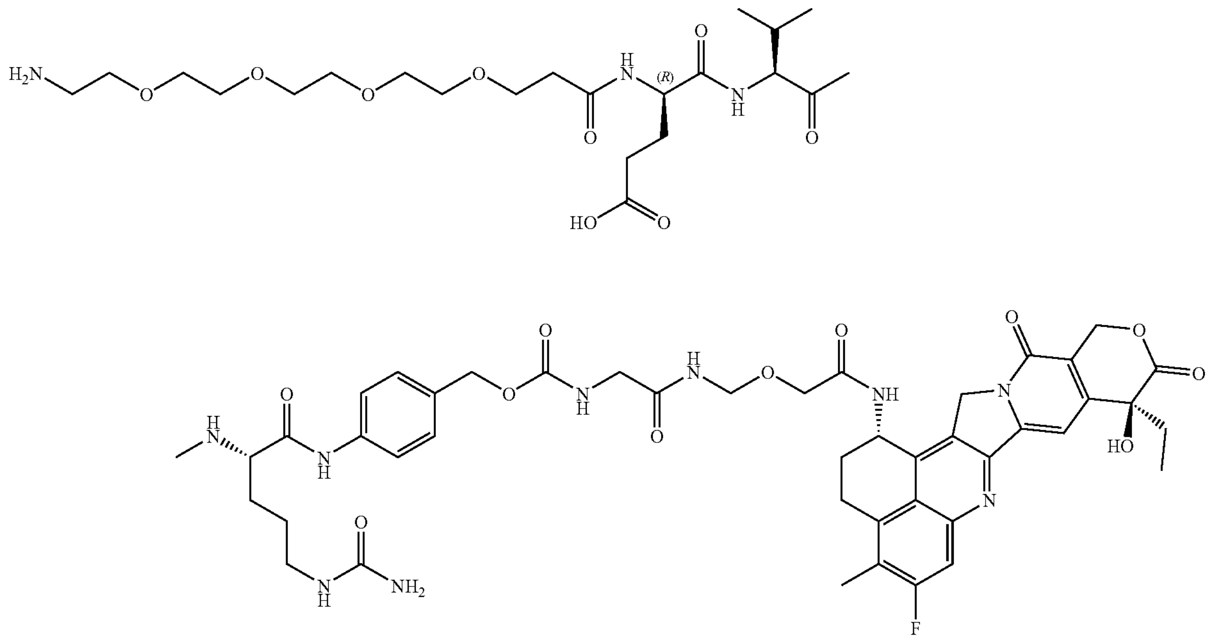

-continued
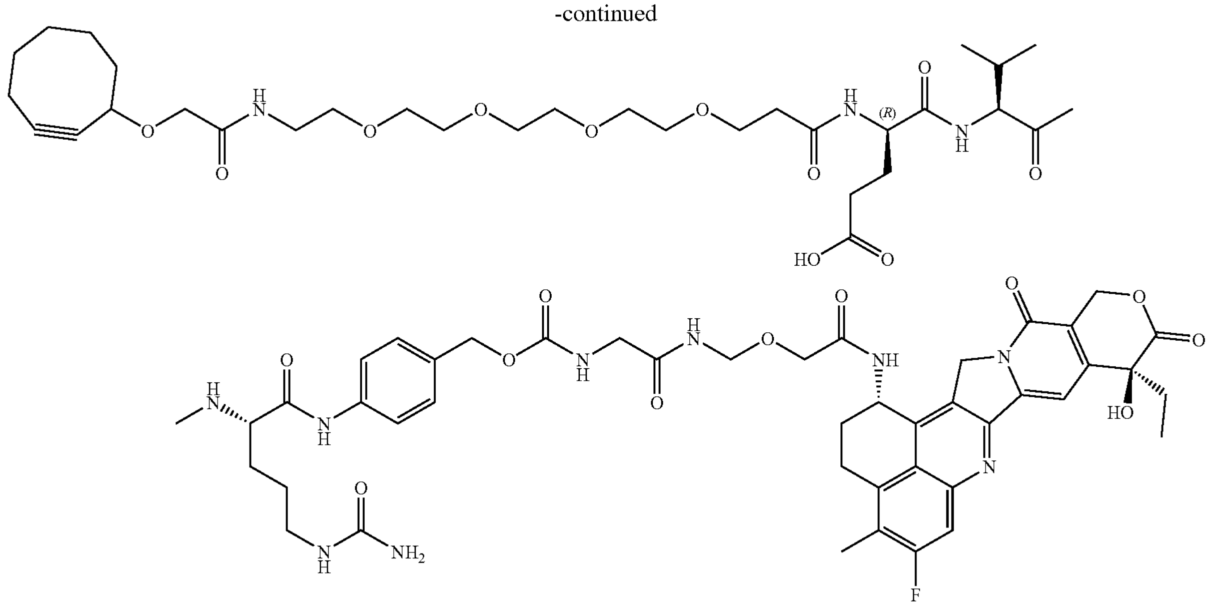
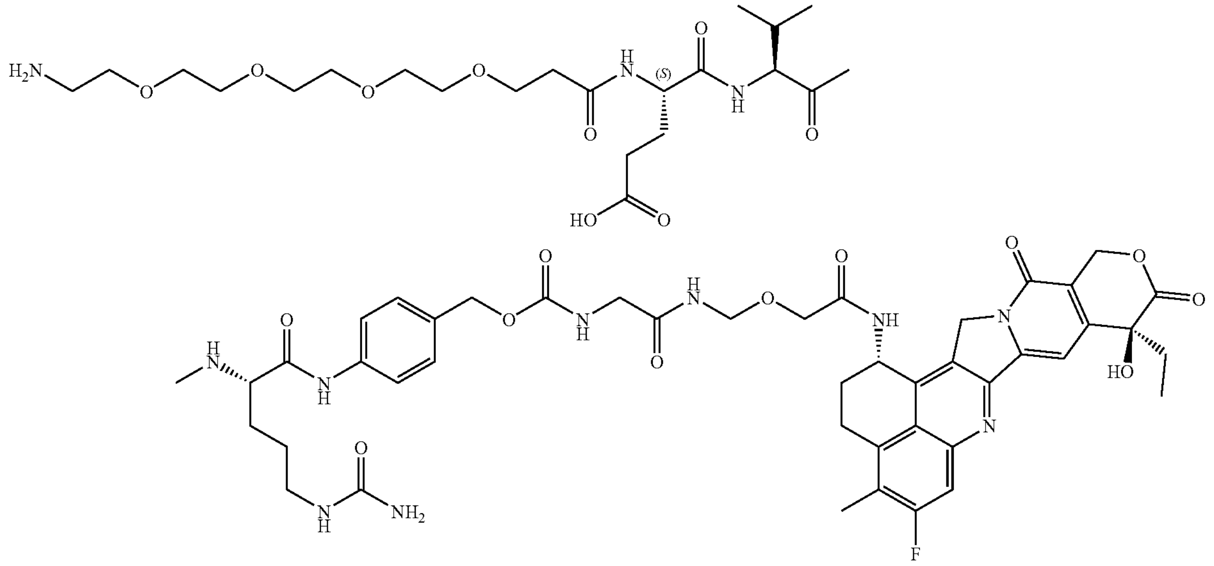
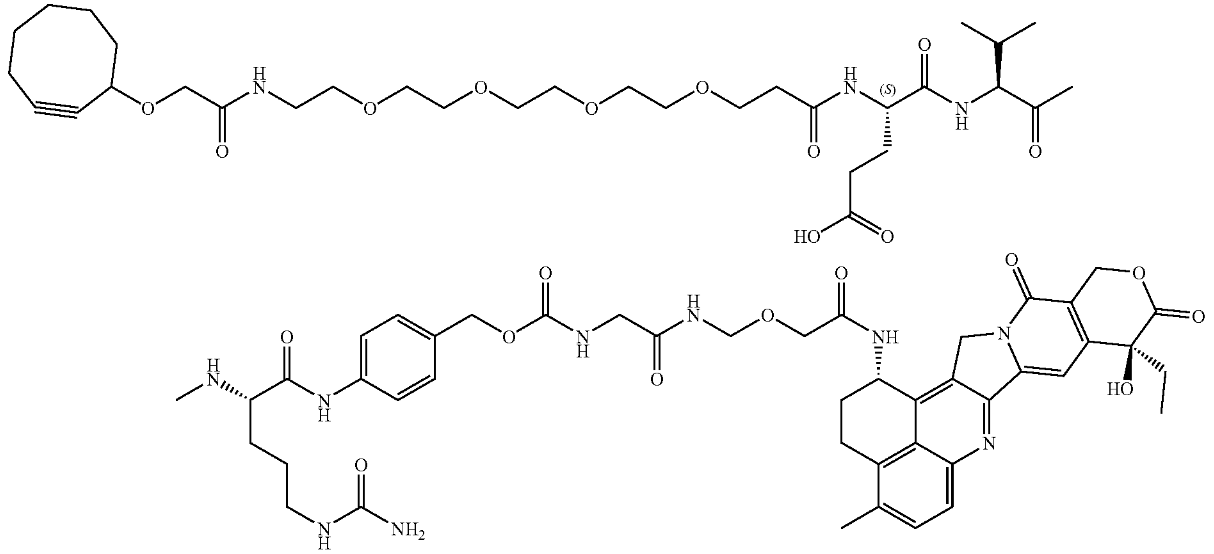

or a pharmaceutically acceptable salt thereof.

Branched Linker2-Payloads (BL2P)

In another aspect, the present disclosure provides L-2-P which comprise one or more branching units. Exemplary branching units B1-B5 according to the disclosure are depicted in Table 1, below.

TABLE 1
| Structures of Branching Units B1-B5 | | | | | |
|---|---|---|---|---|---|
| Branch B | B1 | B2 | B3 | B4 | B5 |
| Structure | 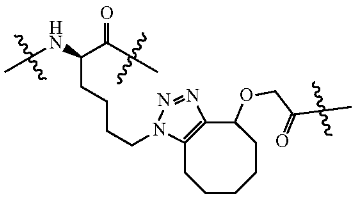 [SMILES: *N[C@H](CCCCn1nnc2c1CCCCCC2OCC(*)=O)C(*)=O] | 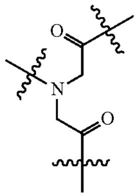 [SMILES: *C(=O)CN(*)CC(*)=O] | 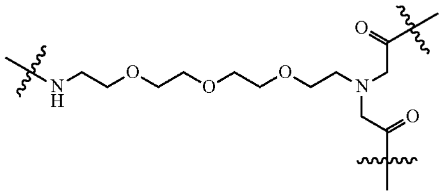 [SMILES: *NCCOCCOCCOCCN(CC(*)=O)CC(*)=O] | 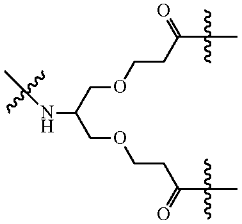 [SMILES: *NC(COCCC(*)=O)COCCC(*)=O] | 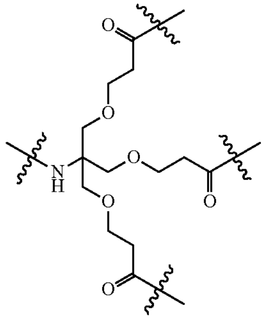 [SMILES: *NC(COCCC(*)=O)(COCCC(*)=O)COCCC(*)=O] |

Table 2, below, provides structures for exemplary branched linker2-payloads (BL2P) according to the disclosure.

TABLE 2
Structures of Branched Linker2-Payloads (BL2P)
| Structures |
| --- |
| 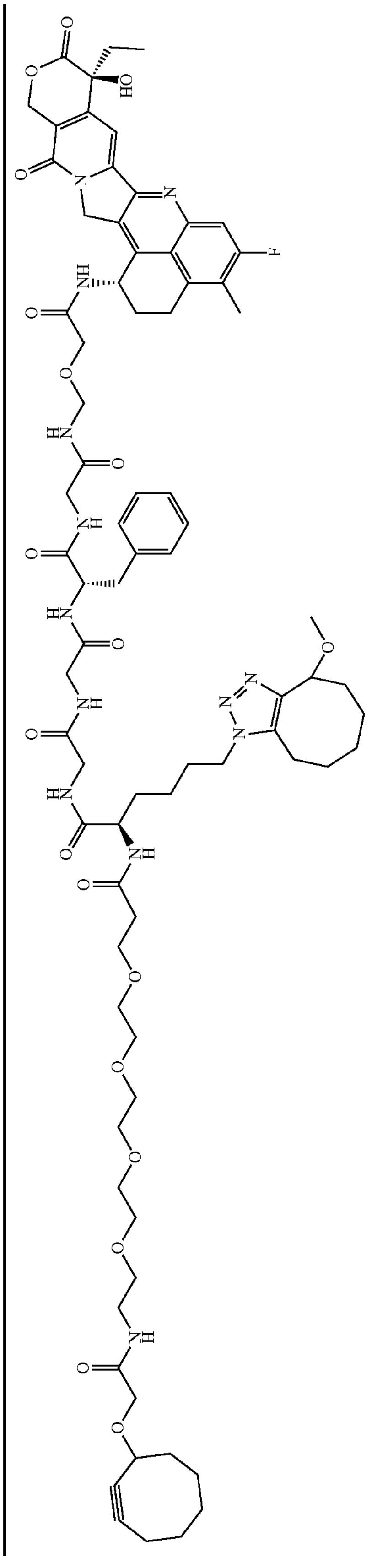 |
| 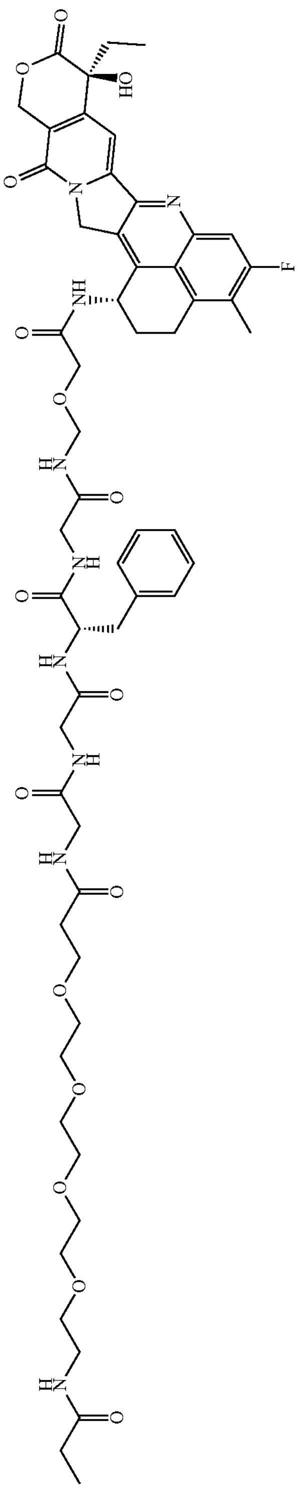 |

TABLE 2-continued
Structures of Branched Linker2-Payloads (BL2P)
Structures
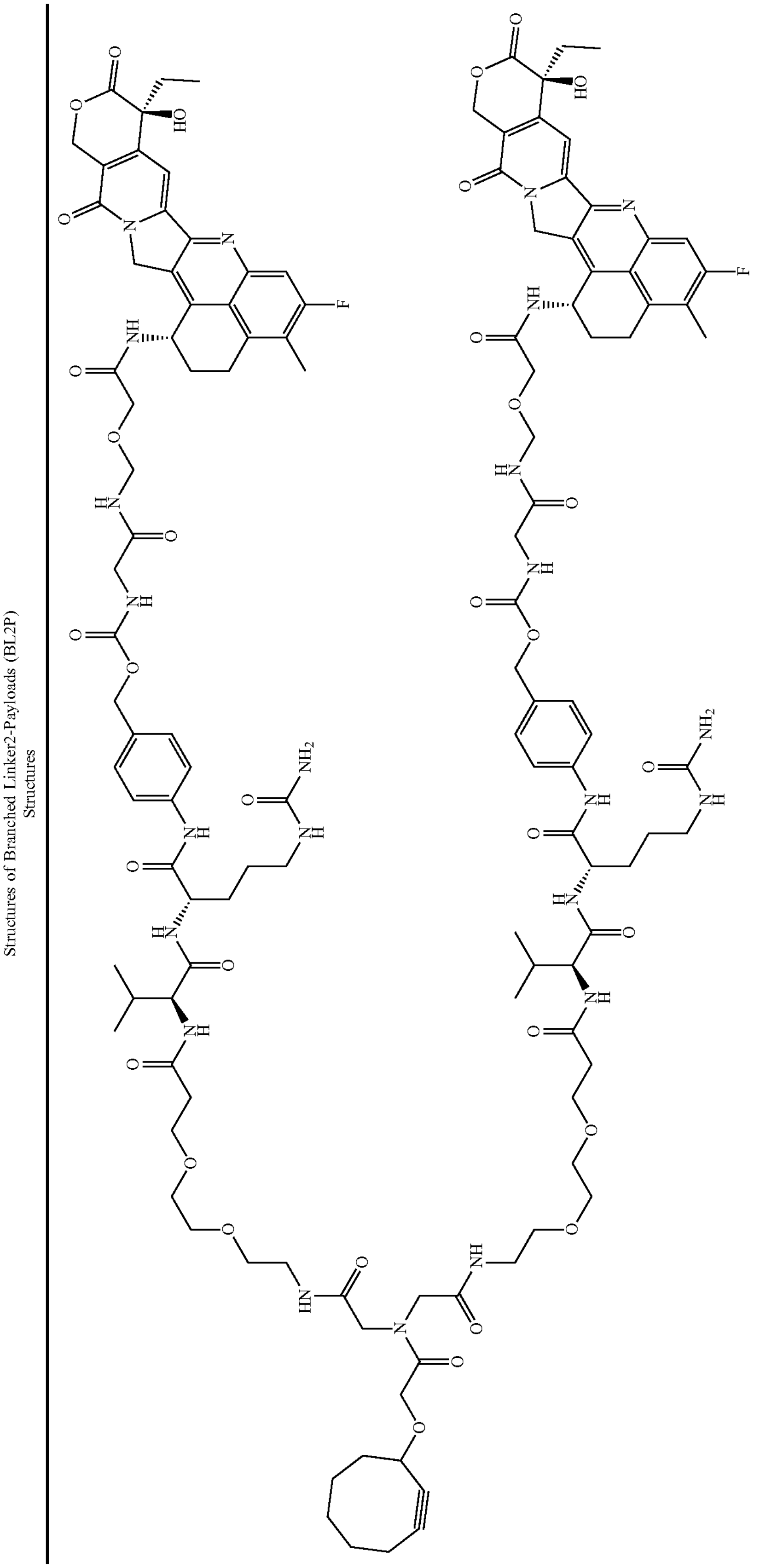

TABLE 2-continued
Structures of Branched Linker2-Payloads (BL2P)
Structures
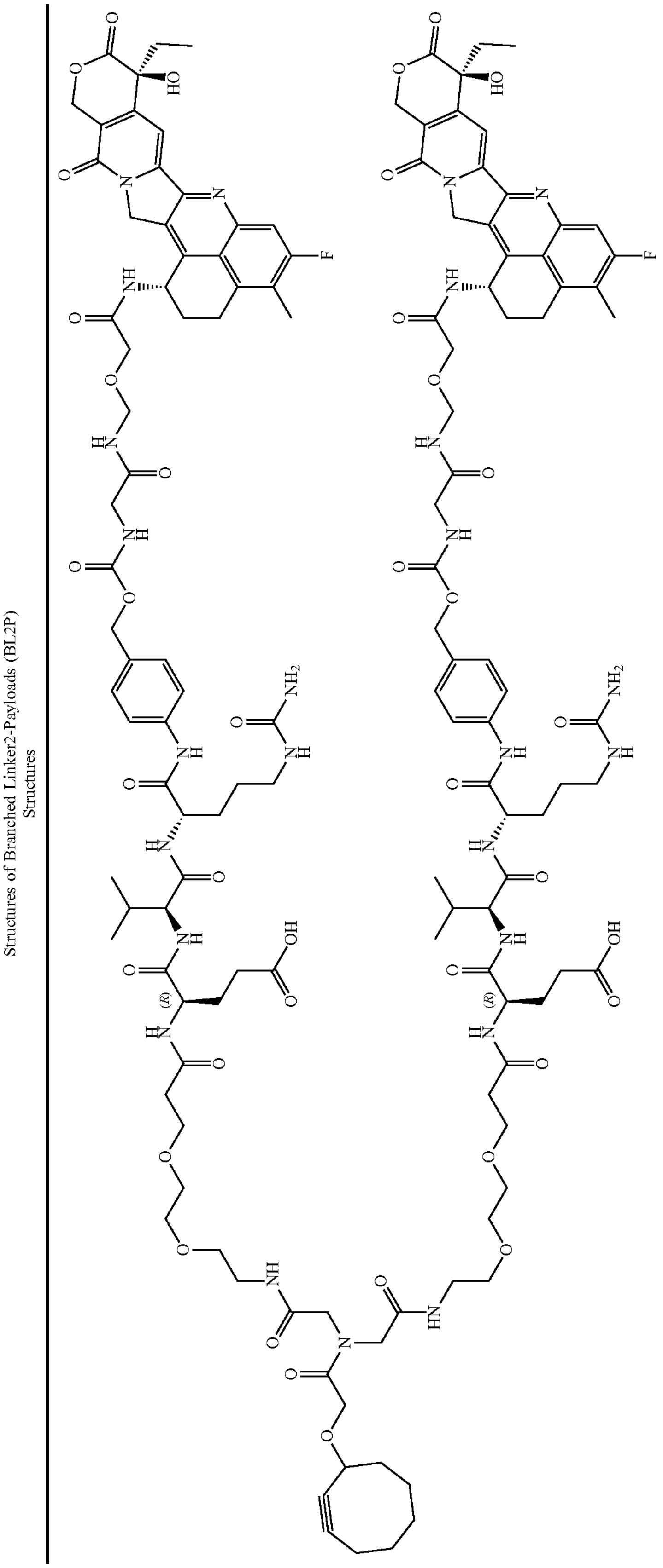

TABLE 2-continued
Structures of Branched Linker2-Payloads (BL2P)
Structures
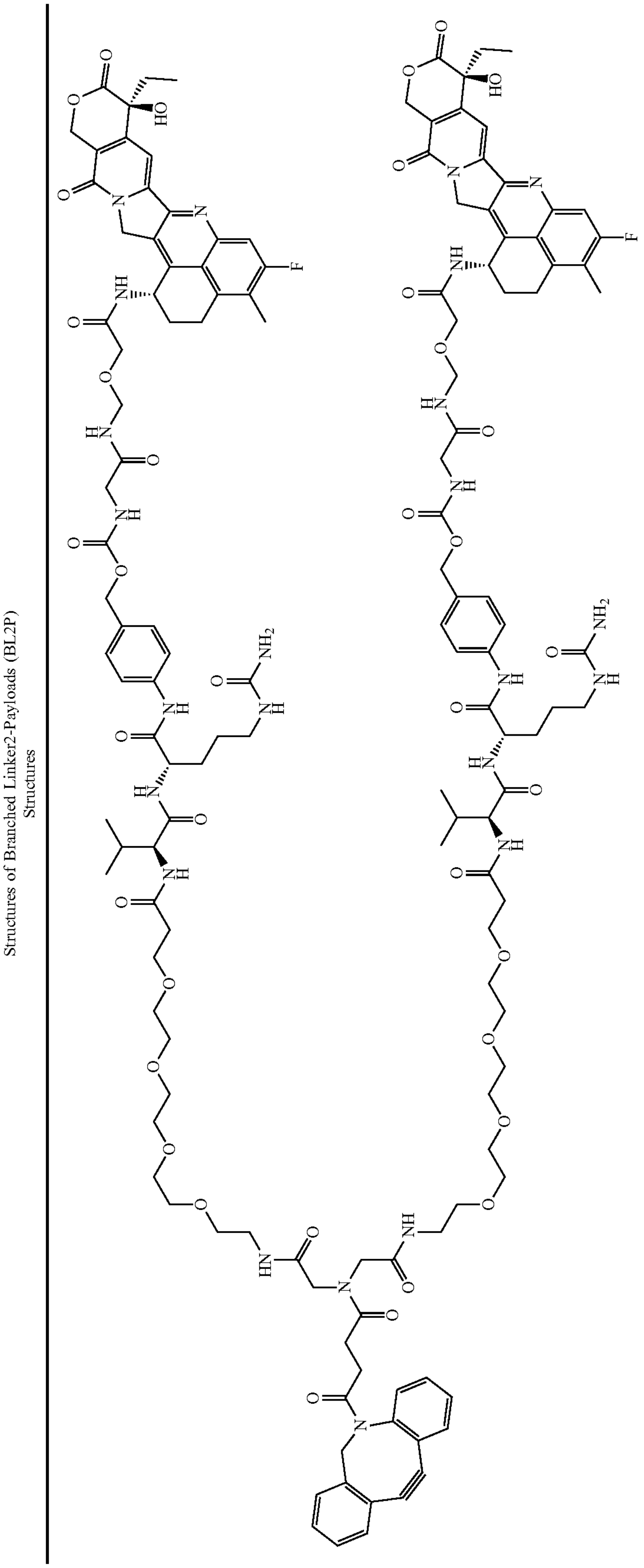

TABLE 2-continued
Structures of Branched Linker2-Payloads (BL2P)
| Structures |
| --- |
| 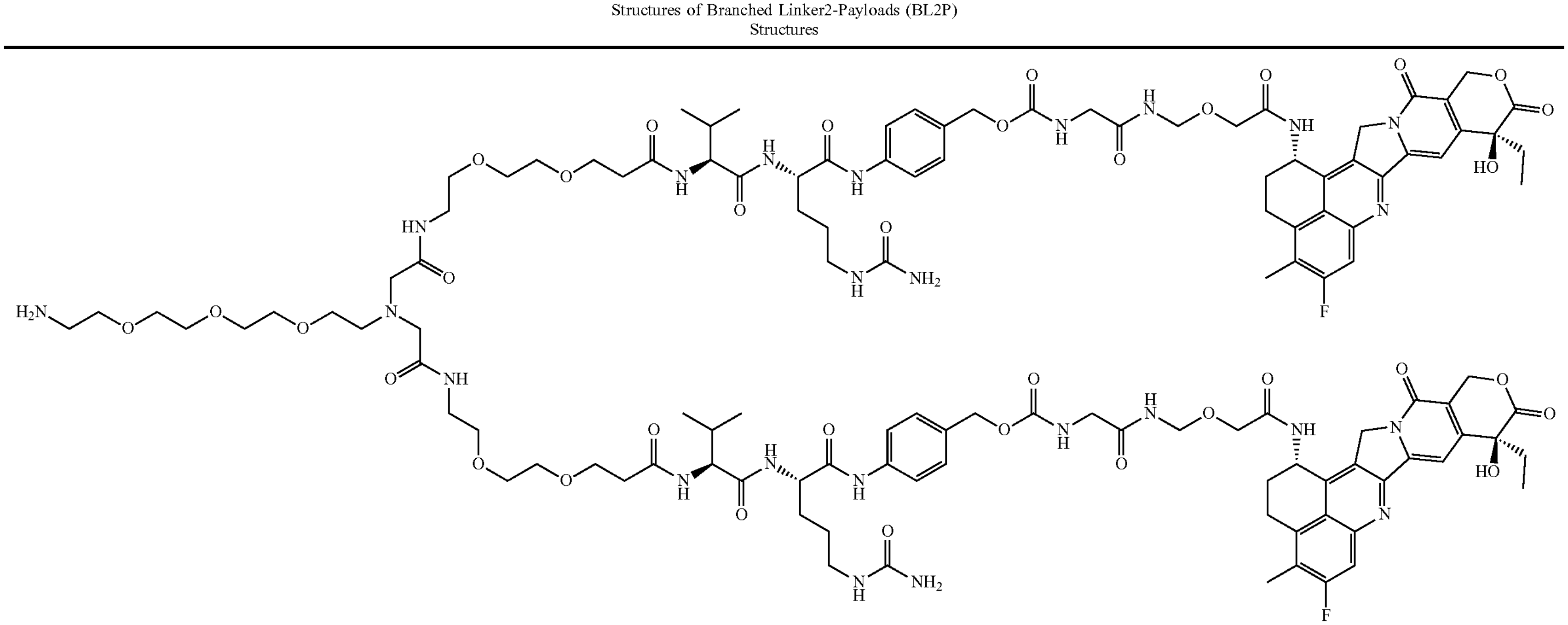 |

TABLE 2-continued
Structures of Branched Linker2-Payloads (BL2P)
| Structures |
| --- |
| 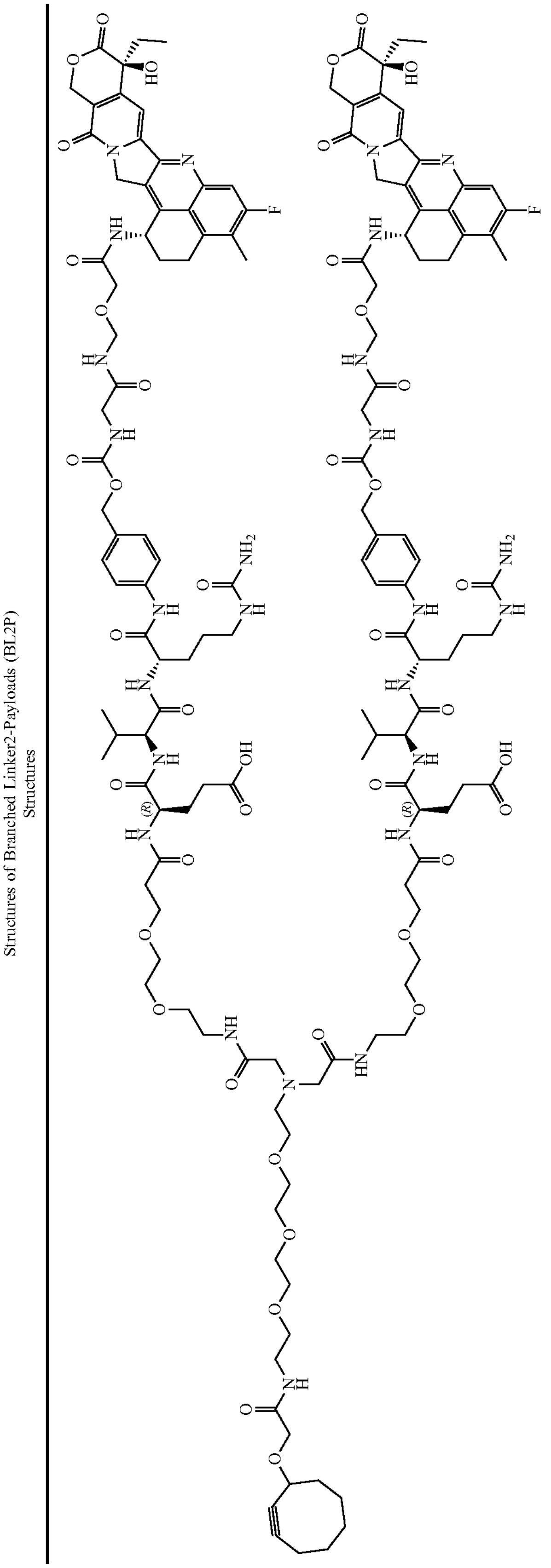 |

TABLE 2-continued
Structures of Branched Linker2-Payloads (BL2P)
| Structures |
| --- |
| 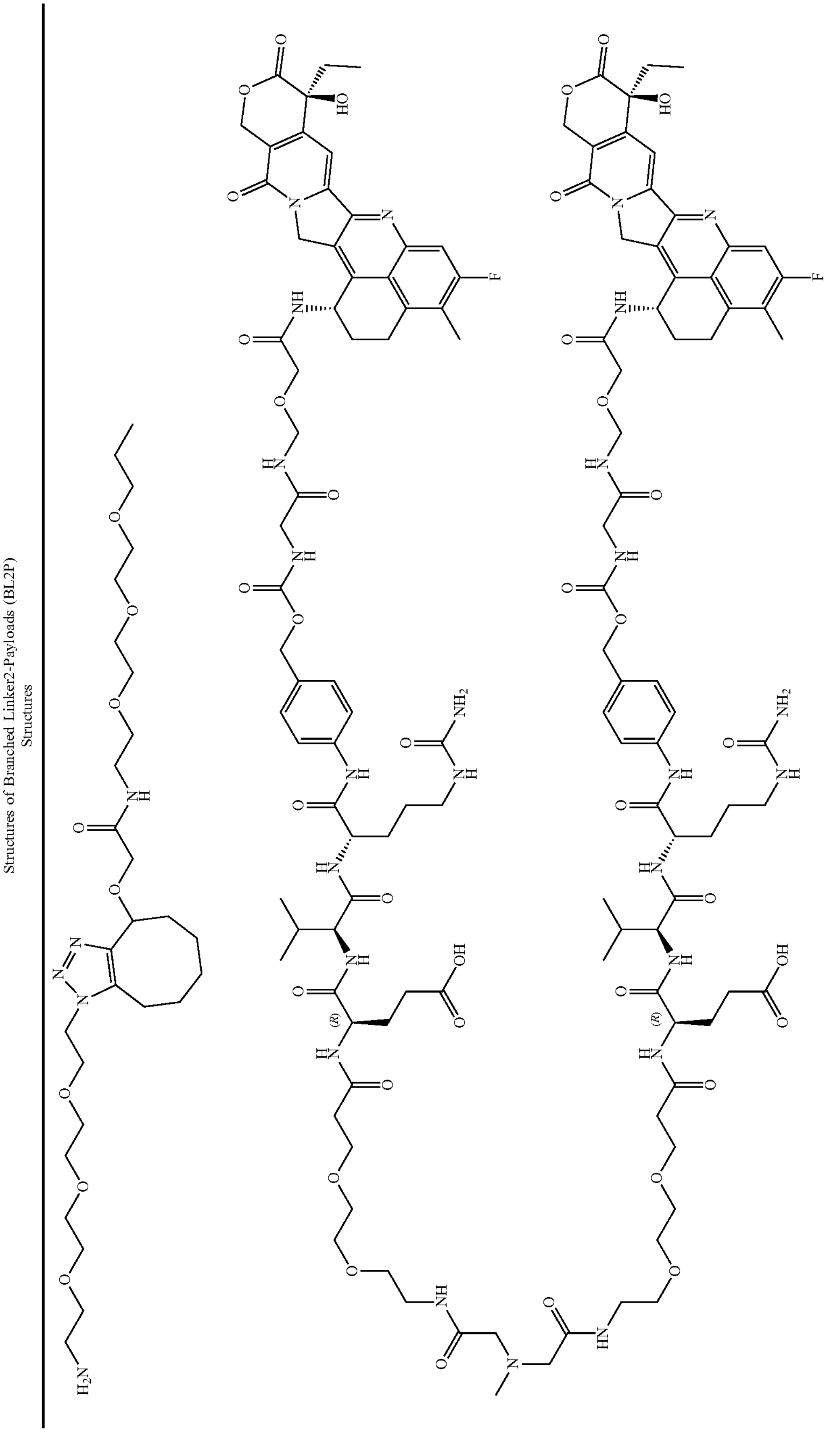 |

TABLE 2-continued
Structures of Branched Linker2-Payloads (BL2P)
Structures
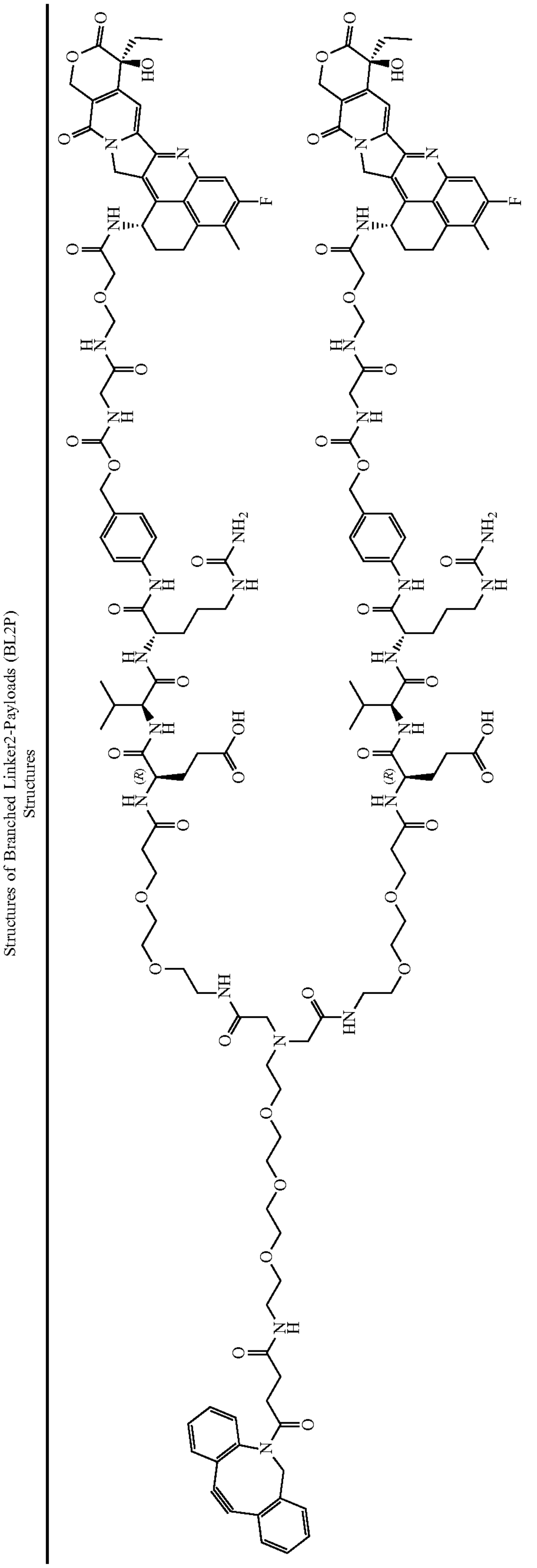

TABLE 2-continued
| Structures of Branched Linker2-Payloads (BL2P) |
| --- |
| Structures |
| 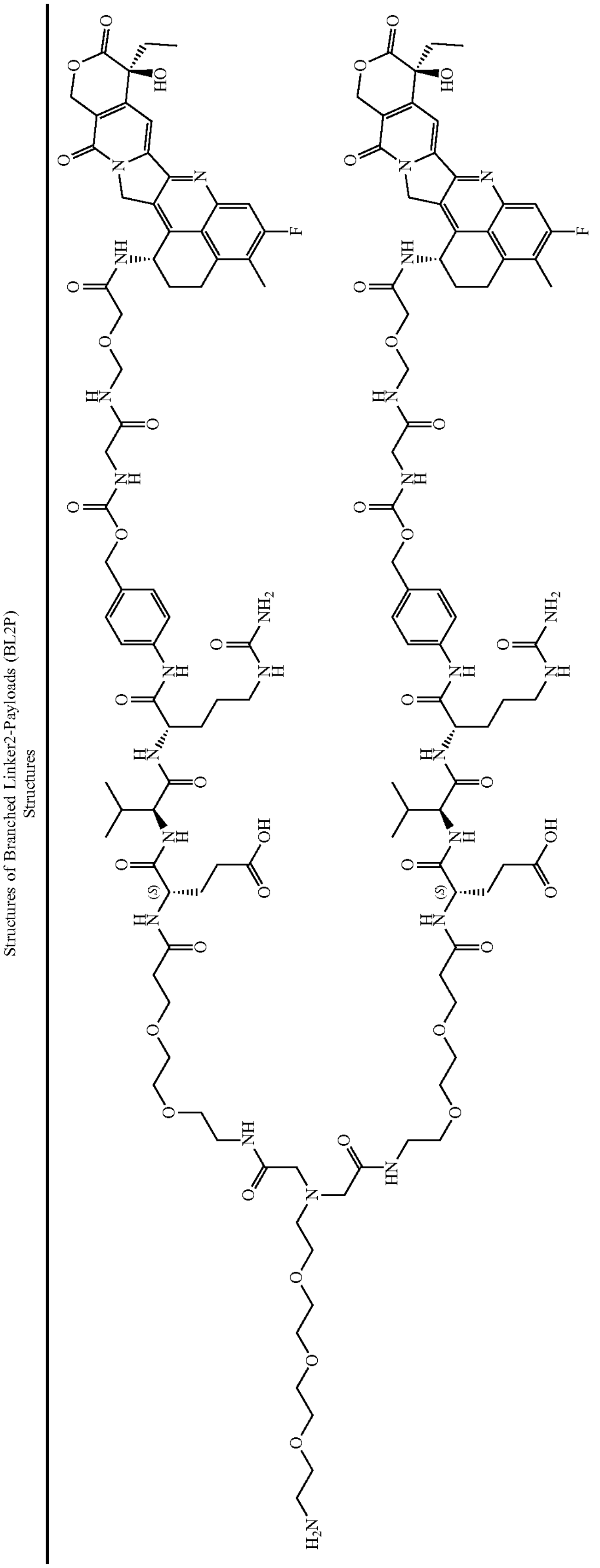 |

TABLE 2-continued
| Structures of Branched Linker2-Payloads (BL2P) |
| --- |
| Structures |
| 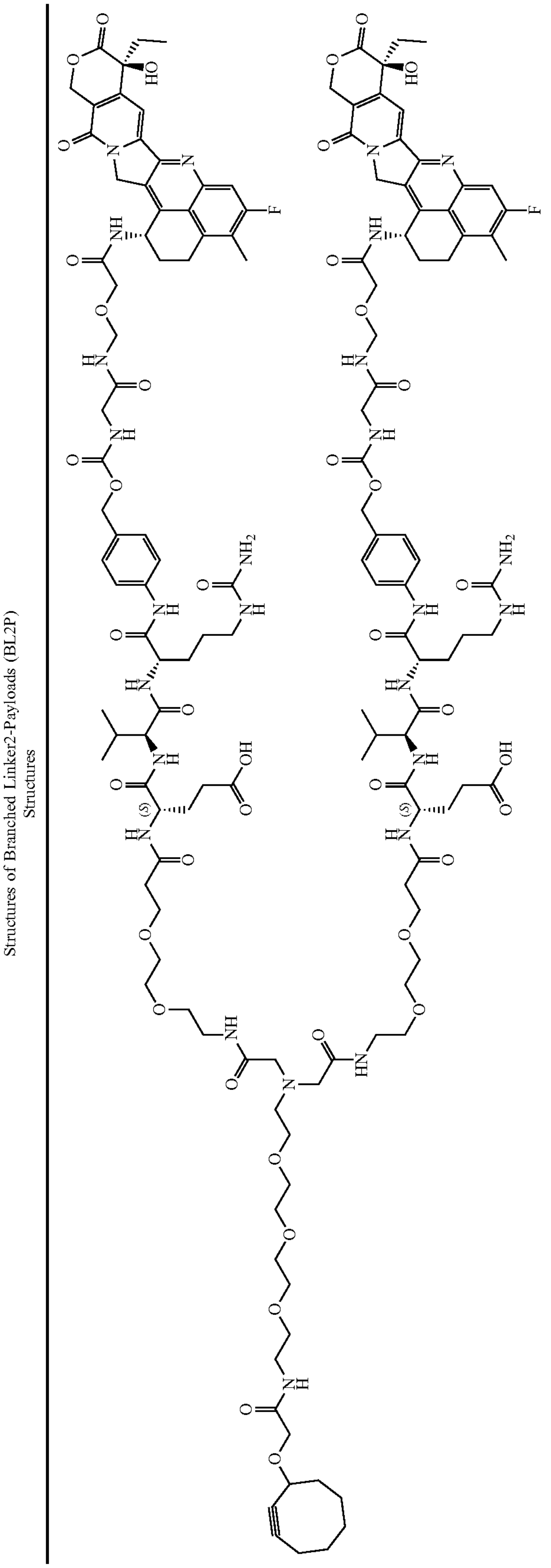 |

TABLE 2-continued
Structures of Branched Linker2-Payloads (BL2P)
Structures
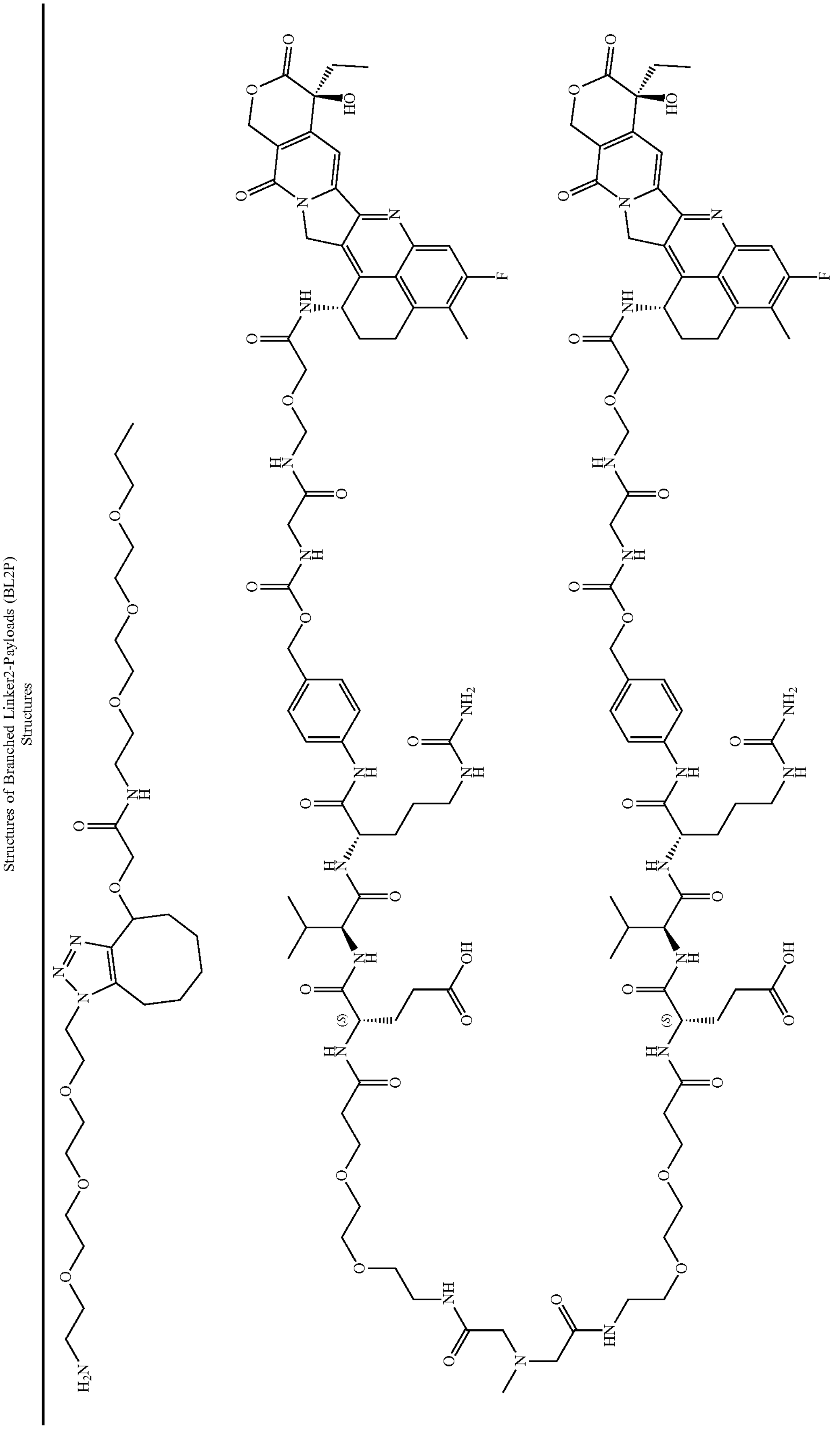

TABLE 2-continued
| Structures of Branched Linker2-Payloads (BL2P) Structures |
|---|
| 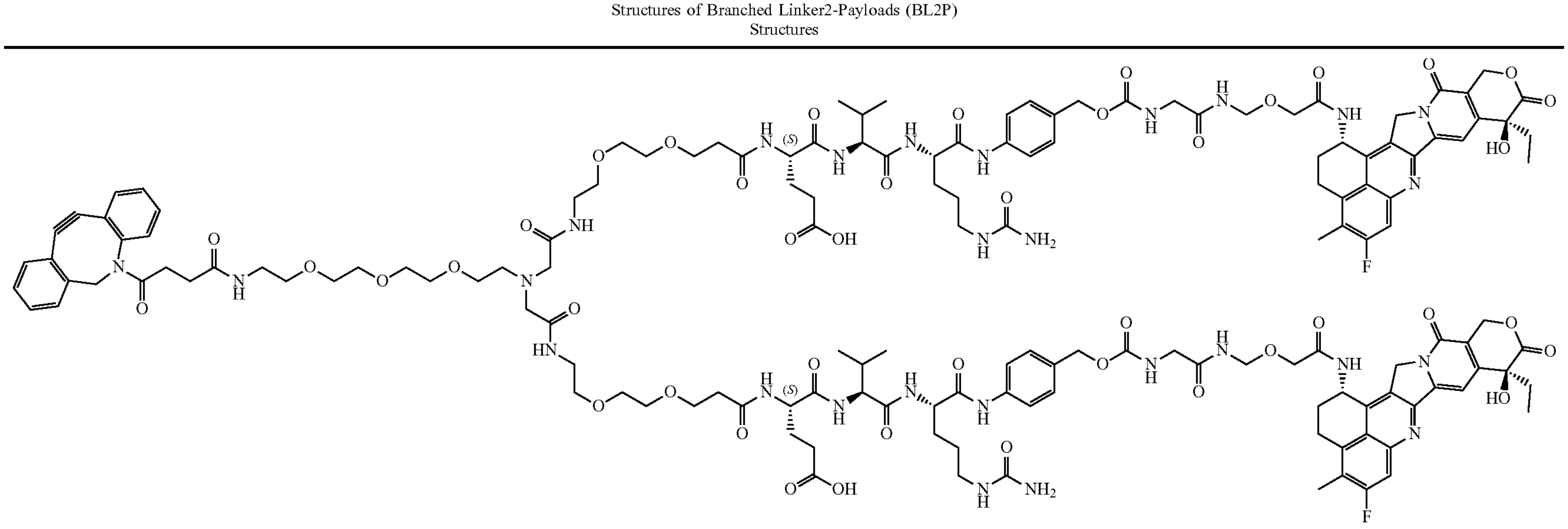 |

TABLE 2-continued
| Structures of Branched Linker2-Payloads (BL2P) Structures |
| --- |
| 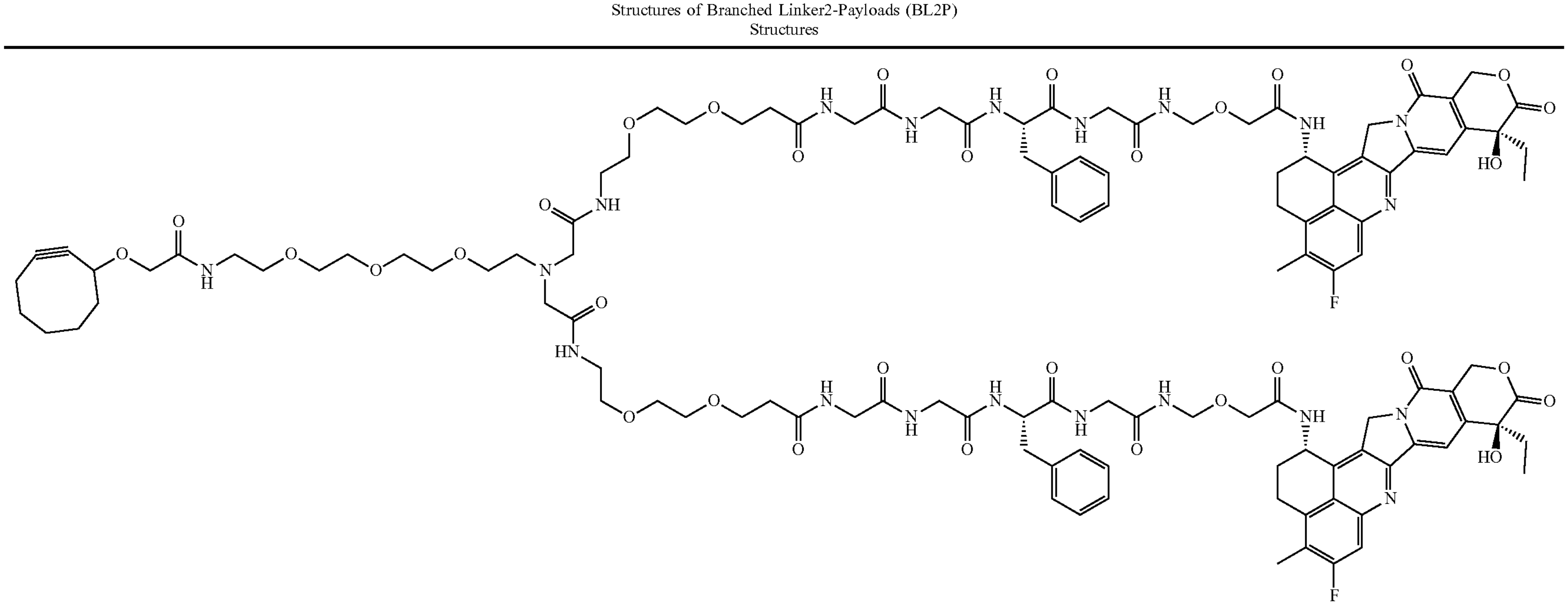 |

TABLE 2-continued
Structures of Branched Linker2-Payloads (BL2P)
Structures
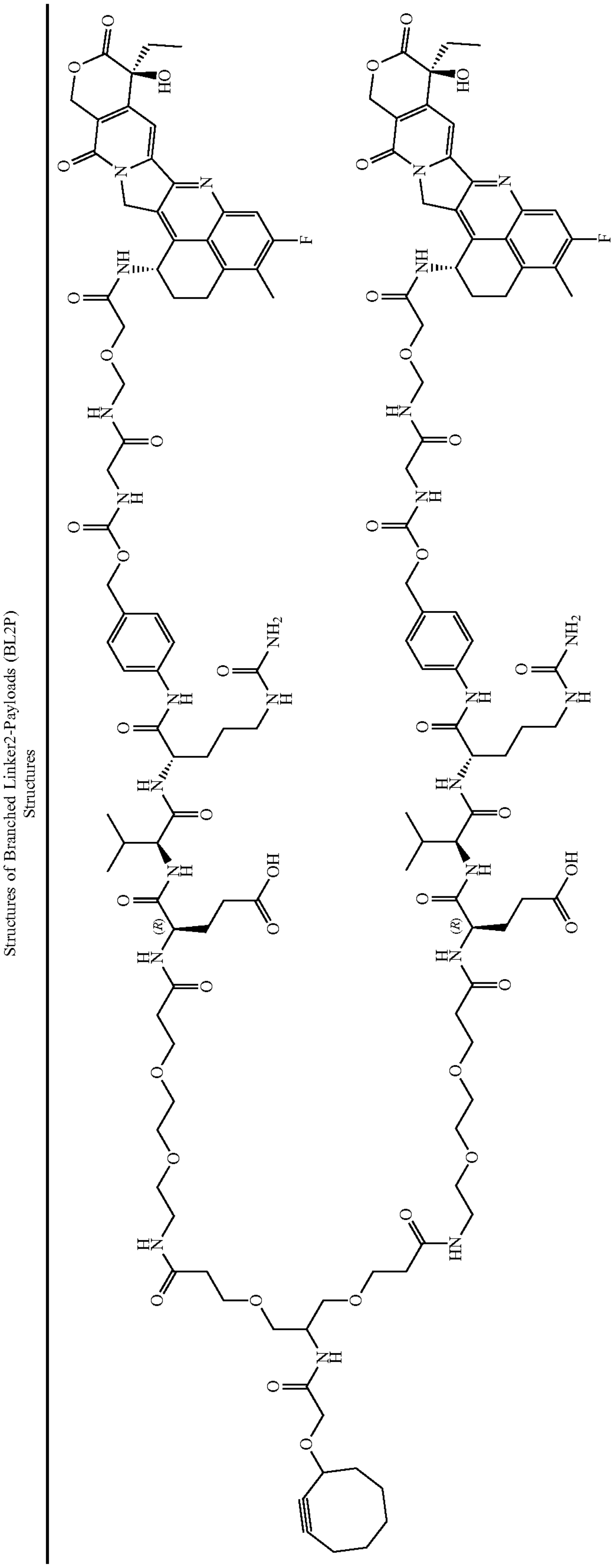

TABLE 2-continued
| Structures of Branched Linker2-Payloads (BL2P) |
| --- |
| Structures |
| 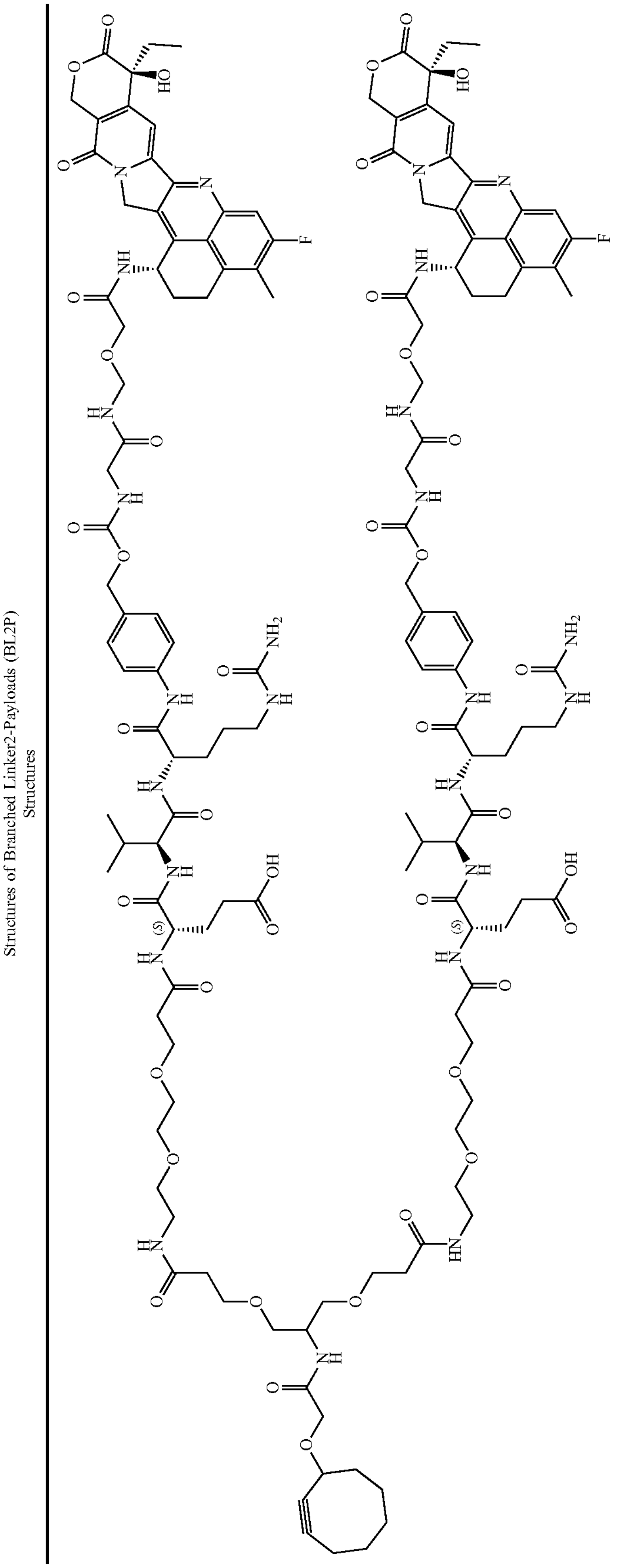 |

TABLE 2-continued
Structures of Branched Linker2-Payloads (BL2P)
Structures
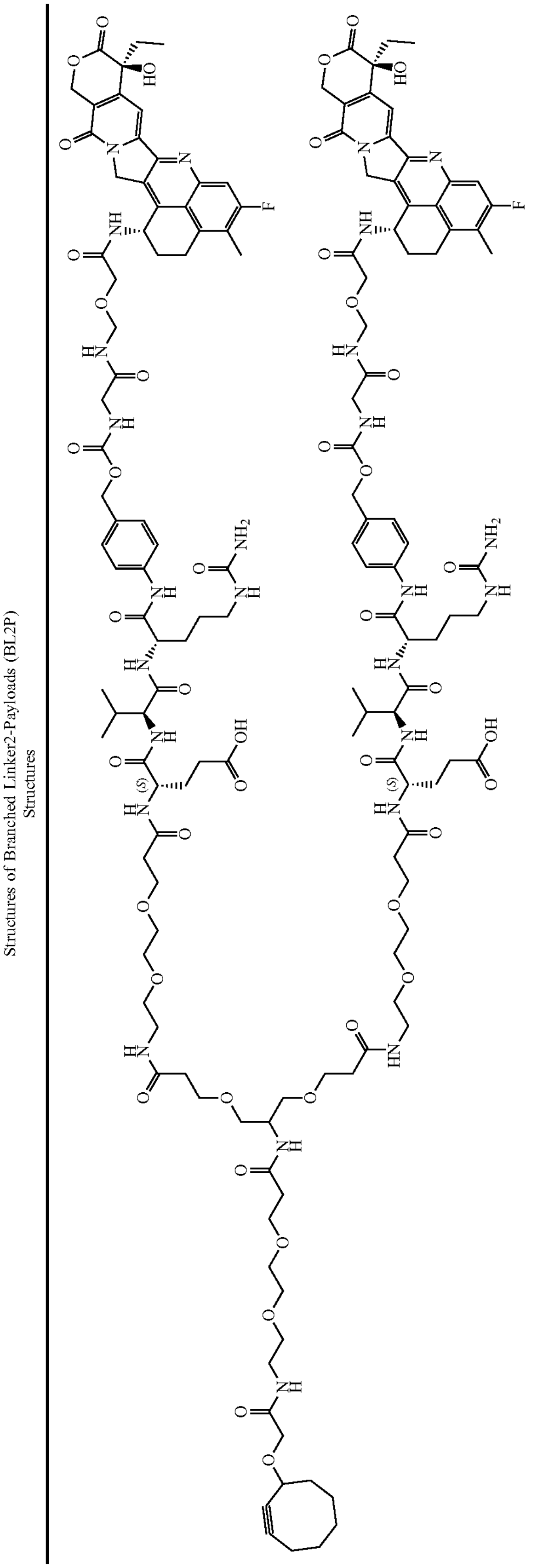

TABLE 2-continued
| Structures of Branched Linker2-Payloads (BL2P) Structures |
|---|
| 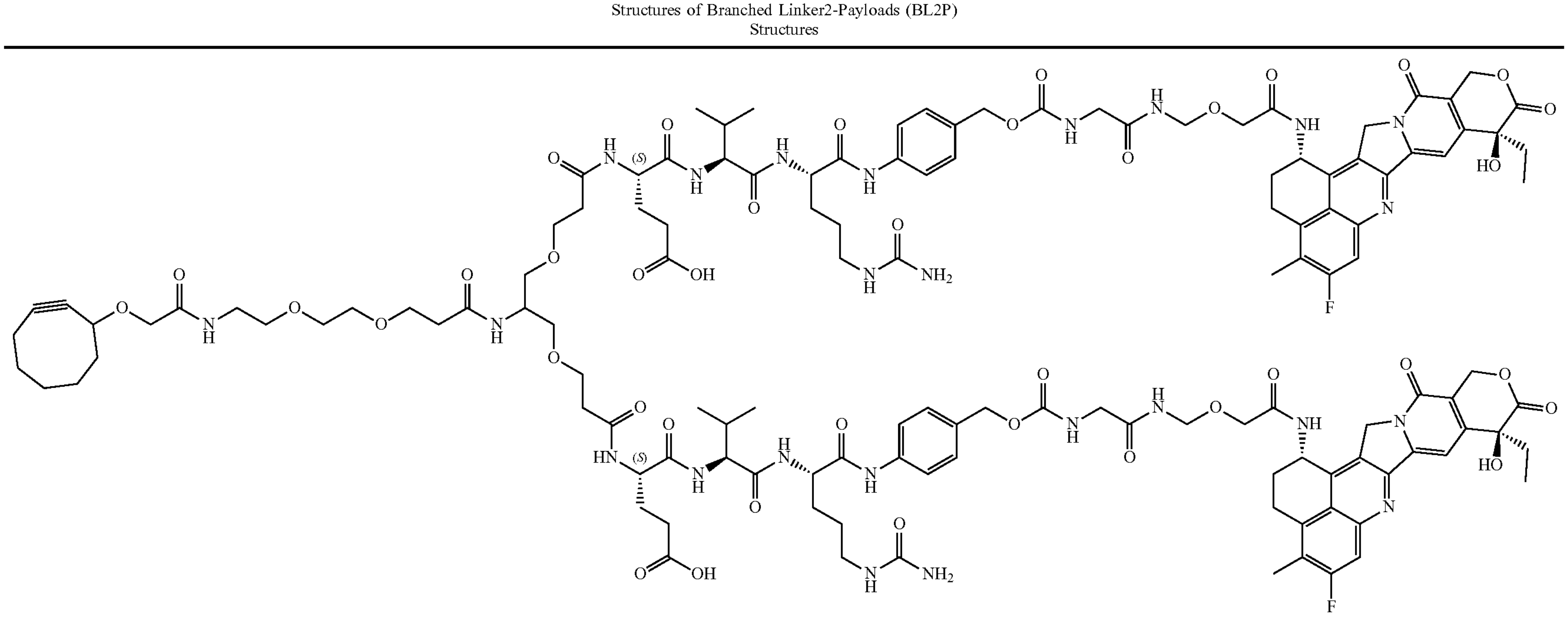 |
| 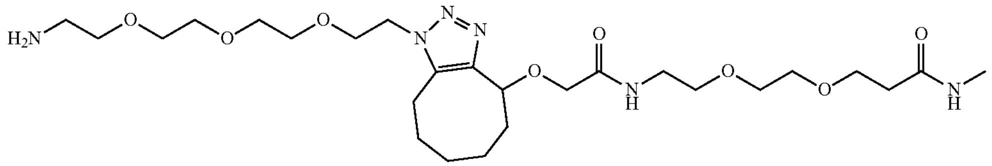 |

TABLE 2-continued
| Structures of Branched Linker2-Payloads (BL2P) |
| --- |
| Structures |
| 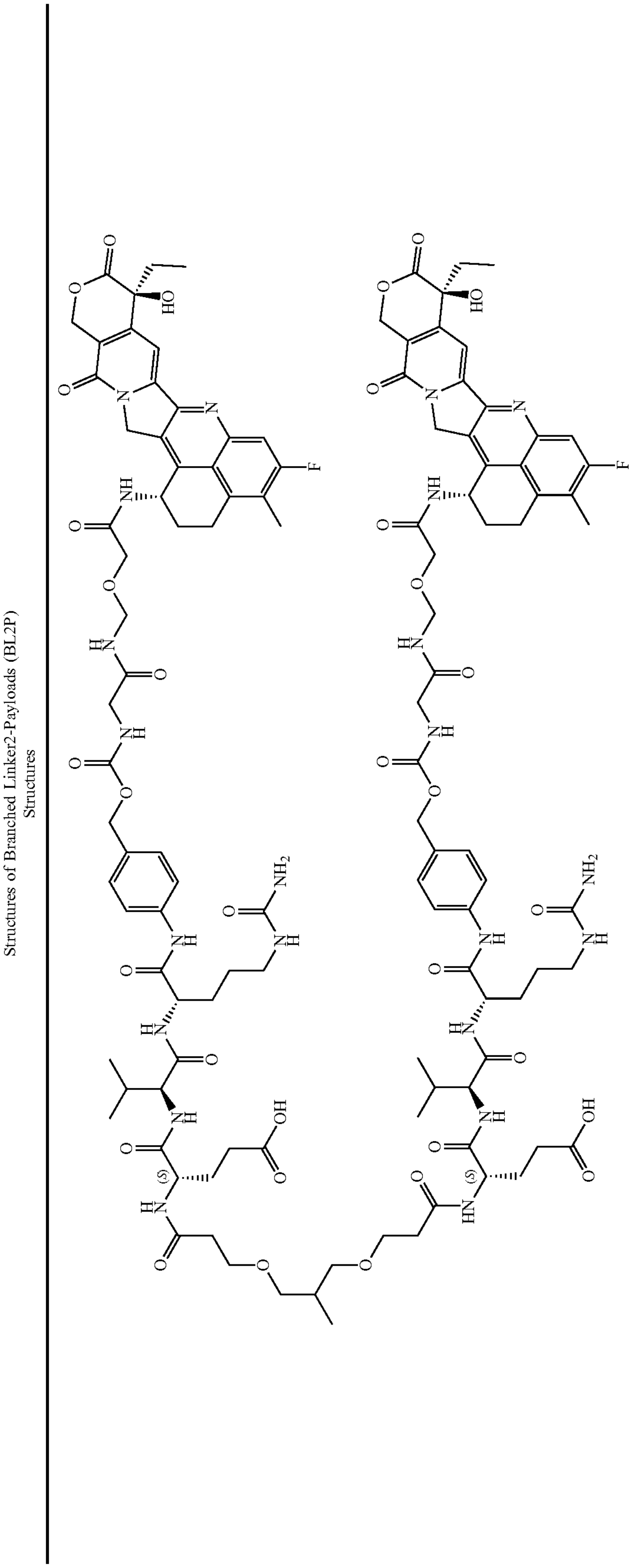 |

TABLE 2-continued
| Structures of Branched Linker2-Payloads (BL2P) Structures |
|---|
| 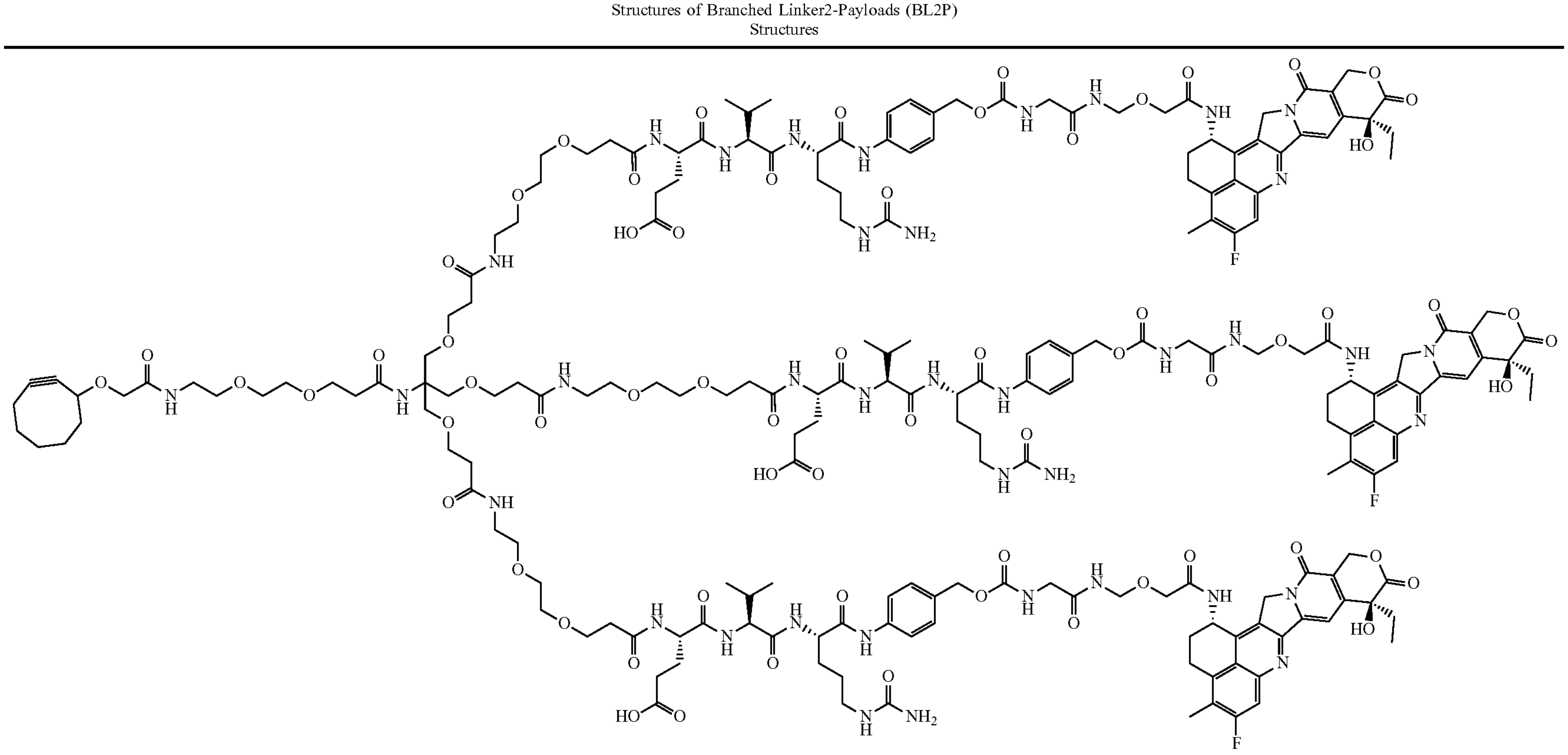 |
| 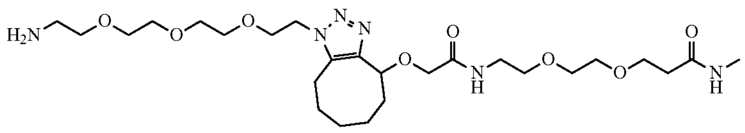 |

TABLE 2-continued
Structures of Branched Linker2-Payloads (BL2P)
Structures
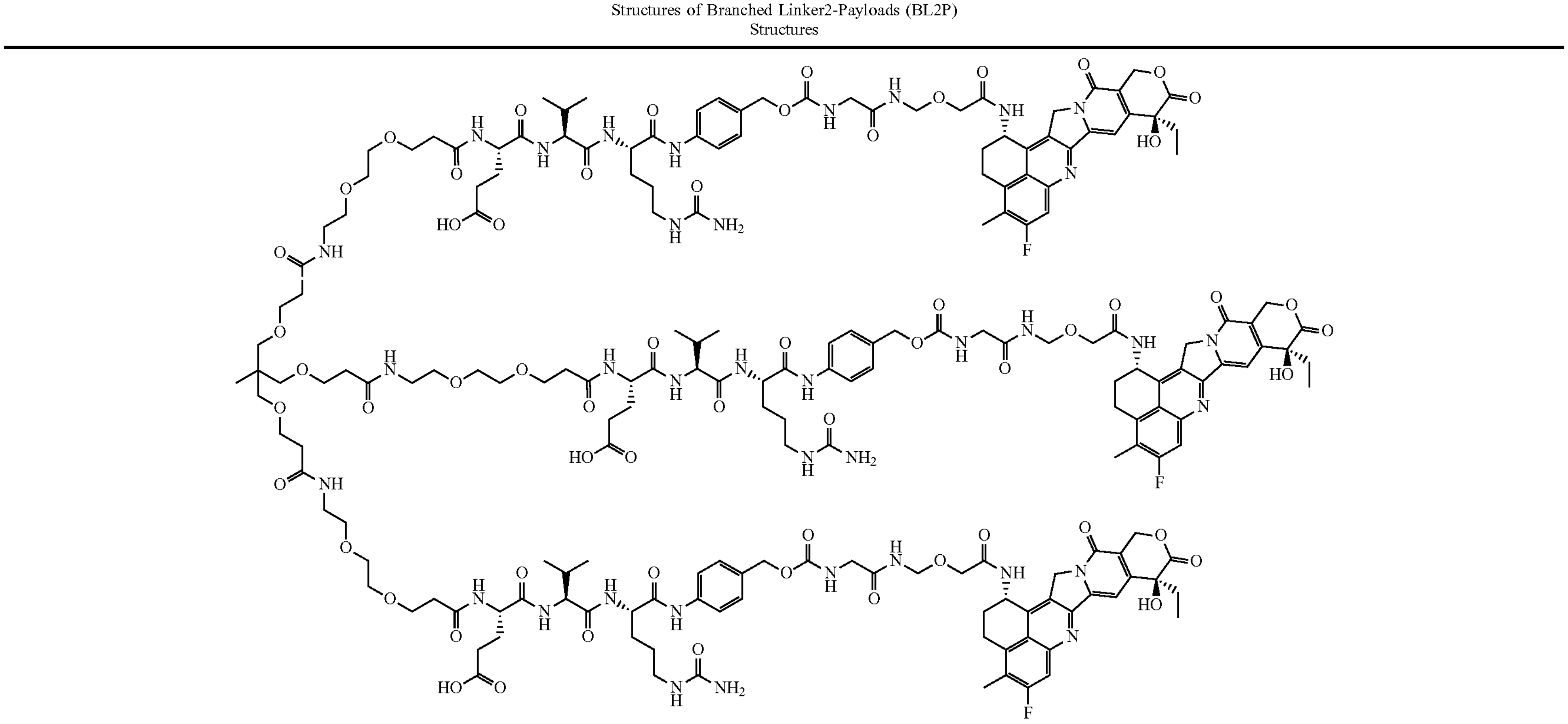

In one embodiment, the compound (i.e., the linker-payload) according to the disclosure has the structure:

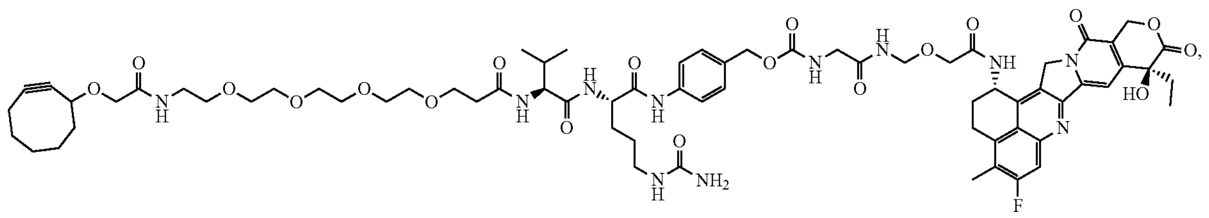 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)OCc1ccc(NC(=O)[C@H](CCCNC(N)=O)NC(=O)[C@@H](NC(=O)CCOCCOCCOCCOCCNC(=O)COC2C#CCCCCC2)C(C)C)cc1)CC3]

or a pharmaceutically acceptable salt thereof.

In some embodiments, the Ab is conjugated to a linker-payload or payload disclosed in WO2015/157592, e.g., compound T32 disclosed therein. In some embodiments, the Ab is conjugated to deruxtecan (DXd), optionally through a linker comprising GGFG.

In some embodiments, Ab is an anti-FGFR2 antibody or antigen-binding fragment thereof comprising the CDRs within the HCVR amino acid sequence of SEQ ID NO: 2 and the CDRs within the LCVR amino acid sequence of SEQ ID NO: 10. In some embodiments, Ab is an anti-FGFR2 antibody or antigen-binding fragment thereof comprising the HCVR amino acid sequence of SEQ ID NO: 2 and the LCVR amino acid sequence of SEQ ID NO: 10.

In some embodiments, Ab is an anti-FGFR2 antibody or antigen-binding fragment thereof comprising the CDRs within the HCVR amino acid sequence of SEQ ID NO: 22 and the CDRs within the LCVR amino acid sequence of SEQ ID NO: 28. In some embodiments, Ab is an anti-FGFR2 antibody or antigen-binding fragment thereof comprising the HCVR amino acid sequence of SEQ ID NO: 22 and the LCVR amino acid sequence of SEQ ID NO: 28.

In some embodiments, Ab is an anti-FGFR2 antibody or antigen-binding fragment thereof comprising the CDRs within the HCVR amino acid sequence of SEQ ID NO: 40 and the CDRs within the LCVR amino acid sequence of SEQ ID NO: 44. In some embodiments, Ab is an anti-FGFR2 antibody or antigen-binding fragment thereof comprising the HCVR amino acid sequence of SEQ ID NO: 40 and the LCVR amino acid sequence of SEQ ID NO: 44.

In some embodiments, L is a cleavable linker. In some embodiments, L is a non-cleavable linker. In some embodiments, L comprises a dipeptide. In some embodiments, L comprises a PAB moiety.

In some embodiments, L comprises a moiety having the following structure:

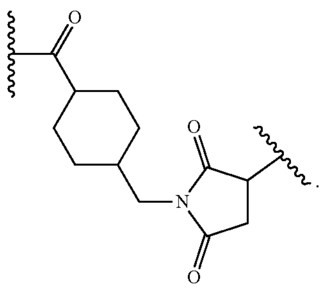 [SMILES: *C(=O)C1CCC(CN2C(=O)CC(*)C2=O)CC1]

In some embodiments, L comprises a moiety having the following structure:

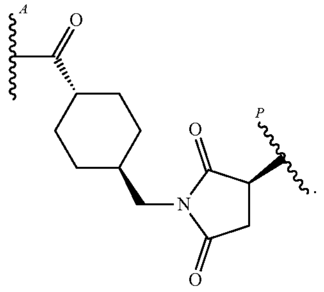

In some embodiments, L comprises a moiety having the following structure:

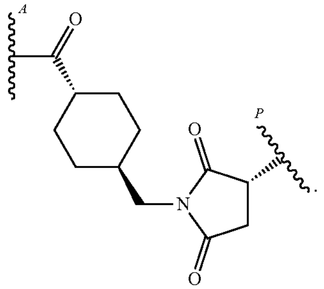

In some embodiments, L comprises a moiety having the following structure:

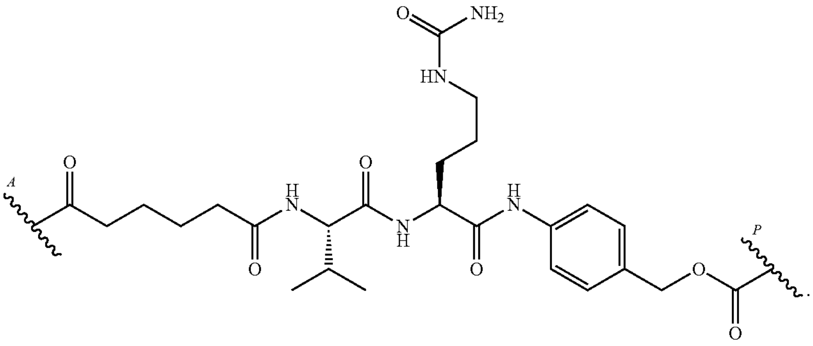
In some embodiments, Pay is a tubulysin.
In some embodiments, Pay is a camptothecin analog.
In some embodiments, Pay is a maytansinoid.
In some embodiments, Pay is:
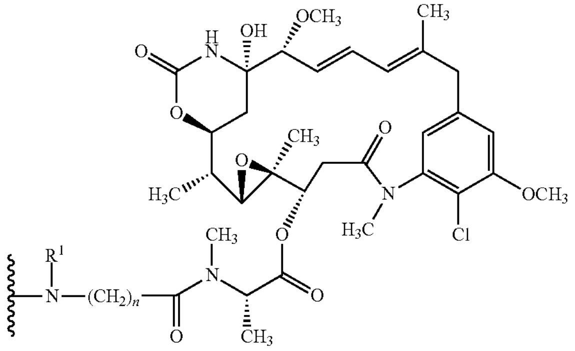
wherein $R^1$ is alkyl.
In some embodiments, Pay is:
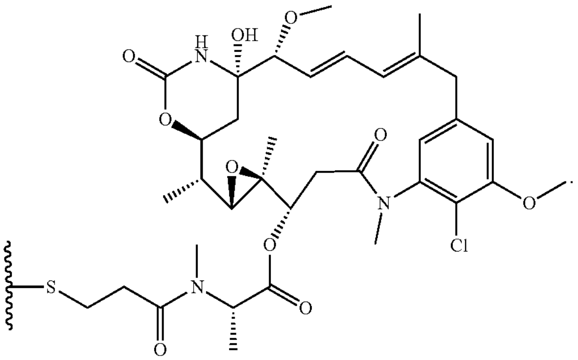 [SMILES: *SCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]
In some embodiments, Pay is:
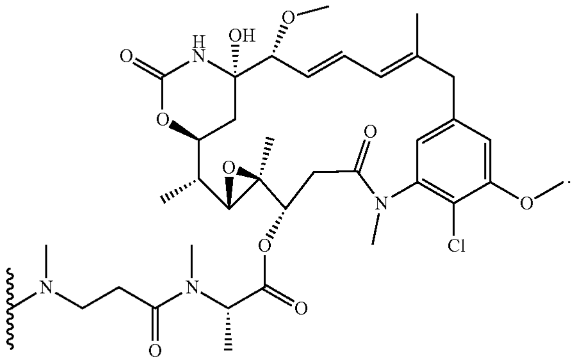 [SMILES: *N(C)CCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]
In some embodiments, n is an integer from 2 to 5.
In some embodiments, -L-Pay is:
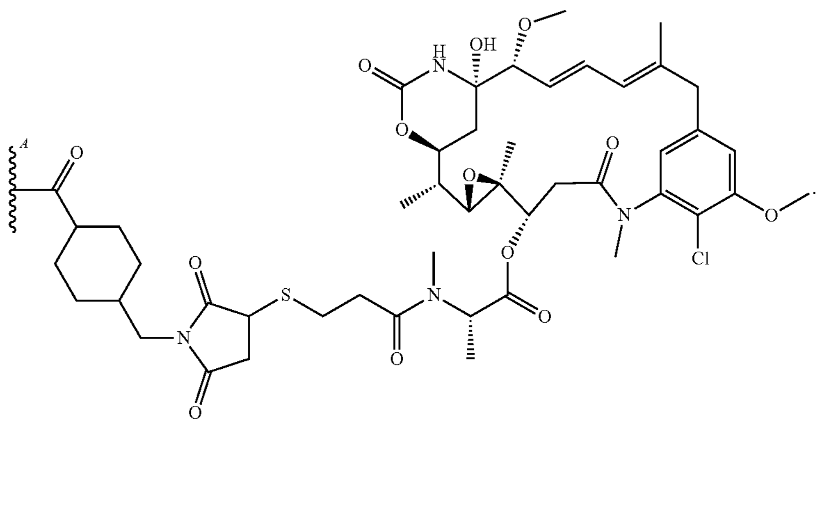

wherein
is a bond to the antibody.
In some embodiments, -L-Pay is:
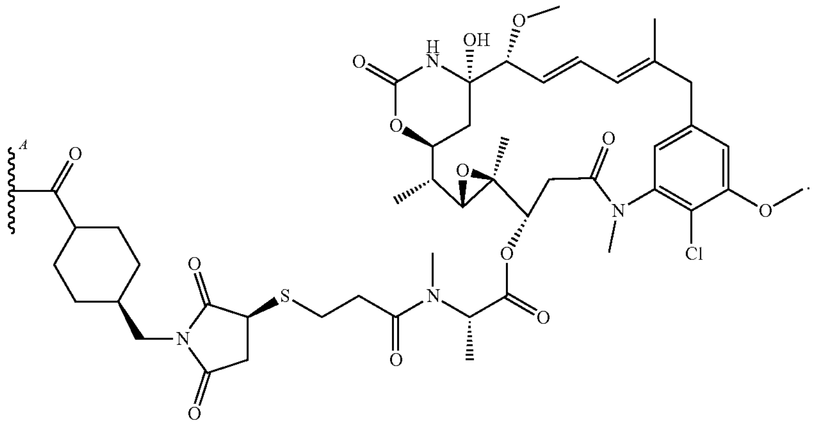
wherein
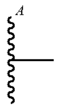
is a bond to the antibody.
In some embodiments, -L-Pay is
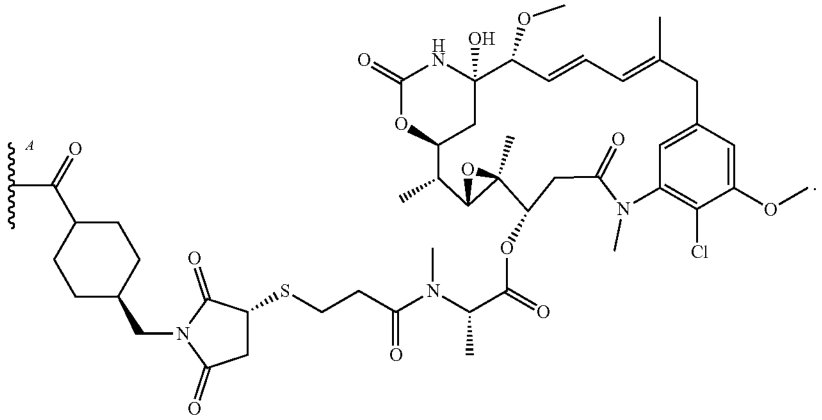
wherein
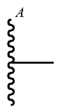
is a bond to the antibody.

In some embodiments, -L-Pay is:

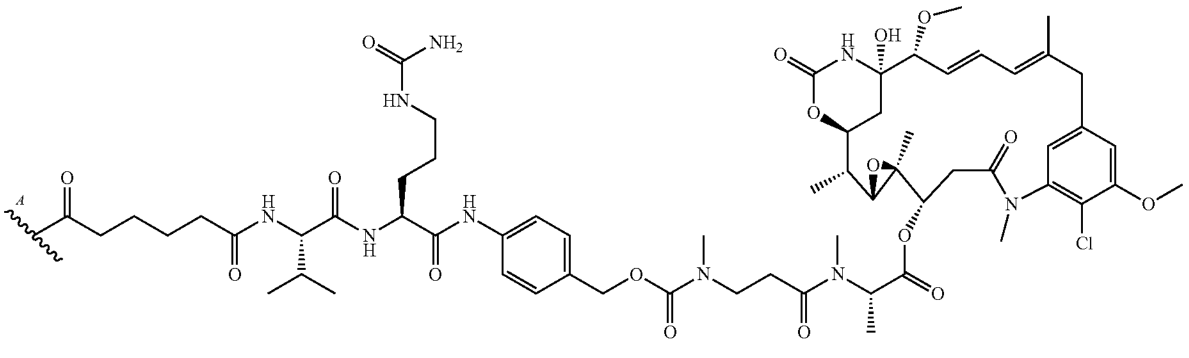

wherein

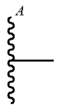

is a bond to the antibody.

In some embodiments, the conjugates have the following structure:

Ab-[L-Pay]$_n$ wherein: Ab is an anti-FGFR2 antibody or antigen-binding fragment thereof comprising:

(i) an HCDR1 having the amino acid sequence of SEQ ID NO: 4; an HCDR2 having the amino acid sequence of SEQ ID NO: 6; an HCDR3 having the amino acid sequence of SEQ ID NO: 8; an LCDR1 having the amino acid sequence of SEQ ID NO: 12; an LCDR2 having the amino acid sequence of GAS; and an LCDR3 having the amino acid sequence of SEQ ID NO: 16;

L-Pay is (maytansinoid 1ALP) wherein

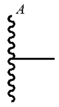

is a bond to the antigen-binding protein; and n is an integer from 2-5.

In some embodiments, the conjugates have the following structure:

Ab-[L-Pay]$_n$ wherein: Ab is an anti-FGFR2 antibody or antigen-binding fragment thereof comprising:

(ii) an HCDR1 having the amino acid sequence of SEQ ID NO: 24; an HCDR2 having the amino acid sequence of SEQ ID NO: 6; an HCDR3 having the amino acid sequence of SEQ ID NO: 26; an LCDR1 having the amino acid sequence of SEQ ID NO: 30; an LCDR2 having the amino acid sequence of KAS; and an LCDR3 having the amino acid sequence of SEQ ID NO: 34;

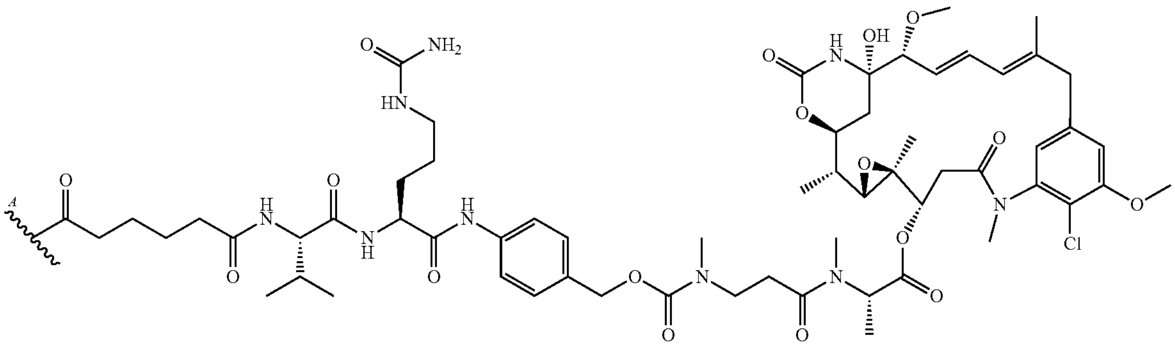

L-Pay is

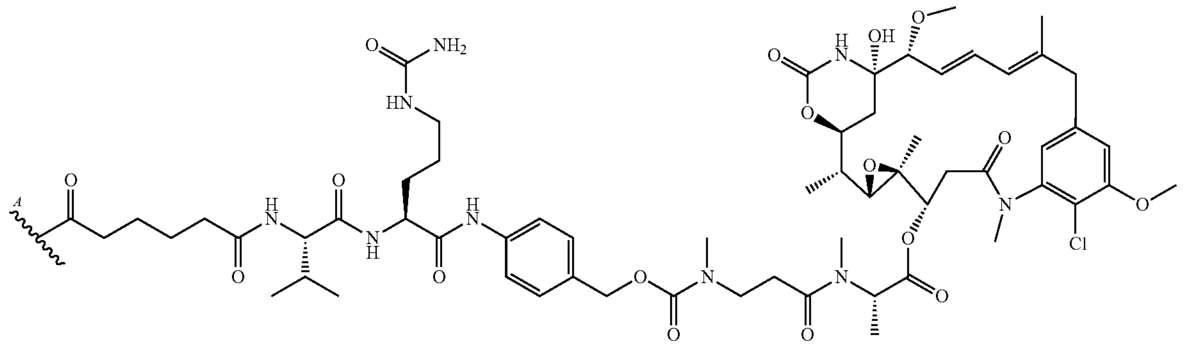

(maytansinoid 1ALP) wherein

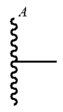

is a bond to the antigen-binding protein; and n is an integer from 2-5.

In some embodiments, the conjugates have the following structure:

Ab-[L-Pay]$_n$ wherein: Ab is an anti-FGFR2 antibody or antigen-binding fragment thereof comprising:

(i) an HCDR1 having the amino acid sequence of SEQ ID NO: 4; an HCDR2 having the amino acid sequence of SEQ ID NO: 6; an HCDR3 having the amino acid sequence of SEQ ID NO: 8; an LCDR1 having the amino acid sequence of SEQ ID NO: 12; an LCDR2 having the amino acid sequence of GAS; and an LCDR3 having the amino acid sequence of SEQ ID NO: 16; Pay is

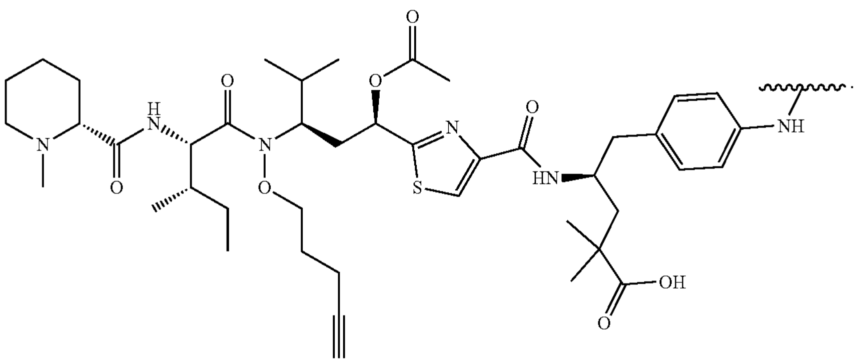 [SMILES: *Nc1ccc(C[C@@H](CC(C)(C)C(=O)O)NC(=O)c2csc([C@@H](C[C@H](C(C)C)N(OCCCC#C)C(=O)[C@@H](NC(=O)[C@H]3CCCCN3C)[C@@H](C)CC)OC(C)=O)n2)cc1]

wherein

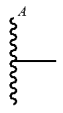

is a bond to the antigen-binding protein; and n is an integer from 2-5.

In some embodiments, the conjugates have the following structure:

Ab-[L-Pay]$_n$ wherein: Ab is an anti-FGFR2 antibody or antigen-binding fragment thereof comprising:

(ii) an HCDR1 having the amino acid sequence of SEQ ID NO: 24; an HCDR2 having the amino acid sequence of SEQ ID NO: 6; an HCDR3 having the amino acid sequence of SEQ ID NO: 26; an LCDR1 having the amino acid sequence of SEQ ID NO: 30; an LCDR2 having the amino acid sequence of KAS; and an LCDR3 having the amino acid sequence of SEQ ID NO: 34;

Pay is

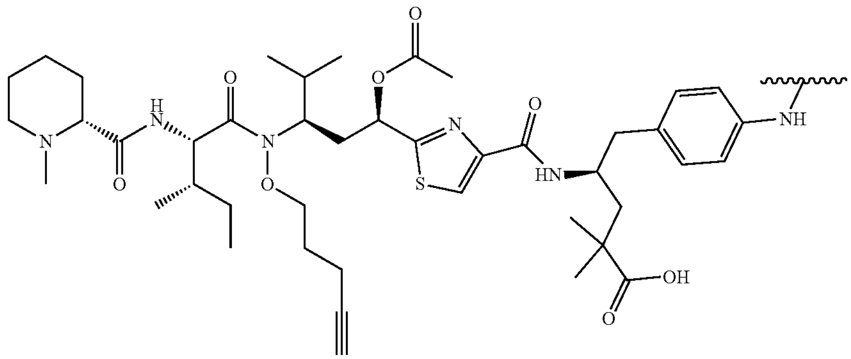 [SMILES: *Nc1ccc(C[C@@H](CC(C)(C)C(=O)O)NC(=O)c2csc([C@@H](C[C@H](C(C)C)N(OCCCC#C)C(=O)[C@@H](NC(=O)[C@H]3CCCCN3C)[C@@H](C)CC)OC(C)=O)n2)cc1]

wherein

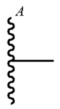

is a bond to the antigen-binding protein; and n is an integer from 2-5.

In some embodiments, the conjugates have the following structure:

Ab-[L-Pay]$_n$ wherein: Ab is an anti-FGFR2 antibody or antigen-binding fragment thereof comprising:

(i) an HCDR1 having the amino acid sequence of SEQ ID NO: 4; an HCDR2 having the amino acid sequence of SEQ ID NO: 6; an HCDR3 having the amino acid sequence of SEQ ID NO: 8; an LCDR1 having the amino acid sequence of SEQ ID NO: 12; an LCDR2 having the amino acid sequence of GAS; and an LCDR3 having the amino acid sequence of SEQ ID NO: 16;

L-Pay is

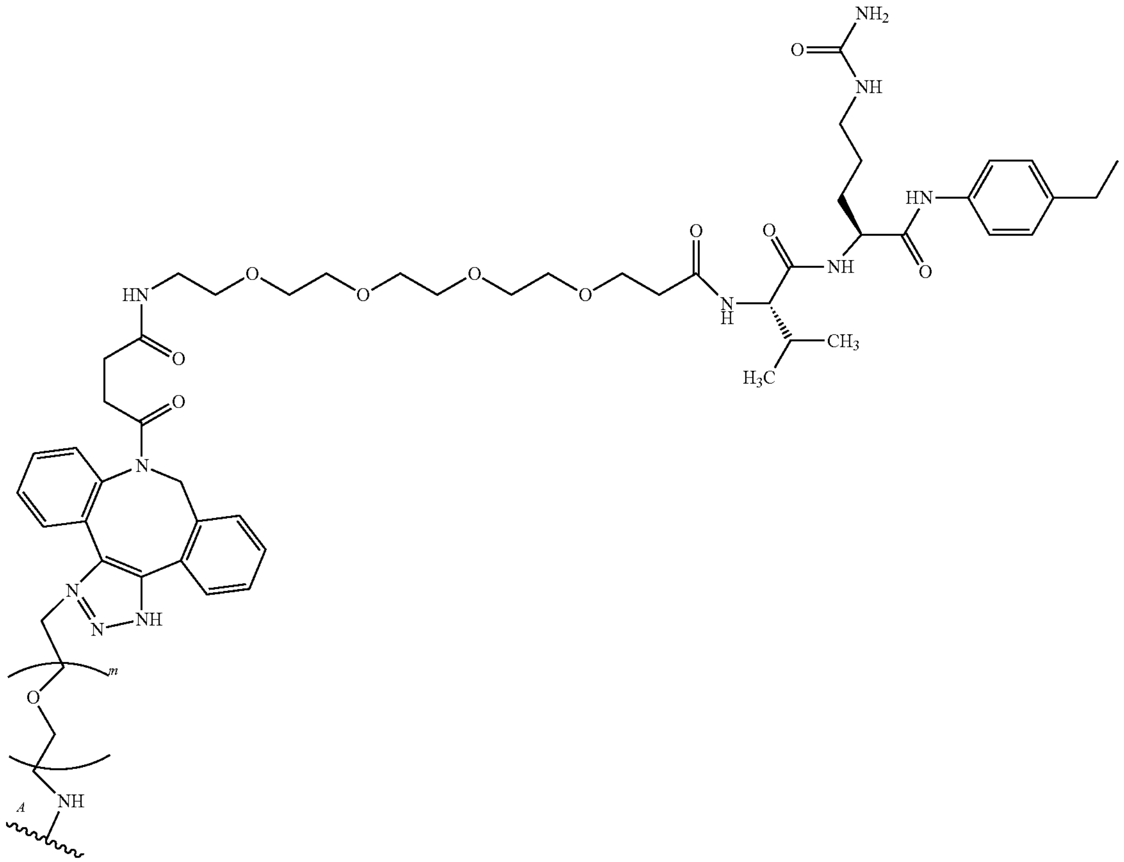

-continued

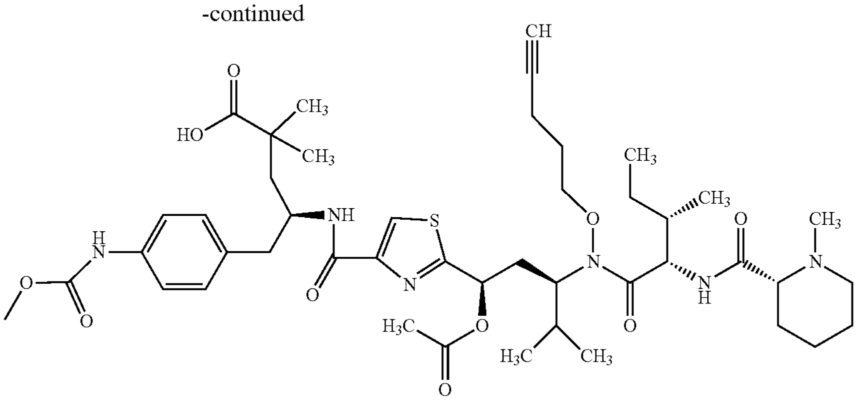

or cycloaddition regioisomer thereof wherein

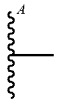

is a bond to a heavy chain glutamine. In some embodiments, n is 2. In certain embodiments, n is 2 and L-Pay is bonded to Q295 glutamines. In some embodiments, n is 4. In certain embodiments, n is 4 and L-Pay is bonded to Q295 and Q297 glutamines.

In some embodiments, the conjugates have the following structure:

Ab-[L-Pay]$_n$ wherein: Ab is an anti-FGFR2 antibody or antigen-binding fragment thereof comprising: (ii) an HCDR1 having the amino acid sequence of SEQ ID NO: 24; an HCDR2 having the amino acid sequence of SEQ ID NO: 6; an HCDR3 having the amino acid sequence of SEQ ID NO: 26; an LCDR1 having the amino acid sequence of SEQ ID NO: 30; an LCDR2 having the amino acid sequence of KAS; and an LCDR3 having the amino acid sequence of SEQ ID NO: 34;

L-Pay is

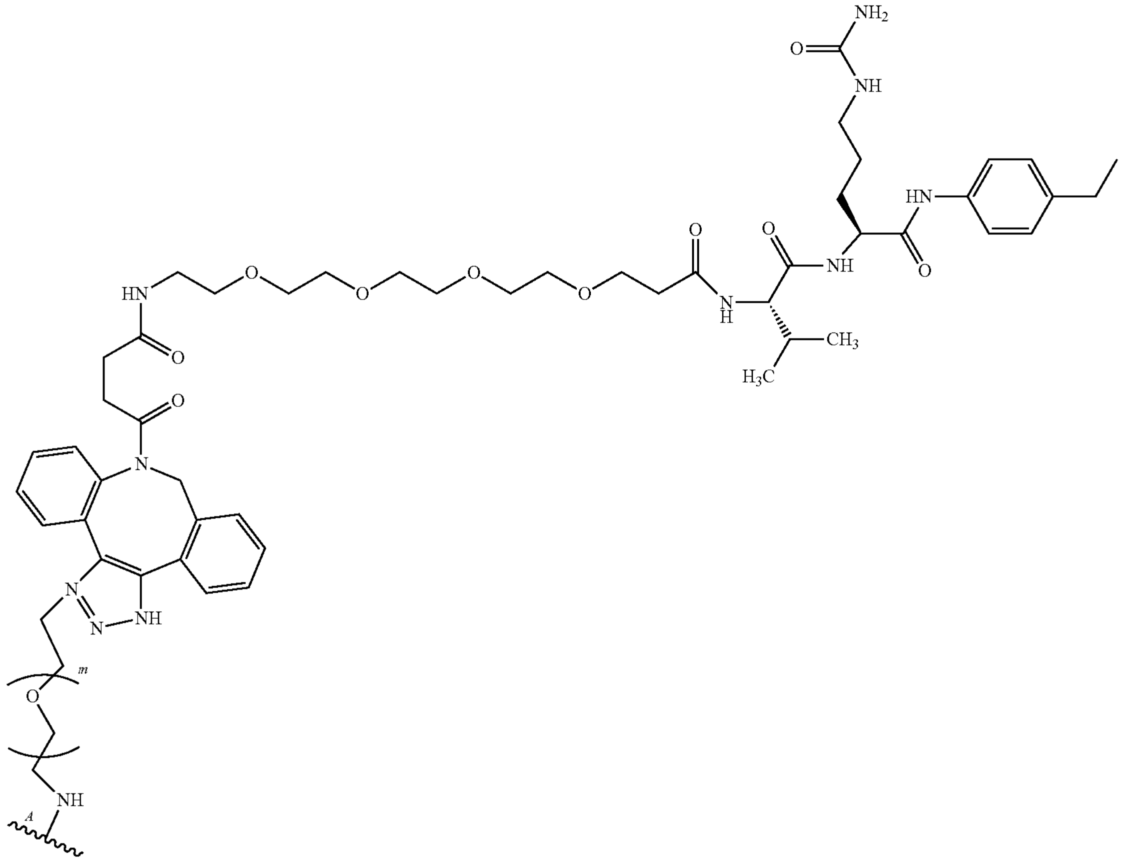

-continued

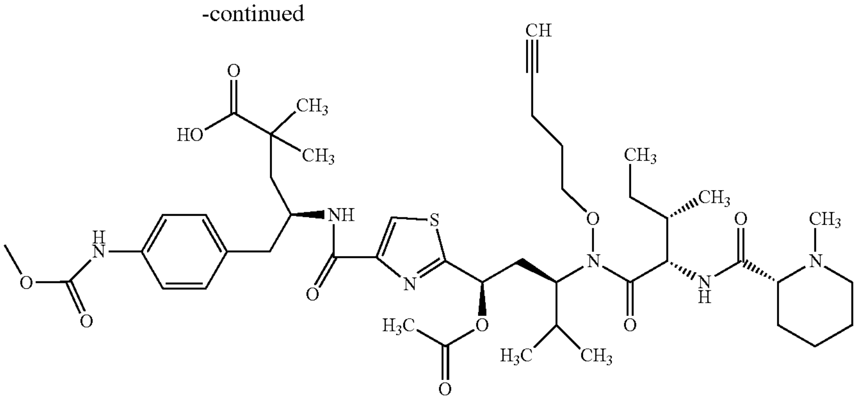

or cycloaddition regioisomer thereof wherein

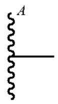

is a bond to a heavy chain glutamine. In some embodiments, n is 2. In certain embodiments, n is 2 and L-Pay is bonded to Q295 glutamines. In some embodiments, n is 4. In certain embodiments, n is 4 and L-Pay is bonded to Q295 and Q297 glutamines.

In some embodiments, the conjugates have the following structure:

Ab-[L-Pay]$^n$ wherein: Ab is an anti-FGFR2 antibody or antigen-binding fragment thereof comprising:

(i) an HCDR1 having the amino acid sequence of SEQ ID NO: 4; an HCDR2 having the amino acid sequence of SEQ ID NO: 6; an HCDR3 having the amino acid sequence of SEQ ID NO: 8; an LCDR1 having the amino acid sequence of SEQ ID NO: 12; an LCDR2 having the amino acid sequence of GAS; and an LCDR3 having the amino acid sequence of SEQ ID NO: 16; Pay is

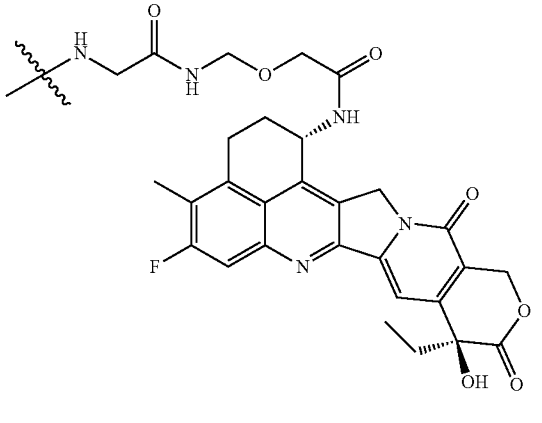

Or

-continued

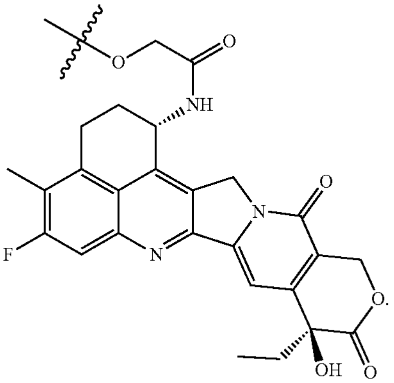

wherein ∿ represents the point of attachment to the antibody, through a linker; and n is an integer from 2-8.

In some embodiments, the conjugates have the following structure:

Ab-[L-Pay]$_n$ wherein: Ab is an anti-FGFR2 antibody or antigen-binding fragment thereof comprising:

(ii) an HCDR1 having the amino acid sequence of SEQ ID NO: 24; an HCDR2 having the amino acid sequence of SEQ ID NO: 6; an HCDR3 having the amino acid sequence of SEQ ID NO: 26; an LCDR1 having the amino acid sequence of SEQ ID NO: 30; an LCDR2 having the amino acid sequence of KAS; and an LCDR3 having the amino acid sequence of SEQ ID NO: 34;

Pay is

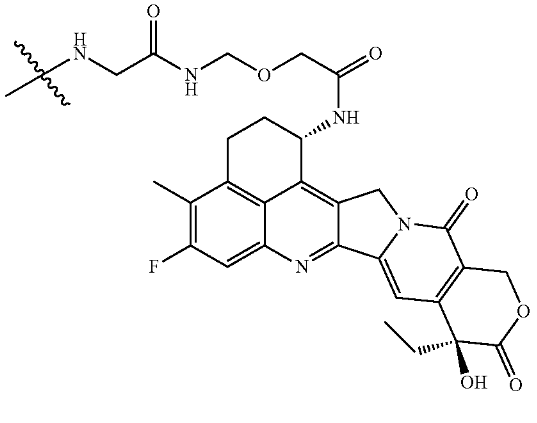

Or

-continued

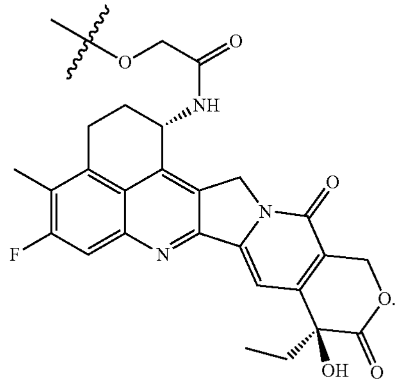

wherein  represents the point of attachment to the antibody, through a linker; and n is an integer from 2-8.

In some embodiments, the conjugates have the following structure:

Ab-[L-Pay]$_n$ wherein: Ab is an anti-FGFR2 antibody or antigen-binding fragment thereof comprising:

(i) an HCDR1 having the amino acid sequence of SEQ ID NO: 4; an HCDR2 having the amino acid sequence of SEQ ID NO: 6; an HCDR3 having the amino acid sequence of SEQ ID NO: 8; an LCDR1 having the amino acid sequence of SEQ ID NO: 12; an LCDR2 having the amino acid sequence of GAS; and an LCDR3 having the amino acid sequence of SEQ ID NO: 16;

L-Pay is

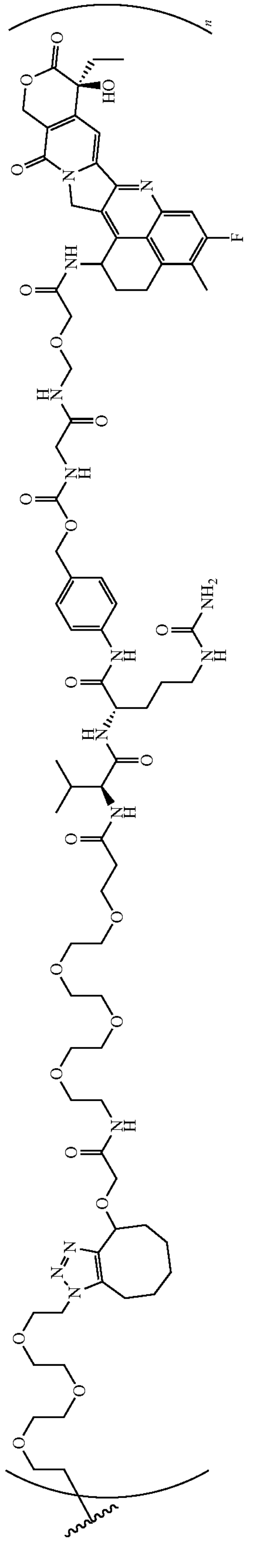
Or
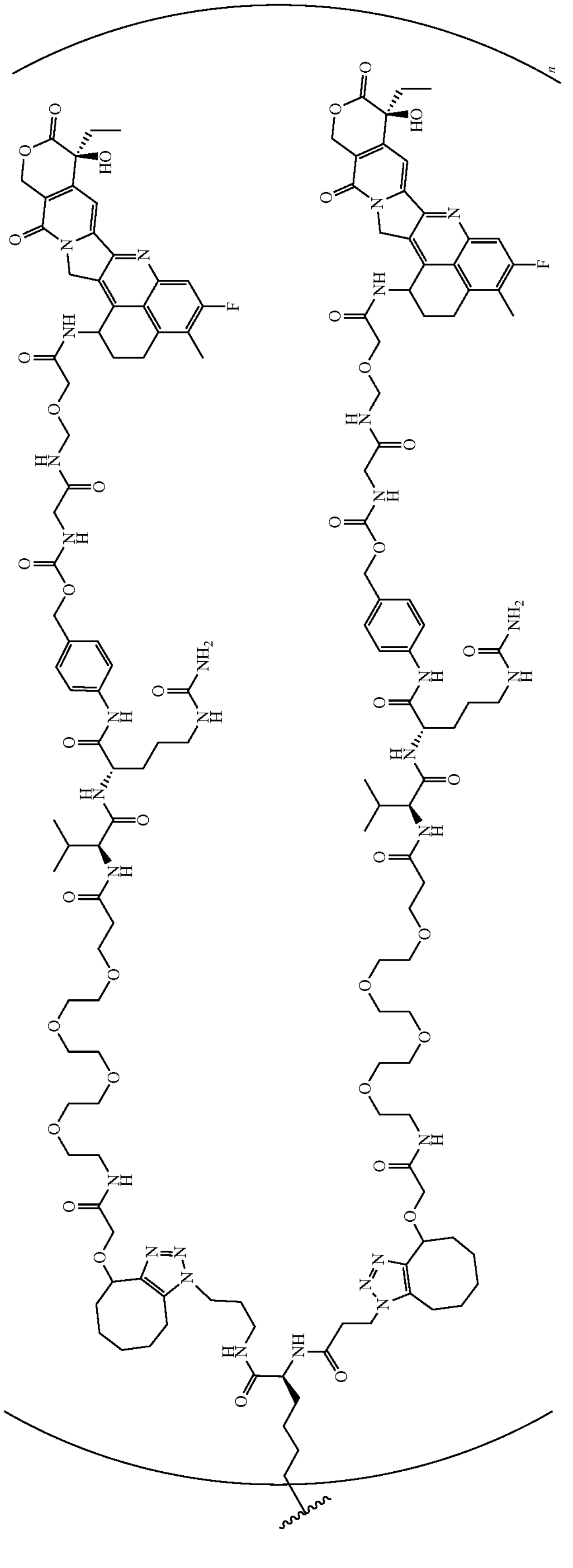

wherein L-pay is bonded to Ab through a heavy chain glutamine. In some embodiments, n is 2. In certain embodiments, n is 2 and L-Pay is bonded to Q295 glutamines. In some embodiments, n is 4. In certain embodiments, n is 4 and L-Pay is bonded to Q295 and Q297 glutamines. In some embodiments, n is 6. In some embodiments, n is 8. In some embodiments, n is 8, L is branched, and L-Pay is bonded to Q295 and Q297.

In some embodiments, the conjugates have the following structure:

Ab-[L-Pay]$_n$ wherein: Ab is an anti-FGFR2 antibody or antigen-binding fragment thereof comprising:

(ii) an HCDR1 having the amino acid sequence of SEQ ID NO: 24; an HCDR2 having the amino acid sequence of SEQ ID NO: 6; an HCDR3 having the amino acid sequence of SEQ ID NO: 26; an LCDR1 having the amino acid sequence of SEQ ID NO: 30; an LCDR2 having the amino acid sequence of KAS; and an LCDR3 having the amino acid sequence of SEQ ID NO: 34;

L-Pay is

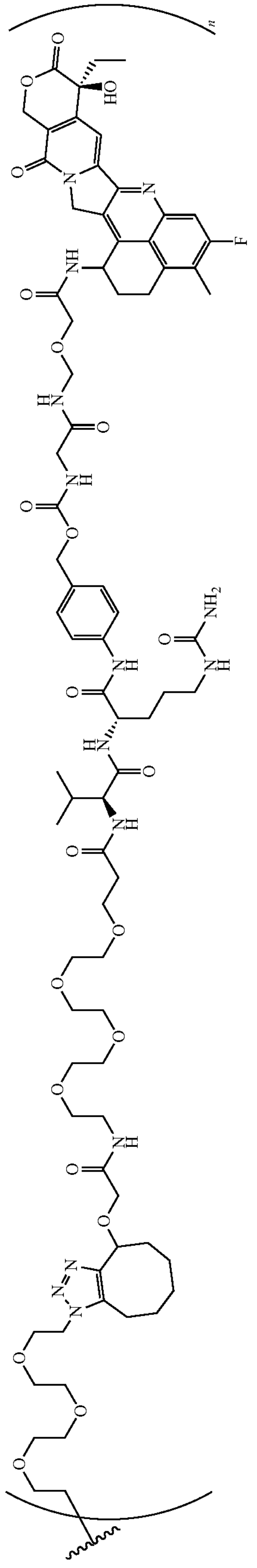
Or
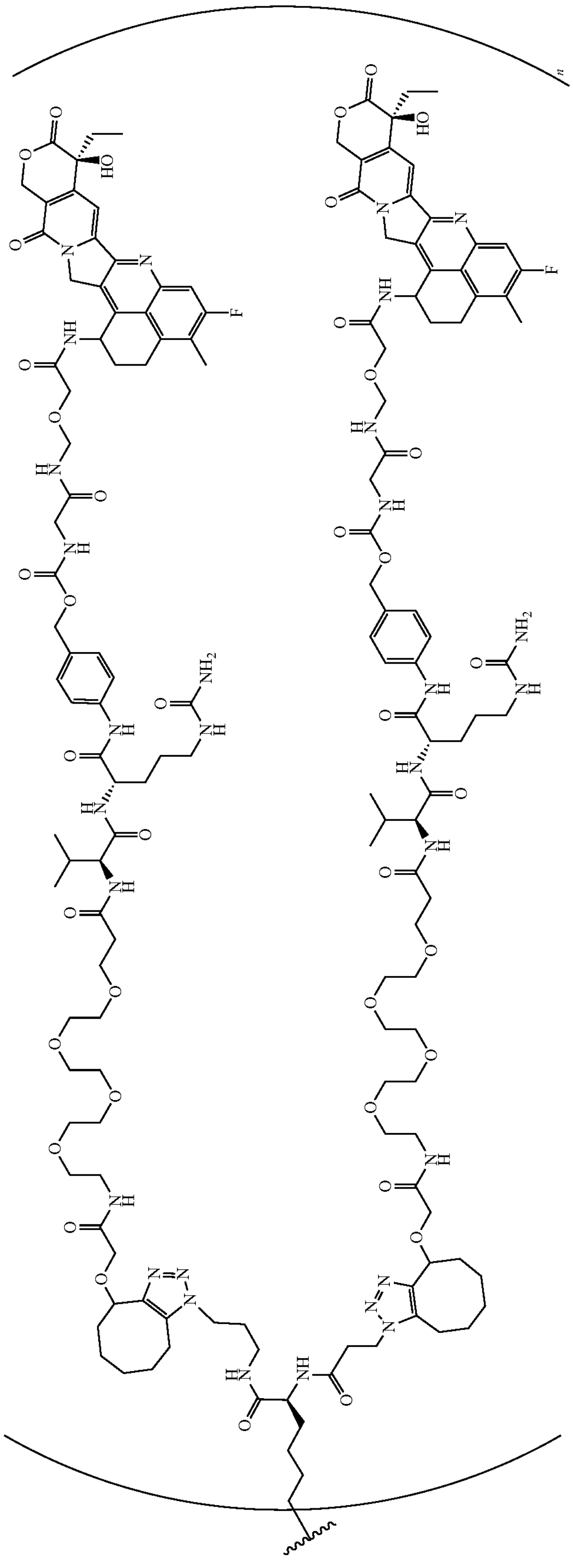

wherein L-pay is bonded to Ab through a heavy chain glutamine. In some embodiments, n is 2. In certain embodiments, n is 2 and L-Pay is bonded to Q295 glutamines. In some embodiments, n is 4. In certain embodiments, n is 4 and L-Pay is bonded to Q295 and Q297 glutamines. In some embodiments, n is 6. In some embodiments, n is 8. In some embodiments, n is 8, L is branched, and L-Pay is bonded to Q295 and Q297.

The antibody drug conjugates described herein can be prepared using conjugation conditions known to those of ordinary skill in the art, (see, e.g., Doronina et al. *Nature Biotechnology* 2003, 21, 7, 778, which is incorporated herein by reference in its entirety). In some embodiments an anti-FGFR2 antibody or antigen-binding fragment thereof antibody drug conjugate is prepared by contacting an anti-FGFR2 antibody or antigen-binding fragment thereof described herein with a compound comprising the desired linker and cytotoxic agent, wherein said linker possesses a moiety that is reactive with the antibody or antigen-binding protein, e.g., at the desired residue of the antibody or antigen-binding protein.

In some embodiments, the antibody drug conjugates provided herein are conjugated at heavy chain Q295 and/or Q297 glutamines. Antibodies comprising heavy chain Q297 glutamines can be prepared using techniques known in the art, e.g., through N297Q mutation. See, e.g., *Bioconjugate Chem.* 2014, 25, 3, 569 (2014). Such conjugation methods can provide antibody drug conjugates having a DAR of 2 or 4. In such embodiments where the linker is branched, the conjugations methods can provide antibody drug conjugates having a DAR of 6 or 8.

In some embodiments, such methods comprise installing a first reactive moiety at the heavy chain glutamines by reacting the antibody with a primary amine compound comprising said first reactive moiety in the presence of transglutaminase to produce an antibody comprising the first reactive moiety at Q295, and optionally Q297. This product can be subsequently reacted with a payload having a linker and complementary second reactive moiety to provide antibody-drug conjugates provided herein. In some embodiments, the first reactive moiety is an azide. In some embodiments, the second reactive moiety is a cycloalkyne. In some embodiments, the payload having a linker and complementary second reactive moiety is:

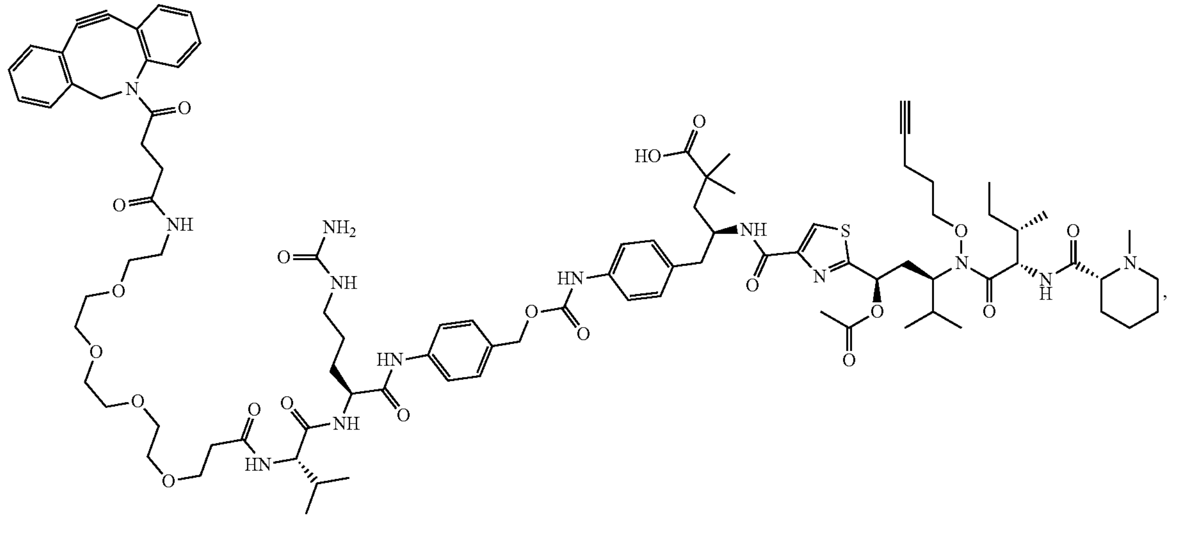 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)OCc3ccc(NC(=O)[C@H](CCCNC(N)=O)NC(=O)[C@@H](NC(=O)CCOCCOCCOCCOCCNC(=O)CCC(=O)N4Cc5ccccc5C#Cc5ccccc54)C(C)C)cc3)cc2)CC(C)(C)C(=O)O)cs1)C(C)C]

which can be prepared using methods described in U.S. patent application Ser. No. 16/724,164 filed Dec. 20, 2019 (e.g., compound LP4 described therein). In certain embodiments, the primary amine compound is

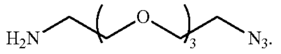

In some embodiments, provided herein are processes for preparing an antibody-drug conjugate comprising contacting an anti-FGFR2 antibody or antigen-binding fragment thereof described herein with a compound

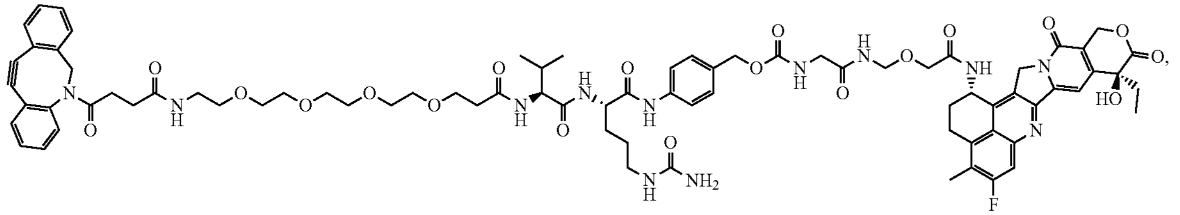 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)OCc1ccc(NC(=O)[C@H](CCCNC(N)=O)NC(=O)[C@@H](NC(=O)CCOCCOCCOCCOCCNC(=O)CCC(=O)N2Cc4ccccc4C#Cc4ccccc42)C(C)C)cc1)CC3]

wherein the anti-FGFR2 is functionalized with an azide.

In some embodiments, provided herein are processes for preparing an antibody-drug conjugate comprising contacting an anti-FGFR2 antibody or antigen-binding fragment thereof described herein with a compound having the following formula $A^1$:

$A^1$

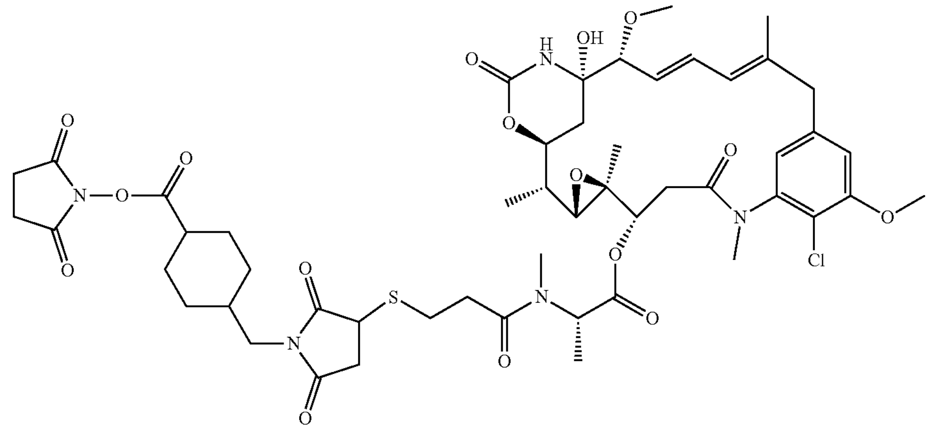

and aqueous diluent.

In some embodiments, the compound of formula $A^1$ is present in stoichiometric excess. In some embodiments, the compound of formula $A^1$ is present in 5-6 fold stoichiometric excess. In some embodiments, the aqueous diluent comprises HEPES. In some embodiments, the aqueous diluent comprises DMA.

In some embodiments, the compound of formula $A^1$ is a compound of formula $A^2$ or $A^3$:

$A^2$

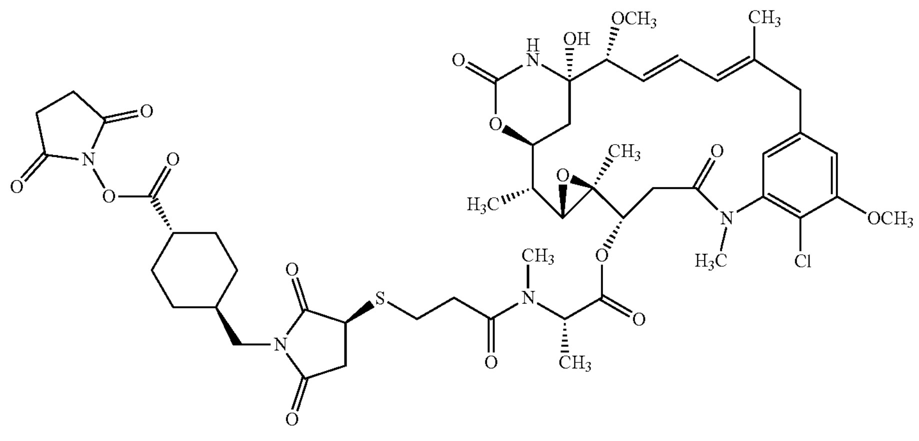

$A^3$

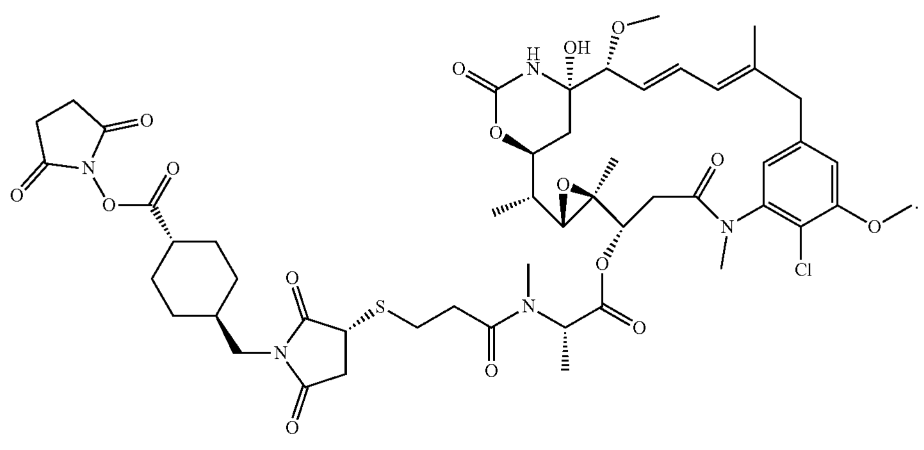

In some embodiments, the compound of formula $A^2$ is $A^3$ stereomerically pure. In some embodiments, the compound of formula $A^1$ comprises a compound of formula $A^1$ or $A^2$, wherein the compound of $A^1$ or $A^2$ is present in a diastereomeric excess of more than 50%. In certain embodiments, the diastereomeric excess is more than 70%. In certain embodiments, the diastereomeric excess is more than 90%. In certain embodiments, the diastereomeric excess is more than 95%.

The term "diastereomeric excess" refers to the difference between the mole fraction of the desired single diastereomer as compared to the remaining diastereomers in a composition. Diastereomeric excess is calculated as follows: (amount of single diastereomer)-(amount of other diastereomers)/1. For example, a composition that contains 90% of 1 and 10% of 2, 3, 4, or a mixture thereof has a diastereomeric excess of 80% [(90-10)/1]. A composition that contains 95% of 1 and 5% of 2, 3, 4, or a mixture thereof has a diastereomeric excess of 90% [(95-5)/1]. A composition that contains 99% of 1 and 1% of 2, 3, 4, or a mixture thereof has a diastereomeric excess of 98% [(99-1)/1]. The diastereomeric excess can similarly be calculated for any one of 1, 2, 3, or 4.

In some embodiments, the compound of formula $A^1$ is prepared by contacting a compound of formula (a):

(a)

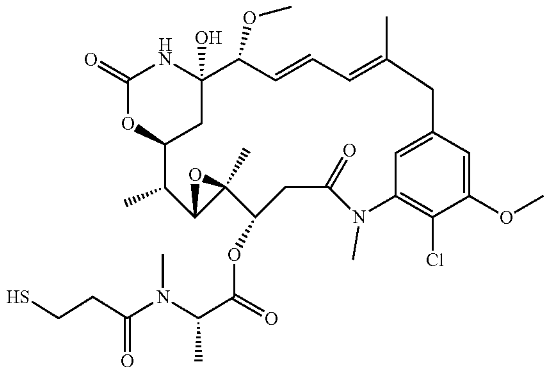

with a compound of formula (b)

(b)

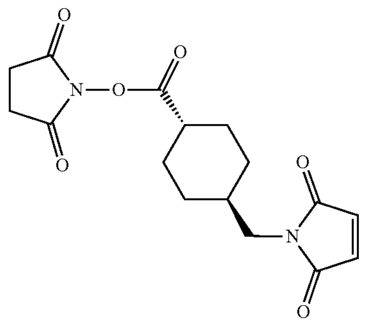

in the presence of silica gel and diluent. In some embodiments, the diluent comprises an organic solvent and water.

Provided herein is also the product prepared by the process of:

(i) contacting a compound of formula (a):

(a)

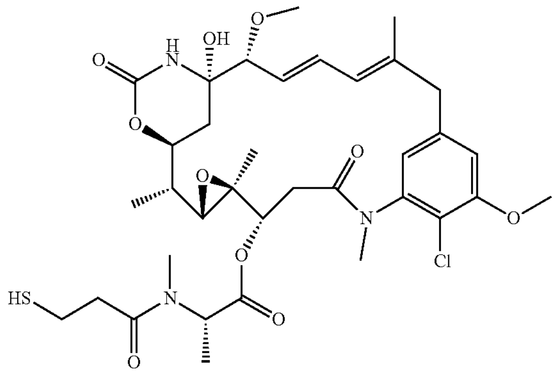

with a compound of formula (b):

(b)

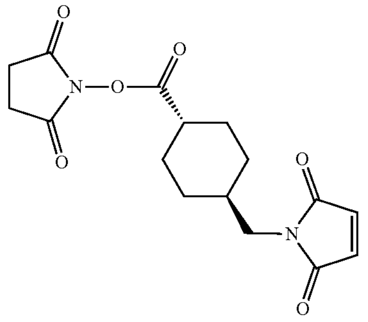

in the presence of silica gel and diluent to synthesize an intermediate; and (ii) contacting an anti-FGFR2 antibody or antigen-binding fragment thereof described herein with the intermediate and aqueous diluent.

In some embodiments, provided herein are processes for preparing an antibody-drug conjugate comprising contacting an anti-FGFR2 antibody or antigen-binding fragment thereof described herein with a compound having the following formula B:

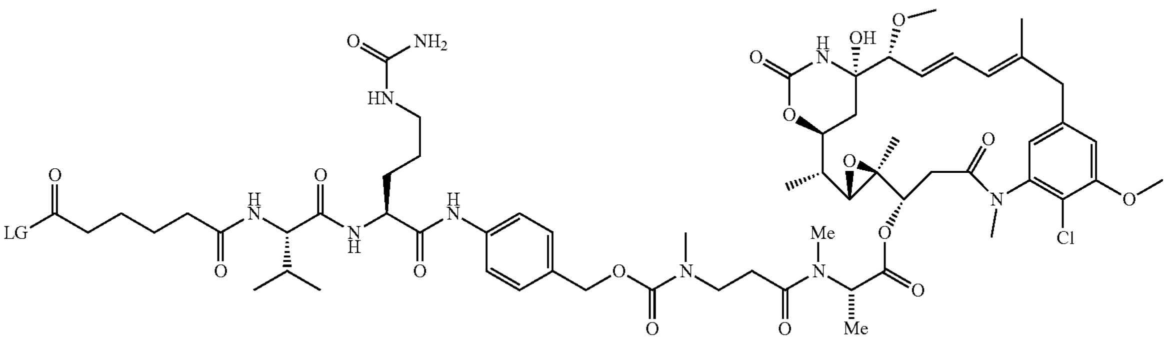

B wherein LG is a leaving group, and aqueous diluent.

In some embodiments, the compound of formula B is present in stoichiometric excess. In some embodiments, the compound of formula B is present in 5-6 fold stoichiometric excess. In some embodiments, the aqueous diluent comprises HEPES. In some embodiments, the aqueous diluent comprises DMA. In some embodiments, the —C(O)-LG is an ester, e.g., NHS or trifluorophenyl ester.

In some embodiments, the compound of formula B is a compound of formula $B^1$:

$B^1$

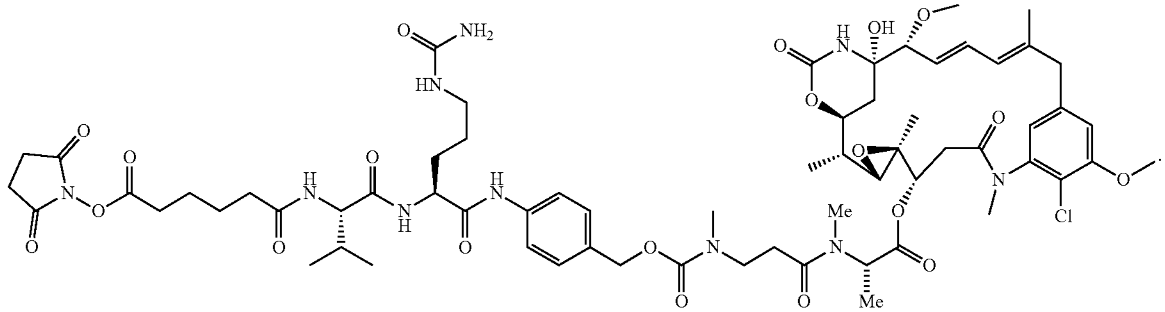

In some embodiments, the compound of formula $B^1$ is prepared by contacting a compound of formula C:

C

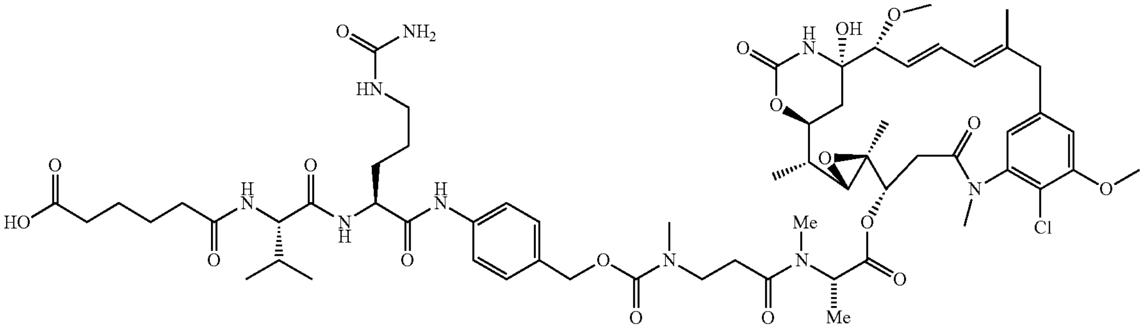

with N-hydroxysuccinimide (NHS), a peptide coupling reagent, and an organic diluent. Suitable peptide coupling reagents include those that activate, i.e., render reactive, carboxylic acid moieties for reaction with a nucleophile. In certain embodiments, the peptide coupling reagent is N-(3-dimethylaminopropyl)-N'-ethylcarbodiimide hydrochloride (EDC). In some embodiments, the organic solvent is dichloromethane.

In some embodiments, the compound of formula C is prepared by contacting a compound of formula D:

D

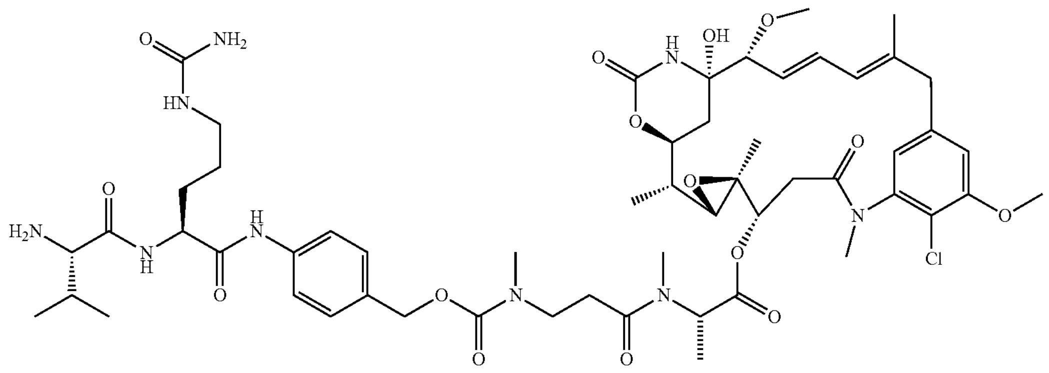

with adipic acid, a peptide coupling agent, and an organic solvent. In certain embodiments, the peptide coupling agent is 2-ethoxy-1-ethoxycarbonyl-1,2-dihydroquinoline (EEDQ). In certain embodiments, the organic solvent comprises dichloromethane. Compound D can be prepared as described in WO2014/145090.

Epitope Mapping and Related Technologies

The term "epitope" refers to a site on an antigen to which B and/or T cells respond. B-cell epitopes can be formed both from contiguous amino acids and noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Provided herein are anti-FGFR2 antibodies that interact with one or more amino acids found within the FGFR2 protein.

The epitope to which the antibodies and antigen-binding fragments thereof bind may consist of a single contiguous sequence of 3 or more (e.g., 3, 4, 5, 6, 7, 8, 9, 10, 11, 12, 13, 14, 15, 16, 17, 18, 19, 20 or more) amino acids of a FGFR2 protein. Alternatively, the relevant epitope may consist of a plurality of non-contiguous amino acids (or amino acid sequences) of FGFR2 (e.g., a conformational epitope).

Various techniques known to persons of ordinary skill in the art can be used to determine the epitope on FGFR2 with which the antibodies and antigen-binding domains of the present disclosure interact. Exemplary techniques that can be used to determine an epitope or binding domain of a particular antibody or antigen-binding domain include, e.g., point mutagenesis (e.g., alanine scanning mutagenesis, arginine scanning mutagenesis, etc.), peptide blots analysis (Reineke, 2004, Methods Mol Biol 248:443-463), protease protection, and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystal structure analysis can also be used to identify the amino acids within a polypeptide with which an antibody interacts.

Further provided herein are anti-FGFR2 antibodies or antigen-binding fragments thereof that bind to the same epitope as any of the specific exemplary antibodies or antigen-binding fragments thereof described herein (e.g., antibodies comprising any of the amino acid sequences as set forth in Table 3 herein). Likewise, also provided herein are anti-FGFR2 antibodies or antigen-binding fragments thereof that compete for binding to FGFR2 with any of the specific exemplary antibodies described herein (e.g., antibodies comprising any of the amino acid sequences as set forth in Table 3 herein).

One can easily determine whether an antibody binds to the same epitope as, or competes for binding with, a reference anti-FGFR2 antibody by using routine methods known in the art and exemplified herein. For example, to determine if a test antibody binds to the same epitope as a reference anti-FGFR2 antibody provided herein, the reference antibody is allowed to bind to a FGFR2 protein. Next, the ability of a test antibody to bind to the FGFR2 molecule is assessed. If the test antibody is able to bind to FGFR2 following saturation binding with the reference anti-FGFR2 antibody, it can be concluded that the test antibody binds to a different epitope than the reference anti-FGFR2 antibody. On the other hand, if the test antibody is not able to bind to the FGFR2 molecule following saturation binding with the reference anti-FGFR2 antibody, then the test antibody may bind to the same epitope as the epitope bound by the reference anti-FGFR2 antibody. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-FGFR2 antibody, the above-described binding methodology is performed in two orientations: In a first orientation, the reference antibody is allowed to bind to a FGFR2 protein under saturating conditions followed by assessment of binding of the test antibody to the FGFR2 molecule. In a second orientation, the test antibody is allowed to bind to a FGFR2 molecule under saturating conditions followed by assessment of binding of the reference antibody to the FGFR2 molecule. If, in both orientations, only the first (saturating) antibody is capable of binding to the FGFR2 molecule, then it is concluded that the test antibody and the reference antibody compete for binding to FGFR2. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

Methods for generating human antibodies in transgenic mice are known in the art. Any such known methods can be used in the context of the present disclosure to make human antibodies that specifically bind to FGFR2. An immunogen comprising any one of the following can be used to generate antibodies to FGFR2. In certain embodiments, the antibodies of the disclosure are obtained from mice immunized with FGFR2b, for example, GenBank accession number NP_075259.4 (SEQ ID NO: 55) or extracellular domain of recombinant human FGFR2b isoform (Accession Number NP_075259.4) fused with a mouse Fc domain (accession number P01863) (SEQ ID NO: 56). Alternatively, the FGFR2 protein or a fragment thereof may be produced using standard biochemical techniques and modified and used as immunogen. In one embodiment, the immunogen is a recombinant FGFR2 protein or fragment thereof. In certain embodiments, the immunogen may be a commercially available FGFR2 protein. In certain embodiments, one or more booster injections may be administered. In certain embodiments, the booster injections may comprise one or more commercially available FGFR2 proteins. In certain embodiments, the immunogen may be a recombinant FGFR2 protein expressed in *E. coli* or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to FGFR2 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody, for example wild-type or modified IgG1 or IgG4. While the constant region selected may vary according to specific use, high affinity antigen-binding and target specificity characteristics reside in the variable region. In certain instances, fully human anti-FGFR2 antibodies are isolated directly from antigen-positive B cells.

Bioequivalents

The anti-FGFR2 antibodies and antibody fragments thereof provided herein encompass proteins having amino acid sequences that vary from those of the described antibodies but that retain the ability to bind human FGFR2. Such variant antibodies and antibody fragments comprise one or more additions, deletions, or substitutions of amino acids when compared to parent sequence, but exhibit biological activity that is essentially equivalent to that of the described antibodies. Likewise, the anti-FGFR2 antibody-encoding DNA sequences of the present disclosure encompass sequences that comprise one or more additions, deletions, or substitutions of nucleotides when compared to the disclosed sequence, but that encode an anti-FGFR2 antibody or antibody fragment that is essentially bioequivalent to an anti-FGFR2 antibody or antibody fragment of the disclosure. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-FGFR2 antibodies or antigen-binding fragments thereof provided herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-FGFR2 antibody variants comprising amino acid changes which modify the glycosylation characteristics of the antibodies, e.g., mutations which eliminate or remove glycosylation.

Species Selectivity and Species Cross-Reactivity

The present disclosure, according to certain embodiments, provides anti-FGFR2 antibodies (and antigen-binding molecules comprising anti-FGFR2 antigen-binding domains) that bind to human FGFR2 but not to FGFR2 from other species. The present disclosure also includes anti-FGFR2 antibodies (and antigen-binding molecules comprising anti-FGFR2 antigen-binding domains) that bind to human FGFR2 and to FGFR2 from one or more non-human species. For example, the anti-FGFR2 antibodies and antigen-binding molecules may bind to human FGFR2 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee FGFR2.

Therapeutic Formulation and Administration

Provided herein are pharmaceutical compositions comprising the anti-FGFR2 antibodies, including anti-FGFR2 ADCs, of the present invention. The pharmaceutical compositions may be formulated with suitable carriers, excipients, and other agents that provide improved transfer, delivery, tolerance, and the like.

In some aspects, the pharmaceutical composition comprising a therapeutically effective amount of one or more isolated human monoclonal antibodies, or antigen-binding fragments thereof, as described herein, together with one or more pharmaceutically acceptable excipients.

Therapeutic Uses of the Antibodies

Provided herein are methods comprising administering to a subject in need thereof a therapeutic composition comprising an anti-FGFR2 antibody or antigen-binding fragment thereof, including anti-FGFR2 antibody ADCs, comprising any of the sequences as set forth herein. The therapeutic composition can comprise any of the anti-FGFR2 antibodies or antigen-binding fragments thereof, including anti-FGFR2 antibody ADCs, disclosed herein, and a pharmaceutically acceptable carrier or diluent. In some aspects, the therapeutic compositions are used in the manufacture of a medicament for the treatment, prevention and/or amelioration of any disease or disorder associated with or mediated by FGFR2 expression, signaling or activity, or treatable by blocking FGFR2 signal transduction, or otherwise inhibiting FGFR2 activity and/or signaling. In some aspects, the therapeutic compositions are used in the manufacture of a medicament for treating cancer.

The anti-FGFR2 antibodies or antigen-binding fragments thereof, including anti-FGFR2 antibody ADCs, are useful, inter alia, for the treatment, prevention and/or amelioration of any disease or disorder associated with or mediated by FGFR2 expression, signaling or activity, or treatable by blocking FGFR2 signal transduction, or otherwise inhibiting FGFR2 activity and/or signaling.

For example, the anti-FGFR2 antibodies or antigen-binding fragments thereof, including anti-FGFR2 antibody ADCs, of the present disclosure are useful for the treatment of tumors that express (or overexpress) FGFR2, in particular, FGFR2b. In some embodiments, the anti-FGFR2 antibodies or antigen-binding fragments thereof, including anti-FGFR2 antibody ADCs, bind cells positive for FGFR2b, e.g., SNU-16 and MFM-223 cells. In some embodiments, the anti-FGFR2 antibodies or antigen-binding fragments thereof, including anti-FGFR2 antibody ADCs, bind minimally with FGFR2c positive cells, e.g., NCI-H716 cells. In some embodiments, the anti-FGFR2 antibodies or antigen-binding fragments thereof, including anti-FGFR2 antibody ADCs, bind poorly to cells lacking FGFR2 expression, e.g., IM-9 cells.

In some embodiments, anti-FGFR2 antibodies or antigen-binding fragments thereof, including anti-FGFR2 antibody ADCs, exhibit cell killing of FGFR2b positive cells but not low FGFR2 expressors. In some aspects, cell killing is less than about 15%, less than about 10%, less than about 5%, or less than about 2% of cells expressing low levels of FGFR2.

In some embodiments, anti-FGFR2 antibodies or antigen-binding fragments thereof, including anti-FGFR2 antibody ADCs, exhibit cell killing of FGFR2b positive cells but not FGFR2c positive cells. In some aspects, cell killing is less than about 35%, less than about 30%, less than about 20%, less than about 10%, or less than about 1% of cells expressing FGFR2c.

In certain embodiments, the anti-FGFR2 antibodies or antigen-binding fragments thereof, including anti-FGFR2 antibody ADCs, are used to treat one or more of the following cancers: astrocytoma, bladder cancer, blood cancer, blood cancer, bone cancer, brain cancer, breast cancer, cervical cancer, clear cell renal cell carcinoma, colorectal cancer, microsatellite-intermediate colorectal cancer, cutaneous squamous cell carcinoma, diffuse large B-cell lymphoma, endometrial cancer, esophageal cancer, fibrosarcoma, gastric cancer, glioblastoma, glioblastoma multiforme, head and neck squamous cell carcinoma, hepatic cell carcinoma, leukemia, liver cancer, leiomyosarcoma, lung cancer, lymphoma, melanoma, mesothelioma, myeloma, nasopharyngeal cancer, non-small cell lung cancer, osteosarcoma, ovarian cancer, pancreatic cancer, primary and/or recurrent cancer, prostate cancer, renal cell carcinoma, rhabdomyosarcoma, small cell lung cancer, squamous cell cancer, synovial sarcoma, thyroid cancer, triple negative breast cancer, uterine cancer, and Wilms' tumor. In some aspects, the cancer is a primary cancer. In some aspects, the cancer is metastatic and/or recurrent cancer.

In some aspects, the anti-FGFR2 antibodies or antigen-binding fragments thereof, including anti-FGFR2 antibody ADCs, may be used to treat primary and/or metastatic tumors positive for FGFR2b, i.e. tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye.

In the context of the methods of treatment described herein, the anti-FGFR2 antibodies or antigen-binding fragments thereof may be administered as a monotherapy (i.e., as the only therapeutic agent), in combination with one or more additional therapeutic agents (examples of which are described elsewhere herein), or as an ADC (examples of which are also described elsewhere herein).

As such, provided herein are methods of treating a cancer in a subject suffering from a tumor overexpressing FGFR2. The methods comprise administering to the subject an anti-FGFR2 antibody or antigen-binding fragment thereof as provided herein. In some aspects, the anti-FGFR2 antibody or antigen-binding fragment thereof comprises: (i) an HCDR1 having the amino acid sequence of SEQ ID NO: 4; an HCDR2 having the amino acid sequence of SEQ ID NO: 6; an HCDR3 having the amino acid sequence of SEQ ID NO: 8; an LCDR1 having the amino acid sequence of SEQ ID NO: 12; an LCDR2 having the amino acid sequence of GAS; and an LCDR3 having the amino acid sequence of SEQ ID NO: 16. In some aspects, the anti-FGFR2 antibody or antigen-binding fragment thereof comprises: (ii) an HCDR1 having the amino acid sequence of SEQ ID NO: 24; an HCDR2 having the amino acid sequence of SEQ ID NO: 6; an HCDR3 having the amino acid sequence of SEQ ID NO: 26; an LCDR1 having the amino acid sequence of SEQ ID NO: 30; an LCDR2 having the amino acid sequence of KAS; and an LCDR3 having the amino acid sequence of SEQ ID NO: 34.

In certain aspects, the cancer is selected from the group consisting of breast invasive ductal carcinoma, gastric adenocarcinoma, esophageal adenocarcinoma, colon adenocarcinoma, and adenocarcinoma of the gastroesophageal junction.

Also provided herein are methods of treating a cancer, reducing tumor growth, and/or causing tumor regression in a subject. The methods comprise administering to a subject in need thereof an antibody-drug conjugate (ADC) comprising an anti-FGFR2 antibody or antigen-binding fragment thereof and a cytotoxin, wherein the anti-FGFR2 antibody or antigen-binding fragment thereof comprises: (i) an HCDR1 having the amino acid sequence of SEQ ID NO: 4; an HCDR2 having the amino acid sequence of SEQ ID NO: 6; an HCDR3 having the amino acid sequence of SEQ ID NO: 8; an LCDR1 having the amino acid sequence of SEQ ID NO: 12; an LCDR2 having the amino acid sequence of GAS; and an LCDR3 having the amino acid sequence of SEQ ID NO: 16; or (ii) an HCDR1 having the amino acid sequence of SEQ ID NO: 24; an HCDR2 having the amino acid sequence of SEQ ID NO: 6; an HCDR3 having the amino acid sequence of SEQ ID NO: 26; an LCDR1 having the amino acid sequence of SEQ ID NO: 30; an LCDR2 having the amino acid sequence of KAS; and an LCDR3 having the amino acid sequence of SEQ ID NO: 34. In some aspects, the cytotoxin is a tubulysin. In some aspects, the cytotoxin is a maytansinoid. In some aspects, the cytotoxin is a camptothecin analog. In some aspects, the cytotoxin is an auristatin.

Combination Therapies and Formulations

Provided herein are compositions and therapeutic formulations comprising any of the anti-FGFR2 antibodies or antigen-binding fragments thereof, including anti-FGFR2 antibody ADCs, described herein in combination with one or more additional therapeutically active components, and methods of treatment comprising administering such combinations to subjects in need thereof.

The anti-FGFR2 antibodies or antigen-binding fragments thereof, including anti-FGFR2 antibody ADCs, may be co-formulated with and/or administered in combination with one or more additional therapeutically active component(s) selected from the group consisting of: another antagonist of FGFR2, for example, an antagonist of FGFR2b (e.g., bemarituzumab or aprutumab, or aprutumab ixadotin), an antagonist of HER2/ErbB2 (e.g., anti-ErbB2 [e.g., Trastuzumab or T-DM1 {KADCYLA®}, or trastuzumab deruxtican {T-SXD; a DNA topoisomerase 1 inhibitor}], or small molecule inhibitor of ErbB2 activity), an antagonist of another EGFR family member such as ErbB3 or ErbB4 (e.g., anti-ErbB3 or anti-ErbB4 antibody or small molecule inhibitor of ErbB3 or ErbB4 activity), a MET antagonist (e.g., an anti-MET antibody [e.g., onartuzumab, emibetuzumab, and H4H14639D] or small molecule inhibitor of MET), an EGFR antagonist (e.g., an anti-EGFR antibody [e.g., cetuximab or panitumumab] or small molecule inhibitor of EGFR [e.g., gefitinib or erlotinib]), an antagonist of EGFRvIII (e.g., an anti-EGFRvIII antibody), an IGF1R antagonist (e.g., an anti-IGF1R antibody), a B-raf inhibitor (e.g., vemurafenib, sorafenib, GDC-0879, PLX-4720), a PDGFR-a inhibitor (e.g., an anti-PDGFR-a antibody), a PDGFR-β inhibitor (e.g., an anti-PDGFR-p antibody or small molecule kinase inhibitor such as, e.g., imatinib mesylate or sunitinib malate), a PDGF ligand inhibitor (e.g., anti-PDGF-A, —B, —C, or -D antibody, aptamer, siRNA, etc.), a VEGF antagonist (e.g., a VEGF-Trap such as aflibercept, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1 H685P), a FOLH1 antagonist (e.g., an anti-FOLH1 antibody), a STEAPI or STEAP2 antagonist (e.g., an anti-STEAPI antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin [e.g., anti-UPK3A] antibody), a MUC16 antagonist (e.g., an anti-MUC16 antibody), a Tn antigen antagonist (e.g., an anti-Tn antibody), a CLEC12A antagonist (e.g., an anti-CLEC12A antibody), a TNFRSF17 antagonist (e.g., an anti-TNFRSF17 antibody), a LGR5 antagonist (e.g., an anti-LGR5 antibody), a monovalent CD20 antagonist (e.g., a monovalent anti-CD20 antibody such as rituximab), a CD20 x CD3 bi-specific antibody, a PD-1 blocking agent (e.g., an anti-PD-1 antibody such as pembrolizumab or nivolumab), etc. Other agents that may be beneficially administered in combination with antibodies provided herein include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

Illustratively, a PD-1 inhibitor such as an anti-PD-1 antibody can be combined with an anti-FGFR2 antibody or antigen-binding fragment thereof, or an antibody-drug conjugate as described herein. The target patient population includes specifically those patients with tumors that overexpress FGFR2, or express a mutated FGFR2, such as a patient with a FGFR2-expressing breast cancer.

Provided herein are compositions and therapeutic formulations comprising any of the anti-FGFR2 antibodies or antigen-binding fragments thereof, including anti-FGFR2 antibody ADCs, described herein in combination with one or more chemotherapeutic agents. Examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The anti-FGFR2 antibodies or antigen-binding fragments thereof, including anti-FGFR2 antibody ADCs, may also be administered and/or co-formulated in combination with antivirals, antibiotics, analgesics, corticosteroids, steroids, oxygen, antioxidants, COX inhibitors, cardioprotectants, metal chelators, IFN-gamma, and/or NSAIDs.

The additional therapeutically active component(s), e.g., any of the agents listed above or derivatives thereof, may be administered just prior to, concurrent with, or shortly after the administration of an anti-FGFR2 antibody or antigen-binding fragment thereof, including an anti-FGFR2 antibody ADC; (for purposes of the present disclosure, such administration regimens are considered the administration of an antibody "in combination with" an additional therapeutically active component). The present disclosure includes pharmaceutical compositions in which an anti-FGFR2 antibody or antigen-binding fragment thereof, including an anti-FGFR2 antibody ADC is co-formulated with one or more of the additional therapeutically active component(s) as described elsewhere herein.

Administration Regimens

According to certain embodiments, multiple doses of an anti-FGFR2 antibody or antigen-binding fragment thereof, including an anti-FGFR2 antibody ADC, or a pharmaceutical composition comprising a combination of an anti-FGFR2 antibody or anti-FGFR2 antibody ADC, and any of the additional therapeutically active agents mentioned herein, may be administered to a subject over a defined time course. The methods according to this aspect comprise sequentially administering to a subject, multiple doses of an anti-FGFR2 antibody or antigen-binding fragment thereof, including an anti-FGFR2 antibody ADC, provided herein. As used herein, "sequentially administering" means that each dose of antibody or ADC is administered to the subject at a different point in time, e.g., on different days separated by a predetermined interval (e.g., hours, days, weeks or months). The present disclosure includes methods which comprise sequentially administering to the patient a single initial dose of an anti-FGFR2 antibody or antigen-binding fragment thereof, including an anti-FGFR2 antibody ADC, followed by one or more secondary doses of the anti-FGFR2 antibody or antigen-binding fragment thereof, or anti-FGFR2 antibody ADC, and optionally followed by one or more tertiary doses of the anti-FGFR2 antibody or antigen-binding fragment thereof or ADC.

The terms "initial dose," "secondary doses," and "tertiary doses," refer to the temporal sequence of administration of the anti-FGFR2 antibody or antigen-binding fragment thereof, or anti-FGFR2 antibody ADC. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the anti-FGFR2 antibody or antigen-binding fragment thereof, or anti-FGFR2 antibody ADC, but generally may differ from one another in terms of frequency of administration. In certain embodiments, however, the amount of antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

Diagnostic Uses of the Antibodies

The anti-FGFR2 antibody or antigen-binding fragment thereof of the present disclosure may also be used to detect and/or measure FGFR2, e.g., FGFR2b, or FGFR2b-expressing cells in a sample, e.g., for diagnostic purposes. For example, an anti-FGFR2 antibody, or fragment thereof, may be used to diagnose a condition or disease characterized by aberrant expression (e.g., over-expression, under-expression, lack of expression, etc.) of FGFR2. Exemplary diagnostic assays for FGFR2 may comprise, e.g., contacting a sample, obtained from a patient, with an anti-FGFR2 antibody or antigen-binding fragment thereof, wherein the antibody is labeled with a detectable label or reporter molecule. Alternatively, an unlabeled anti-FGFR2 antibody can be used in diagnostic applications in combination with a secondary antibody which is itself detectably labeled. The detectable label or reporter molecule can be a radioisotope, such as $^{3}H$, $^{14}$ 32P, $^{35}S$, or $^{125}I$; a fluorescent or chemiluminescent moiety such as fluorescein, or rhodamine; or an enzyme such as alkaline phosphatase, beta-galactosidase, horseradish peroxidase, or luciferase. Specific exemplary assays that can be used to detect or measure FGFR2 in a sample include enzyme-linked immunosorbent assay (ELISA), radioimmunoassay (RIA), immuno-PET (e.g., $^{89}Zr$, $^{64}Cu$, etc.), and fluorescence-activated cell sorting (FACS). In some embodiments, the anti-FGFR2 antibody or antigen-binding fragment thereof is labeled as described in WO 2018/044540, the entirety of which is incorporated herein by reference in its entirety. In some embodiments, the anti-FGFR2 antibody or antigen-binding fragment thereof is labeled to:

In some embodiments, an anti-FGFR2 antibody or antigen-binding fragment thereof comprising an HCVR amino acid sequence of SEQ ID NO: 2 and an LCVR amino acid sequence of SEQ ID NO: 10 is labeled to Biosensor 1.

In some embodiments, an anti-FGFR2 antibody or antigen-binding fragment thereof comprising an HCVR amino acid sequence of SEQ ID NO: 22 and an LCVR amino acid sequence of SEQ ID NO: 28 is labeled to Biosensor 1.

In some embodiments, an anti-FGFR2 antibody or antigen-binding fragment thereof comprising an HCVR amino acid sequence of SEQ ID NO: 40 and an LCVR amino acid sequence of SEQ ID NO: 44 is labeled to Biosensor 1.

Samples that can be used in FGFR2 diagnostic assays according to the present disclosure include any tissue or fluid sample obtainable from a patient. Generally, levels of FGFR2 in a particular sample obtained from a healthy patient (e.g., a patient not afflicted with a disease or condition associated with abnormal FGFR2 levels or activity) will be measured to initially establish a baseline, or standard, level of FGFR2. This baseline level of FGFR2 can then be compared against the levels of FGFR2 measured in samples obtained from individuals suspected of having a FGFR2-related disease or condition.

EXAMPLES

The following examples are put forth so as to provide those of ordinary skill in the art with a complete disclosure and description of how to make and use the methods and compositions provided herein, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

The two comparator antibodies used in the Examples are referred to as Comp1 and Comp2. Comp1 (Five Prime Therapeutics) is a humanized anti-FGFR2b isoform bispecific antibody identified in Catenacci et al. (2020, Phase I Escalation and Expansion Study of Bemarituzumab (FPA144) in Patients With Advanced Solid Tumors and FGFR2b-Selected Gastroesophageal Adenocarcinoma, *J Clin Onc*, DOI https://doi. org/10.1200/JCO.19. 01834). This same bispecific antibody is mentioned in U.S. Pat. No.

Biosensor 1

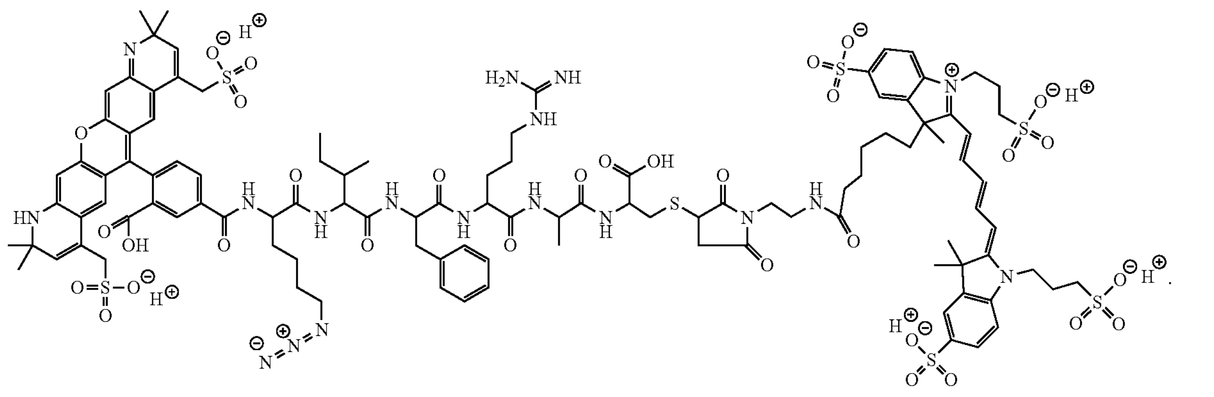

8,603,987 (Galaxy Biotech) as HuGAL-FR21. Comp2 (Bayer) is a humanized IgG1 antibody that binds at the N-terminus of both FGFR2b and FGFR2c. The Comp2 antibody is mentioned in Sommer et al. (2016, Preclinical Efficacy of Auristatin-based antibody-drug conjugate BAY 1187982 for the treatment of FGFR2-positive solid tumors, *Cancer Res,* 76 (21), 6631-6639, doi: 10.1 158/0008-5472.CAN-16-0180) and U.S. Patent Publication No. 2014/0322220. In the patent publication, the Comp2 antibody is referred to as TPP-1402, which is a variant of M048-D01, and has purported heavy chain SEQ ID NO: 133 and light chain SEQ ID NO: 124, according to the U.S. 2014/0322220 publication.

The isotype control antibodies used herein are referred to as IC1 and IC2. Such antibodies can be conjugated to any of the linker payloads including maytansinoid 1 LP, which releases the maytansinoid 1A payload, tubulysin 1 LP, which releases the tubulysin 1A payload, DXd1 LP (branched) and DXd2 LP (unbranched), which release DXd-G or DXd, and the BAY-LP (BAY1187982; see Sommer et al., 2016, Preclinical Efficacy of Auristatin-based Antibody-Drug Conjugate BAY 1187982 for the Treatment of FGFR2-Positive Solid Tumors, *Cancer Res,* 76 (21), 6631-6639, doi: 10.1158/0008-5472.CAN-16-0180)).

Example 1. Generation of Human Antibodies to FGFR2

Human antibodies to FGFR2 were obtained by immunizing a genetically engineered mouse comprising DNA encoding human immunoglobulin heavy and kappa light chain variable regions with an immunogen comprising the extracellular domain of recombinant human FGFR2b isoform (Accession Number NP_075259.4) fused with a mouse Fc domain (accession number P01863) according to SEQ ID NO: 56.

The antibody immune response was monitored by a FGFR2-specific immunoassay. When a desired immune response was achieved splenocytes were harvested and fused with mouse myeloma cells to preserve their viability and form hybridoma cell lines. The hybridoma cell lines were screened and selected to identify cell lines that produce FGFR2-specific antibodies. Using this technique several anti-FGFR2 chimeric antibodies (i.e., antibodies possessing human variable domains and mouse constant domains) were obtained. In addition, several fully human anti-FGFR2 antibodies were isolated directly from antigen-positive B cells without fusion to myeloma cells, as described in U.S. Pat. No. 7,582,298, herein specifically incorporated by reference in its entirety. Using this method, fully human anti-FGFR2 antibodies (i.e., antibodies possessing human variable domains and human constant domains) were obtained.

Certain biological properties of the exemplary anti-FGFR2 antibodies generated in accordance with the methods of this Example are described in detail in the Examples set forth below.

Example 2. Heavy and Light Chain Variable Region Amino Acid Sequences, Heavy and Light Chain Amino Acid Sequences, and Nucleotide Sequences Table 3 sets forth the amino acid sequence identifiers of the heavy and light chain variable regions and CDRs, as well as the heavy chain and light chain sequences, of exemplary anti-FGFR2 antibodies. The corresponding nucleic acid sequence identifiers are set forth in Table 4.

TABLE 3

| Amino Acid Sequence Identifiers | | | | | | | | | | |
|---|---|---|---|---|---|---|---|---|---|---|
| Antibody | SEQ ID NOs: | | | | | | | | | |
| Designation | HCVR | HCDR1 | HCDR2 | HCDR3 | LCVR | LCDR1 | LCDR2 | LCDR3 | HC | LC |
| mAb1 | 2 | 4 | 6 | 8 | 10 | 12 | GAS | 16 | 18 | 20 |
| mAb2 | 22 | 24 | 6 | 26 | 28 | 30 | KAS | 34 | 36 | 38 |
| mAb3 | 40 | 24 | 6 | 42 | 44 | 46 | KAS | 34 | 49 | 51 |

TABLE 4

| Nucleic Acid Sequence Identifiers | | | | | | | | | | |
|---|---|---|---|---|---|---|---|---|---|---|
| Antibody | SEQ ID NOs: | | | | | | | | | |
| Designation | HCVR | HCDR1 | HCDR2 | HCDR3 | LCVR | LCDR1 | LCDR2 | LCDR3 | HC | LC |
| mAb1 | 1 | 3 | 5 | 7 | 9 | 11 | GGTGCATCC | 15 | 17 | 19 |
| mAb2 | 21 | 23 | 5 | 25 | 27 | 29 | AAGGCGTCT | 33 | 35 | 37 |
| mAb3 | 39 | 23 | 5 | 41 | 43 | 45 | AAGGCGTCT | 47 | 48 | 50 |

Antibodies disclosed herein have fully human variable regions but can have mouse constant regions (e.g., a mouse IgG1 Fc or a mouse IgG2 Fc (a or b isotype)) or human constant regions (e.g., a human IgG1 Fc or a human IgG4 Fc). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 3 and 4 will remain the same, and the binding properties to antigen are expected to be identical or substantially similar regard-less of the nature of the Fc domain. In some instances, antibodies disclosed herein have identical heavy chain variable region sequences, but may or may not have an N297Q modification within the Fc domain of the full heavy chain amino acid sequence.

Example 3. Biacore Binding Affinities and Kinetic Constants of Human Monoclonal Anti-FGFR2 Antibodies The equilibrium dissociation constants ($K_D$ values) for hFGFR2b.mmh binding to anti-FGFR2 antibodies conjugated with Tubulysin ("tubulysin 1ALP"), Auristatin ("auristatin LP1"), or mc-VC-PAB-NMe-C3-May ("maytansinoid 1ALP") were determined using a real-time surface plasmon resonance biosensor assay on a Biacore 2000 or a Biacore 4000 instrument. The Biacore sensor surface was derivatized by amine coupling with a monoclonal mouse anti-human Fc antibody (REGN2567 or Jackson Cat. No #109-005-098) to capture anti-FGFR2 ADC and parent unmodified antibodies expressed with human constant regions. Biacore binding studies were performed in HBS-EP running buffer (0.01M HEPES pH 7.4, 0.15M NaCl, 3 mM EDTA, 0.05% v/v Surfactant P20). Human FGFR2b and Human FGFR2c were prepared in-house expressing a C-terminal myc-myc-hexahistidine tag (hFGFR2b-MMH -SEQ ID NO: 57; hFGFR2c-MMH -SEQ ID NO: 58). Different concentrations (3-fold dilutions) of hFGFR2b-MMH or hFGFR2c-MMH (ranging from 30 nM to 1.1 nM) prepared in HBS-EP running buffer were injected over the anti-FGFR2 ADC or antibody captured surface at a flow rate of 50pL/min. Association of hFGFR2b-MMH or hFGFR2c-MMH to each of the captured ADCs and monoclonal antibodies was monitored for 4 minutes. Subsequently, dissociation was monitored for 10 minutes in HBS-EP running buffer. Anti-human Fc surface was regenerated by a brief injection of 20 mM $H_3PO_4$. All binding kinetic experiments were performed at 25° C. Kinetic association ($k_a$) and dissociation ($k_d$) rate constants were determined by fitting the real-time sensorgrams to a 1:1 binding model using Scrubber 2.0c curve fitting software. All sensorgrams were double referenced by subtracting buffer injection sensorgram signal from the corresponding analyte sensorgram, thereby removing artifacts caused by dissociation of the antibody from the capture surface. Binding dissociation equilibrium constants ($K_D$) and dissociative half-lives (t1/2) were calculated from the kinetic rate constants as:

$$K_D(M) = \frac{kd}{ka}, \text{ and } t^{1/2}\text{ (min)} = \frac{\ln(2)}{60 * kd}$$

Binding kinetic parameters for hFGFR2b.mmh binding to the anti-FGFR2 monoclonal antibodies at 25° C. are shown in Table 5a and Table 5b.

TABLE 5a

Binding Kinetics of Anti-FGFR2 Antibodies to hFGFR2b.mmh at 25° C.

| Antibody and ADC | mAb Captured (RU) | Antigen Bound (RU) | ka (1/Ms) | kd (1/s) | $K_D$ (M) | t1/2 (min) |
|---|---|---|---|---|---|---|
| mAb2 | 337.1 ± 2.5 | 62.5 | 5.01E+04 | 4.47E−04 | 8.92E−09 | 25.8 |
| mAb2-maytansinoid 1ALP | 266.8 ± 8.4 | 31.3 | 6.85E+04 | 8.79E−04 | 1.28E−08 | 13.1 |
| mAb2-tubulysin 1ALP | 254.1 ± 3.4 | 32.7 | 5.10E+04 | 1.18E−03 | 2.31E−08 | 9.8 |
| mAb1 | 514.2 ± 9.7 | 70.9 | 4.17E+04 | 1.04E−03 | 2.50E−08 | 11.1 |
| mAb1-maytansinoid 1ALP | 369 ± 7.6 | 42.1 | 2.48E+04 | 1.04E−03 | 4.18E−08 | 11.1 |
| mAb1-tubulysin 1ALP | 305.2 ± 4.9 | 36.4 | 2.21E+04 | 1.06E−03 | 4.81E−08 | 7.4 |
| Comp2 | 1267.6 ± 9.3 | 296.1 | 3.69E+05 | 1.01E−04 | 2.74E−10 | 113.9 |
| Comp2-BAY-LP | 294.7 ± 7.7 | 133.1 | 3.58E+05 | 4.90E−05 | 1.37E−10 | 235.8 |
| Comp1 | 582.6 ± 2.4 | 68.3 | 7.74E+04 | 4.71E−03 | 6.08E−08 | 2.5 |
| IC1 | 480.7 ± 9.1 | 0 | NB | NB | NB | NB |

TABLE 5b

Binding Kinetics of Anti-FGFR2 Antibodies to hFGFR2c.mmh at 25° C.

| Antibody | mAb Captured (RU) | Antigen Bound (RU) | ka (1/Ms) | kd (1/s) | $K_D$ (M) | t1/2 (min) |
|---|---|---|---|---|---|---|
| mAb2 | 351.4 ± 4 | −1.4 | NB | NB | NB | NB |
| mAb1 | 279.3 ± 4.1 | 1.5 | NB | NB | NB | NB |
| Comp2 | 1227.4 ± 2.1 | 295.2 | 1.41E+05 | 1.03E−04 | 7.30E−10 | 112.1 |
| Comp1 | 567.2 ± 0.7 | 0.6 | NB | NB | NB | NB |
| IC1 | 232.6 ± 2.7 | −0.1 | NB | NB | NB | NB |

At 25° C., anti-FGFR2 monoclonal antibodies bound to hFGFR2b.mmh with $K_D$ values of 8.92 nM and 25.0 nM, respectively. The anti-FGFR2 monoclonal antibody conjugates bound to hFGFR2b.mmh with $K_D$ values ranging from 12.8 nM to 48.1 nM. The isotype control antibody IC1 exhibited no binding. See Table 5a. By contrast, the anti-FGFR2 monoclonal antibodies did not bind to hFGFR2c.mmh demonstrating specificity for the FGFR2b protein. Comp2 bound to both hFGFR2b.mmh and hFGFR2c.mmh as expected.

Example 4: Site Specific Conjugation of Anti-FGFR2 Antibodies with Tubulysin 1A In this example, the anti-FGFR2 antibodies were conjugated to the cytotoxin tubulysin 1A, which has the following structure:

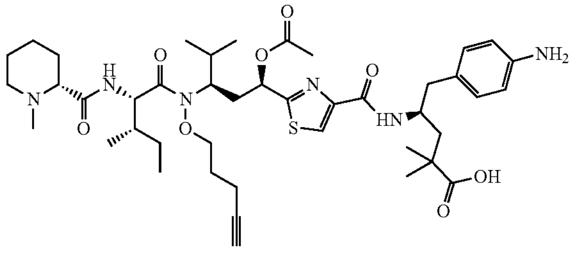 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(N)cc2)CC(C)(C)C(=O)O)cs1)C(C)C]

The antibody was conjugated through a linker moiety as described in the procedure below, providing an ADC having the following structure, and/or its cycloaddition regioisomer thereof.

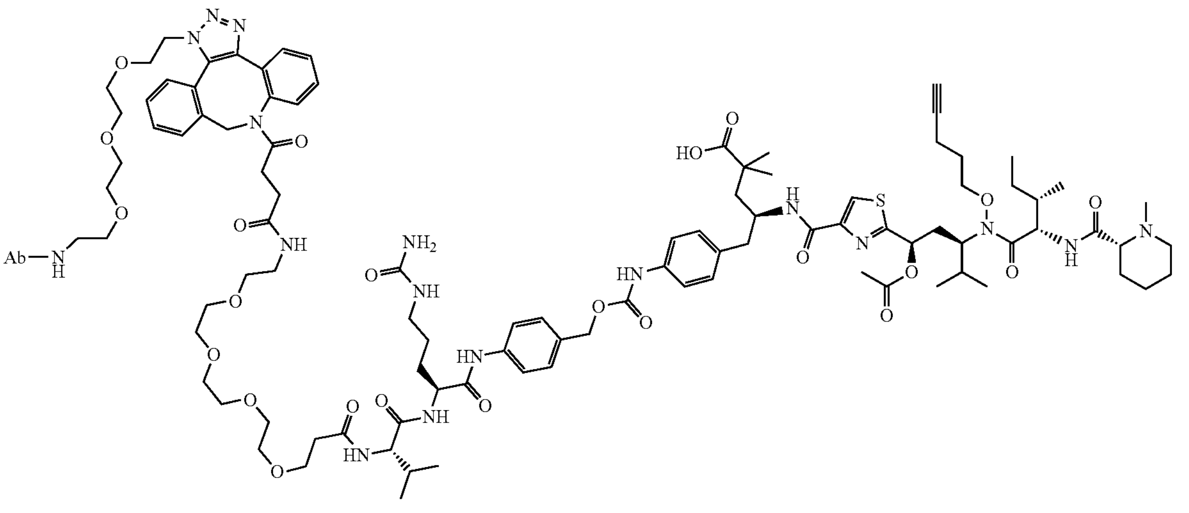

wherein Ab is the anti-FGFR2 antibody.

Site-specific conjugates of a cyclooctyne-spacer-payload to a wild-type antibody or antigen-binding fragment thereof were produced in three steps. In the first step, deglycosylation of a wild-type antibody was performed. In the second step, microbial transglutaminase (MTG) based enzymatic attachment of a spacer moiety suitable for subsequent elaboration, e.g., via cycloaddition, such as an azido-$PEG_3$-amine spacer, to the Q295 site of the deglycosylated antibody, was performed (hereinafter "MTG-based" conjugation). In the third step, attachment of a cyclooctyne-spacer-payload to the azido-functionalized antibody was performed via a [2+3] cycloaddition for example, the 1,3-dipolar cycloaddition between an azide and a cyclooctyne (aka copper-free click chemistry). See, Baskin, J. M.; Prescher, J. A.; Laughlin, S. T.; Agard, N. J.; Chang, P. V.; Miller, I. A.; Lo, A.; Codelli, J. A.; Bertozzi, C. R. PNAS 2007, 104 (43), 16793-7. FIG. 1A is an example of a linker-spacer-payload having a DIBAC moiety conjugated with an azido-functionalized antibody via a [2+3]cycloaddition. This process provided site-specific and stoichiometric conjugates in about 50-80% isolated yield. FIG. 1 B is an example of 3-step site specific conjugation carried out as follows:

Step 1: Preparation of a deglycosylated antibody.

Deglycosylation was performed to expose the conjugation site. An anti-FGFR2 human IgG4 antibody (30 mg, 40 mg/mL in PBS; pH5.5-8.0) was mixed with PNGase F enzyme (New England BioLabs, 500,000 U/mL, 2 uL enzyme per 1 mg antibody, so 60 uL total). The reaction mixture was incubated at 37° C. overnight while gently shaking. The deglycosylation was monitored by ESI-MS. Upon reaction completion, the reaction mixture was used directly in next step.

Step 2: Preparation of an azido-functionalized antibody.

The deglycosylated anti-FGFR2 antibody (30 mg) in 1.5 mL PBS (pH 7.2) was incubated with 200 molar equivalents of the azido-$PEG_3$-amine (MW=218.26 g/mol) in the presence of MTG (ACTIVA TI, Ajinomoto, Japan) (0.06 mg MTG per mg antibody). The reaction was incubated at 37° C. for 4 h then 25° C. overnight while gently mixing. The reaction was monitored by ESI-MS. Upon reaction completion, excess azido-$PEG_3$-amine and MTG were removed by SEC (Superdex 200 PG, GE Healthcare), to generate the azido-functionalized antibody. The azido-$PEG_3$-amine added to two Q295 sites on the antibody resulting in a 404 Da increase for the 2DAR antibody-$PEG_3$-azide conjugate.

This process can also be carried out on antibodies having an N297Q modification in one or both heavy chains. In this instance, the azido-$PEG_3$-amine would be added to two Q295 sites and at least one 297Q site on the antibody resulting in a 3DAR or 4DAR antibody-$PEG_3$-azide conjugate.

Step 3: Preparation of site-specific conjugates by a [2+3] click reaction between the azido-functionalized glutaminyl-modified antibodies and cyclooctyne containing linker-payload (LPs).

In general, an azido-functionalized antibody-LP conjugate was prepared by incubating the azido-functionalized glutaminyl-modified antibody with >6 molar equivalents of LP, e.g., the compound of the following structure:

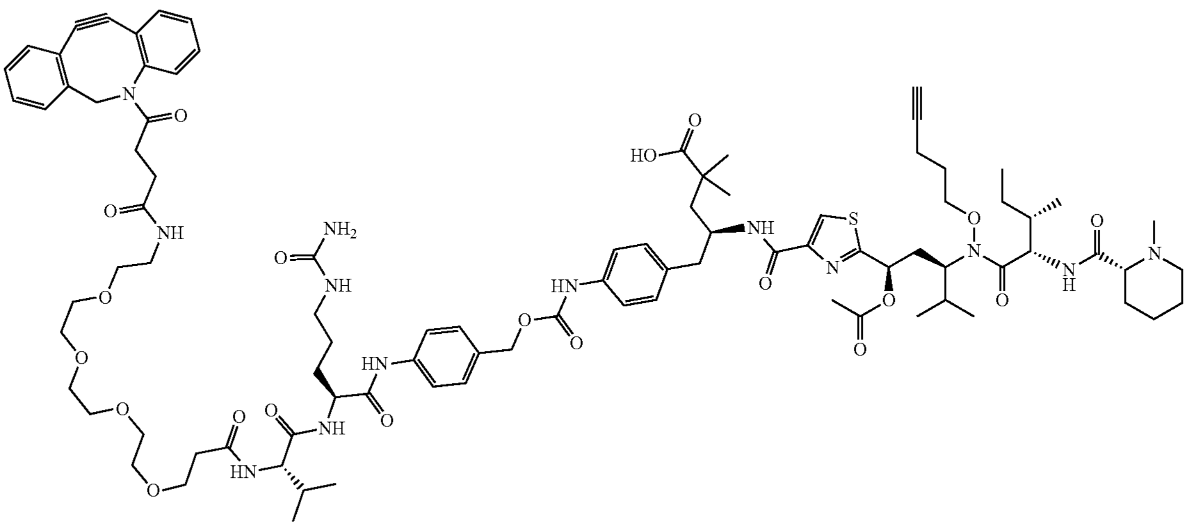 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)OCc3ccc(NC(=O)[C@H](CCCNC(N)=O)NC(=O)[C@@H](NC(=O)CCOCCOCCOCCOCCNC(=O)CCC(=O)N4Cc5ccccc5C#Cc5ccccc54)C(C)C)cc3)cc2)CC(C)(C)C(=O)O)cs1)C(C)C]

dissolved in a suitable organic solvent (e.g., DMSO, DMF or DMA; reaction mixture contains 10-20% organic solvent, v/v) at 25° C. to 37° C. for 3-24 h. The progress of the reaction was monitored by ESI-MS. Absence of azido-functionalized antibody (mAb-$PEG_3$-$N_3$) indicated completion of the conjugation. The excess linker-payload (LP) and organic solvent were removed by desalting column or size exclusion chromatography (SEC). The purified conjugate was analyzed by SEC-HPLC and ESI-MS. Conjugates' monomer purity was >99% by SEC-HPLC analysis.

In a specific example, the azido-functionalized anti-FGFR2 antibodies, e.g., mAb1 and mAb2, (23 mg) in 3.2 mL PBS were treated with six equivalents of Tubulysin 1A -LP (conc. 10 mg/mL in DMA) at 30° C. overnight. The excess linker payload (LP) was removed by SEC (Superdex 200 PG, GE Healthcare). The final product was characterized by UV, SEC-HPLC (see FIG. 2), and ESI-MS.

Shown in Table 6 is a list of DAR (ESI-MS) values for antibody tubulysin conjugates (ADCs).

Characterization of Antibody and ADCs by SEC-HPLC and LC-ESI-MS

The purified conjugates were analyzed by SEC-HPLC and ESI-MS, with representative SEC and ESI-MS.

Analytical SEC experiments were run using a Waters 1515 instrument, on a Superdex™ 200 Increase (1.0×30 cm) column, at flow rate of 0.80 mL/min using PBS pH 7.2 and monitored at λ=280 nm using a Waters 2998 PDA. An analytic sample was composed of 30-80 μL of test sample. The SEC results in FIG. 2 indicate typical retention times for monomeric mAb and conjugates thereof, with minimal aggregation or degradation.

Measurement of intact mass for the ADC samples by LC-ESI-MS was performed to determine drug-payload distribution profiles and to calculate the average DAR. Each testing sample (20-50 ng, 5 μL) was reduced by DTT then loaded onto an Acquity UPLC Protein BEH C4 column (10K psi, 300 Å, 1.7 μm, 75 μm×100 mm; Cat No. 186003810). After desalting for 3 min, the protein was eluted, and mass spectra were acquired by a Waters Synapt G2-Si mass spectrometer.

TABLE 6

Antibody Drug Conjugate DARs

| | ADC | DAR (by ESI-MS) |
|---|---|---|
| mAb1-Tubulysin 1A-LP | Anti FGFR2 mAb1-$PEG_3$-$N_3$-Tubulysin 1A-LP | 2.1 |
| mAb2-Tubulysin 1A-LP | Anti FGFR2 mAb2-$PEG_3$-$N_3$-Tubulysin 1A-LP | 2.1 |
| IC1-Tubulysin 1A-LP | Isotype mAb-$PEG_3$-$N_3$-Tubulysin 1A-LP | 2.0 |

The ADCs generated in this experiment were used in the following Examples.

Example 5: Conjugation of Anti-FGFR2 Antibodies with Maytansinoid Linker Payload In this example, the anti-FGFR2 antibodies were conjugated to the cytotoxin maytansinoid 1A, which was the following structure:

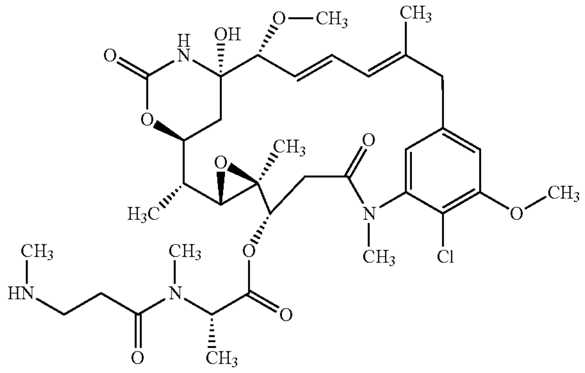 [SMILES: CNCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

The antibody was conjugated through a linker moiety as described in the procedure below, providing an ADC having the following structure:

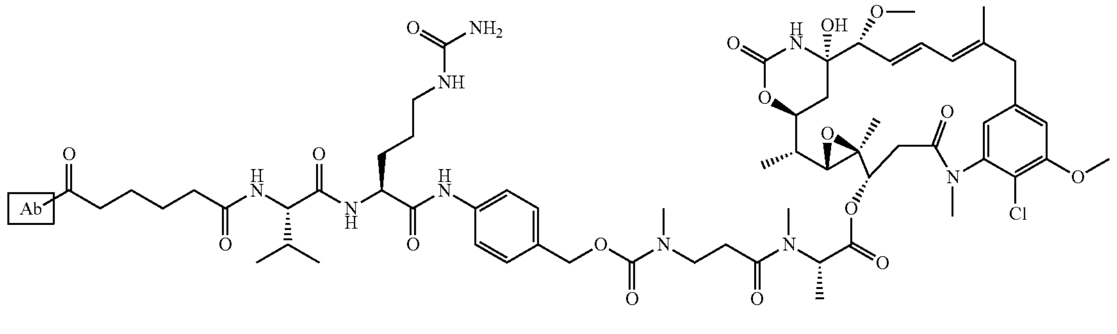

wherein Ab is the anti-FGFR2 antibody.

The antibodies (10-20 mg/ml) in 50 mM HEPES, 150 mM NaCl, pH 8.0, and 10-15% (v/v) DMA were conjugated with a 5-6 fold excess of the following compounds:

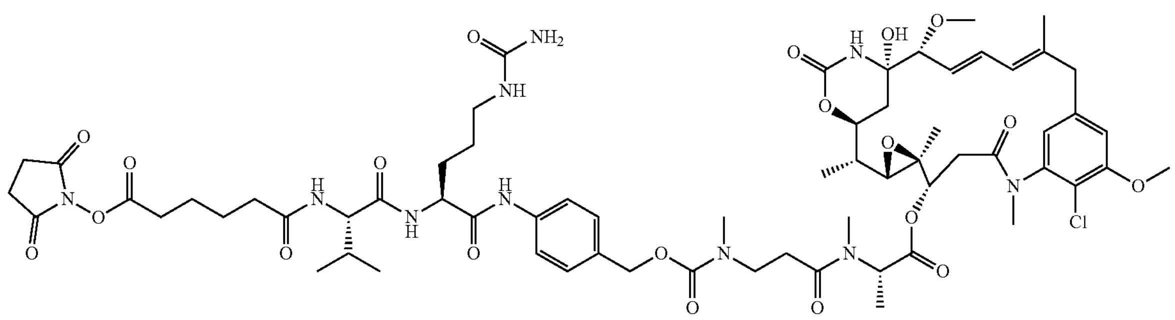 [SMILES: COc1cc2cc(c1Cl)N(C)C(=O)C[C@H](OC(=O)[C@H](C)N(C)C(=O)CCN(C)C(=O)OCc1ccc(NC(=O)[C@H](CCCNC(N)=O)NC(=O)[C@@H](NC(=O)CCCCC(=O)ON3C(=O)CCC3=O)C(C)C)cc1)[C@]1(C)O[C@H]1[C@H](C)[C@@H]1C[C@@](O)(NC(=O)O1)[C@H](OC)/C=C/C=C(\C)C2]

2 hours at ambient temperature. The conjugates were purified by size exclusion chromatography or extensive ultrafiltration and sterile filtered. Protein concentrations were determined by UV spectral analysis. Size-exclusion HPLC established that all conjugates used were >90% monomeric, and RP-HPLC established that there was <1% unconjugated linker payload. All conjugated antibodies were analyzed by UV for linker payload loading values according to Hamblett et al(American Association for Cancer Research. 2004 Oct. 15; 10(20):7063-70) and/or by mass difference, native versus conjugated. Payload to antibody ratios (DARs) are shown in Table 7.

TABLE 7

Percent Yield and Payload to Antibody Ratios for Each Antibody Drug Conjugate

| Antibody | Yield (%) | DAR (ESI-MS) |
|---|---|---|
| mAb3-maytansinoid 1ALP | 70 | 2.2 |
| mAb2-maytansinoid 1ALP | 70 | 1.9 |
| mAb1-maytansinoid 1ALP | 70 | 2.5 |
| IC1-maytansinoid 1ALP | 80 | 2.0 |

Characterization of Conjugates by Liquid Chromatography-Mass Spectrometry

To determine the loading of the linker-payloads on the antibody, the conjugates were deglycosylated, and analyzed by LC-MS.

For the assay, 50 μg of the conjugate was diluted with milli-Q water to a final concentration of 1 mg/mL. Ten μL of PNGase F solution [PNGase F solution was prepared by adding 150 μL of PNGase F stock (New England Biolabs, Cat #P0704L) and 850 μL of milli-Q water and mixed well] was added to the diluted conjugate solution and then incubated at 37° C. overnight. Injections of 5 μL of each sample were made onto LC-MS (Waters Synat G2-Si) and eluted with 0.1 mL/minute of a gradient mobile phase 20-40% over 25 minutes (Mobile Phase A: 0.1% v/v FA in $H_2O$; Mobile Phase B: 0.1% v/v FA in Acetonitrile). The LC separation was achieved on a Waters Acquity BEH C4 column (1.0×50 mM, 1.7 pM) at 80° C.

The mass spectrometry spectra were deconvoluted using Masslynx software and the drug to antibody ratio (DAR) was calculated using the following equations.

1. Relative percentage (%) of drug (Dn) by distribution peak intensity (PI):

Dn %=PIn/Σ(PI0+PI1+PI2. . . +PIi)×100,(n=0,1,2, 3, . . . ,i)

2. Average DAR calculation:

DAR=Σ(1×D1%+2×D2%+3×D3%+. . . +ixDi %)

Example 6: In Vitro Cytotoxicity Assay of Anti-FGFR2 Antibody Drug Conjugates in Tumor Cell Lines To test the ability of anti-FGFR2 antibody drug conjugates (ADCs) disclosed herein to kill human cell lines, an in vitro cytotoxicity assay was performed. In vitro cytotoxicity of the anti-FGFR2 ADCs, isotype control ADCs, and reference free payloads were evaluated using the CellTiter-Glo 2.0 Assay Kit (Promega, Cat #G9243), in which the quantity of ATP present is used to determine the number of viable cells in culture. The payloads Maytansinoid 1A, Maytansinoid 1A* (a cell permeable equivalent of Maytansinoid 1A), and Tubulysin 1A were tested as free payloads, and the unconjugated antibodies, including comparator antibodies, were used as controls.

For the assay, SNU-16, MFM-223, NCI-H716, or IM-9 cells were seeded at 2000 cells/well in poly-D-lysine coated white 96 well BioCoat plates (Corning #356693) in complete growth medium and grown overnight at 37° C. in 5% $CO_2$. Five-fold serial dilutions of anti-FGFR2 ADCs or isotype control ADCs were prepared in dilution media (Optimem+0.1% BSA) and added to cells at final concentrations ranging from 20 nM to 0.051 pM (concentrations were corrected for the DAR and are dosed based on the effective payload concentration). Five-fold serial dilutions of free payloads were prepared in 100% DMSO, transferred to fresh dilution media, and then added to the cells at a final constant DMSO concentration of 0.2% and final payload concentrations ranging from 20 nM to 0.051 pM. The last well in each dilution series served as an untreated control and included media alone or media plus 0.2% DMSO and was plotted as a continuation of the 5-fold serial dilution. Six days later, 100 μL of CellTiter Glo 2.0 was added to each well, plates were mixed for 2 minutes on an orbital shaker, and plates were incubated at room temperature for 10 minutes. Relative light units (RLUs) were measured on an Envision luminometer (PerkinElmer) and cell viability was expressed as a percentage of the untreated (100% viable) cells. $IC_{50}$values were determined using a four-parameter logistic equation over a 10-point dose response curve (GraphPad Prism). The maximum % kill was also determined for each test article as follows: 100-minimum percent viability. The $IC_{50}$value and maximum % kill of each test article are shown in Table 8.

As shown in Table 8, mAb2-tubulysin 1A-LP and mAb1-tubulysin 1A-LP (anti-FGFR2 ADCs conjugated to a tubulysin payload) killed FGFR2b positive SNU-16 and MFM-223 cells with $IC_{50}$values ranging from of 37.0 pM to 125 pM and maximum % kill values ranging from 90.0% to 95.4%. These same anti-FGFR2 ADCs were weakly cytotoxic in NCI-H716 cells (low FGFR2b but high FGFR2c expressing cell line) and in non-FGFR2 expressing IM-9 cells with $IC_{50}$values>20 nM. The free payload tubulysin 1A (the payload of tubulysin 1A-LP) killed all tested cells with $IC_{50}$values ranging from 3.69 pM to 74.3 pM. A non-binding control antibody conjugated to the tubulysin payload (IC1-tubulysin 1A-LP) was weakly cytotoxic in all tested cells with $IC_{50}$values ranging from 1.98 nM to >20 nM. The mAb2-maytansinoid 1A-LP and mAb1-maytansinoid 1A-LP (anti-FGFR2 ADCs conjugated to a maytansinoid payload) antibody conjugates also killed FGFR2b positive SNU-16 and MFM-223 cells with $IC_{50}$values ranging from of 172 pM to 268 pM and maximum % kill values ranging from 85.5% to 95.0%. The free payload maytansinoid 1A (the payload in maytansinoid 1A-LP) and a non-binding control antibody conjugated to the maytansinoid payload (IC1-maytansinoid 1A-LP) had little to no killing activity at the tested concentrations with $IC_{50}$values ranging from 4.63 nM to >20 nM. The cell permeable equivalent of maytansinoid 1A (informative for bystander effect) did kill all tested lines with $IC_{50}$values ranging from 113 pM to 5.45 nM suggesting that none of the tested cell lines are generally resistant to the class of maytansinoid payloads.

A comparator anti-FGFR2 ADO that recognizes both FGFR2b and FGFR2c and is conjugated to an auristatin payload (Comp2-BAY-LP) was also tested for cytotoxicity. Similar to the other tested anti-FGFR2 AD9s, Comp2-BAY-LP killed SNU-16 and MFM-223 cells with 87.pM and 63.8 pM $IC_{50}$values, respectively. In contrast to the other tested anti-FGFR2 ADCs which only bind FGFR2b, the dual FGFR2b+FGFR2c binder, Comp2-BAY-LP, also killed NCI-H71 6 cells (expressing high FGFR2c levels but low FGFR2b) with an $IC_{50}$value of 349 pM. Comp2-BAY-LP was weakly cytotoxic in FGFR2 negative IM-9 cells and the non-binding control conjugated to the auristatin payload ((C2-BAY-LP) was weakly cytotoxic in all tested lines with % $C_5$o ranging from 6.06 nM to greater than 20 nM. All of the unconjugated antibodies including an FGFR2b selective comparator antibody, Compi, were weakly cytotoxic in all tested lines with EC50s greater than 20 nM.

TABLE 8

Cytotoxicity of Anti-FGFR2 ADCs in SNU-16, NCI-H716, MFM-223, MFE-296, and IM-9 Cells

| | IM-9 | | MFM-223 | | NCI-H716 | | SNU-16 | |
|---|---|---|---|---|---|---|---|---|
| Test Article | IC50 (M) | Max % Kill | IC50 (M) | Max % Kill | IC50 (M) | Max % Kill | IC50 (M) | Max % Kill |
| mAb2-tubulysin 1ALP | >2.00E−08 | 6.9 | 6.36E−11 | 90.0 | >2.00E−08 | 30.9 | 3.70E−11 | 95.3 |
| mAb1-tubulysin 1ALP | >2.00E−08 | 13.4 | 1.25E−10 | 91.1 | >2.00E−08 | 19.3 | 4.34E−11 | 95.4 |
| IC1-tubulysin 1ALP (Control) | 1.45E−08 | 95.2 | 1.98E−09 | 89.6 | >2.00E−08 | 7.1 | 3.40E−09 | 94.9 |
| Tubulysin 1A | 2.12E−11 | 94.6 | 3.76E−12 | 89.7 | 7.43E−11 | 84.9 | 3.69E−12 | 95.1 |
| mAb2-maytansinoid 1ALP | >2.00E−08 | 9.5 | 1.72E−10 | 91.1 | >2.00E−08 | 17.0 | 2.06E−10 | 95.0 |
| mAb1-maytansinoid 1ALP | >2.00E−08 | 0.0 | 2.14E−10 | 85.5 | >2.00E−08 | 0.5 | 2.68E−10 | 93.1 |
| IC1-maytansinoid 1ALP (control) | >2.00E−08 | 4.0 | 4.63E−09 | 84.3 | >2.00E−08 | 3.3 | >2.00E−08 | 6.0 |
| maytansinoid 1A | >2.00E−08 | 3.7 | >2.00E−08 | 18.1 | >2.00E−08 | 6.4 | >2.00E−08 | 9.2 |
| Cell Permeable Maytansinoid 1A* | 2.99E−10 | 95.3 | 1.13E−10 | 92.0 | 5.45E−09 | 59.5 | 1.89E−10 | 95.9 |
| Comp2-BAY-LP | >2.00E−08 | 2.2 | 6.38E−11 | 90.4 | 3.49E−10 | 77.2 | 8.71E−11 | 94.7 |
| IC2-BAY-LP (control) | >2.00E−08 | 10.5 | 6.06E−09 | 89.3 | >2.00E−08 | 19.0 | 1.31E−08 | 66.1 |

TABLE 8-continued

Cytotoxicity of Anti-FGFR2 ADCs in SNU-16, NCI-H716, MFM-223, MFE-296, and IM-9 Cells

| | IM-9 | | MFM-223 | | NCI-H716 | | SNU-16 | |
|---|---|---|---|---|---|---|---|---|
| Test Article | IC50 (M) | Max % Kill | IC50 (M) | Max % Kill | IC50 (M) | Max % Kill | IC50 (M) | Max % Kill |
| Comp1 (Unconjugated) | >2.00E−08 | 3.8 | >2.00E−08 | 0.8 | >2.00E−08 | 9.9 | >2.00E−08 | 0.0 |
| Comp2 (Unconjugated) | >2.00E−08 | 7.6 | >2.00E−08 | 7.8 | >2.00E−08 | 0.6 | >2.00E−08 | 12.0 |
| mAb2 (Unconjugated) | >2.00E−08 | 6.4 | >2.00E−08 | 4.5 | >2.00E−08 | 7.8 | >2.00E−08 | 10.3 |
| mAb1 (Unconjugated) | >2.00E−08 | 4.4 | >2.00E−08 | 4.5 | >2.00E−08 | 7.8 | >2.00E−08 | 5.4 |
| IC1 (Unconjugated Control) | >2.00E−08 | 1.6 | >2.00E−08 | 2.9 | >2.00E−08 | 12.6 | >2.00E−08 | 6.0 |
| IC2 (Unconjugated Control) | >2.00E−08 | 6.2 | >2.00E−08 | 8.5 | >2.00E−08 | 3.5 | >2.00E−08 | 2.1 |

Co-Cultures and the Bystander Effect

The ability of the anti-FGFR2 ADCs to induce cytotoxicity in FGFR2 negative cells through release of the payload in FGFR2 positive cells, i.e., bystander activity, was also assessed. In this assay, 10,000 FGFR2 positive SNU-16 cells, 10,000 FGFR2 negative NALM-6 cells, or a 1:1 mixture of 5,000 cells each of SNU-16 and NALM-6 cells, were seeded into 96-well assay plates (Corning #355691) and incubated overnight at 37° C. and 5% $CO_2$. Cytotoxicity was assessed as described previously for tumor cell lines except that three-fold serial dilutions were performed for all test articles with concentrations ranging from 100 nM to 15.2 pM, and cells were incubated with test articles for 5 days.

TABLE 9

Cytotoxicity of Anti-FGFR2 ADCs in An in Vitro Bystander Assay

| | SNU-16 cells | | NALM-6 cells | | SNU-16 + NALM-6 Cells | |
|---|---|---|---|---|---|---|
| Test Article | IC50 (M) | Max % Kill | IC50 (M) | Max % Kill | IC50 (M) | Max % Kill |
| mAb2-tubulysin 1ALP | 2.73E−11 | 97.2 | >1.0E−07 | 0.0 | 1.16E−08 | 97.7 |
| mAb1-tubulysin 1ALP | 6.69E−11 | 97.1 | >1.0E−07 | 0.0 | 4.97E−08 | 87.8 |
| IC1-tubulysin 1ALP | 4.11E−08 | 91.0 | >1.0E−07 | 3.7 | >1.0E−07 | 17.0 |
| Tubulysin 1A | 1.84E−11 | 99.3 | 7.09E−11 | 99.9 | 1.66E−10 | 99.5 |
| mAb2-maytansinoid 1ALP | 6.45E−10 | 94.8 | >1.0E−07 | 5.0 | >1.0E−07 | 18.3 |
| IC1-maytansinoid 1ALP (control) | >1.0E−07 | 9.8 | >1.0E−07 | 0.0 | >1.0E−07 | 3.6 |
| Comp2-BAY-LP | 2.34E−10 | 95.6 | >1.0E−07 | 0.0 | >1.0E−07 | 21.2 |
| IC2-BAY-LP (control) | 5.68E−08 | 76.9 | >1.0E−07 | 7.8 | >1.0E−07 | 19.3 |

As shown in Table 9, mAb2-tubulysin 1ALP and mAb1-tubulysin 1ALP antibody conjugates killed FGFR2 positive SNU-16 monocultures with maximum % killing of 97.2 and 97.1, respectively, but were not cytotoxic in FGFR2 negative NALM-6 monocultures. The mAb2-tubulysin 1ALP and mAb1-tubulysin 1ALP antibody conjugates also killed SNU-16+NALM-6 cocultures with maximum % killing of 97.7 and 87.8 suggestive of bystander killing activity. The non-binding ADC control (IC1-tubulysin 1ALP) was weakly cytotoxic in the SNU-16+NALM-6 coculture with max % killing of 17.0%. mAb2-maytansinoid 1ALP demonstrated cytotoxicity in FGFR2-positive SNU-16 cell monocultures ($EC_{50}$ value of 64.5 pM and 94.8% max kill) and did not have cytotoxic activity in FGFR2-negative NALM-6 cell monocultures (5.0% max kill). In cocultures of SNU-16 and NLAM-6 cells prepared at a 1:1 ratio, mAb2-maytansinoid 1ALP exhibited a maximum cytotoxicity of approximately 18.3%, suggesting there was little to no bystander killing of the FGFR2-negative NALM-6 cell population. The non-binding control IC1-maytansinoid 1ALP was weakly cytotoxic under all tested conditions (<10% max kill). The Comparator ADC, Comp2-BAY-LP, also exhibited weak bystander activity as evidenced by its robust killing activity in SNU-16 cells (max % kill of 95.6%) and weak killing activity in the SNU-16+NALM16 coculture (max % kill of 21.2%).

Figure 4:
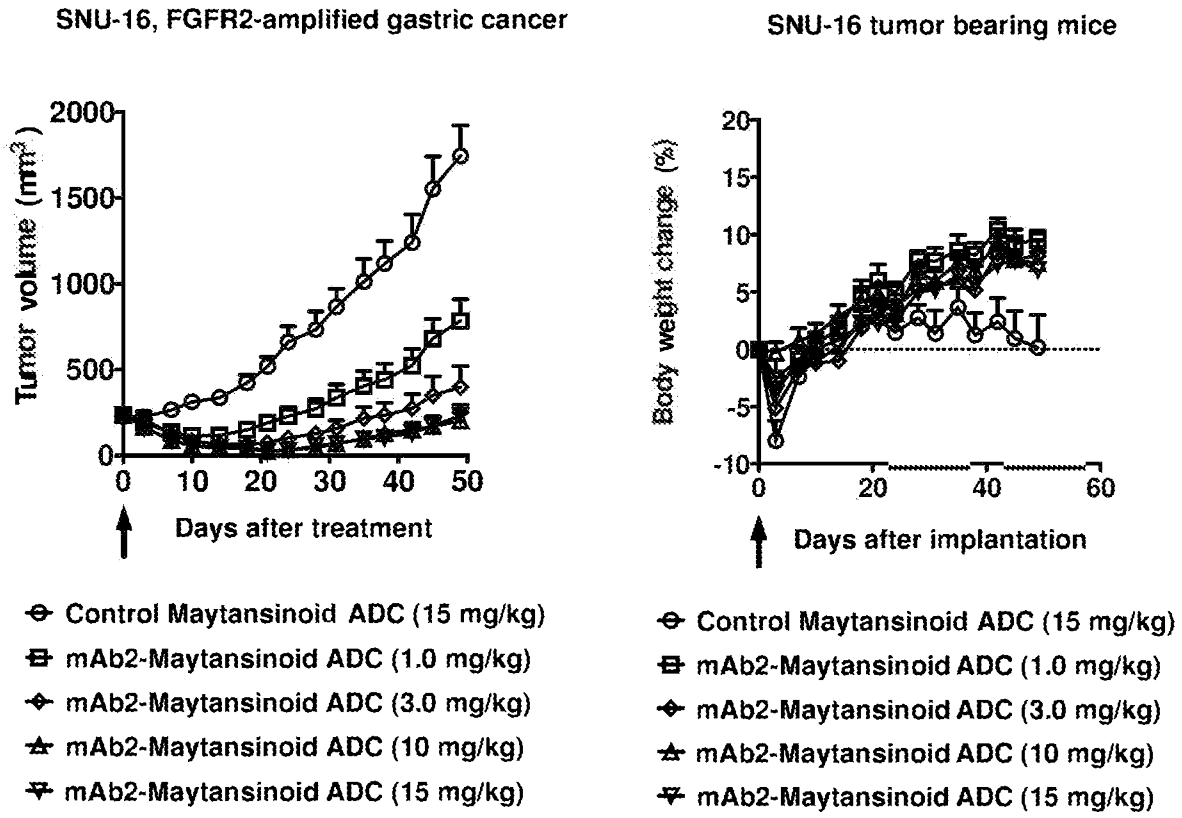
FIG. 4 shows change in tumor volume and body weight in mice having human gastric cancer xenografts over time with treatment using different dosages of Anti-FGFR2 antibody-maytansinoid conjugate. Anti-FGFR2 maytansinoid ADC demonstrated significant anti-tumor efficacy against SNU-16 human gastric cancer xenografts.

Example 7: In Vivo Efficacy of Anti-FGFR2 Antibody Drug Conjugates (ADC) on the Growth of SNU-16 Gastric Cancer Xenografts FGFR2 tubulysin ADC mAb1-tubulysin 1ALP was tested in Experiment A (FIG. 3), and FGFR2 maytansinoid ADC mAb2-maytansinoid 1ALP was tested in Experiment B (FIG. 4), for their ability to inhibit the growth of SNU-16 human gastric cancer xenografts at different doses. Briefly, $5\times10^6$ SNU-16 cells (ATCC) mixed with Matrigel (BD Biosciences) were implanted subcutaneously into the flank of male BALB/c SCID mice (6-8 weeks old, Jackson Laboratory). After tumors reached an average volume of 200-250 $mm^3$, mice were randomized into groups for treatment (n=5-6 mice per group for Experiment A and n=6-7 mice per group for Experiment B). Mice were administered a human Fc isotype control tubulysin ADC IC1-tubulysin 1ALP (3.0 mg/kg) or an FGFR2 tubulysin ADC mAb1-tubulysin 1ALP (0.1, 0.3, 1.0 or 3.0 mg/kg) in Experiment A, and a human Fc isotype control maytansinoid ADC IC1-maytansinoid 1ALP or an FGFR2 maytansinoid ADC mAb2-maytansinoid 1ALP (1.0, 3.0, 10 or 15 mg/kg) in Experiment B. All ADCs were administered once via subcutaneous injection. Tumor volumes were measured twice per week over the course of the experiment. Averages (mean+/−standard deviation) of the tumor growth (change in tumor volume from the start of treatment through the end of the experiment) were calculated for each treatment group. The percent decrease of tumor growth was calculated from comparison to the isotype control group, and the percent regression of tumors at the end of the experiment was calculated from comparison to the tumor volume at the start of treatment. The results are shown in Table 10.

TABLE 10

Inhibition of SNU-16 Xenograft Growth in BALB/c SCID Mice

| Antibody (mg/kg) | Total Payload Dose (ug/kg) | Tumor growth in mm3 from start of treatment (mean ± SD) | Average % Decrease in Tumor Growth | Average % Tumor Regression |
|---|---|---|---|---|
| Experiment A | | | | |
| IC1-tubulysin 1ALP (3.0 mg/kg) | 36 | 519.3 ± 576.8 | | |
| mAb1-tubulysin 1ALP (0.1 mg/kg) | 1.2 | 435.2 ± 189.7 | 16.2 | |
| mAb1-tubulysin 1ALP (0.3 mg/kg) | 3.6 | 141.8 ± 141.5 | 72.7 | |
| mAb1-tubulysin 1ALP (1.0 mg/kg) | 12 | −168.8 ± 37.8 | | 79.3 |
| mAb1-tubulysin 1ALP (3.0 mg/kg) | 36 | −202.5 ± 48.7 | | 88.3 |
| Experiment B | | | | |
| IC1-maytansinoid 1ALP (15 mg/kg) | 190 | 1516.2 ± 413.9 | | |
| mAb2-maytansinoid 1ALP (1.0 mg/kg) | 14 | 547.6 ± 292.3 | 63.9 | |
| mAb2-maytansinoid 1ALP (3.0 mg/kg) | 42 | 164.1 ± 245.5 | 89.2 | |
| mAb2-maytansinoid 1ALP (10 mg/kg) | 140 | −35.1 ± 102.7 | | 18.2 |
| mAb2-maytansinoid 1ALP (15 mg/kg) | 210 | −5.8 ± 145.6 | | 8.4 |

These results demonstrate that ADCs targeting FGFR2b isoforms induced complete regression of SNU-16 tumor xenografts in a dose dependent manner, with maximal efficacy provided by the 1.0 mg/kg dose of tubulysin FGFR2 ADC, and by the 10 mg/kg dose of maytansinoid FGFR2 ADC.

Figure 5:
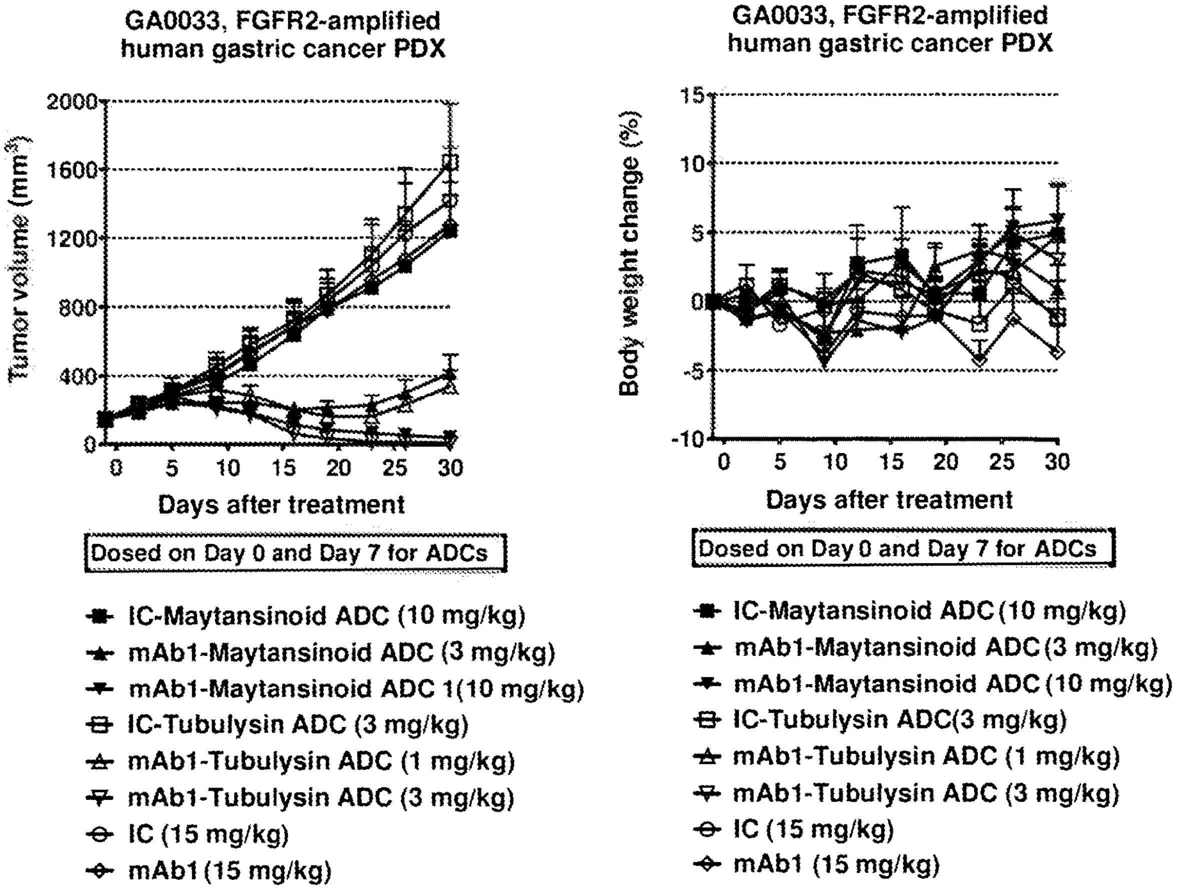
FIG. 5 shows change in tumor volume and body weight in mice with human gastric cancer PDX GA0033 tumors over time with treatment using different dosages of Anti-FGFR2 antibody-tubulysin conjugate and Anti-FGFR2 antibody-maytansinoid conjugate. Mice were dosed on day 0 and day 7 with the respective ADCs or control antibodies. Anti-FGFR2b ADCs demonstrated significant anti-tumor efficacy against human gastric cancer PDX GA0033 tumors.

Example 8: In Vivo Efficacy of Anti-FGFR2b Antibody Drug Conjugates (ADC) on the Growth of Human Gastric Cancer PDX GA0033 Tumors FGFR2 maytansinoid ADC mAb1-maytansinoid 1ALP and FGFR2 tubulysin ADC mAb1-tubulysin 1ALP were tested in this experiment (FIG. 5), for their ability to inhibit the growth of human gastric cancer PDX GA0033 tumors at different doses. Briefly, HuPrime® primary human gastric cancer PDX GA0033 tumor fragments 2-3 mm in diameter (Crown Bioscience) were implanted subcutaneously into the right flank of female BALB/c nude mice (5-9 weeks old, GemPharmatech). After tumors reached an average volume of 100-200 $mm^3$, mice were randomized into groups for treatment (n=6 mice per group). Mice were administered a human Fc isotype control maytansinoid ADC IC-maytansinoid 1ALP (10 mg/kg), an FGFR2 maytansinoid ADC mAb1-maytansinoid 1ALP (3 or 10 mg/kg), a human Fc isotype control tubulysin ADC IC-tubulysin 1ALP (3 mg/kg), an FGFR2 tubulysin ADC mAb1-tubulysin 1ALP (1 or 3 mg/kg), a human Fc isotype control naked antibody IC (15 mg/kg), or an FGFR2 naked antibody mAb1 (15 mg/kg). All ADCs were administered once per week via subcutaneous injection for two treatments, and all naked antibodies were administered twice per week via subcutaneous injection throughout the experiment. Tumor volumes were measured twice per week over the course of the experiment. Averages (mean+/−standard deviation) of the tumor growth (change in tumor volume from the start of treatment through the end of the experiment) were calculated for each treatment group. The percent decrease of tumor growth was calculated from comparison to the corresponding isotype control group, and the percent regression of tumors at the end of the experiment was calculated from comparison to the tumor volume at the start of treatment. The results are shown in Table 11.

TABLE 11

| Inhibition of Human Gastric Cancer PDX GA0033 Tumor Growth in BALB/c Nude Mice | | | | |
|---|---|---|---|---|
| Antibody (mg/kg) | Total Payload Dose (ug/kg) | Tumor growth in $mm^3$ from start of treatment (mean ± SD) | Average % Decrease in Tumor Growth | Average % Tumor Regression |
| IC-maytansinoid 1ALP (10 mg/kg) | 132 × 2 | 1099.4 ± 676.3 | | |
| mAb1-maytansinoid 1ALP (3 mg/kg) | 40 × 2 | 273.6 ± 241.9 | 75.1 | |
| mAb1-maytansinoid 1ALP (10 mg/kg) | 132 × 2 | −104.2 ± 20.6 | | 75.0 |
| IC-tubulysin 1ALP (3 mg/kg) | 36 × 2 | 1497.7 ± 839.5 | | |
| mAb1-tubulysin 1ALP (1 mg/kg) | 12 × 2 | 197.3 ± 201.7 | 86.8 | |
| mAb1-tubulysin 1 ALP (3 mg/kg) | 36 × 2 | −138.4 ± 27.6 | | 96.5 |
| IC (15 mg/kg) | N/A | 1273.7 ± 750.2 | | |
| mAb1 (15 mg/kg) | N/A | 1135.3 ± 391.3 | 10.9 | |

These results demonstrate that ADCs targeting FGFR2b isoforms induced complete regression of human gastric cancer PDX GA0033 tumors in a dose dependent manner, with maximal efficacy provided by the 3.0 mg/kg dose of tubulysin FGFR2 ADC, and by the 10 mg/kg dose of maytansinoid FGFR2 ADO.

Example 9: Synthesis of Camptothecin Derivatives (Payloads)

TABLE 12

| Exemplary Camptothecin Analog Payloads P1-P4 | | | | | | | | |
|---|---|---|---|---|---|---|---|---|
| # | Name | Structures | cLogP | MF | MW | Purity (%) | m/z | Salt |
| P1 | Exatecan | 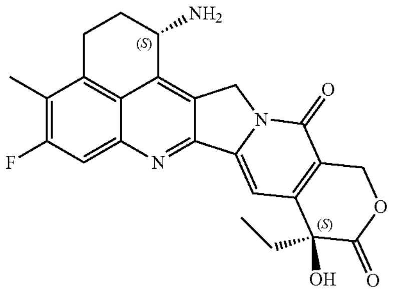 | 1.45 | $C_{24}H_{22}FN_3O_4 \bullet CH_4O_3S$ | 531.56 | 97 | 436.1 [M + H], 893.2 [2M + Na] | MsOH |
| P2 | Dxd | 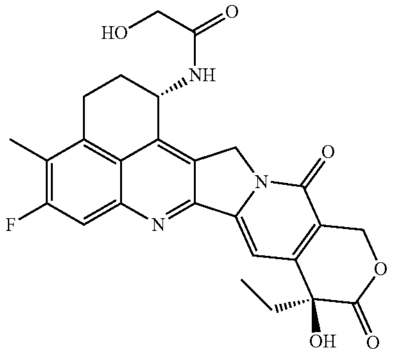 [SMILES: CC[C@@]1(O)C(=O)OCc2c1cc1n(c2=O)Cc2c-1nc1cc(F)c(C)c3c1c2[C@@H](NC(=O)CO)CC3] | 0.55 | $C_{26}H_{24}FN_3O_6$ | 493.48 | 100 | 494.2 [M + H] | NA |

TABLE 12-continued

Exemplary Camptothecin Analog Payloads P1-P4

| # | Name | Structures | cLogP | MF | MW | Purity (%) | m/z | Salt |
|---|---|---|---|---|---|---|---|---|
| P3 | | 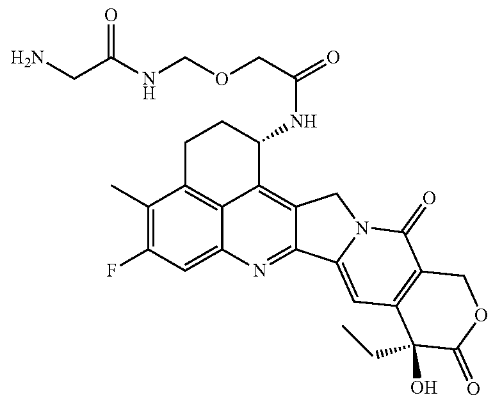 [SMILES: CC[C@@]1(O)C(=O)OCc2c1cc1n(c2=O)Cc2c-1nc1cc(F)c(C)c3c1c2[C@@H](NC(=O)COCNC(=O)CN)CC3] | −0.60 | $C_{29}H_{30}FN_5O_7 \bullet C_2HF_3O_2$ | 693.59 | 97 | 580.2 [M + H], 1159.2 [2M + H] | TFA |
| P4 | | 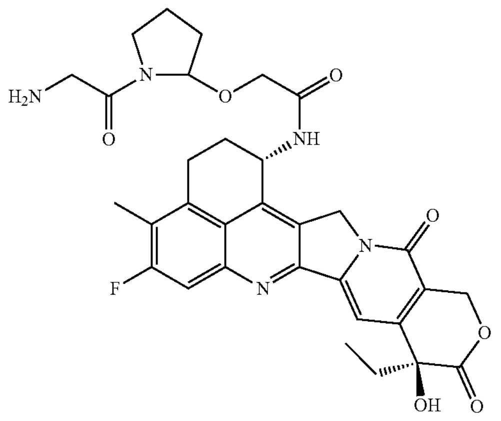 [SMILES: CC[C@@]1(O)C(=O)OCc2c1cc1n(c2=O)Cc2c-1nc1cc(F)c(C)c3c1c2[C@@H](NC(=O)COC1CCCN1C(=O)CN)CC3] | 0.02 | $C_{32}H_{34}FN_5O_7$ | 619.64 | 88 | 620.3 [M + H] | NA |

Payload P1, Exatecan mesylate, was commercially obtained from MOE. Payloads P2 and P3 were synthesized as described in WO2015155998, incorporated herein by reference, and camptothecin derivative payload P4 was synthesized as described in Scheme 1A and according to the synthetic steps outlined in Examples 9A-1 E:

Scheme 1: Synthesis of Camptothecin derivatives (payloads) P3 and P4

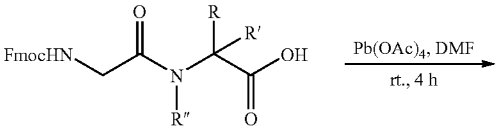

P3-1, R = R′ = R″ = H

P4-1, R = H; R′, R″ = $—(CH_2)_3—$

-continued

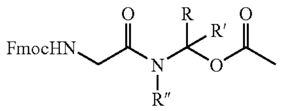

P3-2, R = R′ = R″ = H

P4-2, R = H; R′, R″ = $—(CH_2)_3—$

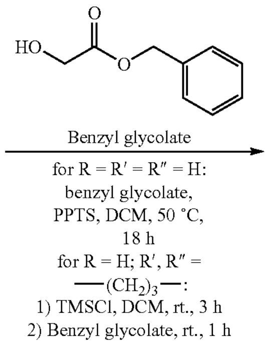

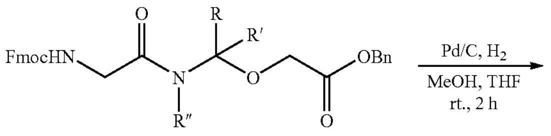

P3-3, R = R′ = R″ = H

P4-3, R = H; R′, R″ = $—(CH_2)_3—$

-continued

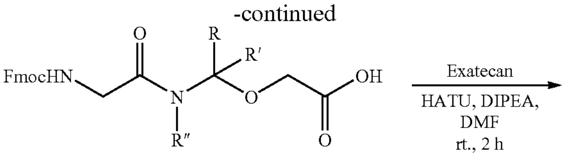

P3-4, R = R′ = R″ = H

P4-4, R = H; R′, R″ = $-(CH_2)_3-$

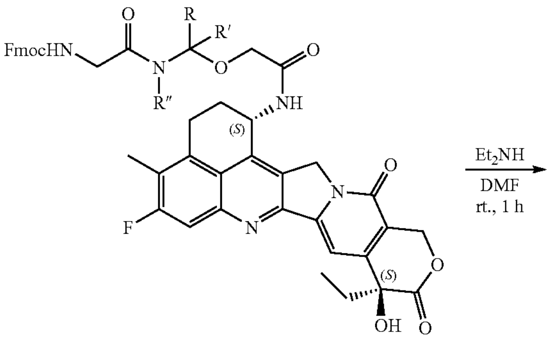

P3-5, R = R′ = R″ = H

P4-5, R = H; R′, R″ = $-(CH_2)_3-$

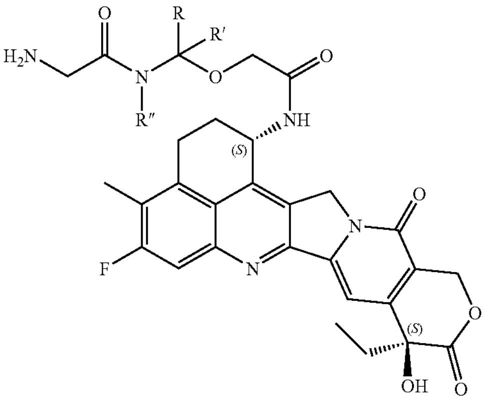

P3, P4

P3, R = R′ = R″ = H

P4, R = H; R′, R″ = $-(CH_2)_3-$

Example 9A: Synthesis of 9H-Fluoren-9-ylmethyl N-[2-(2-hydroxypyrrolidin-1-yl)-2-oxoethyl]carbamate (P4-2)

(P4-2)

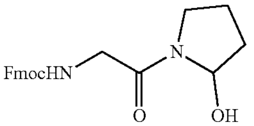

To a mixture of Fmoc-Gly-Pro-OH P4-1 (0.10 g, 0.26 mmol) in dry DMF (1 mL) was added lead tetraacetate (0.14 g, 0.31 mmol). The resulting mixture was stirred at RT for 30 minutes; reaction progress was monitored by LCMS. The resulting mixture was filtered through Celite, and the filtrate was diluted with ethyl acetate, washed with water and brine, dried over anhydrous sodium sulfate, and concentrated in vacuo. The residue was purified by silica gel column chromatography (0-10% ethyl acetate in petroleum ether) to give compound P4-2 (50 mg, 53% yield) as a white solid, and no acetate intermediate was obtained. ESI m/z: 389 (M+23)+. $^1$H NMR (400 MHz, DMSO) δ 7.90 (d, J=7.4 Hz, 2H), 7.73 (d, J=7.5 Hz, 2H), 7.47-7.37 (m, 3H), 7.33 (t, J=7.3 Hz, 2H), 5.86 (br s, 1H), 5.48 (d, J=4.0 Hz, 0.25H), 5.39 (d, J=4.0 Hz, 0.75H), 4.33-4.18 (m, 3H), 3.96 (d, J=6.0 Hz, 1.5H), 3.75 (d, J=6.0 Hz, 0.5H), 3.59-3.33 (m, 1H), 3.22-3.11 (m, 1H), 2.00-1.59 (m, 4H) ppm.

Example 9B: Synthesis of Benzyl 2-{[1-(2-{[(9H-fluoren-9-ylmethoxy)carbonyl]amino}acetyl) pyrrolidin-2-yl]oxy}acetate (P4-3)

(P4-3)

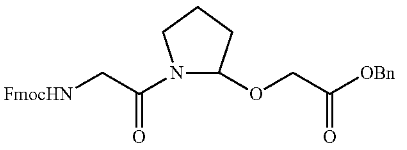

To a solution of compound P4-2 (0.30 g, 0.82 mmol) in DCM (25 mL) was added chlorotrimethylsilane (TMSCl) (0.27 g, 2.5 mmol). The reaction mixture was stirred at RT for 3 hours; reaction progress was monitored by LCMS. The resulting mixture was concentrated in vacuo and the residue was diluted with DCM (25 mL). To the solution were added benzyl glycolate (0.27 g, 1.6 mmol) and DIPEA (0.21 g, 1.6 mmol), and the reaction mixture was stirred at RT for an hour; the completion of the reaction was monitored by LCMS. The resulting mixture was concentrated in vacuo and the residue was purified by reversed phase flash chromatography (0-100% acetonitrile in aq. ammonium bicarbonate (0.05%)) to give compound P4-3 (0.11 g, 25% yield, with purity>99% and 50 mg, with purity 75%) as a white solid. ESI m/z: 537.3 (M+Na)+. $^1$H NMR (400 MHz, $DMSO_{d6}$) δ 7.91-7.89 (m, 2H), 7.74-7.69 (m, 2H), 7.63-7.48 (m, 1H), 7.42-7.25 (m, 9H), 5.51-5.09 (m, 2H), 4.35-4.21 (m, 5H), 4.00-3.77 (m, 2H), 3.52-3.38 (m, 2H), 3.30-3.18 (m, 1H), 2.19-1.64 (m, 4H) ppm.

Example 9C: Synthesis of 2-{[1-(2-{[(9H-Fluoren-9-ylmethoxy)carbonyl]amino}acetyl)pyrrolidin-2-yl]oxy}acetic acid (P4-4)

(P4-4)

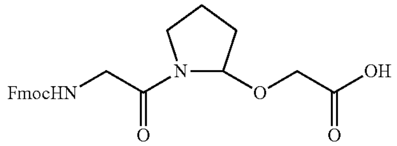

To a solution of compound P4-3 (89 mg, 0.17 mmol) in methanol (3 mL) and THE (7 mL) was added wet palladium on carbon (10% Pd, 20 mg) under nitrogen protection. The mixture was degassed and stirred under hydrogen balloon pressure at RT for 2 hours, and the completion of the reaction was monitored by LCMS. The reaction mixture was filtered through Celite and the filtrate was concentrated in vacuo. The residue was purified by reversed phase flash chromatography (0-100% acetonitrile in aq. ammonium bicarbonate (0.05%)) to give compound P4-4 (36 mg, 49% yield) as a white solid. ESI m/z: 447.1 (M+Na)+.

Example 9D: 9H-Fluoren-9-ylmethyl N-{2-[2-({[(10S,23S)-10-ethyl-18-fluoro-10-hydroxy-19-methyl-5,9-dioxo-8-oxa-4,15-diazahexacyclo [14.7.1.$0^{2}$,$^{14}$0.$0^{4}$,$^{13}$.$0^{6}$,$^{11}$ 0.$^{20}$,$^{24}$]tetracosa-1,6(11),12,14,16,18,20(24)-heptaen-23-yl]carbamoyl}methoxy) pyrrolidin-1-yl]-2-oxoethyl}carbamate (P4-5)

(P4-5)

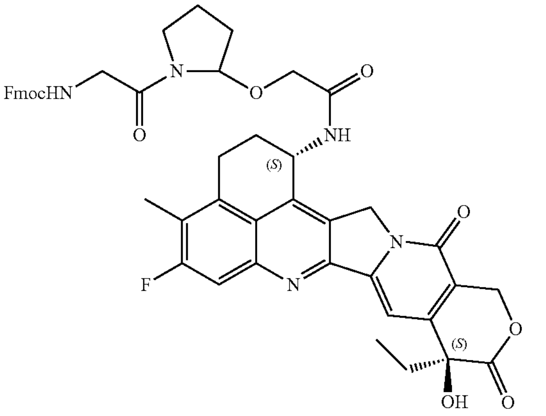

To a mixture of compound P4-4 (63 mg, 0.15 mmol) and Exatecan mesylate (66 mg, 0.12 mmol) in DMF (2 mL) were added HATU (61 mg, 0.16 mmol) and DIPEA (46 mg, 0.36 mmol), and the mixture was stirred at RT for 2 hours; reaction completion was monitored by LCMS. The reaction mixture was directly purified by reversed phase flash chromatography (0-100% acetonitrile in aq. ammonium bicarbonate (10 mM)) to give compound P4-5 (45 mg, 44% yield) as a yellow solid. ESI m/z: 842.3 (M+H)+.

Example 9E: 2-{[1-(2-Aminoacetyl)pyrrolidin-2-yl] oxy}-N-[(10S,23S)-10-ethyl-18-fluoro-10-hydroxy-19-methyl-5,9-dioxo-8-oxa-4,15-diazahexacyclo [14.7.1.$0^{2}$,$^{14}$0.$^{4}$,$^{13}$.$0^{6}$,$^{11}$.$0^{20}$,$^{24}$]tetracosa-1,6(11),12,14,16,18,20(24)-heptaen-23-yl]acetamide (P4)

(P4)

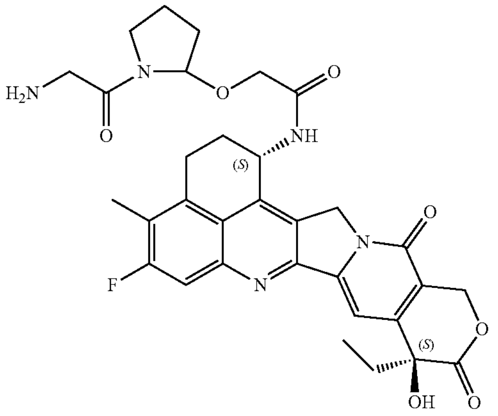

To a solution of compound P4-5 (45 mg, 54 μmol) in DCM (4 mL) was added diethylamine (20 mg, 0.27 mmol), and the mixture was stirred at RT overnight. Reaction completion was monitored by LCMS. The reaction mixture was concentrated in vacuo and the residue was purified by silica gel flash chromatography (0-10% methanol in DCM) to give compound P4 (9.5 mg, 28% yield) as colorless oil. ESI m/z: 620.3 $(M+H)^+$.

Example 10: Synthesis of vcPAB-Carbamate Linker-Payloads

Linker-payloads LP1 and LP2 were synthesized as described in Scheme 2 and in Examples 10A-10C (for LP1) and 10D (for LP2), below. Starting materials L1-1 (CAS 2226472-26-8) and L2-3 (CAS 2226472-28-0) were synthesized according to WO2018089373A2, incorporated by reference herein in its entirety.

Scheme 2. Synthesis of vcPAB-carbamate linker-payloads

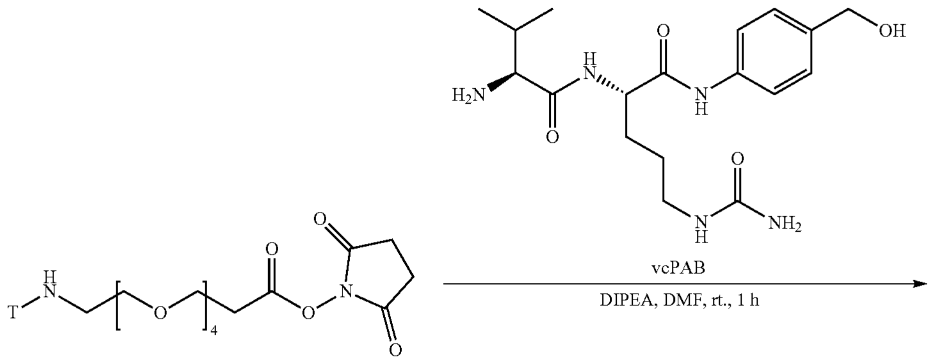

L1-1
L2-1

-continued
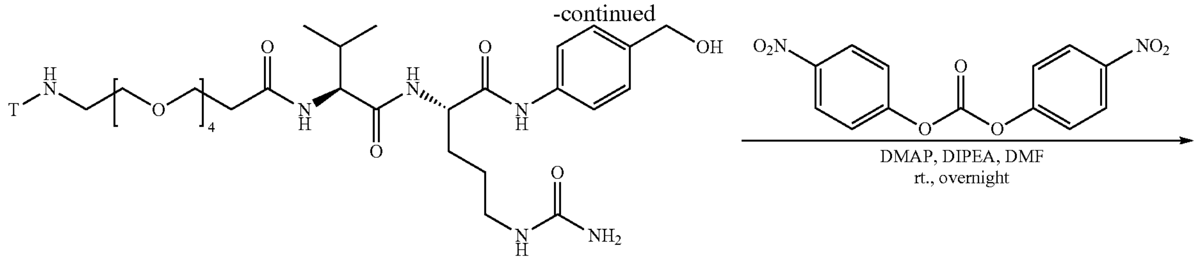
L1-2
L2-2
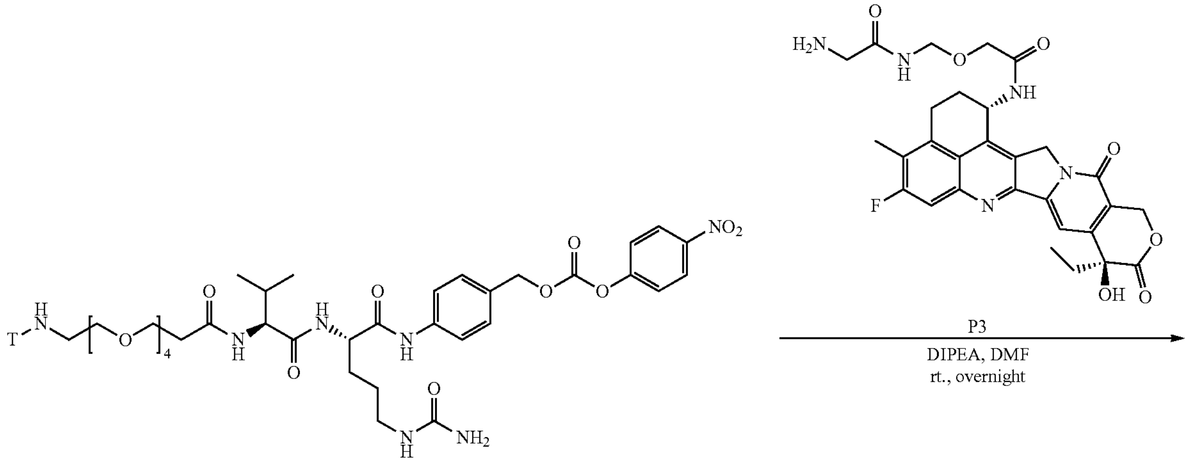
L1-3
L2-3
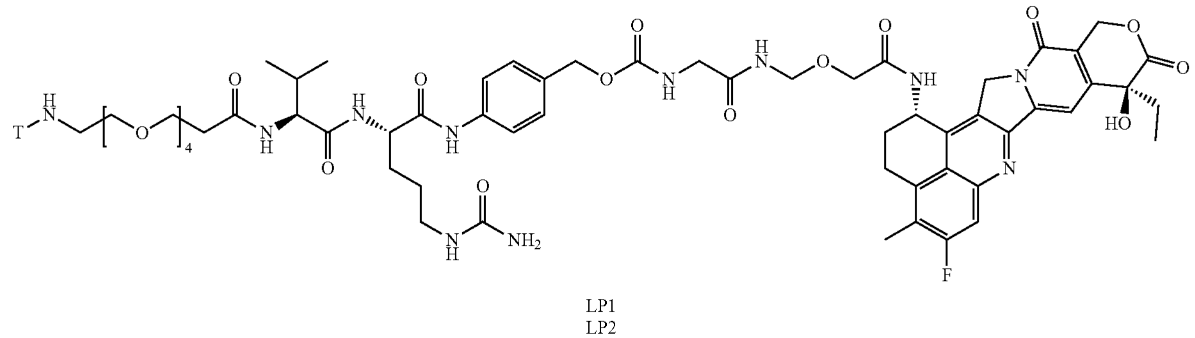
LP1
LP2
L1, LP1, T =
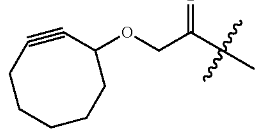
L2, LP2, T =
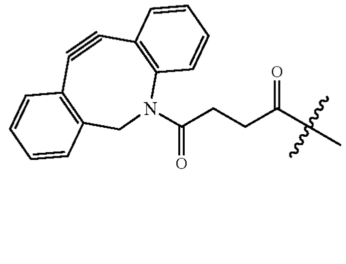

Example 10A: N-[(1 S)-1-{[(1 S)-4-(Carbamoylamino)-1-{[4-(hydroxymethyl)phenyl]carbamoyl}butyl]carbamoyl}-2-methylpropyl]-1-[2-(cyclooct-2-yn-1-yloxy)acetamido]-3,6,9,12-tetraoxapentadecan-15-amide (L1-2)

(L1-2)

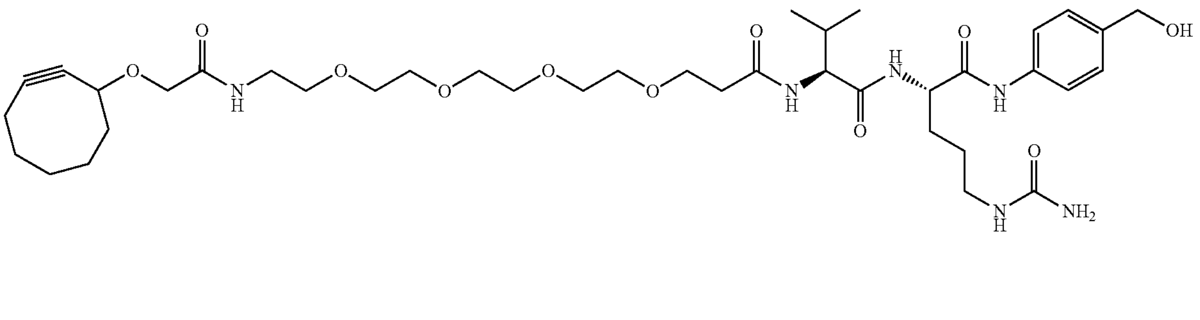

To a solution of compound L1-1 (0.17 g, 0.33 mmol) in DMF (10 mL) were added DIPEA (0.13 g, 1.0 mmol) and vcPAB (0.13 g, 0.34 mmol) successively, and the reaction mixture was stirred at RT for an hour. Reaction completion was monitored by LCMS. The resulting mixture was directly purified by reversed phase flash chromatography (0-80% acetonitrile in water) to give compound L1-2 (0.18 g, 70% yield) as a colorless oil. ESI m/z: 791.3 $(M+H)^+$. $^1H$ NMR (400 MHz, $DMSO_{d6}$) δ 9.91 (s, 1H), 8.11 (d, J=8.4 Hz, 1H), 7.89 (d, J=8.8 Hz, 1H), 7.61 (t, J=5.6 Hz, 1H), 7.55 (d, J=8.4 Hz, 2H), 7.23 (d, J=8.4 Hz, 2H), 5.98 (t, J=5.6 Hz, 1H), 5.42 (s, 2H), 5.10 (br s, 1H), ), 4.43 (s, 2H), 4.39-4.37 (m, 1H), 4.30-4.21 (m, 2H), 3.87 (d, J=14.8 Hz, 1H), 3.75 (d, J=14.8 Hz, 1H), 3.62-3.58 (m, 2H), 3.50-3.46 (m, 12H), 3.43 (t, J=6.0 Hz, 2H), 3.27-3.22 (m, 2H), 3.06-2.92 (m, 2H), 2.41-2.32 (m, 2H), 2.26-2.05 (m, 3H), 1.99-1.66 (m, 6H), 1.62-1.55 (m, 3H), 1.44-1.35 (m, 3H), 0.89 (d, J=6.8 Hz, 3H), 0.83 (d, J=6.8 Hz, 3H) ppm.

Example 10B: {4-[(2S)-5-(Carbamoylamino)-2-[(2S)-2-{1-[2-(cyclooct-2-yn-1-yloxy) acetamido]-3,6,9,12-tetraoxapentadecan-15-amido}-3-methylbutanamido]pentanamido]phenyl}methyl 4-nitrophenyl carbonate (L1-3)

(L1-3)

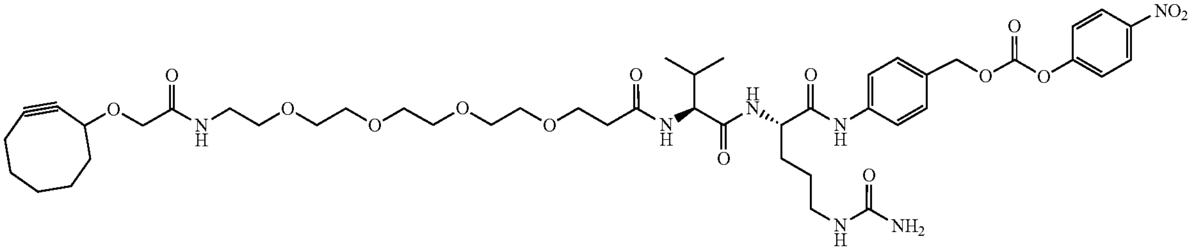

A suspension of compound L1-2 (80 mg, 0.10 mmol), DMAP (12 mg, 0.10 mmol) and DIPEA (26 mg, 0.20 mmol) in dry DMF (5 mL) was stirred at RT for 10 minutes before the addition of bis(4-nitrophenyl) carbonate (61 mg, 0.20 mmol). The reaction mixture was stirred at RT for 2 hours. Reaction completion was monitored by LCMS. The resulting mixture was directly purified by reversed phase flash chromatography (0-80% acetonitrile in water) to give compound L1-3 (53 mg, 55% yield) as a white solid. ESI m/z: 956.3 $(M+H)^+$.

Example 10C: {4-[(2S)-5-(Carbamoylamino)-2-[(2S)-2-{1-[2-(cyclooct-2-yn-1-yloxy)acetamido]-3,6,9,12-tetraoxapentadecan-15-amido}-3-methylbutanamido]pentanamido]phenyl}methyl N-({[({[(10S,23S)-10-ethyl-18-fluoro-10-hydroxy-19-methyl-5,9-dioxo-8-oxa-4,15-diazahexacyclo [14.7.1.$0^{2}$,$^{14}$.$^{4}$,$^{13}$.$0^{6}$,$^{11}$.$0^{20}$,$^{24}$]tetracosa-i1,6(11),12,14,16,18,20(24)-heptaen-23-yl]carbamoyl}methoxy)methyl]carbamoyl}methyl)carbamate (LP1)

(LP1)

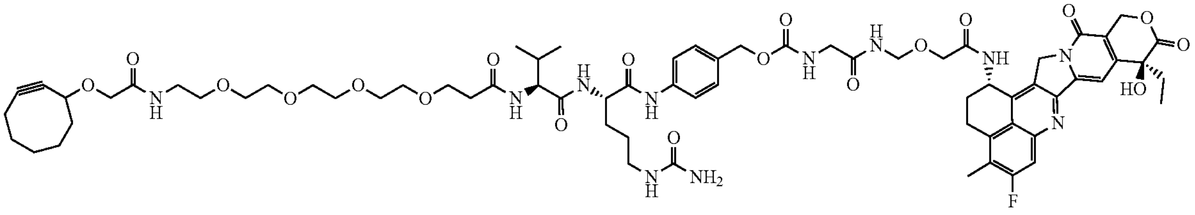

To a yellow solution of compound L1-3 (16 mg, 17 μmol) and P3 (12 mg, 17 μmol) in dry DMF (2 mL) was added DIPEA (6.5 mg, 51 μmol), and the clear reaction solution was stirred at RT for 2 hours. Reaction completion was monitored by LCMS. The resulting mixture was directly purified by reversed phase flash chromatography (0-60% acetonitrile in aq. TFA (0.01%)) to give linker-payload LP1 (15 mg, 63% yield as TFA salt) as a white solid. ESI m/z: 698.8 $(M/2+H)^+$. $^1H$ NMR (400 MHz, $DMSO_{d6}$) δ 9.99 (s, 1H), 8.80 (t, J=6.8 Hz, 1H), 8.50 (d, J=9.2 Hz, 1H), 8.12 (d, J=7.2 Hz, 1H), 7.87 (d, J=8.8 Hz, 1H), 7.79 (d, J=10.8 Hz, 1H), 7.62-7.58 (m, 3H), 7.42 (t, J=6.0 Hz, 1H), 7.31 (s, 1H), 7.28 (d, J=8.4 Hz, 2H), 6.53 (br s, 1H), 5.98 (t, J=5.2 Hz, 1H), 5.63-5.57 (m, 1H), 5.46-5.37 (m, 3H), 5.21 (s, 2H), 4.93 (s, 2H), 4.63 (d, J=6.4 Hz, 2H), 4.41-4.35 (m, 1H), 4.29-4.21 (m, 2H), 4.02 (s, 2H), 3.87 (d, J=14.4 Hz, 1H), 3.75 (d, J=14.8 Hz, 1H), 3.63-3.58 (m, 4H), 3.50-3.48 (m, 12H), 3.46-3.41 (m, 2H), 3.27-3.24 (m, 2H), 3.23-3.12 (m, 2H), 3.07-2.91 (m, 2H), 2.47-2.45 (m, 0.5H), 2.41-2.33 (m, 4.5H), 2.25-2.04 (m, 5H), 1.99-1.69 (m, 9H), 1.63-1.54 (m, 3H), 1.44-1.33 (m, 3H), 0.88-0.82 (m, 9H) ppm. (The proton of TFA was not observed). $^{17}F$ NMR (376 MHz, $DMSO_{d6}$) δ-74 (TFA), −111 (Ar-F) ppm.

Example 10D: {4-[(2S)-2-[(2S)-2-[1-(4-{2-Azatricyclo[10.4.0.$0^{4}$,$^{9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino) pentanamido]phenyl}methyl N-({[({[(10S,23S)-10-ethyl-18-fluoro-10-hydroxy-19-methyl-5,9-dioxo-8-oxa-4,15-diazahexacyclo [14.7.1.$0^{2}$,$^{14}$0.$0^{4}$,$^{13}$.$0^{6}$,$^{11}$.$0^{20}$,$^{24}$]tetracosa-1,6(11),12,14,16,18,20(24)-heptaen-23-yl]carbamoyl}methoxy)methyl]carbamoyl}methyl)carbamate (LP2)

(LP2)

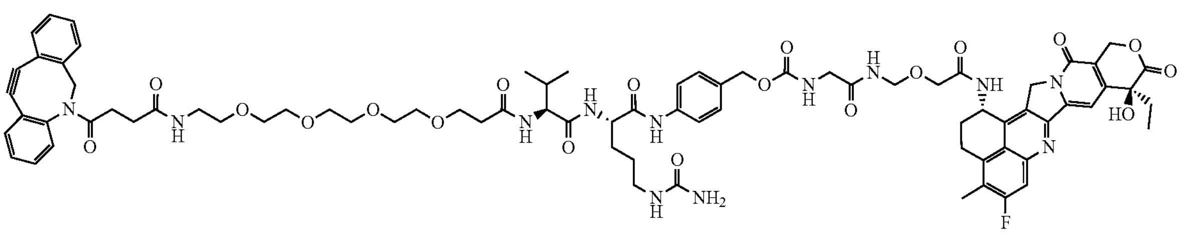

Following the procedure to make LP1 except substituting L2-3 for L1-3, linker-payload LP2 (12 mg, 46% yield) was obtained as a mixture of the lactone product (LP2, pictured above) and the ring-opening product (LP2-RO, pictured below) as a white solid after purification by reversed phase flash chromatography (0-100% methanol in aq. ammonium bicarbonate (10 mM)).

(LP2-RO)

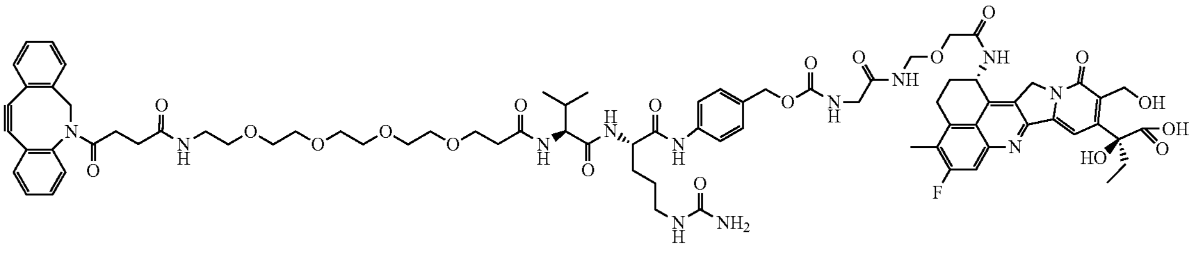

Lactone LP2: HPLC purity: 67%, retention time: 7.41 min, ESI m/z: 507.3 $(M/3+H)^+$, 760.5 $(M/2+H)^+$; Ring-opening product LP2-RO: HPLC purity: 33%, retention time: 6.61 min, ESI m/z: 513.3 $(M/3+H)^+$, 769.5 $(M/2+H)^+$.

Lactone product and ring-opening product mixture $^1H$ NMR (400 MHz, $DMSO_{d6}$) δ 9.99 (s, 1H), 8.80 (t, J=6.4 Hz, 1H), 8.50 (d, J=8.8 Hz, 1H), 8.12 (d, J=7.2 Hz, 1H), 7.87 (d, J=8.4 Hz, 1H), 7.80-7.75 (m. 2H), 7.69-7.67 (m, 1H), 7.63-7.58 (m, 3H), 7.51-7.46 (m, 3H), 7.45-7.33 (m, 3H), 7.32-7.26 (m, 4H), 6.53 (s, 1H), 5.98 (t, J=6.0 Hz, 1H), 5.63-5.57 (m, 1H), 5.42 (s, 4H), 5.21 (s, 2H), 5.03 (d, J=14.0 Hz, 1H), 4.93 (s, 2H), 4.63 (d, J=6.8 Hz, 2H), 4.41-4.35 (m, 1H), 4.25-4.21 (m, 1H), 4.02 (s, 2H), 3.62-3.57 (m, 5H), 3.48-3.45 (m, 12H), 3.31-3.28 (m, 2H), 3.23-3.14 (m, 2H), 3.11-3.07 (m, 2H), 3.05-2.98 (m, 1H), 2.96-2.91 (m, 1H), 2.60-2.55 (m, 1H), 2.46-2.44 (m, 1H), 2.39 (s, 3H), 2.35-2.33 (m, 1H), 2.26-2.15 (m, 3H), 2.03-1.94 (m, 2H), 1.88-1.67 (m, 4H), 1.63-1.57 (m, 1H), 1.46-1.33 (m, 2H), 0.88-0.81 (m, 9H) ppm. $^{19}F$ NMR (376 MHz, $DMSO_{d6}$) δ −111 ppm.

Example 11: FGFR2b-Camptothecin Conjugation

This example demonstrates a method for site-specific conjugation according to an embodiment of the disclosure, generally, of a payload to an anti-FGFR2b antibody or an antigen-binding fragment thereof. The first step is microbial transglutaminase (MTG) mediated attachment of Linker 1 (L1-B'), such as bis azido-alkyl substituted amine (BL7) or azide-$PEG_3$-amine (AL1), to the FGFR2b antibody, wherein an excess of the amine reagent was used to avoid potential cross-linking of antibody chains. The second step attached the alkyne-linked payload linker payload (L2P) to the $N_3$-tagged conjugate via a strain-promoted azide-alkyne cycloaddition (SPAAC). The number of L2P molecules added to the antibody is dependent on the number of conjugation sites and the number of azide functional groups (n) within $L_1$ (AL, n=1; BL, n≥2). For antibodies with a WT Fc domain that were enzymatically deglycosylated or have an N297D Fc mutation and then azido functionalized with AL or BL linkers, the expected DAR=2 times n times m, where n is the number of azide functional groups B' on each L1 linker, and m is the number of L2P payloads, respectively. For antibodies with an N297Q Fc mutation then azido functionalized with AL or BL linkers, the expected DAR=4×(n)×(m).

Example 11A: Step 1: Making a Site-Specific Azido-Functionalized Antibody Drug Conjugate Containing 2, 4 or 8 Azido Groups Anti-FGFR2b human IgG antibody containing an N297Q mutation or an isotype control antibody was mixed with 150 molar equivalents of azido-PEG3-amine (AL1, MW 218.26 g/mol) or bis azido-alkyl substituted amine (BL7, MW 325.38 g/mL). The resulting solution was mixed with transglutaminase (25U/mL; 1 U mTG per mg of antibody, Zedira, Darmstadt, Germany) resulting in a final concentration of the antibody at 1-20 mg/mL. The reaction mixture was incubated at 25-37° C. for 4-24 hours while gently shaking while monitored by ESI-MS. Upon completion, the excess amine and mTG were removed by size exclusion chromatography (SEC) or protein A column chromatography. The conjugate was characterized by UV-Vis, SEC and ESI-MS. The azido linkers attached antibody resulting in an 804 Da or 1232 Da mass increase for the DAR=4 conjugate with AL1 and BL7 respectively. Conjugates' monomer purity was >99% by SEC.

Example 11 B: Step 2: Making Site-Specific Conjugates Via 1,3-Cycloaddition ("Click") Reactions Between Azido-Functionalized Antibodies and Alkyne Containing Linker-Payload A site-specific antibody drug conjugate was prepared by incubating azido-functionalized antibody (1-20 mg/mL) in PBS (pH 7.4) with ≥6 molar equivalents of a linker-payload dissolved in an organic solvent such as DMSO or DMA (10 mg/mL) to have the reaction mixture containing 5-15% organic solvent (v/v), at 25-37° C. for 1-48 hours while gently shaking. The reaction was monitored by ESI-MS. Upon completion, the excess amount of linker-payload and protein aggregates were removed by size exclusion chromatography (SEC). The purified conjugate was concentrated, sterile filtered and characterized by UV-Vis, SEC and ESI-MS. Conjugates' monomer purity was >99% by SEC.

Example 12: ADC Conjugation: Three Approaches

The present disclosure depicts three exemplary approaches to attach branched linker-payloads to anti-FGFR2b antibody Q295/297 sites.

Approaches I and II include a two-step process for the antibody-drug conjugations. The first step is microbial transglutaminase (MTG) mediated attachment of a small molecular amine, e.g., AL1 or BL2, to the mAb-Q sites, wherein an excess of the amine reagent is used to avoid potential cross-linking of antibody chains (WO2017/147542, incorporated by reference herein in its entirety). The second step is attaching an alkyne-linked linker payload ($L_2P$) to the $N_3$-tagged conjugate via, e.g., a strain-promoted azide-alkyne cycloaddition (SPAAC, aka copper-free click chemistry). Where the reactive group (RG) is a DIBAC or COT moiety, the conjugation is carried out with an azido functionalized antibody via a [2+3]cycloaddition. This process provides the site-specific and stoichiometric conjugates. The number of $L_2P$ molecules added to the antibody is dependent on the number of conjugation sites and the number of azide functional groups (n) within $L_1$ (e.g., for AL, n=1; for BL, n≥2).

Approach I is to conjugate a small molecular amine linker L1 (e.g., AL1) to the antibody Q295/297 sites to generate antibody-azido tag (Ab-N3), which is then covalently reacted (e.g., via the "click" cycloaddition) with an alkyne-tethered linear linker-payload (LL2P) to generate 4DAR ADCs and with an alkyne tethered branched linker-payload (BL2P) to generate 8DAR ADCs.

Approach II is to conjugate a small molecular branched azido-amine (e.g., BL2) to the antibody Q295/297 sites to generate antibody branched-azido tag (Ab-branch-2N3), which is then covalently reacted (e.g., via the "click" cycloaddition) with a linear linker-Payload to generate 8DAR ADCs and with an alkyne tethered branched linker-2 Payload to generate 16DAR ADCs or a branched tethered-3 Payload to generate 24DAR ADCs. Similarly, the site-specific ADC conjugations on antibody Q295 sites with the linear or branched linker-Payload could generate DAR2 to DAR12 ADCs.

In the conjugations of Approach Ill, the MTG mediated attachment of an amine-branched linker-payload to the antibody Q295/297 sites was achieved using >20 molar equivalents of the amine reagents in a single step MTG-mediated reaction.

For antibodies with a WT Fc domain that were enzymatically deglycosylated or have an N297D Fc mutation and then azido functionalized with AL or BL linkers, the expected DAR per azido-tag on 2 Fc=2n. For antibodies with an N297Q Fc mutation which were azido-functionalized with AL or BL linkers, the expected DAR per azido-tag on 2 Fc=4n. For antibodies conjugated with each linker-Payload having m×payload ($P_m$), the expected ADC-DAR=(2n x m) for N297D mutated antibodies and (4n×m) for N297Q mutated antibodies.

Generic procedures for making site-specific conjugates in two steps:

Example 12A: Step 1: Making a Site-Specific Azido-Functionalized Antibody Drug Conjugate Containing 2, 4 or 8 Azido Group Aglycosylated human anti-FGFR2b antibody IgG (IgG1, IgG4, etc.) containing an N297Q mutation or N297D mutation in BupH buffer (pH7.4) was mixed with >=150 molar equivalents of azido-PEG3-amine (AL1) or bis azido-alkyl substituted amine (BL2). The resulting solution was mixed with transglutaminase (25U/mL; 1 U mTG per mg of antibody, Zedira, Darmstadt, Germany; or 10U/mL; 5.5U MTG per mg of antibody, Modernist Pantry-ACTIVA TI contains Maltodextrin from Ajinomoto, Japan) resulting in a final concentration of the antibody at 0.5-20 mg/mL. The reaction mixture was incubated at 25-37° C. for 24 hours while gently shaking while monitored by ESI-MS. Upon completion, the excess amine and mTG were removed by size exclusion chromatography (SEC) or protein A column chromatography. The conjugate was characterized by UV-Vis, SEC and ESI-MS. The azido linkers attached to the antibody resulted in an 804 Da or 1232 Da mass increase for the 4DAR conjugates with AL1 and BL2, respectively, and in a 2768 Da increase for the 8DAR antibody-BL2-(azide)s conjugate. Conjugates' monomer purity was >99% by SEC.

Example 12B: Step 2: Making Site-Specific Conjugates Via [2+3] Click Reactions Between Azido-Functionalized Antibodies and an Alkyne Containing Linker-Payloa A site-specific antibody drug conjugate with a human IgG (IgG1, IgG4, etc) was prepared by the [2+3]azide-alkyne "click" reaction between the azido-functionalized antibody and an alkyne-functionalized linker-payload. The azido-functionalized antibody (1-20 mg/mL) in PBS (pH7.4) was incubated with >6 molar equivalents of a linker-payload (LP) dissolved in an organic solvent such as DMSO or DMA (10 mg/mL) to have the reaction mixture containing 5-15% organic solvent (v/v) at 25-37° C. for 1-48 hours while gently shaking. The reaction was monitored by ESI-MS. Upon completion, the excess amount of LP and organic solvent were removed by desalting column with BupH (pH 7.4) and protein aggregates (if any) were removed by size exclusion chromatography (SEC). The purified conjugate was concentrated, sterile filtered and characterized by UV-Vis, SEC and ESI-MS. Conjugates' monomer purity was >99% by SEC.

Example 13: Effect of FGFR2b Antibody Drug Conjugates (ADC) on the Growth of SNU-16 Gastric Cancer Xenografts To assess the anti-tumor activity of FGFR2b Camptothecin ADCs against SNU16 xenografts (human gastric cancer xenografts), 5×10$^6$ SNU-16 cells (ATCC) mixed with Matrigel (BD Biosciences) were implanted subcutaneously into the flank of male BALB/c SCID mice (6-8 weeks old, Jackson Laboratory). After tumors reached an average volume of 200-250 mm$^3$, mice were randomized into groups for treatment (n=6 mice per group). Camptothecin-LP1 and Camptothecin-LP2 are shown in Table 13. All ADCs were administered via subcutaneous injection at the dosages shown in Table 14. Mice treated with the anti-FGFR2 Camptothecin-LP1 ADC (DAR8) were dosed on day 0; mice treated with anti-FGFR2 Camptothecin-LP2 ADC (DAR4) were dose twice, first on day 0 and then again on day 7.

TABLE 13
| Camptothecin Derivatives | |
|---|---|
| Campto-thecin-LP1 | 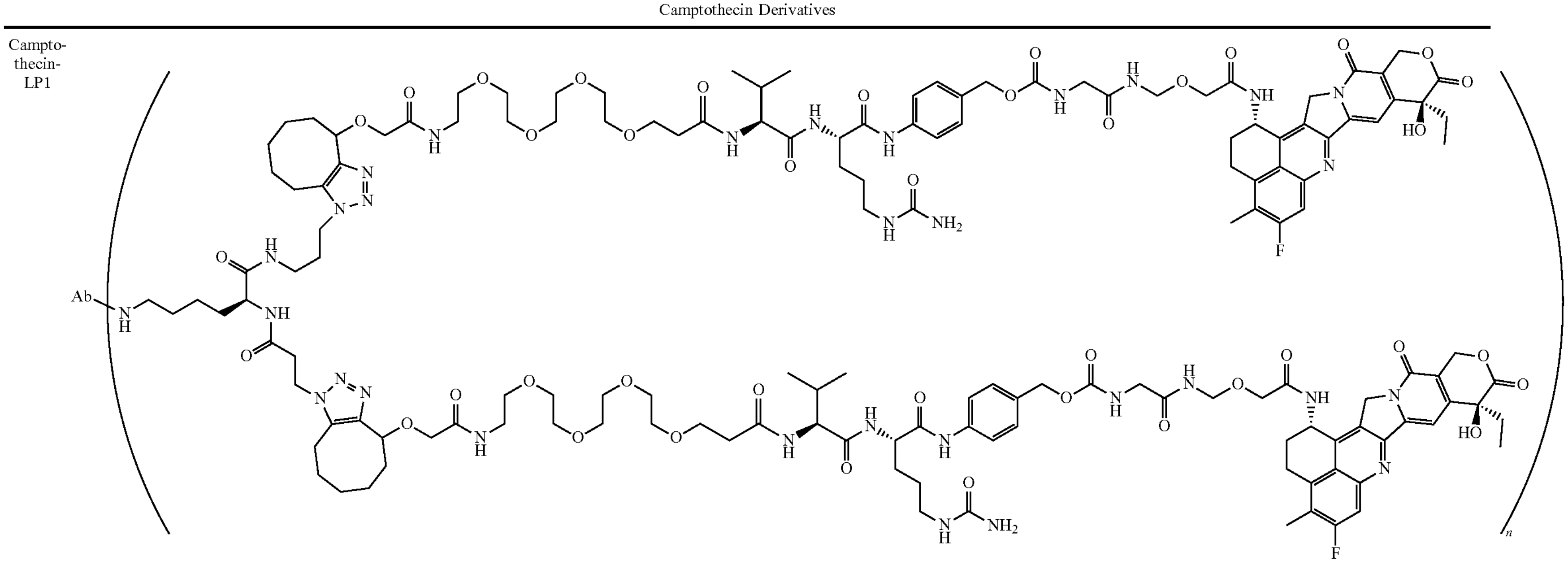 |
| Campto-thecin-LP2 | 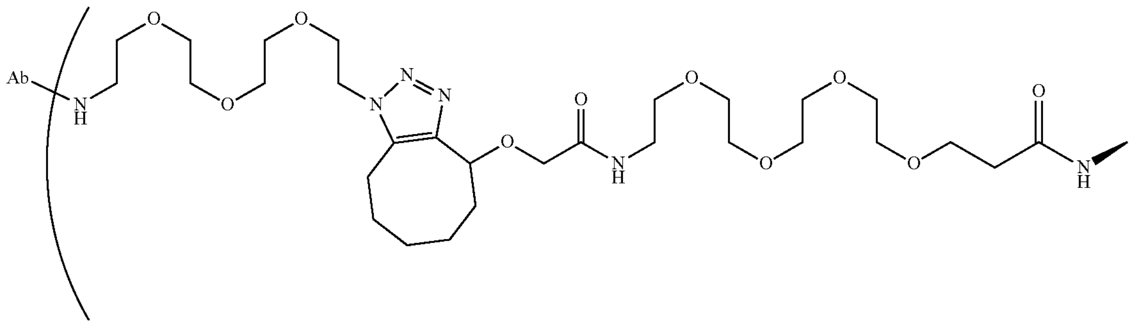 |

TABLE 13-continued
Camptothecin Derivatives
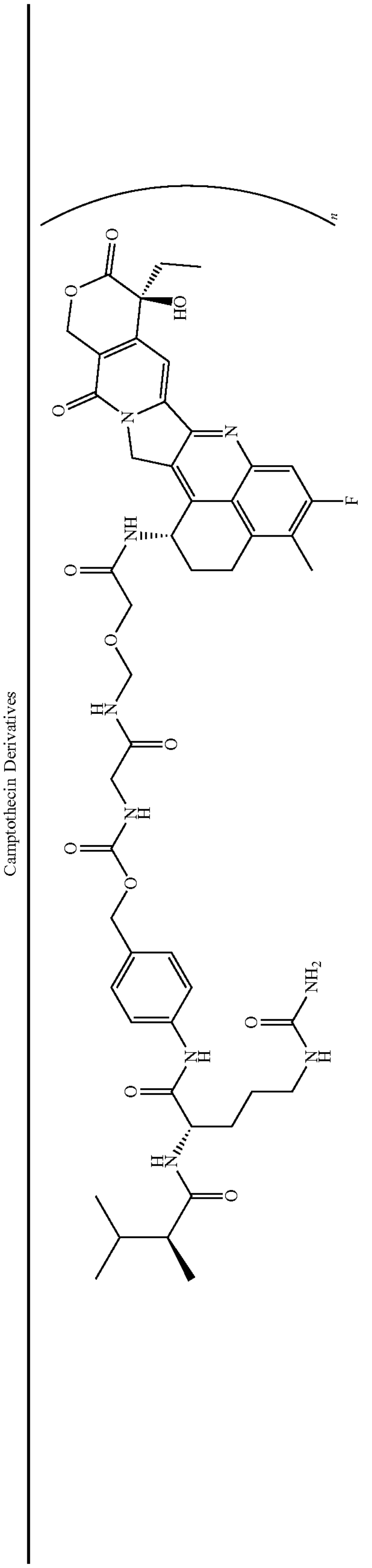

The constructs comprise the camptothecin analog:

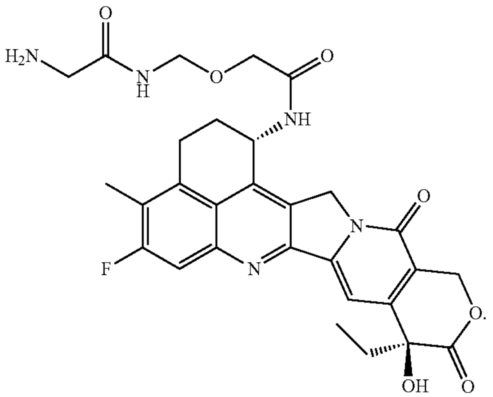 [SMILES: CC[C@@]1(O)C(=O)OCc2c1cc1n(c2=O)Cc2c-1nc1cc(F)c(C)c3c1c2[C@@H](NC(=O)COCNC(=O)CN)CC3]

TABLE 14

| Antibody-Camptothecin Derivative-Linker Payloads and Respective Dosages | | | | |
|---|---|---|---|---|
| Antibody-LP | Fc modification | Site of Conjugation | DAR | Dose |
| IC-Camptothecin-LP1 ADC | N297Q | Q295, Q297 | 7.9 | 10 mg/kg |
| mAb2-Camptothecin-LP1 ADC | N297Q | Q295, Q297 | 7.5 | 1, 3 or 10 mg/kg |
| mAb1-Camptothecin-LP1 ADC | N297Q | Q295, Q297 | 7.9 | 1, 3 or 10 mg/kg |
| IC-Camptothecin-LP2 ADC | N297Q | Q295, Q297 | 3.7 | 3 mg/kg |
| mAb1-Camptothecin-LP2 ADC | N297Q | Q295, Q297 | 3.7 | 0.3, 1 or 3 mg/kg |

Figure 6:
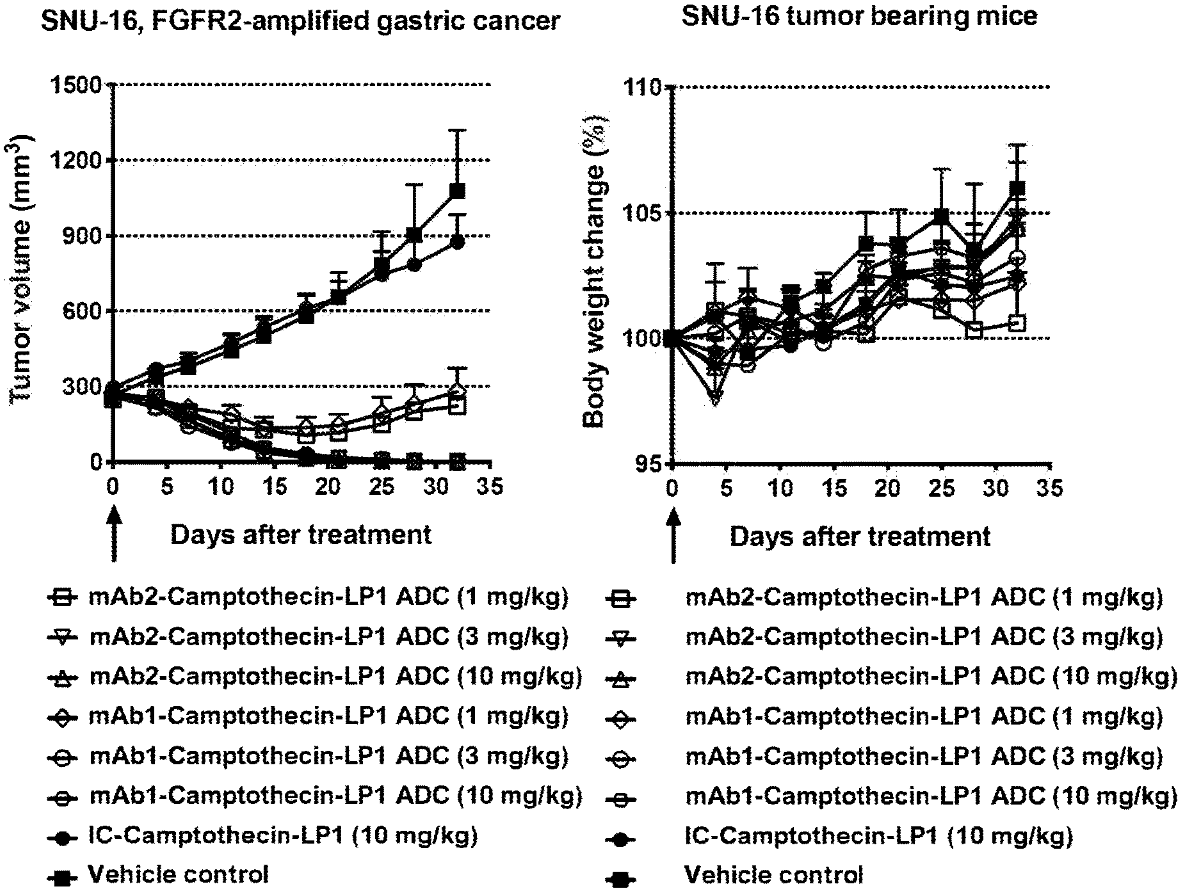
FIG. 6 shows change in tumor volume and body weight in mice with SNU-16 human gastric cancer xenografts over time with treatment using different dosages of Anti-FGFR2 antibody-camptothecin analog conjugates (DAR8). Mice were dosed on day 0 with the respective conjugates and dosages. FGFR2b Camptothecin ADCs (Camptothecin-LP1, DAR8) demonstrated significant anti-tumor efficacy against SNU-16 human gastric cancer xenografts.
Figure 7:
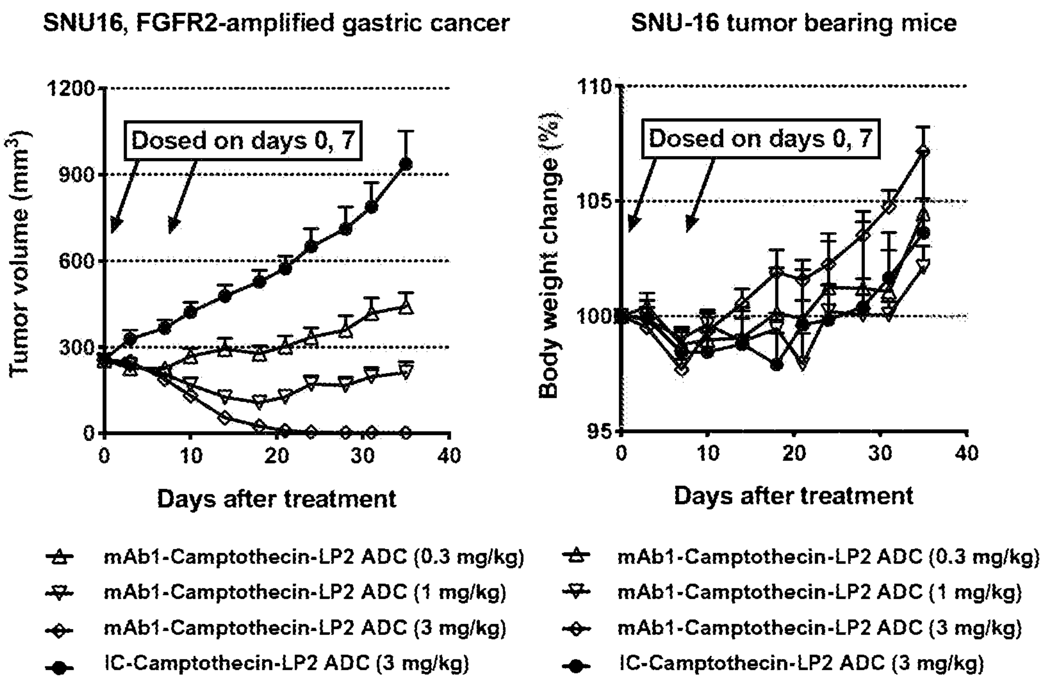
FIG. 7 shows change in tumor volume and body weight in mice with SNU-16 human gastric cancer xenografts over time with treatment using different dosages of an Anti-FGFR2 antibody camptothecin analog conjugate (DAR4). Mice were dosed on day 0 and day 7 with the respective dosages. FGFR2b Camptothecin ADCs (Camptothecin-LP2, DAR4) demonstrated significant anti-tumor efficacy against SNU-16 human gastric cancer xenografts.

Tumor volumes were measured twice per week over the course of the experiment. Averages (mean+/−standard deviation) of the tumor growth (change in tumor volume from the start of treatment through the end of the experiment) were calculated for each treatment group. The percent decrease of tumor growth was calculated from comparison to the isotype control group, and the percent regression of tumors at the end of the experiment was calculated from comparison to the tumor volume at the start of treatment. The results from two separate experiments utilizing ADCs with different DARs are shown in Table 15 and FIGS. 6 and 7. The results demonstrate that FGFR2b Camptothecin Derivative ADCs induce complete regression of SNU-16 tumor xenografts in a dose dependent manner.

TABLE 15

| Inhibition of SNU-16 Xenograft Growth in BALB/c SCID Mice | | | | |
|---|---|---|---|---|
| Antibody (mg/kg) | Total Payload Dose (ug/kg) | Tumor growth in mm3 from start of treatment (mean ± SD) | Average % Decrease in Tumor Growth | Average % Tumor Regression |
| Experiment 1 (DAR 8 ADCs) | | | | |
| mAb2 Camptothecin-LP1ADC (1 mg/kg) | 25 | −27.2 ± 89.2 | 103.3 | 11.0 |
| mAb2 Camptothecin-LP1 ADC (3 mg/kg) | 76 | −254.4 ± 34.1 | 131.4 | 99.1 |
| mAb2 Camptothecin-LP1 ADC (10 mg/kg) | 254 | −259.0 ± 25.8 | 131.9 | 100 |
| mAb1 Camptothecin-LP1 ADC (1 mg/kg) | 26 | 4.7 ± 181.9 | 99.4 | 6.7 |
| mAb1 Camptothecin-LP1 ADC (3 mg/kg) | 79 | −259.8 ± 40.1 | 132.0 | 99.8 |
| mAb1 Camptothecin-LP1 ADC (10 mg/kg) | 264 | −260.8 ± 25.0 | 132.1 | 100 |
| IC Camptothecin-LP1 ADC (10 mg/kg) | 264 | 579.5 ± 229.3 | 28.6 | −192.9 |
| Vehicle control | | 811.5 ± 556.1 | | −291.8 |

TABLE 15-continued

Inhibition of SNU-16 Xenograft Growth in BALB/c SCID Mice

| Antibody (mg/kg) | Total Payload Dose (ug/kg) | Tumor growth in mm3 from start of treatment (mean ± SD) | Average % Decrease in Tumor Growth | Average % Tumor Regression |
|---|---|---|---|---|
| Experiment 2 (DAR 4 ADCs) | | | | |
| mAb1 Camptothecin-LP2 ADC (0.3 mg/kg) | 4 | 187.0 ± 117.1 | 72.5 | −74.8 |
| mAb1 Camptothecin-LP2 ADC (1 mg/kg) | 13 | -43.5 ± 91.6 | 106.4 | 16.3 |
| mAb1 Camptothecin-LP2 ADC (3 mg/kg) | 38 | -254.2 ± 30.2 | 137.4 | 99.7 |
| IC Camptothecin-LP2 ADC (3 mg/kg) | 38 | 679.0 ± 253.1 | | −259.1 |

Example 14: Effect of FGFR2b Antibody Drug Conjugates (ADC) on the Growth of Gastric Cancer Patient Derived Xenografts (GA1224)

To assess the anti-tumor activity of FGFR2b Camptothecin-LP2 ADCs (Table 13) against patient derived gastric cancer xenografts (GA1224), tumor fragments (2-3 mm in diameter) were implanted subcutaneously into the flank of female BALB/c Nude mice (6-9 weeks old, GemPharmatech Co., Ltd). After tumors reached an average volume of 100-150 $mm^3$, mice were randomized into groups for treatment (n=6 mice per group). Tumor bearing mice were administered once per week for two weeks via intravenous injection at the doses shown in Table 16.

TABLE 16

Antibody-Camptothecin Derivative-Linker Payloads and Respective Dosages

| Antibody-LP | Fc modification | Site of Conjugation | DAR | Dose |
|---|---|---|---|---|
| IC | N297Q | NA | NA | 20 mg/kg |
| mAb1 | N297Q | NA | NA | 20 mg/kg |
| IC-Camptotecin-LP2 ADC | N297Q | Q295, Q297 | 4.0 | 20 mg/kg |
| mAb1-Camptothecin-LP2 ADC | N297Q | Q295, Q297 | 4.0 | 5, 10 or 20 mg/kg |

Figure 10:
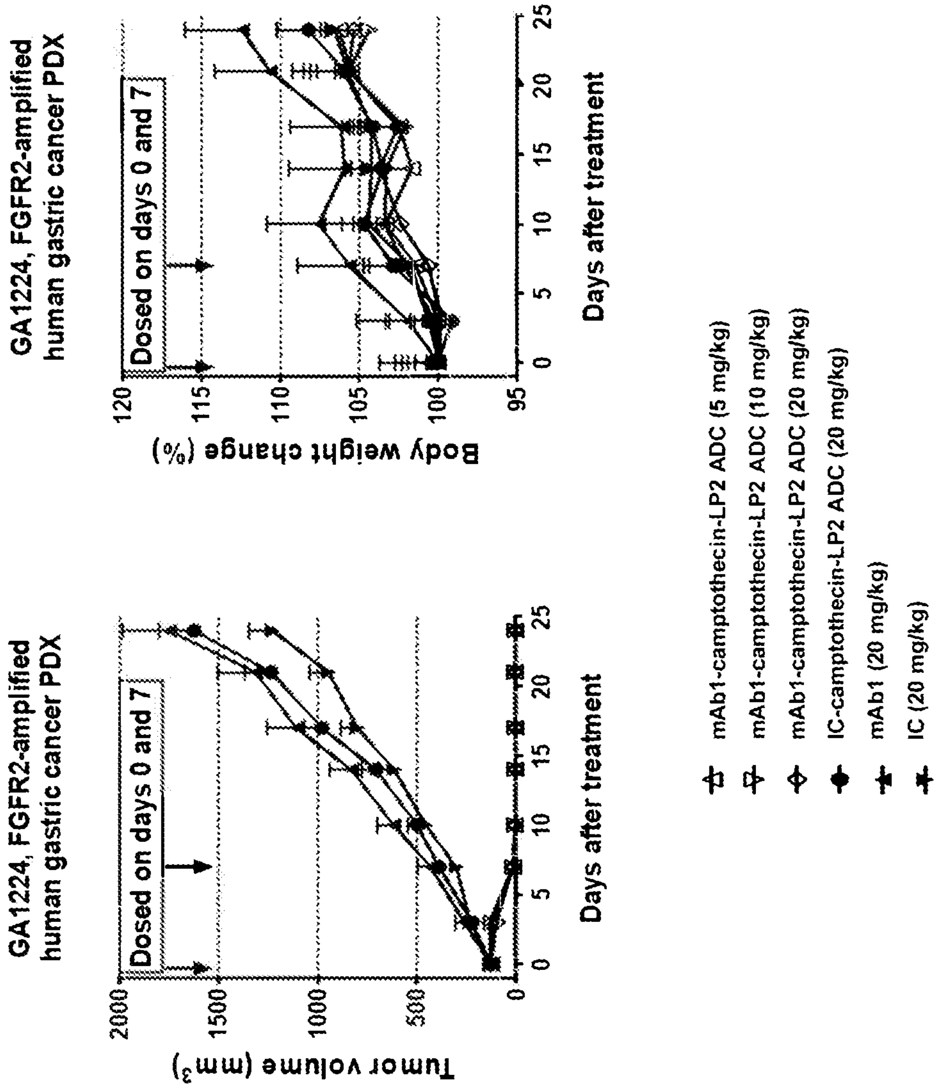
FIG. 10 shows change in tumor volume and body weight in mice with GA1224 human PDX tumors over time with treatment using different dosages of Anti-FGFR2 antibody camptothecin ADC (DAR4). Mice were dosed on day 0 and day 7 with the respective dosages. Anti-FGFR2b Camptothecin ADCs (DAR4) demonstrated significant anti-tumor efficacy against GA1224 human gastric cancer PDX tumors.

Tumor volumes were measured twice per week over the course of the experiment. Averages (mean+/−standard deviation) of the tumor growth (change in tumor volume from the start of treatment through the end of the experiment) were calculated for each treatment group. The percent decrease of tumor growth was calculated from comparison to the isotype control antibody group, and the percent regression of tumors at the end of the experiment was calculated from comparison to the tumor volume at the start of treatment. The results are shown in Table 17 and FIG. 10. These results demonstrate that DXd ADCs targeting FGFR2b isoforms induced complete regression of GA1224 PDX tumors at all tested doses.

TABLE 17

Inhibition of GA1224 PDX Growth in BALB/c Nude Mice

| Antibody (mg/kg) | Total Payload Dose (ug/kg) | Tumor growth in mm3 from start of treatment (mean ± SD) | Average % Decrease in Tumor Growth | Average % Tumor Regression |
|---|---|---|---|---|
| mAb1-Camptothecin-LP2 ADC (5 mg/kg) | 68 | −124.9 ± 31.2 | 111.3 | 100 |
| mAb1-Camptothecin-LP2 ADC (10 mg/kg) | 136 | −124.9 ± 36.5 | 111.3 | 100 |
| mAb1-Camptothecin-LP2 ADC (20 mg/kg) | 272 | −125.1 ± 34.8 | 111.3 | 100 |
| IC-Camptotecin-LP2 ADC (20 mg/kg) | 272 | 1499.7 ± 432.8 | −35.9 | −1265.4 |
| mAb 1 | NA | 1627.8 ± 551.9 | −47.5 | −1300.5 |
| IC | NA | 1103.5 ± 289.7 | NA | −923.2 |

Figure 12:
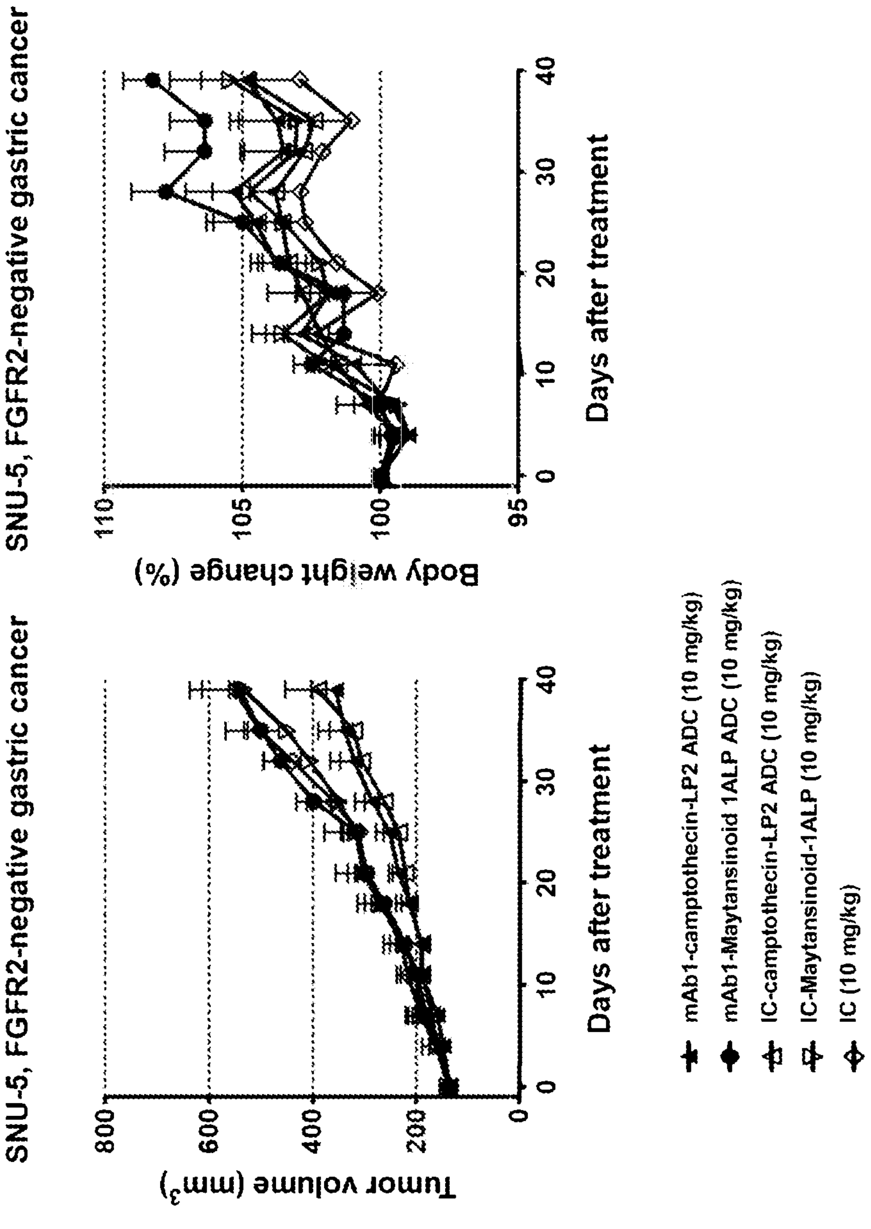
FIG. 12 shows change in tumor volume and body weight in mice with SNU-5 human gastric cancer xenografts (FGFR2b negative) over time with treatment using an Anti-FGFR2 antibody camptothecin ADC (DAR4) or Anti-FGFR2 antibody maytansinoid ADC. Both anti-FGFR2b Camptothecin ADC and anti-FGFR2b Maytansinoid ADC demonstrated no anti-tumor efficacy against SNU5 human gastric cancer xenografts.
Figure 13:
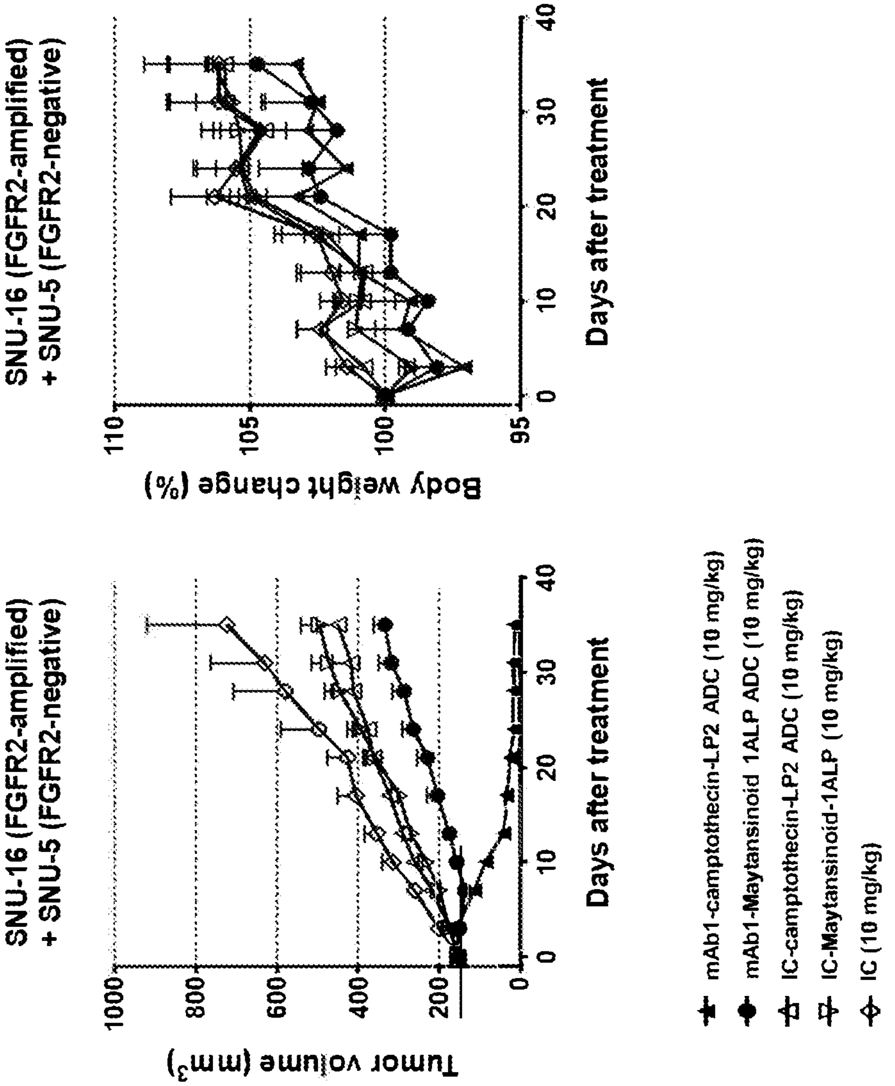
FIG. 13 shows change in tumor volume and body weight in mice co-implanted at a ratio of 2:1 with SNU-16 (FGFR2b positive) and SNU-5 (FGFR2b negative) human gastric cancer xenografts with treatment using an Anti-FGFR2 antibody camptothecin ADC (DAR4) or Anti-FGFR2 antibody maytansinoid ADC. Anti-FGFR2b Camptothecin ADC, but not anti-FGFR2b maytansinoid ADC, demonstrated significant anti-tumor efficacy against SNU-16+SNU5 co-inoculated human gastric cancer xenografts.

Example 15: In Vivo Bystander Killing Effect of Anti-FGFR2b Antibody Drug Conjugates (ADC) on the Growth of Co-Inoculated SNU-16/SNU-5 Gastric Cancer Xenografts The ability of the anti-FGFR2 ADCs to induce tumor regression in FGFR2 negative cells through release of the payload in FGFR2 positive cells, i.e., bystander activity, was also assessed. The ability of FGFR2b Camptothecin ADC and FGFR2b Maytansinoid ADC to inhibit tumor growth was tested on FGFR2-amplified SNU-16 human gastric cancer xenografts (FIG. 11), on FGFR2-negative SNU-5 human gastric cancer xenografts (FIG. 12), or on co-inoculated SNU-16 and SNU-5 xenografts implanted at a ratio of 2:1 (FIG. 13).

Briefly, $5\times10^6$ SNU-16 and/or SNU-5 cancer cells (ATCC) mixed with Matrigel (BD Biosciences) were implanted subcutaneously into the flank of male BALB/c SCID mice (6-8 weeks old, Jackson Laboratory). After tumors reached an average volume of 200-250 $mm^3$, mice were randomized into groups for treatment (n=6 mice per group). Tumor bearing mice were administered a single dose via subcutaneous injection at the doses shown in Table 18.

TABLE 18

Antibody-Camptothecin-Linker Payloads and Antibody-Maytansinoid-Linker Payloads and Respective Dosages

| Antibody-LP | Fc modification | Site of Conjugation | DAR | Dose |
|---|---|---|---|---|
| mAb1-Camptothecin-LP2 ADC | N297Q | Q295/Q297 | 3.7 | 10 mg/kg |
| mAb1-Maytansinoid 1ALP ADC | N297Q | Q295/Q297 | 3.0 | 10 mg/kg |
| IC-Camptothecin-LP2 ADC | N297Q | Lys | 3.7 | 10 mg/kg |
| IC-Maytansinoid 1ALP ADC | N297Q | Lys | 3.0 | 10 mg/kg |
| IC | N297Q | NA | NA | 10 mg/kg |

Tumor volumes were measured twice per week over the course of the experiment. Averages (mean+/−standard deviation) of the tumor growth (change in tumor volume from the start of treatment through the end of the experiment) were calculated for each treatment group. The percent decrease of tumor growth was calculated from comparison to the isotype control group, and the percent regression of tumors at the end of the experiment was calculated from comparison to the tumor volume at the start of treatment. The results are shown in Table 19.

These results demonstrate that Camptothecin ADCs targeting FGFR2b isoforms induced complete regression of SNU-16 xenografts (FGFR2b positive), did not inhibit the growth of SNU-5 xenografts (FGFR2b negative), but induced complete regression of SNU-16 and SNU-5 co-inoculated xenografts, suggesting there was significant bystander killing of the FGFR2-negative SNU-5 cell population. Maytansinoid ADCs targeting FGFR2b isoforms induced complete regression of SNU-16 xenografts, did not inhibit the growth of SNU-5 xenografts, and only partially inhibited the growth of SNU-16 and SNU-5 co-inoculated xenografts, suggesting there was little to no bystander killing of the FGFR2b-negative SNU-5 cell population.

TABLE 19

Inhibition of SNU-16 and/or SNU-5 xenograft growth in BALB/c SCID mice

Figure 11:
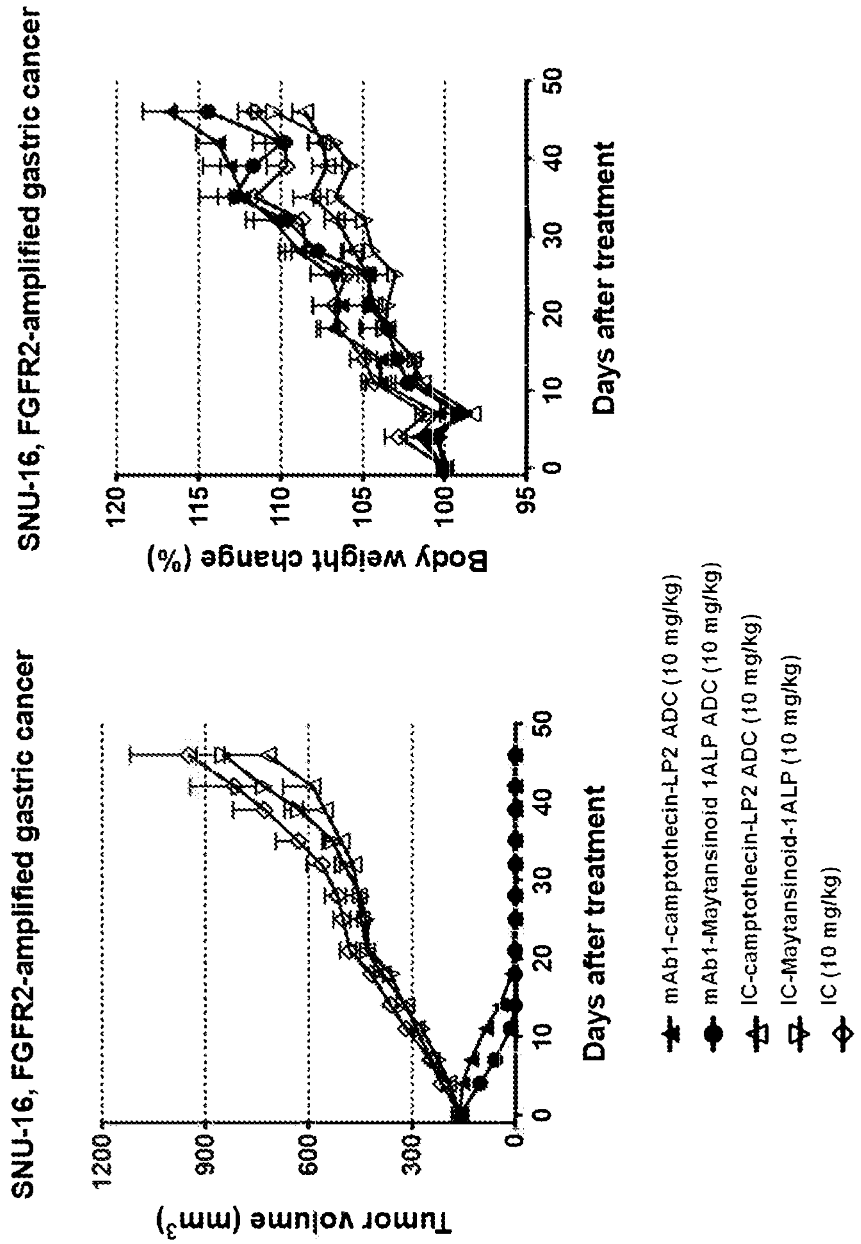
FIG. 11 shows change in tumor volume and body weight in mice with SNU-16 human gastric cancer xenografts (FGFR2b positive) over time with treatment using an Anti-FGFR2 antibody camptothecin ADC (DAR4) or Anti-FGFR2 antibody maytansinoid ADC. Both anti-FGFR2b Camptothecin ADC and anti-FGFR2b Maytansinoid ADC demonstrated significant anti-tumor efficacy against SNU-16 human gastric cancer xenografts.

| Antibody (mg/kg) | Total Payload Dose (ug/kg) | Tumor growth in $mm^3$ from start of treatment (mean ± SD) | Average % Decrease in Tumor Growth | Average % Tumor Regression |
|---|---|---|---|---|
| FIG. 11: SNU16 (FGFR2b positive cells) | | | | |
| mAb1-camptothecin-LP2 ADC (10 mg/kg) | 130 | −158.4 ± 25.4 | 120.1 | 98.9 |
| mAb1-Maytansinoid 1ALP ADC (10 mg/kg) | 147 | −160.7 ± 28.4 | 120.4 | 100 |
| IC-camptothecin-LP2 ADC (10 mg/kg) | 130 | 560.2 ± 302.0 | 29 | −363.5 |
| IC-Maytansinoid-1ALP (10 mg/kg) | 147 | 686.0 ± 174.5 | 13.1 | −472.3 |
| IC (10 mg/kg) | NA | 789.2 ± 413.5 | | −493.8 |
| FIG. 12: SNU5 (FGFR2b negative cells) | | | | |
| mAb1-camptothecin-LP2 ADC (10 mg/kg) | 130 | 220.6 ± 103.8 | 46.9 | −164 |
| mAb1-Maytansinoid 1ALP ADC (10 mg/kg) | 147 | 401.6 ± 74.4 | 3.4 | −311.8 |
| IC-camptothecin-LP2 ADC (10 mg/kg) | 130 | 252.1 ± 159.6 | 39.4 | −195.6 |
| IC-Maytansinoid-1ALP (10 mg/kg) | 147 | 395.6 ± 225.0 | 4.8 | −272.7 |
| IC (10 mg/kg) | | 415.7 ± 160.3 | | −323.4 |
| FIG. 13: SNU16 and SNU5 Co-Inoculated (2:1 ratio) | | | | |
| mAb1-camptothecin-LP2 ADC (10 mg/kg) | 130 | −140.6 ± 18.5 | 124.7 | 91.8 |
| mAb1-Maytansinoid 1ALP ADC (10 mg/kg) | 147 | 181.1 ± 57.0 | 68.2 | −118.3 |
| IC-camptothecin-LP2 ADC (10 mg/kg) | 130 | 291.8 ± 131.3 | 48.7 | −189.8 |

TABLE 19-continued

Inhibition of SNU-16 and/or SNU-5 xenograft growth in BALB/c SCID mice

| Antibody (mg/kg) | Total Payload Dose (ug/kg) | Tumor growth in $mm^3$ from start of treatment (mean ± SD) | Average % Decrease in Tumor Growth | Average % Tumor Regression |
|---|---|---|---|---|
| IC-Maytansinoid-1ALP (10 mg/kg) | 147 | 342.3 ± 101.3 | 39.9 | −222.9 |
| IC (10 mg/kg) | | 569.4 ± 480.7 | | −380.5 |

SEQUENCE LISTING

| SEQ ID NO | Sequence | Description |
|---|---|---|
| 1 | CAGGTGCAGCTGGTGGAGTCTGGGGGAGGCGTGGTCCAGCCTGGGAGGTC CCTGAGACTCTCCTGTGCAGCGTCTGGATTCACCTTCAGTAGCTATGGCATG CACTGGGTCCGCCAGGCTCCAGGCAAGGGACTGGAGTGGGTGGCAGTTAT ATGGTATGATGGAAGTAATAAATACTATGCAGACTCCGTGAAGGGCCGATTC ACCATCTCCAGAGACAATTCCAAGAACACGCTGTATCTGCAAATGAACAGCC TGAGAGCCGAGGACACGGCTGTGTATTACTGTGCGAGAGAGGAAAGCAGC GCGTCCGGGGTTGACTACTGGGGCCAGGGAACCCTGGTCACCGTCTCCTC A | mAb1 Heavy Chain Variable Region |
| 2 | QVQLVESGGGVVQPGRSLRLSCAASGFTFSSYGMHWVRQAPGKGLEWVAVI WYDGSNKYYADSVKGRFTISRDNSKNTLYLQMNSLRAEDTAVYYCAREESSAS GVDYWGQGTLVTVSS | mAb1 Heavy Chain Variable Region |
| 3 | GGATTCACCTTCAGTAGCTATGGC | mAb1 HCDR1 |
| 4 | GFTFSSYG | mAb1 HCDR1 |
| 5 | ATATGGTATGATGGAAGTAATAAA | mAb1, mAb2, and mAb3 HCDR2 |
| 6 | IWYDGSNK | mAb1, mAb2, and mAb3 HCDR2 |
| 7 | GCGAGAGAGGAAAGCAGCGCGTCCGGGGTTGACTAC | mAb1 HCDR3 |
| 8 | AREESSASGVDY | mAb1 HCDR3 |
| 9 | GAAATTGTGTTGACGCAGTCTCCAGGCACCCTGTCCTTGTCTCCAGGGGAA AGAGCCACCCTCTCCTGCAGGGCCAGTCAGAGTGTTAGCACCAGGTACTTA GCCTGGTACCAGCAGAAACGTGGCCAGGCTCCCAGGCTCCTCATCTATGGT GCATCCAGCAGGGCCACTGGCATCCCAGACAGGTTCAGTGGCAGTGGGTC TGGGACAGACTTCACTCTCACCATCAGCAGACTGGAGCCTGAAGATTTTGCA GTGTATTACTGTCAGGAGTATGGTAGCTCATCGATCACCTTCGGCCAAGGGA CACGACTGGAGATTAAA | mAb1 Light Chain Variable Region |
| 10 | EIVLTQSPGTLSLSPGERATLSCRASQSVSTRYLAWYQQKRGQAPRLLIYGASS RATGIPDRFSGSGSGTDFTLTISRLEPEDFAVYYCQEYGSSSITFGQGTRLEIK | mAb1 Light Chain Variable Region |
| 11 | CAGAGTGTTAGCACCAGGTAC | mAb1 LCDR1 |
| 12 | QSVSTRY | mAb1 LCDR1 |
| 13 | GGTGCATCC | mAb1 LCDR2 |
| 14 | GAS | mAb1 LCDR2 |
| 15 | CAGGAGTATGGTAGCTCATCGATCACC | mAb1 LCDR3 |

-continued

SEQUENCE LISTING

| SEQ ID NO | Sequence | Description |
|---|---|---|
| 16 | QEYGSSSIT | mAb1<br>LCDR3 |
| 17 | CAGGTGCAGCTGGTGGAGTCTGGGGGAGGCGTGGTCCAGCCTGGGAGGTC<br>CCTGAGACTCTCCTGTGCAGCGTCTGGATTCACCTTCAGTAGCTATGGCATG<br>CACTGGGTCCGCCAGGCTCCAGGCAAGGGACTGGAGTGGGTGGCAGTTAT<br>ATGGTATGATGGAAGTAATAAATACTATGCAGACTCCGTGAAGGGCCGATTC<br>ACCATCTCCAGAGACAATTCCAAGAACACGCTGTATCTGCAAATGAACAGCC<br>TGAGAGCCGAGGACACGGCTGTGTATTACTGTGCGAGAGAGGAAAGCAGC<br>GCGTCCGGGGTTGACTACTGGGGCCAGGGAACCCTGGTCACCGTCTCCTC<br>AGCCTCCACCAAGGGCCCATCGGTCTTCCCCCTGGCGCCCTGCTCCAGGA<br>GCACCTCCGAGAGCACAGCCGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCAG<br>CGTGGTGACCGTGCCCTCCAGCAGCTTGGGCACGAAGACCTACACCTGCAA<br>CGTAGATCACAAGCCCAGCAACACCAAGGTGGACAAGAGAGTTGAGTCCAA<br>ATATGGTCCCCCATGCCCACCCTGCCCAGCACCTGAGTTCCTGGGGGGACC<br>ATCAGTCTTCCTGTTCCCCCCAAAACCCAAGGACACTCTCATGATCTCCCGG<br>ACCCCTGAGGTCACGTGCGTGGTGGTGGACGTGAGCCAGGAAGACCCCGA<br>GGTCCAGTTCAACTGGTACGTGGATGGCGTGGAGGTGCATAATGCCAAGAC<br>AAAGCCGCGGGAGGAGCAGTTCAACAGCACGTACCGTGTGGTCAGCGTCC<br>TCACCGTCCTGCACCAGGACTGGCTGAACGGCAAGGAGTACAAGTGCAAGG<br>TCTCCAACAAAGGCCTCCCGTCCTCCATCGAGAAAACCATCTCCAAAGCCAA<br>AGGGCAGCCCCGAGAGCCACAGGTGTACACCCTGCCCCCATCCCAGGAGG<br>AGATGACCAAGAACCAGGTCAGCCTGACCTGCCTGGTCAAAGGCTTCTACC<br>CCAGCGACATCGCCGTGGAGTGGGAGAGCAATGGGCAGCCGGAGAACAAC<br>TACAAGACCACGCCTCCCGTGCTGGACTCCGACGGCTCCTTCTTCCTCTACA<br>GCAGGCTCACCGTGGACAAGAGCAGGTGGCAGGAGGGGAATGTCTTCTCA<br>TGCTCCGTGATGCATGAGGCTCTGCACAACCACTACACACAGAAGTCCCTCT<br>CCCTGTCTCTGGGTAAATGA | mAb1<br>Heavy Chain |
| 18 | QVQLVESGGGVVQPGRSLRLSCAASGFTFSSYGMHWVRQAPGKGLEWVAVI<br>WYDGSNKYYADSVKGRFTISRDNSKNTLYLQMNSLRAEDTAVYYCAREESSAS<br>GVDYWGQGTLVTVSSASTKGPSVFPLAPCSRSTSESTAALGCLVKDYFPEPVT<br>VSWNSGALTSGVHTFPAVLQSSGLYSLSSVVTVPSSSLGTKTYTCNVDHKPSN<br>TKVDKRVESKYGPPCPPCPAPEFLGGPSVFLFPPKPKDTLMISRTPEVTCVVVD<br>VSQEDPEVQFNWYVDGVEVHNAKTKPREEQFNSTYRVVSVLTVLHQDWLNGK<br>EYKCKVSNKGLPSSIEKTISKAKGQPREPQVYTLPPSQEEMTKNQVSLTCLVKG<br>FYPSDIAVEWESNGQPENNYKTTPPVLDSDGSFFLYSRLTVDKSRWQEGNVFS<br>CSVMHEALHNHYTQKSLSLSLGK* | mAb1<br>Heavy Chain |
| 19 | GAAATTGTGTTGACGCAGTCTCCAGGCACCCTGTCCTTGTCTCCAGGGGAA<br>AGAGCCACCCTCTCCTGCAGGGCCAGTCAGAGTGTTAGCACCAGGTACTTA<br>GCCTGGTACCAGCAGAAACGTGGCCAGGCTCCCAGGCTCCTCATCTATGGT<br>GCATCCAGCAGGGCCACTGGCATCCCAGACAGGTTCAGTGGCAGTGGGTC<br>TGGGACAGACTTCACTCTCACCATCAGCAGACTGGAGCCTGAAGATTTTGCA<br>GTGTATTACTGTCAGGAGTATGGTAGCTCATCGATCACCTTCGGCCAAGGGA<br>CACGACTGGAGATTAAACGAACTGTGGCTGCACCATCTGTCTTCATCTTCCC<br>GCCATCTGATGAGCAGTTGAAATCTGGAACTGCCTCTGTTGTGTGCCTGCTG<br>AATAACTTCTATCCCAGAGAGGCCAAAGTACAGTGGAAGGTGGATAACGCC<br>CTCCAATCGGGTAACTCCCAGGAGAGTGTCACAGAGCAGGACAGCAAGGAC<br>AGCACCTACAGCCTCAGCAGCACCCTGACGCTGAGCAAAGCAGACTACGAG<br>AAACACAAAGTCTACGCCTGCGAAGTCACCCATCAGGGCCTGAGCTCGCCC<br>GTCACAAAGAGCTTCAACAGGGGAGAGTGTTAG | mAb1<br>Light Chain |
| 20 | EIVLTQSPGTLSLSPGERATLSCRASQSVSTRYLAWYQQKRGQAPRLLIYGASS<br>RATGIPDRFSGSGSGTDFTLTISRLEPEDFAVYYCQEYGSSSITFGQGTRLEIKR<br>TVAAPSVFIFPPSDEQLKSGTASVVCLLNNFYPREAKVQWKVDNALQSGNSQE<br>SVTEQDSKDSTYSLSSTLTLSKADYEKHKVYACEVTHQGLSSPVTKSFNRGEC* | mAb1<br>Light Chain |
| 21 | CAGGTGCAGCTGGTGGAGTCTGGGGGAGGCGTGGTCCAGCCTGGGAAGTC<br>CCTGAGACTCTCCTGTGCAGCGTCTGGATTCACCTTCAGTAACTATGGCATG<br>CACTGGGTCCGCCAAACTCCAGTCAAGGGACTGGAGTGGGTGACACTTATA<br>TGGTATGATGGAAGTAATAAATACTATACAGACTCCGTGAAGGGCCGATTCA<br>CCATCTCCAGAGACAATTCCAAGAACACGCTGTATCTGCAAATGAACAGCCT<br>GAGATCCGAGGACACGGCTGTGTATTACTGTGCGAGAGAGGGGAACTGGAA<br>CTACGGGCATGCTTTTGATATCTGGGGCCAAGGGACAATGGTCACCGTCTC<br>TTCA | mAb2<br>Heavy Chain Variable<br>Region |
| 22 | QVQLVESGGGVVQPGKSLRLSCAASGFTFSNYGMHWVRQTPVKGLEWVTLIW<br>YDGSNKYYTDSVKGRFTISRDNSKNTLYLQMNSLRSEDTAVYYCAREGNWNYG<br>HAFDIWGQGTMVTVSS | mAb2<br>Heavy Chain Variable<br>Region |

-continued

SEQUENCE LISTING

| SEQ ID NO | Sequence | Description |
|---|---|---|
| 23 | GGATTCACCTTCAGTAACTATGGC | mAb2 and mAb3 HCDR1 |
| 24 | GFTFSNYG | mAb2 and mAb3 HCDR1 |
| 25 | GCGAGAGAGGGGAACTGGAACTACGGGCATGCTTTTGATATC | mAb2 HCDR3 |
| 26 | AREGNWNYGHAFDI | mAb2 HCDR3 |
| 27 | GACATCCAGATGACCCAGTCTCCTTCCACCCTGTCTGCATCTGTAGGAGACA GAGTCACCATCACTTGCCGGGCCAGTCAGAATATTGGTAACTGGTTGGCCT GGTATCAGCAGAAACCAGGGAAAGCCCCTAACCTCCTGATTTATAAGGCGT CTACTTTAGAAAGTGGGGTCCCATCAAGGTTCAGCGGCAGTGGATCTGGGA CAGAATTCACTCTCACCATCAGCAGCCTGCAGCCTGATGATTTTGCAACTTA TAACTGCCAACAGTATAATAGTTATTCTCCCACTTTTGGCCAGGGGACCAAG CTGGAGATCAAA | mAb2 Light Chain Variable Region |
| 28 | DIQMTQSPSTLSASVGDRVTITCRASQNIGNWLAWYQQKPGKAPNLLIYKASTL ESGVPSRFSGSGSGTEFTLTISSLQPDDFATYNCQQYNSYSPTFGQGTKLEIK | mAb2 Light Chain Variable Region |
| 29 | CAGAATATTGGTAACTGG | mAb2 LCDR1 |
| 30 | QNIGNW | mAb2 LCDR1 |
| 31 | AAGGCGTCT | mAb2 and mAb3 LCDR2 |
| 32 | KAS | mAb2 and mAb3 LCDR2 |
| 33 | CAACAGTATAATAGTTATTCTCCCACT | mAb2 LCDR3 |
| 34 | QQYNSYSPT | mAb2 and mAb3 LCDR3 |
| 35 | CAGGTGCAGCTGGTGGAGTCTGGGGGAGGCGTGGTCCAGCCTGGGAAGTC CCTGAGACTCTCCTGTGCAGCGTCTGGATTCACCTTCAGTAACTATGGCATG CACTGGGTCCGCCAAACTCCAGTCAAGGGACTGGAGTGGGTGACACTTATA TGGTATGATGGAAGTAATAAATACTATACAGACTCCGTGAAGGGCCGATTCA CCATCTCCAGAGACAATTCCAAGAACACGCTGTATCTGCAAATGAACAGCCT GAGATCCGAGGACACGGCTGTGTATTACTGTGCGAGAGAGGGGAACTGGAA CTACGGGCATGCTTTTGATATCTGGGGCCAAGGGACAATGGTCACCGTCTC TTCAGCCTCCACCAAGGGCCCATCGGTCTTCCCCCTGGCGCCCTGCTCCAG GAGCACCTCCGAGAGCACAGCCGCCCTGGGCTGCCTGGTCAAGGACTACT TCCCCGAACCGGTGACGGTGTCGTGGAACTCAGGCGCCCTGACCAGCGGC GTGCACACCTTCCCGGCTGTCCTACAGTCCTCAGGACTCTACTCCCTCAGCA GCGTGGTGACCGTGCCCTCCAGCAGCTTGGGCACGAAGACCTACACCTGC AACGTAGATCACAAGCCCAGCAACACCAAGGTGGACAAGAGAGTTGAGTCC AAATATGGTCCCCCATGCCCACCCTGCCCAGCACCTGAGTTCCTGGGGGGA CCATCAGTCTTCCTGTTCCCCCCAAAACCCAAGGACACTCTCATGATCTCCC GGACCCCTGAGGTCACGTGCGTGGTGGTGGACGTGAGCCAGGAAGACCCC GAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGT CCTCACCGTCCTGCACCAGGACTGGCTGAACGGCAAGGAGTACAAGTGCAA GGTCTCCAACAAAGGCCTCCCGTCCTCCATCGAGAAAACCATCTCCAAAGC CAAAGGGCAGCCCCGAGAGCCACAGGTGTACACCCTGCCCCCATCCCAGG AGGAGATGACCAAGAACCAGGTCAGCCTGACCTGCCTGGTCAAAGGCTTCT ACCCCAGCGACATCGCCGTGGAGTGGGAGAGCAATGGGCAGCCGGAGAAC AACTACAAGACCACGCCTCCCGTGCTGGACTCCGACGGCTCCTTCTTCCTCT ACAGCAGGCTCACCGTGGACAAGAGCAGGTGGCAGGAGGGGAATGTCTTC TCATGCTCCGTGATGCATGAGGCTCTGCACAACCACTACACACAGAAGTCC CTCTCCCTGTCTCTGGGTAAATGA | mAb2 Heavy Chain |
| 36 | QVQLVESGGGVVQPGKSLRLSCAASGFTFSNYGMHWVRQTPVKGLEWVTLIW YDGSNKYYTDSVKGRFTISRDNSKNTLYLQMNSLRSEDTAVYYCAREGNWNYG HAFDIWGQGTMVTVSSASTKGPSVFPLAPCSRSTSESTAALGCLVKDYFPEPVT | mAb2 Heavy Chain |

-continued

SEQUENCE LISTING

| SEQ ID NO | Sequence | Description |
|---|---|---|
| | VSWNSGALTSGVHTFPAVLQSSGLYSLSSVVTVPSSSLGTKTYTCNVDHKPSN TKVDKRVESKYGPPCPPCPAPEFLGGPSVFLFPPKPKDTLMISRTPEVTCVVVD VSQEDPEVQFNWYVDGVEVHNAKTKPREEQFNSTYRVVSVLTVLHQDWLNGK EYKCKVSNKGLPSSIEKTISKAKGQPREPQVYTLPPSQEEMTKNQVSLTCLVKG FYPSDIAVEWESNGQPENNYKTTPPVLDSDGSFFLYSRLTVDKSRWQEGNVFS CSVMHEALHNHYTQKSLSLSLGK* | |
| 37 | GACATCCAGATGACCCAGTCTCCTTCCACCCTGTCTGCATCTGTAGGAGACA GAGTCACCATCACTTGCCGGGCCAGTCAGAATATTGGTAACTGGTTGGCCT GGTATCAGCAGAAACCAGGGAAAGCCCCTAACCTCCTGATTTATAAGGCGT CTACTTTAGAAAGTGGGGTCCCATCAAGGTTCAGCGGCAGTGGATCTGGGA CAGAATTCACTCTCACCATCAGCAGCCTGCAGCCTGATGATTTTGCAACTTA TAACTGCCAACAGTATAATAGTTATTCTCCCACTTTTGGCCAGGGGACCAAG CTGGAGATCAAACGAACTGTGGCTGCACCATCTGTCTTCATCTTCCCGCCAT CTGATGAGCAGTTGAAATCTGGAACTGCCTCTGTTGTGTGCCTGCTGAATAA CTTCTATCCCAGAGAGGCCAAAGTACAGTGGAAGGTGGATAACGCCCTCCA ATCGGGTAACTCCCAGGAGAGTGTCACAGAGCAGGACAGCAAGGACAGCA CCTACAGCCTCAGCAGCACCCTGACGCTGAGCAAAGCAGACTACGAGAAAC ACAAAGTCTACGCCTGCGAAGTCACCCATCAGGGCCTGAGCTCGCCCGTCA CAAAGAGCTTCAACAGGGGAGAGTGTTAG | mAb2 Light Chain |
| 38 | DIQMTQSPSTLSASVGDRVTITCRASQNIGNWLAWYQQKPGKAPNLLIYKASTL ESGVPSRFSGSGSGTEFTLTISSLQPDDFATYNCQQYNSYSPTFGQGTKLEIKR TVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC* | mAb2 Light Chain |
| 39 | CAGGTGCAGCTGGTGGAGTCTGGGGGAGGCGTGGTCCAGCCTGGGAGGTC CCTGAGACTCTCCTGTGCAGCGTCTGGATTCACCTTCAGTAACTATGGCATG CACTGGGTCCGCCAGGCTCCAGGCAAGGGGCTGGAGTGGGTGGCACTTAT ATGGTATGATGGAAGTAATAAATACTATGCAGACTCCGTGAAGGGCCGATTC ACCATCTCCAGAGACAATTCCAAGAACACGCTTTTTCTGCAAATGAACAGCC TGAGAGCCGATGACACGGCTGTGTATTACTGTGCGCGAGAGATGGAGAGCA GCTCGGGCTTCGATCTCTGGGGCCGTGGCACCCTGGTCACTGTCTCCTCA | mAb3 Heavy Chain Variable Region |
| 40 | QVQLVESGGGVVQPGRSLRLSCAASGFTFSNYGMHWVRQAPGKGLEWVALI WYDGSNKYYADSVKGRFTISRDNSKNTLFLQMNSLRADDTAVYYCAREMESSS GFDLWGRGTLVTVSS | mAb3 Heavy Chain Variable Region |
| 41 | GCGCGAGAGATGGAGAGCAGCTCGGGCTTCGATCTC | mAb3 HCDR3 |
| 42 | AREMESSSGFDL | mAb3 HCDR3 |
| 43 | GACATCCAGATGACCCAGTCTCCTTCCACCCTGTCTGCATCTGTAGGAGACA GAGTCACCATCACTTGCCGGGCCAGTCAGAGTATTAGTAGGTGGTTGGCCT GGTATCAGCAGAAACCAGGGAAAGCCCCTAAGCTCCTGATCTATAAGGCGT CTAGTTTACAAAGTGGGGTCCCTTCAAGGTTCAGCGGCAGTGGATCTGGGA CAGAATTCACTCTCACCATCAGCAGCCTGCAGCCTGATGATTTTGCAACTTA TTACTGCCAACAGTATAATAGTTATTCTCCGACGTTCGGCCAAGGGACCAAG GTGGAAATCAAA | mAb3 Light Chain Variable Region |
| 44 | DIQMTQSPSTLSASVGDRVTITCRASQSISRWLAWYQQKPGKAPKLLIYKASSL QSGVPSRFSGSGSGTEFTLTISSLQPDDFATYYCQQYNSYSPTFGQGTKVEIK | mAb3 Light Chain Variable Region |
| 45 | CAGAGTATTAGTAGGTGG | mAb3 LCDR1 |
| 46 | QSISRW | mAb3 LCDR1 |
| 47 | CAACAGTATAATAGTTATTCTCCGACG | mAb3 LCDR3 |
| 48 | CAGGTGCAGCTGGTGGAGTCTGGGGGAGGCGTGGTCCAGCCTGGGAGGTC CCTGAGACTCTCCTGTGCAGCGTCTGGATTCACCTTCAGTAACTATGGCATG CACTGGGTCCGCCAGGCTCCAGGCAAGGGGCTGGAGTGGGTGGCACTTAT ATGGTATGATGGAAGTAATAAATACTATGCAGACTCCGTGAAGGGCCGATTC ACCATCTCCAGAGACAATTCCAAGAACACGCTTTTTCTGCAAATGAACAGCC TGAGAGCCGATGACACGGCTGTGTATTACTGTGCGCGAGAGATGGAGAGCA GCTCGGGCTTCGATCTCTGGGGCCGTGGCACCCTGGTCACTGTCTCCTCAG CCTCCACCAAGGGCCCATCGGTCTTCCCCCTGGCGCCCTGCTCCAGGAGCA CCTCCGAGAGCACAGCCGCCCTGGGCTGCCTGGTCAAGGACTACTTCCCC | mAb3 Heavy Chain |

-continued

SEQUENCE LISTING

| SEQ ID NO | Sequence | Description |
|---|---|---|
| | GAACCGGTGACGGTGTCGTGGAACTCAGGCGCCCTGACCAGCGGCGTGCA CACCTTCCCGGCTGTCCTACAGTCCTCAGGACTCTACTCCCTCAGCAGCGT GGTGACCGTGCCCTCCAGCAGCTTGGGCACGAAGACCTACACCTGCAACGT AGATCACAAGCCCAGCAACACCAAGGTGGACAAGAGAGTTGAGTCCAAATA TGGTCCCCCATGCCCACCCTGCCCAGCACCTGAGTTCCTGGGGGGACCATC AGTCTTCCTGTTCCCCCCAAAACCCAAGGACACTCTCATGATCTCCCGGACC CCTGAGGTCACGTGCGTGGTGGTGGACGTGAGCCAGGAAGACCCCGAGGT CCAGTTCAACTGGTACGTGGATGGCGTGGAGGTGCATAATGCCAAGACAAA GCCGCGGGAGGAGCAGTTCAACAGCACGTACCGTGTGGTCAGCGTCCTCA CCGTCCTGCACCAGGACTGGCTGAACGGCAAGGAGTACAAGTGCAAGGTCT CCAACAAAGGCCTCCCGTCCTCCATCGAGAAAACCATCTCCAAAGCCAAAG GGCAGCCCCGAGAGCCACAGGTGTACACCCTGCCCCCATCCCAGGAGGAG ATGACCAAGAACCAGGTCAGCCTGACCTGCCTGGTCAAAGGCTTCTACCCC AGCGACATCGCCGTGGAGTGGGAGAGCAATGGGCAGCCGGAGAACAACTA CAAGACCACGCCTCCCGTGCTGGACTCCGACGGCTCCTTCTTCCTCTACAG CAGGCTCACCGTGGACAAGAGCAGGTGGCAGGAGGGGAATGTCTTCTCAT GCTCCGTGATGCATGAGGCTCTGCACAACCACTACACACAGAAGTCCCTCT CCCTGTCTCTGGGTAAATGA | |
| 49 | QVQLVESGGGVVQPGRSLRLSCAASGFTFSNYGMHWVRQAPGKGLEWVALI WYDGSNKYYADSVKGRFTISRDNSKNTLFLQMNSLRADDTAVYYCAREMESSS GFDLWGRGTLVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDV SQEDPEVQFNWYVDGVEVHNAKTKPREEQFNSTYRVVSVLTVLHQDWLNGKE YKCKVSNKGLPSSIEKTISKAKGQPREPQVYTLPPSQEEMTKNQVSLTCLVKGF YPSDIAVEWESNGQPENNYKTTPPVLDSDGSFFLYSRLTVDKSRWQEGNVFSC SVMHEALHNHYTQKSLSLSLGK* | mAb3 Heavy Chain |
| 50 | GACATCCAGATGACCCAGTCTCCTTCCACCCTGTCTGCATCTGTAGGAGACA GAGTCACCATCACTTGCCGGGCCAGTCAGAGTATTAGTAGGTGGTTGGCCT GGTATCAGCAGAAACCAGGGAAAGCCCCTAAGCTCCTGATCTATAAGGCGT CTAGTTTACAAAGTGGGGTCCCTTCAAGGTTCAGCGGCAGTGGATCTGGGA CAGAATTCACTCTCACCATCAGCAGCCTGCAGCCTGATGATTTTGCAACTTA TTACTGCCAACAGTATAATAGTTATTCTCCGACGTTCGGCCAAGGGACCAAG GTGGAAATCAAACGAACTGTGGCTGCACCATCTGTCTTCATCTTCCCGCCAT CTGATGAGCAGTTGAAATCTGGAACTGCCTCTGTTGTGTGCCTGCTGAATAA CTTCTATCCCAGAGAGGCCAAAGTACAGTGGAAGGTGGATAACGCCCTCCA ATCGGGTAACTCCCAGGAGAGTGTCACAGAGCAGGACAGCAAGGACAGCA CCTACAGCCTCAGCAGCACCCTGACGCTGAGCAAAGCAGACTACGAGAAAC ACAAAGTCTACGCCTGCGAAGTCACCCATCAGGGCCTGAGCTCGCCCGTCA CAAAGAGCTTCAACAGGGGAGAGTGTTAG | mAb3 Light Chain |
| 51 | DIQMTQSPSTLSASVGDRVTITCRASQSISRWLAWYQQKPGKAPKLLIYKASSL QSGVPSRFSGSGSGTEFTLTISSLQPDDFATYYCQQYNSYSPTFGQGTKVEIKR TVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC* | mAb3 Light Chain |
| 52 | QVQLVESGGGVVQPGRSLRLSCAASGFTFSSYGMHWVRQAPGKGLEWVAVI WYDGSNKYYADSVKGRFTISRDNSKNTLYLQMNSLRAEDTAVYYCAREESSAS GVDYWGQGTLVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPSN TKVDKRVESKYGPPCPPCPAPEFLGGPSVFLFPPKPKDTLMISRTPEVTCVVVD VSQEDPEVQFNWYVDGVEVHNAKTKPREEQFQSTYRVVSVLTVLHQDWLNGK EYKCKVSNKGLPSSIEKTISKAKGQPREPQVYTLPPSQEEMTKNQVSLTCLVKG FYPSDIAVEWESNGQPENNYKTTPPVLDSDGSFFLYSRLTVDKSRWQEGNVFS CSVMHEALHNHYTQKSLSLSLGK* | mAb1 Heavy Chain with N297Q Modification |
| 53 | QVQLVESGGGVVQPGKSLRLSCAASGFTFSNYGMHWVRQTPVKGLEWVTLIW YDGSNKYYTDSVKGRFTISRDNSKNTLYLQMNSLRSEDTAVYYCAREGNWNYG HAFDIWGQGTMVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPSN TKVDKRVESKYGPPCPPCPAPEFLGGPSVFLFPPKPKDTLMISRTPEVTCVVVD VSQEDPEVQFNWYVDGVEVHNAKTKPREEQFQSTYRVVSVLTVLHQDWLNGK EYKCKVSNKGLPSSIEKTISKAKGQPREPQVYTLPPSQEEMTKNQVSLTCLVKG FYPSDIAVEWESNGQPENNYKTTPPVLDSDGSFFLYSRLTVDKSRWQEGNVFS CSVMHEALHNHYTQKSLSLSLGK* | mAb2 Heavy Chain with N297Q Modification |
| 54 | QVQLVESGGGVVQPGRSLRLSCAASGFTFSNYGMHWVRQAPGKGLEWVALI WYDGSNKYYADSVKGRFTISRDNSKNTLFLQMNSLRADDTAVYYCAREMESSS GFDLWGRGTLVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDV SQEDPEVQFNWYVDGVEVHNAKTKPREEQFQSTYRVVSVLTVLHQDWLNGKE | mAb3 Heavy Chain with N297Q Modification |

-continued

SEQUENCE LISTING

| SEQ ID NO | Sequence | Description |
|---|---|---|
| | YKCKVSNKGLPSSIEKTISKAKGQPREPQVYTLPPSQEEMTKNQVSLTCLVKGF YPSDIAVEWESNGQPENNYKTTPPVLDSDGSFFLYSRLTVDKSRWQEGNVFSC SVMHEALHNHYTQKSLSLSLGK* | |
| 55 | MVSWGRFICLVVVTMATLSLARPSFSLVEDTTLEPEEPPTKYQISQPEVYVAAP GESLEVRCLLKDAAVISWTKDGVHLGPNNRTVLIGEYLQIKGATPRDSGLYACTA SRTVDSETWYFMVNVTDAISSGDDEDDTDGAEDFVSENSNNKRAPYWTNTEK MEKRLHAVPAANTVKFRCPAGGNPMPTMRWLKNGKEFKQEHRIGGYKVRNQH WSLIMESVVPSDKGNYTCVVENEYGSINHTYHLDVVERSPHRPILQAGLPANAS TVVGGDVEFVCKVYSDAQPHIQWIKHVEKNGSKYGPDGLPYLKVLKHSGINSSN AEVLALFNVTEADAGEYICKVSNYIGQANQSAWLTVLPKQQAPGREKEITASPD YLEIAIYCIGVFLIACMVVTVILCRMKNTTKKPDFSSQPAVHKLTKRIPLRRQVTVS AESSSSMNSNTPLVRITTRLSSTADTPMLAGVSEYELPEDPKWEFPRDKLTLGK PLGEGCFGQVVMAEAVGIDKDKPKEAVTVAVKMLKDDATEKDLSDLVSEMEMM KMIGKHKNIINLLGACTQDGPLYVIVEYASKGNLREYLRARRPPGMEYSYDINRV PEEQMTFKDLVSCTYQLARGMEYLASQKCIHRDLAARNVLVTENNVMKIADFGL ARDINNIDYYKKTTNGRLPVKWMAPEALFDRVYTHQSDVWSFGVLMWEIFTLG GSPYPGIPVEELFKLLKEGHRMDKPANCTNELYMMMRDCWHAVPSQRPTFKQ LVEDLDRILTLTTNEEYLDLSQPLEQYSPSYPDTRSSCSSGDDSVFSPDPMPYE PCLPQYPHINGSVKT | FGFR2b NCBI accession No. NP_075259.4 |
| 56 | RPSFSLVEDTTLEPEEPPTKYQISQPEVYVAAPGESLEVRCLLKDAAVISWTKDG VHLGPNNRTVLIGEYLQIKGATPRDSGLYACTASRTVDSETWYFMVNVTDAISS GDDEDDTDGAEDFVSENSNNKRAPYWTNTEKMEKRLHAVPAANTVKFRCPAG GNPMPTMRWLKNGKEFKQEHRIGGYKVRNQHWSLIMESVVPSDKGNYTCVVE NEYGSINHTYHLDVVERSPHRPILQAGLPANASTVVGGDVEFVCKVYSDAQPHI QWIKHVEKNGSKYGPDGLPYLKVLKHSGINSSNAEVLALFNVTEADAGEYICKV SNYIGQANQSAWLTVLPKQQAPGREKEITASPDYLEIEPRGPTIKPCPPCKCPAP NLLGGPSVFIFPPKIKDVLMISLSPIVTCVVVDVSEDDPDVQISWFVNNVEVHTAQ TQTHREDYNSTLRVVSALPIQHQDWMSGKEFKCKVNNKDLPAPIERTISKPKGS VRAPQVYVLPPPEEEMTKKQVTLTCMVTDFMPEDIYVEWTNNGKTELNYKNTE PVLDSDGSYFMYSKLRVEKKNWVERNSYSCSVVHEGLHNHHTTKSFSRTPGK | extracellular domain of recombinant human FGFR2b isoform (Accession Number NP_075259.4) fused with a mouse Fc domain (accession number P01863) |
| 57 | RPSFSLVEDTTLEPEEPPTKYQISQPEVYVAAPGESLEVRCLLKDAAVISWTKDG VHLGPNNRTVLIGEYLQIKGATPRDSGLYACTASRTVDSETWYFMVNVTDAISS GDDEDDTDGAEDFVSENSNNKRAPYWTNTEKMEKRLHAVPAANTVKFRCPAG GNPMPTMRWLKNGKEFKQEHRIGGYKVRNQHWSLIMESVVPSDKGNYTCVVE NEYGSINHTYHLDVVERSPHRPILQAGLPANASTVVGGDVEFVCKVYSDAQPHI QWIKHVEKNGSKYGPDGLPYLKVLKHSGINSSNAEVLALFNVTEADAGEYICKV SNYIGQANQSAWLTVLPKQQAPGREKEITASPDYLEIEQKLISEEDLGGEQKLIS EEDLHHHHHH | hFGFR2b-MMH |
| 58 | RPSFSLVEDTTLEPEEPPTKYQISQPEVYVAAPGESLEVRCLLKDAAVISWTKDG VHLGPNNRTVLIGEYLQIKGATPRDSGLYACTASRTVDSETWYFMVNVTDAISS GDDEDDTDGAEDFVSENSNNKRAPYWTNTEKMEKRLHAVPAANTVKFRCPAG GNPMPTMRWLKNGKEFKQEHRIGGYKVRNQHWSLIMESVVPSDKGNYTCVVE NEYGSINHTYHLDVVERSPHRPILQAGLPANASTVVGGDVEFVCKVYSDAQPHI QWIKHVEKNGSKYGPDGLPYLKVLKAAGVNTTDKEIEVLYIRNVTFEDAGEYTCL AGNSIGISFHSAWLTVLPAPGREKEITASPDYLEEQKLISEEDLGGEQKLISEEDL HHHHHH | hFGFR2c-MMH |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A nucleic acid molecule comprising a polynucleotide sequence that encodes a heavy chain variable region (HCVR) and/or a polynucleotide sequence that encodes a light chain variable region (LCVR) of a human monoclonal antibody or antigen-binding fragment thereof that binds to FGFR2, wherein the antibody or antigen-binding fragment thereof comprises:

three heavy chain complementarity determining regions (CDRs) (HCDR1, HCDR2 and HCDR3) contained within the HCVR sequence set forth in SEQ ID NO: 2, SEQ ID NO: 22 or SEQ ID NO: 40; and three light chain CDRs (LCDR1, LCDR2 and LCDR3) contained within the LCVR sequence set forth in SEQ ID NO: 10, SEQ ID NO: 28 or SEQ ID NO: 44.

2. The nucleic acid molecule of claim 1 comprising:

(a) a polynucleotide sequence that encodes an HCVR comprising an HCDR1 comprising the amino acid sequence of SEQ ID NO: 4; an HCDR2 comprising the amino acid sequence of SEQ ID NO: 6; and an HCDR3 comprising the amino acid sequence of SEQ ID NO: 8; or (b) a polynucleotide sequence that encodes an HCVR comprising an HCDR1 comprising the amino acid sequence of SEQ ID NO: 24; an HCDR2 comprising the amino acid sequence of SEQ ID NO: 6; and an HCDR3 comprising the amino acid sequence of SEQ ID NO: 26; or (c) a polynucleotide sequence that encodes an HCVR comprising an HCDR1 comprising the amino acid sequence of SEQ ID NO: 24; an HCDR2 comprising the amino acid sequence of SEQ ID NO: 6; and an HCDR3 comprising the amino acid sequence of SEQ ID NO: 42.

3. The nucleic acid molecule of claim 2, wherein the polynucleotide encodes an HCVR comprising the amino acid sequence of SEQ ID NO: 2.

4. The nucleic acid molecule of claim 3 comprising a nucleotide sequence as set forth in SEQ ID NO: 1 or a substantially identical sequence having at least 95% homology thereto.

5. The nucleic acid molecule of claim 2, wherein the polynucleotide encodes a heavy chain comprising the amino acid sequence of SEQ ID NO: 18.

6. The nucleic acid molecule of claim 5 comprising a nucleotide sequence as set forth in SEQ ID NO: 17 or a substantially identical sequence having at least 95% homology thereto.

7. The nucleic acid molecule of claim 2, wherein the polynucleotide encodes an HCVR comprising the amino acid sequence of SEQ ID NO: 22.

8. The nucleic acid molecule of claim 7 comprising a nucleotide sequence as set forth in SEQ ID NO: 21 or a substantially identical sequence having at least 95% homology thereto.

9. The nucleic acid molecule of claim 2, wherein the polynucleotide encodes a heavy chain comprising the amino acid sequence of SEQ ID NO: 36.

10. The nucleic acid molecule of claim 9 comprising a nucleotide sequence as set forth in SEQ ID NO: 35 or a substantially identical sequence having at least 95% homology thereto.

11. The nucleic acid molecule of claim 2, wherein the polynucleotide encodes an HCVR comprising the amino acid sequence of SEQ ID NO: 40.

12. The nucleic acid molecule of claim 11 comprising a nucleotide sequence as set forth in SEQ ID NO: 39 or a substantially identical sequence having at least 95% homology thereto.

13. The nucleic acid molecule of claim 2, wherein the polynucleotide encodes a heavy chain comprising the amino acid sequence of SEQ ID NO: 49.

14. The nucleic acid molecule of claim 13 comprising a nucleotide sequence as set forth in SEQ ID NO: 48 or a substantially identical sequence having at least 95% homology thereto.

15. The nucleic acid molecule of claim 1 comprising:

(a) a polynucleotide sequence that encodes an LCVR comprising an LCDR1 comprising the amino acid sequence of SEQ ID NO: 12; an LCDR2 comprising the amino acid sequence of GAS; and an LCDR3 comprising the amino acid sequence of SEQ ID NO: 16; or (b) a polynucleotide sequence that encodes an LCVR comprising an LCDR1 comprising the amino acid sequence of SEQ ID NO: 30; an LCDR2 comprising the amino acid sequence of KAS; and an LCDR3 comprising the amino acid sequence of SEQ ID NO: 34; or (c) a polynucleotide sequence that encodes an LCVR comprising an LCDR1 comprising the amino acid sequence of SEQ ID NO: 46; an LCDR2 comprising the amino acid sequence of KAS; and an LCDR3 comprising the amino acid sequence of SEQ ID NO: 34.

16. The nucleic acid molecule of claim 15, wherein the polynucleotide encodes an LCVR comprising the amino acid sequence of SEQ ID NO: 10.

17. The nucleic acid molecule of claim 16 comprising a nucleotide sequence as set forth in SEQ ID NO: 9 or a substantially identical sequence having at least 95% homology thereto.

18. The nucleic acid molecule of claim 15, wherein the polynucleotide encodes a light chain comprising the amino acid sequence of SEQ ID NO: 20.

19. The nucleic acid molecule of claim 18 comprising a nucleotide sequence as set forth in SEQ ID NO: 19 or a substantially identical sequence having at least 95% homology thereto.

20. The nucleic acid molecule of claim 15, wherein the polynucleotide encodes an LCVR comprising the amino acid sequence of SEQ ID NO: 28.

21. The nucleic acid molecule of claim 20 comprising a nucleotide sequence as set forth in SEQ ID NO: 27 or a substantially identical sequence having at least 95% homology thereto.

22. The nucleic acid molecule of claim 15, wherein the polynucleotide encodes a light chain comprising the amino acid sequence of SEQ ID NO: 38.

23. The nucleic acid molecule of claim 22 comprising a nucleotide sequence as set forth in SEQ ID NO: 37 or a substantially identical sequence having at least 95% homology thereto.

24. The nucleic acid molecule of claim 15, wherein the polynucleotide encodes an LCVR comprising the amino acid sequence of SEQ ID NO: 44.

25. The nucleic acid molecule of claim 15 comprising a nucleotide sequence as set forth in SEQ ID NO: 43 or a substantially identical sequence having at least 95% homology thereto.

26. The nucleic acid molecule of claim 15, wherein the polynucleotide encodes a light chain comprising the amino acid sequence of SEQ ID NO: 51.

27. The nucleic acid molecule of claim 26 comprising a nucleotide sequence as set forth in SEQ ID NO: 50 or a substantially identical sequence having at least 95% homology thereto.

28. The nucleic acid molecule of claim 1, comprising a polynucleotide sequence that encodes (i) an HCVR comprising an HCDR1 comprising the amino acid sequence of SEQ ID NO: 4, an HCDR2 comprising the amino acid sequence of SEQ ID NO: 6, and an HCDR3 comprising the amino acid sequence of SEQ ID NO: 8; and (ii) an LCVR comprising an LCDR1 comprising the amino acid sequence of SEQ ID NO: 12, an LCDR2 comprising the amino acid sequence of GAS, and an LCDR3 comprising the amino acid sequence of SEQ ID NO: 16.

29. The nucleic acid molecule of claim 1 comprising a polynucleotide sequence that encodes (i) an HCVR comprising an HCDR1 comprising the amino acid sequence of SEQ ID NO: 24, an HCDR2 comprising the amino acid sequence of SEQ ID NO: 6, and an HCDR3 comprising the amino acid sequence of SEQ ID NO: 26; and (ii) an LCVR comprising an LCDR1 comprising the amino acid sequence of SEQ ID NO: 30, an LCDR2 comprising the amino acid sequence of KAS, and an LCDR3 comprising the amino acid sequence of SEQ ID NO: 34.

30. The nucleic acid molecule of claim 1 comprising a polynucleotide sequence that encodes (i) an HCVR comprising an HCDR1 comprising the amino acid sequence of SEQ ID NO: 24, an HCDR2 comprising the amino acid sequence of SEQ ID NO: 6, and an HCDR3 comprising the amino acid sequence of SEQ ID NO: 42; and (ii) an LCVR comprising an LCDR1 comprising the amino acid sequence of SEQ ID NO: 46, an LCDR2 comprising the amino acid sequence of KAS, and an LCDR3 comprising the amino acid sequence of SEQ ID NO: 34.

31. A composition comprising a first nucleic acid molecule and a second nucleic acid molecule, wherein:

a) the first nucleic acid molecule comprises a polynucleotide sequence encoding an HCVR of a human monoclonal antibody or antigen-binding fragment thereof that binds to FGFR2, wherein the HCVR comprises an HCDR1 comprising the amino acid sequence of SEQ ID NO: 4, an HCDR2 comprising the amino acid sequence of SEQ ID NO: 6, and an HCDR3 comprising the amino acid sequence of SEQ ID NO: 8; and the second nucleic acid molecule comprises a polynucleotide sequence encoding an LCVR of the human monoclonal antibody or antigen-binding fragment thereof that binds to FGFR2, wherein the LCVR comprises an LCDR1 comprising the amino acid sequence of SEQ ID NO: 12, an LCDR2 comprising the amino acid sequence of GAS, and an LCDR3 comprising the amino acid sequence of SEQ ID NO: 16; or b) the first nucleic acid molecule comprises a polynucleotide sequence encoding an HCVR of a human monoclonal antibody or antigen-binding fragment thereof that binds to FGFR2, wherein the HCVR comprises an HCDR1 comprising the amino acid sequence of SEQ ID NO: 24, an HCDR2 comprising the amino acid sequence of SEQ ID NO: 6, and an HCDR3 comprising the amino acid sequence of SEQ ID NO: 26; and the second nucleic acid molecule comprises a polynucleotide sequence encoding an LCVR of the human monoclonal antibody or antigen-binding fragment thereof that binds to FGFR2, wherein the LCVR comprises an LCDR1 comprising the amino acid sequence of SEQ ID NO: 30, an LCDR2 comprising the amino acid sequence of KAS, and an LCDR3 comprising the amino acid sequence of SEQ ID NO: 34; or c) the first nucleic acid molecule comprises a polynucleotide sequence encoding an HCVR of a human monoclonal antibody or antigen-binding fragment thereof that binds to FGFR2, wherein the HCVR comprises an HCDR1 comprising the amino acid sequence of SEQ ID NO: 24, an HCDR2 comprising the amino acid sequence of SEQ ID NO: 6, and an HCDR3 comprising the amino acid sequence of SEQ ID NO: 42; and the second nucleic acid molecule comprises a polynucleotide sequence encoding an LCVR of the human monoclonal antibody or antigen-binding fragment thereof that binds to FGFR2, wherein the LCVR comprises an LCDR1 comprising the amino acid sequence of SEQ ID NO: 46, an LCDR2 comprising the amino acid sequence of KAS, and an LCDR3 comprising the amino acid sequence of SEQ ID NO: 34.

32. An expression vector comprising the nucleic acid molecule of claim 1.

33. An isolated host cell expressing the expression vector of claim 13.

34. A method of producing an anti-FGFR2 antibody or antigen-binding fragment thereof, the method comprising growing the host cell of claim 33 under conditions permitting production of the anti-FGFR2 antibody or antigen-binding fragment thereof, and optionally recovering the anti-FGFR2 antibody or antigen-binding fragment thereof so produced.

35. An expression vector comprising a first nucleic acid molecule and a second nucleic acid molecule, wherein:

a) the first nucleic acid molecule comprises a polynucleotide sequence that encodes an HCVR comprising the amino acid sequence of SEQ ID NO: 2, and the second nucleic acid molecule comprises a polynucleotide sequence that encodes an LCVR comprising the amino acid sequence of SEQ ID NO: 10; or b) the first nucleic acid molecule comprises a polynucleotide sequence that encodes an HCVR comprising the amino acid sequence of SEQ ID NO: 22, and the second nucleic acid molecule comprises a polynucleotide sequence that encodes an LCVR comprising the amino acid sequence of SEQ ID NO: 28; or c) the first nucleic acid molecule comprises a polynucleotide sequence that encodes an HCVR comprising the amino acid sequence of SEQ ID NO: 40, and the second nucleic acid molecule comprises a polynucleotide sequence that encodes an LCVR comprising the amino acid sequence of SEQ ID NO: 44.

36. An isolated host cell expressing the expression vector of claim 35.

37. A method of producing an anti-FGFR2 antibody or antigen-binding fragment thereof, the method comprising growing the host cell of claim 36 under conditions permitting production of the anti-FGFR2 antibody or antigen-binding fragment thereof, and optionally recovering the antibody or antigen-binding fragment thereof so produced.

* * * * *

SEQUENCE LISTING

```
Sequence total quantity: 58
SEQ ID NO: 1            moltype = DNA  length = 357
FEATURE                 Location/Qualifiers
misc_feature            1..357
                        note = Synthetic
source                  1..357
                        mol_type = other DNA
                        organism = synthetic construct
SEQUENCE: 1
caggtgcagc tggtggagtc tgggggaggc gtggtccagc ctgggaggtc cctgagactc  60
tcctgtgcag cgtctggatt caccttcagt agctatggca tgcactgggt ccgccaggct  120
ccaggcaagg gactggagtg ggtggcagtt atatggtatg atggaagtaa taaatactat  180
```

-continued

```
gcagactccg tgaagggccg attcaccatc tccagagaca attccaagaa cacgctgtat  240
ctgcaaatga acagcctgag agccgaggac acggctgtgt attactgtgc gagagaggaa  300
agcagcgcgt ccggggttga ctactggggc cagggaaccc tggtcaccgt ctcctca     357

SEQ ID NO: 2            moltype = AA  length = 119
FEATURE                 Location/Qualifiers
REGION                  1..119
                        note = Synthetic
source                  1..119
                        mol_type = protein
                        organism = synthetic construct
SEQUENCE: 2
QVQLVESGGG VVQPGRSLRL SCAASGFTFS SYGMHWVRQA PGKGLEWVAV IWYDGSNKYY  60
ADSVKGRFTI SRDNSKNTLY LQMNSLRAED TAVYYCAREE SSASGVDYWG QGTLVTVSS   119

SEQ ID NO: 3            moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 3
ggattcacct tcagtagcta tggc                                         24

SEQ ID NO: 4            moltype = AA  length = 8
FEATURE                 Location/Qualifiers
REGION                  1..8
                        note = Synthetic
source                  1..8
                        mol_type = protein
                        organism = synthetic construct
SEQUENCE: 4
GFTFSSYG                                                           8

SEQ ID NO: 5            moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 5
atatggtatg atggaagtaa taaa                                         24

SEQ ID NO: 6            moltype = AA  length = 8
FEATURE                 Location/Qualifiers
REGION                  1..8
                        note = Synthetic
source                  1..8
                        mol_type = protein
                        organism = synthetic construct
SEQUENCE: 6
IWYDGSNK                                                           8

SEQ ID NO: 7            moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 7
gcgagagagg aaagcagcgc gtccggggtt gactac                            36

SEQ ID NO: 8            moltype = AA  length = 12
FEATURE                 Location/Qualifiers
REGION                  1..12
                        note = Synthetic
source                  1..12
                        mol_type = protein
                        organism = synthetic construct
SEQUENCE: 8
AREESSASGV DY                                                      12

SEQ ID NO: 9            moltype = DNA  length = 324
FEATURE                 Location/Qualifiers
misc_feature            1..324
                        note = Synthetic
```

```
source                1..324
                      mol_type = other DNA
                      organism = synthetic construct
SEQUENCE: 9
gaaattgtgt tgacgcagtc tccaggcacc ctgtccttgt ctccagggga aagagccacc  60
ctctcctgca gggccagtca gagtgttagc accaggtact tagcctggta ccagcagaaa  120
cgtggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag gagtatggta gctcatcgat caccttcggc  300
caagggacac gactggagat taaa                                         324

SEQ ID NO: 10         moltype = AA  length = 108
FEATURE               Location/Qualifiers
REGION                1..108
                      note = Synthetic
source                1..108
                      mol_type = protein
                      organism = synthetic construct
SEQUENCE: 10
EIVLTQSPGT LSLSPGERAT LSCRASQSVS TRYLAWYQQK RGQAPRLLIY GASSRATGIP  60
DRFSGSGSGT DFTLTISRLE PEDFAVYYCQ EYGSSSITFG QGTRLEIK               108

SEQ ID NO: 11         moltype = DNA  length = 21
FEATURE               Location/Qualifiers
misc_feature          1..21
                      note = Synthetic
source                1..21
                      mol_type = other DNA
                      organism = synthetic construct
SEQUENCE: 11
cagagtgtta gcaccaggta c                                            21

SEQ ID NO: 12         moltype = AA  length = 7
FEATURE               Location/Qualifiers
REGION                1..7
                      note = Synthetic
source                1..7
                      mol_type = protein
                      organism = synthetic construct
SEQUENCE: 12
QSVSTRY                                                            7

SEQ ID NO: 13         moltype =   length =
SEQUENCE: 13
000

SEQ ID NO: 14         moltype =   length =
SEQUENCE: 14
000

SEQ ID NO: 15         moltype = DNA  length = 27
FEATURE               Location/Qualifiers
misc_feature          1..27
                      note = Synthetic
source                1..27
                      mol_type = other DNA
                      organism = synthetic construct
SEQUENCE: 15
caggagtatg gtagctcatc gatcacc                                      27

SEQ ID NO: 16         moltype = AA  length = 9
FEATURE               Location/Qualifiers
REGION                1..9
                      note = Synthetic
source                1..9
                      mol_type = protein
                      organism = synthetic construct
SEQUENCE: 16
QEYGSSSIT                                                          9

SEQ ID NO: 17         moltype = DNA  length = 1341
FEATURE               Location/Qualifiers
misc_feature          1..1341
                      note = Synthetic
source                1..1341
                      mol_type = other DNA
                      organism = synthetic construct
SEQUENCE: 17
caggtgcagc tggtggagtc tgggggaggc gtggtccagc ctgggaggtc cctgagactc  60
```

-continued

```
tcctgtgcag cgtctggatt caccttcagt agctatggca tgcactgggt ccgccaggct  120
ccaggcaagg gactggagtg ggtggcagtt atatggtatg atggaagtaa taaatactat  180
gcagactccg tgaagggccg attcaccatc tccagagaca attccaagaa cacgctgtat  240
ctgcaaatga acagcctgag agccgaggac acggctgtgt attactgtgc gagagaggaa  300
agcagcgcgt ccggggttga ctactggggc cagggaaccc tggtcaccgt ctcctcagcc  360
tccaccaagg gcccatcggt cttccccctg gcgccctgct ccaggagcac ctccgagagc  420
acagccgccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac gaagacctac  600
acctgcaacg tagatcacaa gcccagcaac accaaggtgg acaagagagt tgagtccaaa  660
tatggtcccc catgcccacc ctgcccagca cctgagttcc tggggggacc atcagtcttc  720
ctgttccccc caaaacccaa ggacactctc atgatctccc ggacccctga ggtcacgtgc  780
gtggtggtgg acgtgagcca ggaagacccc gaggtccagt tcaactggta cgtggatggc  840
gtggaggtgc ataatgccaa gacaaagccg cgggaggagc agttcaacag cacgtaccgt  900
gtggtcagcg tcctcaccgt cctgcaccag gactggctga acggcaagga gtacaagtgc  960
aaggtctcca acaaaggcct cccgtcctcc atcgagaaaa ccatctccaa agccaaaggg  1020
cagccccgag agccacaggt gtacaccctg cccccatccc aggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacgc ctcccgtgct ggactccgac  1200
ggctccttct tcctctacag caggctcacc gtggacaaga gcaggtggca ggaggggaat  1260
gtcttctcat gctccgtgat gcatgaggct ctgcacaacc actacacaca gaagtccctc  1320
tccctgtctc tgggtaaatg a                                            1341

SEQ ID NO: 18          moltype = AA  length = 446
FEATURE                Location/Qualifiers
REGION                 1..446
                       note = Synthetic
source                 1..446
                       mol_type = protein
                       organism = synthetic construct
SEQUENCE: 18
QVQLVESGGG VVQPGRSLRL SCAASGFTFS SYGMHWVRQA PGKGLEWVAV IWYDGSNKYY  60
ADSVKGRFTI SRDNSKNTLY LQMNSLRAED TAVYYCAREE SSASGVDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                      446

SEQ ID NO: 19          moltype = DNA  length = 648
FEATURE                Location/Qualifiers
misc_feature           1..648
                       note = Synthetic
source                 1..648
                       mol_type = other DNA
                       organism = synthetic construct
SEQUENCE: 19
gaaattgtgt tgacgcagtc tccaggcacc ctgtccttgt ctccagggga aagagccacc  60
ctctcctgca gggccagtca gagtgttagc accaggtact tagcctggta ccagcagaaa  120
cgtggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag gagtatggta gctcatcgat caccttcggc  300
caagggacac gactggagat taaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag              648

SEQ ID NO: 20          moltype = AA  length = 215
FEATURE                Location/Qualifiers
REGION                 1..215
                       note = Synthetic
source                 1..215
                       mol_type = protein
                       organism = synthetic construct
SEQUENCE: 20
EIVLTQSPGT LSLSPGERAT LSCRASQSVS TRYLAWYQQK RGQAPRLLIY GASSRATGIP  60
DRFSGSGSGT DFTLTISRLE PEDFAVYYCQ EYGSSSITFG QGTRLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 21          moltype = DNA  length = 363
FEATURE                Location/Qualifiers
misc_feature           1..363
                       note = Synthetic
source                 1..363
                       mol_type = other DNA
```

-continued

```
                         organism = synthetic construct
SEQUENCE: 21
caggtgcagc tggtggagtc tgggggaggc gtggtccagc ctgggaagtc cctgagactc  60
tcctgtgcag cgtctggatt caccttcagt aactatggca tgcactgggt ccgccaaact  120
ccagtcaagg gactggagtg ggtgacactt atatggtatg atggaagtaa taaatactat  180
acagactccg tgaagggccg attcaccatc tccagagaca attccaagaa cacgctgtat  240
ctgcaaatga acagcctgag atccgaggac acggctgtgt attactgtgc gagagagggg  300
aactggaact acgggcatgc ttttgatatc tggggccaag ggacaatggt caccgtctct  360
tca                                                                363

SEQ ID NO: 22            moltype = AA  length = 121
FEATURE                  Location/Qualifiers
REGION                   1..121
                         note = Synthetic
source                   1..121
                         mol_type = protein
                         organism = synthetic construct
SEQUENCE: 22
QVQLVESGGG VVQPGKSLRL SCAASGFTFS NYGMHWVRQT PVKGLEWVTL IWYDGSNKYY  60
TDSVKGRFTI SRDNSKNTLY LQMNSLRSED TAVYYCAREG NWNYGHAFDI WGQGTMVTVS  120
S                                                                  121

SEQ ID NO: 23            moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 23
ggattcacct tcagtaacta tggc                                         24

SEQ ID NO: 24            moltype = AA  length = 8
FEATURE                  Location/Qualifiers
REGION                   1..8
                         note = Synthetic
source                   1..8
                         mol_type = protein
                         organism = synthetic construct
SEQUENCE: 24
GFTFSNYG                                                           8

SEQ ID NO: 25            moltype = DNA  length = 42
FEATURE                  Location/Qualifiers
misc_feature             1..42
                         note = Synthetic
source                   1..42
                         mol_type = other DNA
                         organism = synthetic construct
SEQUENCE: 25
gcgagagagg ggaactggaa ctacgggcat gcttttgata tc                     42

SEQ ID NO: 26            moltype = AA  length = 14
FEATURE                  Location/Qualifiers
REGION                   1..14
                         note = Synthetic
source                   1..14
                         mol_type = protein
                         organism = synthetic construct
SEQUENCE: 26
AREGNWNYGH AFDI                                                    14

SEQ ID NO: 27            moltype = DNA  length = 321
FEATURE                  Location/Qualifiers
misc_feature             1..321
                         note = Synthetic
source                   1..321
                         mol_type = other DNA
                         organism = synthetic construct
SEQUENCE: 27
gacatccaga tgacccagtc tccttccacc ctgtctgcat ctgtaggaga cagagtcacc  60
atcacttgcc gggccagtca gaatattggt aactggttgg cctggtatca gcagaaacca  120
gggaaagccc ctaacctcct gatttataag gcgtctactt tagaaagtgg ggtcccatca  180
aggttcagcg gcagtggatc tgggacagaa ttcactctca ccatcagcag cctgcagcct  240
gatgattttg caacttataa ctgccaacag tataatagtt attctcccac ttttggccag  300
gggaccaagc tggagatcaa a                                            321

SEQ ID NO: 28            moltype = AA  length = 107
FEATURE                  Location/Qualifiers
```

-continued

```
REGION                  1..107
                        note = Synthetic
source                  1..107
                        mol_type = protein
                        organism = synthetic construct
SEQUENCE: 28
DIQMTQSPST LSASVGDRVT ITCRASQNIG NWLAWYQQKP GKAPNLLIYK ASTLESGVPS  60
RFSGSGSGTE FTLTISSLQP DDFATYNCQQ YNSYSPTFGQ GTKLEIK                107

SEQ ID NO: 29           moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 29
cagaatattg gtaactgg                                                18

SEQ ID NO: 30           moltype = AA  length = 6
FEATURE                 Location/Qualifiers
REGION                  1..6
                        note = Synthetic
source                  1..6
                        mol_type = protein
                        organism = synthetic construct
SEQUENCE: 30
QNIGNW                                                             6

SEQ ID NO: 31           moltype =   length =
SEQUENCE: 31
000

SEQ ID NO: 32           moltype =   length =
SEQUENCE: 32
000

SEQ ID NO: 33           moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 33
caacagtata atagttattc tcccact                                      27

SEQ ID NO: 34           moltype = AA  length = 9
FEATURE                 Location/Qualifiers
REGION                  1..9
                        note = Synthetic
source                  1..9
                        mol_type = protein
                        organism = synthetic construct
SEQUENCE: 34
QQYNSYSPT                                                          9

SEQ ID NO: 35           moltype = DNA  length = 1347
FEATURE                 Location/Qualifiers
misc_feature            1..1347
                        note = Synthetic
source                  1..1347
                        mol_type = other DNA
                        organism = synthetic construct
SEQUENCE: 35
caggtgcagc tggtggagtc tgggggaggc gtggtccagc ctgggaagtc cctgagactc  60
tcctgtgcag cgtctggatt caccttcagt aactatggca tgcactgggt ccgccaaact  120
ccagtcaagg gactggagtg ggtgacactt atatggtatg atggaagtaa taaatactat  180
acagactccg tgaagggccg attcaccatc tccagagaca attccaagaa cacgctgtat  240
ctgcaaatga acagcctgag atccgaggac acggctgtgt attactgtgc gagagagggg  300
aactggaact acgggcatgc ttttgatatc tggggccaag ggacaatggt caccgtctct  360
tcagcctcca ccaagggccc atcggtcttc cccctggcgc cctgctccag gagcacctcc  420
gagagcacag ccgccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacgaag  600
acctacacct gcaacgtaga tcacaagccc agcaacacca aggtggacaa gagagttgag  660
tccaaatatg gtcccccatg cccaccctgc ccagcacctg agttcctggg gggaccatca  720
gtcttcctgt tccccccaaa acccaaggac actctcatga tctcccggac ccctgaggtc  780
acgtgcgtgg tggtggacgt gagccaggaa gaccccgagg tccagttcaa ctggtacgtg  840
```

```
gatggcgtgg aggtgcataa tgccaagaca aagccgcggg aggagcagtt caacagcacg  900
taccgtgtgg tcagcgtcct caccgtcctg caccaggact ggctgaacgg caaggagtac  960
aagtgcaagg tctccaacaa aggcctcccg tcctccatcg agaaaaccat ctccaaagcc  1020
aaagggcagc cccgagagcc acaggtgtac accctgcccc catcccagga ggagatgacc  1080
aagaaccagg tcagcctgac ctgcctggtc aaaggcttct accccagcga catcgccgtg  1140
gagtgggaga gcaatgggca gccggagaac aactacaaga ccacgcctcc cgtgctggac  1200
tccgacggct ccttcttcct ctacagcagg ctcaccgtgg acaagagcag gtggcaggag  1260
gggaatgtct tctcatgctc cgtgatgcat gaggctctgc acaaccacta cacacagaag  1320
tccctctccc tgtctctggg taaatga                                      1347

SEQ ID NO: 36          moltype = AA  length = 448
FEATURE                Location/Qualifiers
REGION                 1..448
                       note = Synthetic
source                 1..448
                       mol_type = protein
                       organism = synthetic construct
SEQUENCE: 36
QVQLVESGGG VVQPGKSLRL SCAASGFTFS NYGMHWVRQT PVKGLEWVTL IWYDGSNKYY  60
TDSVKGRFTI SRDNSKNTLY LQMNSLRSED TAVYYCAREG NWNYGHAFDI WGQGTMVTVS  120
SASTKGPSVF PLAPCSRSTS ESTAALGCLV KDYFPEPVTV SWNSGALTSG VHTFPAVLQS  180
SGLYSLSSVV TVPSSSLGTK TYTCNVDHKP SNTKVDKRVE SKYGPPCPPC PAPEFLGGPS  240
VFLFPPKPKD TLMISRTPEV TCVVVDVSQE DPEVQFNWYV DGVEVHNAKT KPREEQFNST  300
YRVVSVLTVL HQDWLNGKEY KCKVSNKGLP SSIEKTISKA KGQPREPQVY TLPPSQEEMT  360
KNQVSLTCLV KGFYPSDIAV EWESNGQPEN NYKTTPPVLD SDGSFFLYSR LTVDKSRWQE  420
GNVFSCSVMH EALHNHYTQK SLSLSLGK                                     448

SEQ ID NO: 37          moltype = DNA  length = 645
FEATURE                Location/Qualifiers
misc_feature           1..645
                       note = Synthetic
source                 1..645
                       mol_type = other DNA
                       organism = synthetic construct
SEQUENCE: 37
gacatccaga tgacccagtc tccttccacc ctgtctgcat ctgtaggaga cagagtcacc  60
atcacttgcc gggccagtca gaatattggt aactggttgg cctggtatca gcagaaacca  120
gggaaagccc ctaacctcct gatttataag gcgtctactt tagaaagtgg ggtcccatca  180
aggttcagcg gcagtggatc tgggacagaa ttcactctca ccatcagcag cctgcagcct  240
gatgattttg caacttataa ctgccaacag tataatagtt attctcccac ttttggccag  300
gggaccaagc tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 38          moltype = AA  length = 214
FEATURE                Location/Qualifiers
REGION                 1..214
                       note = Synthetic
source                 1..214
                       mol_type = protein
                       organism = synthetic construct
SEQUENCE: 38
DIQMTQSPST LSASVGDRVT ITCRASQNIG NWLAWYQQKP GKAPNLLIYK ASTLESGVPS  60
RFSGSGSGTE FTLTISSLQP DDFATYNCQQ YNSYSPTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 39          moltype = DNA  length = 357
FEATURE                Location/Qualifiers
misc_feature           1..357
                       note = Synthetic
source                 1..357
                       mol_type = other DNA
                       organism = synthetic construct
SEQUENCE: 39
caggtgcagc tggtggagtc tgggggaggc gtggtccagc ctgggaggtc cctgagactc  60
tcctgtgcag cgtctggatt caccttcagt aactatggca tgcactgggt ccgccaggct  120
ccaggcaagg ggctggagtg ggtggcactt atatggtatg atggaagtaa taaatactat  180
gcagactccg tgaagggccg attcaccatc tccagagaca attccaagaa cacgcttttt  240
ctgcaaatga acagcctgag agccgatgac acggctgtgt attactgtgc gcgagagatg  300
gagagcagct cgggcttcga tctctggggc cgtggcaccc tggtcactgt ctcctca     357

SEQ ID NO: 40          moltype = AA  length = 119
FEATURE                Location/Qualifiers
REGION                 1..119
                       note = Synthetic
```

```
source                  1..119
                        mol_type = protein
                        organism = synthetic construct
SEQUENCE: 40
QVQLVESGGG VVQPGRSLRL SCAASGFTFS NYGMHWVRQA PGKGLEWVAL IWYDGSNKYY  60
ADSVKGRFTI SRDNSKNTLF LQMNSLRADD TAVYYCAREM ESSSGFDLWG RGTLVTVSS   119

SEQ ID NO: 41           moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 41
gcgcgagaga tggagagcag ctcgggcttc gatctc                           36

SEQ ID NO: 42           moltype = AA  length = 12
FEATURE                 Location/Qualifiers
REGION                  1..12
                        note = Synthetic
source                  1..12
                        mol_type = protein
                        organism = synthetic construct
SEQUENCE: 42
AREMESSSGF DL                                                     12

SEQ ID NO: 43           moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 43
gacatccaga tgacccagtc tccttccacc ctgtctgcat ctgtaggaga cagagtcacc  60
atcacttgcc gggccagtca gagtattagt aggtggttgg cctggtatca gcagaaacca  120
gggaaagccc ctaagctcct gatctataag gcgtctagtt tacaaagtgg ggtcccttca  180
aggttcagcg gcagtggatc tgggacagaa ttcactctca ccatcagcag cctgcagcct  240
gatgattttg caacttatta ctgccaacag tataatagtt attctccgac gttcggccaa  300
gggaccaagg tggaaatcaa a                                           321

SEQ ID NO: 44           moltype = AA  length = 107
FEATURE                 Location/Qualifiers
REGION                  1..107
                        note = Synthetic
source                  1..107
                        mol_type = protein
                        organism = synthetic construct
SEQUENCE: 44
DIQMTQSPST LSASVGDRVT ITCRASQSIS RWLAWYQQKP GKAPKLLIYK ASSLQSGVPS  60
RFSGSGSGTE FTLTISSLQP DDFATYYCQQ YNSYSPTFGQ GTKVEIK               107

SEQ ID NO: 45           moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 45
cagagtatta gtaggtgg                                               18

SEQ ID NO: 46           moltype = AA  length = 6
FEATURE                 Location/Qualifiers
REGION                  1..6
                        note = Synthetic
source                  1..6
                        mol_type = protein
                        organism = synthetic construct
SEQUENCE: 46
QSISRW                                                            6

SEQ ID NO: 47           moltype = DNA  length = 27
FEATURE                 Location/Qualifiers
misc_feature            1..27
                        note = Synthetic
source                  1..27
                        mol_type = other DNA
```

```
                         organism = synthetic construct
SEQUENCE: 47
caacagtata atagttattc tccgacg                                         27

SEQ ID NO: 48            moltype = DNA  length = 1341
FEATURE                  Location/Qualifiers
misc_feature             1..1341
                         note = Synthetic
source                   1..1341
                         mol_type = other DNA
                         organism = synthetic construct
SEQUENCE: 48
caggtgcagc tggtggagtc tgggggaggc gtggtccagc ctgggaggtc cctgagactc  60
tcctgtgcag cgtctggatt caccttcagt aactatggca tgcactgggt ccgccaggct  120
ccaggcaagg ggctggagtg ggtggcactt atatggtatg atggaagtaa taaatactat  180
gcagactccg tgaagggccg attcaccatc tccagagaca attccaagaa cacgcttttt  240
ctgcaaatga acagcctgag agccgatgac acggctgtgt attactgtgc gcgagagatg  300
gagagcagct cgggcttcga tctctggggc cgtggcaccc tggtcactgt ctcctcagcc  360
tccaccaagg gcccatcggt cttccccctg gcgccctgct ccaggagcac ctccgagagc  420
acagccgccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac gaagacctac  600
acctgcaacg tagatcacaa gcccagcaac accaaggtgg acaagagagt tgagtccaaa  660
tatggtcccc catgcccacc ctgcccagca cctgagttcc tggggggacc atcagtcttc  720
ctgttccccc caaaacccaa ggacactctc atgatctccc ggacccctga ggtcacgtgc  780
gtggtggtgg acgtgagcca ggaagacccc gaggtccagt tcaactggta cgtggatggc  840
gtggaggtgc ataatgccaa gacaaagccg cgggaggagc agttcaacag cacgtaccgt  900
gtggtcagcg tcctcaccgt cctgcaccag gactggctga acggcaagga gtacaagtgc  960
aaggtctcca acaaaggcct cccgtcctcc atcgagaaaa ccatctccaa agccaaaggg  1020
cagccccgag agccacaggt gtacaccctg cccccatccc aggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacgc ctcccgtgct ggactccgac  1200
ggctccttct tcctctacag caggctcacc gtggacaaga gcaggtggca ggaggggaat  1260
gtcttctcat gctccgtgat gcatgaggct ctgcacaacc actacacaca gaagtccctc  1320
tccctgtctc tgggtaaatg a                                               1341

SEQ ID NO: 49            moltype = AA  length = 446
FEATURE                  Location/Qualifiers
REGION                   1..446
                         note = Synthetic
source                   1..446
                         mol_type = protein
                         organism = synthetic construct
SEQUENCE: 49
QVQLVESGGG VVQPGRSLRL SCAASGFTFS NYGMHWVRQA PGKGLEWVAL IWYDGSNKYY  60
ADSVKGRFTI SRDNSKNTLF LQMNSLRADD TAVYYCAREM ESSSGFDLWG RGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                          446

SEQ ID NO: 50            moltype = DNA  length = 645
FEATURE                  Location/Qualifiers
misc_feature             1..645
                         note = Synthetic
source                   1..645
                         mol_type = other DNA
                         organism = synthetic construct
SEQUENCE: 50
gacatccaga tgacccagtc tccttccacc ctgtctgcat ctgtaggaga cagagtcacc  60
atcacttgcc gggccagtca gagtattagt aggtggttgg cctggtatca gcagaaacca  120
gggaaagccc ctaagctcct gatctataag gcgtctagtt tacaaagtgg ggtcccttca  180
aggttcagcg gcagtggatc tgggacagaa ttcactctca ccatcagcag cctgcagcct  240
gatgattttg caacttatta ctgccaacag tataatagtt attctccgac gttcggccaa  300
gggaccaagg tggaaatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                     645

SEQ ID NO: 51            moltype = AA  length = 214
FEATURE                  Location/Qualifiers
REGION                   1..214
                         note = Synthetic
source                   1..214
                         mol_type = protein
```

```
                         organism = synthetic construct
SEQUENCE: 51
DIQMTQSPST LSASVGDRVT ITCRASQSIS RWLAWYQQKP GKAPKLLIYK ASSLQSGVPS  60
RFSGSGSGTE FTLTISSLQP DDFATYYCQQ YNSYSPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 52            moltype = AA  length = 446
FEATURE                  Location/Qualifiers
REGION                   1..446
                         note = Synthetic
source                   1..446
                         mol_type = protein
                         organism = synthetic construct
SEQUENCE: 52
QVQLVESGGG VVQPGRSLRL SCAASGFTFS SYGMHWVRQA PGKGLEWVAV IWYDGSNKYY  60
ADSVKGRFTI SRDNSKNTLY LQMNSLRAED TAVYYCAREE SSASGVDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFQSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                       446

SEQ ID NO: 53            moltype = AA  length = 448
FEATURE                  Location/Qualifiers
REGION                   1..448
                         note = Synthetic
source                   1..448
                         mol_type = protein
                         organism = synthetic construct
SEQUENCE: 53
QVQLVESGGG VVQPGKSLRL SCAASGFTFS NYGMHWVRQT PVKGLEWVTL IWYDGSNKYY  60
TDSVKGRFTI SRDNSKNTLY LQMNSLRSED TAVYYCAREG NWNYGHAFDI WGQGTMVTVS  120
SASTKGPSVF PLAPCSRSTS ESTAALGCLV KDYFPEPVTV SWNSGALTSG VHTFPAVLQS  180
SGLYSLSSVV TVPSSSLGTK TYTCNVDHKP SNTKVDKRVE SKYGPPCPPC PAPEFLGGPS  240
VFLFPPKPKD TLMISRTPEV TCVVVDVSQE DPEVQFNWYV DGVEVHNAKT KPREEQFQST  300
YRVVSVLTVL HQDWLNGKEY KCKVSNKGLP SSIEKTISKA KGQPREPQVY TLPPSQEEMT  360
KNQVSLTCLV KGFYPSDIAV EWESNGQPEN NYKTTPPVLD SDGSFFLYSR LTVDKSRWQE  420
GNVFSCSVMH EALHNHYTQK SLSLSLGK                                     448

SEQ ID NO: 54            moltype = AA  length = 446
FEATURE                  Location/Qualifiers
REGION                   1..446
                         note = Synthetic
source                   1..446
                         mol_type = protein
                         organism = synthetic construct
SEQUENCE: 54
QVQLVESGGG VVQPGRSLRL SCAASGFTFS NYGMHWVRQA PGKGLEWVAL IWYDGSNKYY  60
ADSVKGRFTI SRDNSKNTLF LQMNSLRADD TAVYYCAREM ESSSGFDLWG RGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFQSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                       446

SEQ ID NO: 55            moltype = AA  length = 822
FEATURE                  Location/Qualifiers
REGION                   1..822
                         note = Synthetic
source                   1..822
                         mol_type = protein
                         organism = synthetic construct
SEQUENCE: 55
MVSWGRFICL VVVTMATLSL ARPSFSLVED TTLEPEEPPT KYQISQPEVY VAAPGESLEV  60
RCLLKDAAVI SWTKDGVHLG PNNRTVLIGE YLQIKGATPR DSGLYACTAS RTVDSETWYF  120
MVNVTDAISS GDDEDDTDGA EDFVSENSNN KRAPYWTNTE KMEKRLHAVP AANTVKFRCP  180
AGGNPMPTMR WLKNGKEFKQ EHRIGGYKVR NQHWSLIMES VVPSDKGNYT CVVENEYGSI  240
NHTYHLDVVE RSPHRPILQA GLPANASTVV GGDVEFVCKV YSDAQPHIQW IKHVEKNGSK  300
YGPDGLPYLK VLKHSGINSS NAEVLALFNV TEADAGEYIC KVSNYIGQAN QSAWLTVLPK  360
QQAPGREKEI TASPDYLEIA IYCIGVFLIA CMVVTVILCR MKNTTKKPDF SSQPAVHKLT  420
KRIPLRRQVT VSAESSSSMN SNTPLVRITT RLSSTADTPM LAGVSEYELP EDPKWEFPRD  480
KLTLGKPLGE GCFGQVVMAE AVGIDKDKPK EAVTVAVKML KDDATEKDLS DLVSEMEMMK  540
MIGKHKNIIN LLGACTQDGP LYVIVEYASK GNLREYLRAR RPPGMEYSYD INRVPEEQMT  600
FKDLVSCTYQ LARGMEYLAS QKCIHRDLAA RNVLVTENNV MKIADFGLAR DINNIDYYKK  660
TTNGRLPVKW MAPEALFDRV YTHQSDVWSF GVLMWEIFTL GGSPYPGIPV EELFKLLKEG  720
HRMDKPANCT NELYMMMRDC WHAVPSQRPT FKQLVEDLDR ILTLTTNEEY LDLSQPLEQY  780
```

-continued

```
SPSYPDTRSS CSSGDDSVFS PDPMPYEPCL PQYPHINGSV KT                       822

SEQ ID NO: 56           moltype = AA  length = 591
FEATURE                 Location/Qualifiers
REGION                  1..591
                        note = Synthetic
source                  1..591
                        mol_type = protein
                        organism = synthetic construct
SEQUENCE: 56
RPSFSLVEDT TLEPEEPPTK YQISQPEVYV AAPGESLEVR CLLKDAAVIS WTKDGVHLGP  60
NNRTVLIGEY LQIKGATPRD SGLYACTASR TVDSETWYFM VNVTDAISSG DDEDDTDGAE  120
DFVSENSNNK RAPYWTNTEK MEKRLHAVPA ANTVKFRCPA GGNPMPTMRW LKNGKEFKQE  180
HRIGGYKVRN QHWSLIMESV VPSDKGNYTC VVENEYGSIN HTYHLDVVER SPHRPILQAG  240
LPANASTVVG GDVEFVCKVY SDAQPHIQWI KHVEKNGSKY GPDGLPYLKV LKHSGINSSN  300
AEVLALFNVT EADAGEYICK VSNYIGQANQ SAWLTVLPKQ QAPGREKEIT ASPDYLEIEP  360
RGPTIKPCPP CKCPAPNLLG GPSVFIFPPK IKDVLMISLS PIVTCVVVDV SEDDPDVQIS  420
WFVNNVEVHT AQTQTHREDY NSTLRVVSAL PIQHQDWMSG KEFKCKVNNK DLPAPIERTI  480
SKPKGSVRAP QVYVLPPPEE EMTKKQVTLT CMVTDFMPED IYVEWTNNGK TELNYKNTEP  540
VLDSDGSYFM YSKLRVEKKN WVERNSYSCS VVHEGLHNHH TTKSFSRTPG K            591

SEQ ID NO: 57           moltype = AA  length = 386
FEATURE                 Location/Qualifiers
REGION                  1..386
                        note = Synthetic
source                  1..386
                        mol_type = protein
                        organism = synthetic construct
SEQUENCE: 57
RPSFSLVEDT TLEPEEPPTK YQISQPEVYV AAPGESLEVR CLLKDAAVIS WTKDGVHLGP  60
NNRTVLIGEY LQIKGATPRD SGLYACTASR TVDSETWYFM VNVTDAISSG DDEDDTDGAE  120
DFVSENSNNK RAPYWTNTEK MEKRLHAVPA ANTVKFRCPA GGNPMPTMRW LKNGKEFKQE  180
HRIGGYKVRN QHWSLIMESV VPSDKGNYTC VVENEYGSIN HTYHLDVVER SPHRPILQAG  240
LPANASTVVG GDVEFVCKVY SDAQPHIQWI KHVEKNGSKY GPDGLPYLKV LKHSGINSSN  300
AEVLALFNVT EADAGEYICK VSNYIGQANQ SAWLTVLPKQ QAPGREKEIT ASPDYLEIEQ  360
KLISEEDLGG EQKLISEEDL HHHHHH                                       386

SEQ ID NO: 58           moltype = AA  length = 384
FEATURE                 Location/Qualifiers
REGION                  1..384
                        note = Synthetic
source                  1..384
                        mol_type = protein
                        organism = synthetic construct
SEQUENCE: 58
RPSFSLVEDT TLEPEEPPTK YQISQPEVYV AAPGESLEVR CLLKDAAVIS WTKDGVHLGP  60
NNRTVLIGEY LQIKGATPRD SGLYACTASR TVDSETWYFM VNVTDAISSG DDEDDTDGAE  120
DFVSENSNNK RAPYWTNTEK MEKRLHAVPA ANTVKFRCPA GGNPMPTMRW LKNGKEFKQE  180
HRIGGYKVRN QHWSLIMESV VPSDKGNYTC VVENEYGSIN HTYHLDVVER SPHRPILQAG  240
LPANASTVVG GDVEFVCKVY SDAQPHIQWI KHVEKNGSKY GPDGLPYLKV LKAAGVNTTD  300
KEIEVLYIRN VTFEDAGEYT CLAGNSIGIS FHSAWLTVLP APGREKEITA SPDYLEEQKL  360
ISEEDLGGEQ KLISEEDLHH HHHH                                         384
```